US008110726B2

(12) United States Patent
Bloksberg et al.

(10) Patent No.: US 8,110,726 B2
(45) Date of Patent: Feb. 7, 2012

(54) POLYNUCLEOTIDES ENCODING CELLULOSE SYNTHASE FROM PINUS RADIATA AND METHODS OF USE FOR REGULATING POLYSACCHARIDES OF A PLANT

(75) Inventors: Leonard N. Bloksberg, Remuera (NZ); Marie B. Connett-Porceddu, Charleston, SC (US); Sarah Jane Emerson, Sandringham (AU); Michael J. Frost, Remuera (NZ); Richard Llewellyn Syndey Forster, Blockhouse Bay (NZ); Murray Robert Grigor, St. Heilers (NZ); Ilkka Havukkala, Remura (NZ); Colleen M. Higgins, Parnell (NZ); Robert J. Kodrzycki, Summerville, SC (US); Steven Troy Lund, Vancouver (CA); Andreas Magusin, Auckland (NZ)

(73) Assignee: Arborgen Inc., Summerville, SC (US)

( * ) Notice: Subject to any disclaimer, the term of this patent is extended or adjusted under 35 U.S.C. 154(b) by 26 days.

(21) Appl. No.: 12/697,484

(22) Filed: Feb. 1, 2010

(65) Prior Publication Data
US 2010/0186118 A1 Jul. 22, 2010

Related U.S. Application Data

(63) Continuation of application No. 10/861,910, filed on Jun. 7, 2004, now Pat. No. 7,671,188.

(60) Provisional application No. 60/476,239, filed on Jun. 6, 2003.

(51) Int. Cl.
C12N 15/82 (2006.01)
A01H 5/00 (2006.01)
C07H 21/04 (2006.01)

(52) U.S. Cl. ........ 800/285; 800/284; 800/286; 800/295; 800/298; 800/319; 536/23.2; 536/23.6; 536/23.1; 536/24.5; 435/419; 435/468

(58) Field of Classification Search ................. None
See application file for complete search history.

(56) References Cited

U.S. PATENT DOCUMENTS

| | | | |
|---|---|---|---|
| 5,159,135 A | 10/1992 | Umbeck | |
| 5,593,867 A | 1/1997 | Walker et al. | |
| 5,702,933 A * | 12/1997 | Klee et al. .................. | 800/283 |
| 5,824,859 A * | 10/1998 | Cashmore et al. ........... | 800/290 |
| 5,891,859 A | 4/1999 | Thomashow et al. | |
| 5,892,009 A | 4/1999 | Thomashow et al. | |
| 5,914,451 A | 6/1999 | Martinell et al. | |
| 5,929,305 A | 7/1999 | Thomashow et al. | |
| 5,965,705 A | 10/1999 | Thomashow et al. | |
| 5,981,840 A | 11/1999 | Zhao et al. | |
| 6,132,970 A | 10/2000 | Stemmer | |
| 6,271,443 B1 | 8/2001 | Stalker et al. | |
| 6,287,862 B1 | 9/2001 | delCardayre et al. | |
| 6,326,204 B1 | 12/2001 | delCardayre et al. | |
| 6,335,198 B1 | 1/2002 | delCardayre et al. | |
| 6,352,859 B1 | 3/2002 | delCardayre et al. | |
| 6,379,964 B1 | 4/2002 | del Cardayre et al. | |
| 6,436,675 B1 | 8/2002 | Welch et al. | |
| 6,500,617 B1 | 12/2002 | Stemmer et al. | |
| 6,500,639 B2 | 12/2002 | Subramanian | |
| 2002/0100083 A1 | 7/2002 | Connett-Porceddu et al. | |
| 2002/0107644 A1 | 8/2002 | Meglen et al. | |
| 2002/0113212 A1 | 8/2002 | Meglen et al. | |
| 2002/0120124 A1 * | 8/2002 | Allen ........................... | 536/23.6 |
| 2003/0229922 A1 * | 12/2003 | Bloksberg .................... | 800/284 |

FOREIGN PATENT DOCUMENTS

| | | |
|---|---|---|
| EP | 0 154 204 B1 | 1/1994 |
| EP | 0 271 988 B1 | 8/1995 |
| EP | 0875575 A2 | 4/1998 |
| JP | 10-276782 A | 10/1998 |
| JP | 2002-527056 A | 8/2002 |
| WO | WO 92/04449 | 3/1992 |
| WO | WO 95/11755 | 5/1995 |
| WO | WO 99/32660 | 7/1999 |
| WO | WO 00/04166 | 1/2000 |
| WO | WO 00/09706 | 2/2000 |
| WO | WO 00/12715 | 3/2000 |
| WO | WO 00/22092 | 4/2000 |
| WO | WO 00/70058 | 11/2000 |
| WO | WO 01/75164 | 10/2001 |

OTHER PUBLICATIONS

Lazar et al. Transforming growth factor alpha: mutation of aspartic acid 47 and leucine 48 results in different biological activities. (1988) Mol. Cell. Biol. 8:1247-1252.*
Hill et al. Functional analysis of conserved histidines in SDP-Glucose phyrophosphorylase from *Escherichia coli*. (1998) Biochem. Biophys. Res. Comm. 244:573-577.*
Guo et al. Protein tolerance to random amino acid change. (2004) Proc. Natl. Acad. Sci. USA 101: 9205-9210.*
Elomaa et al. Transformation of antisense constructs of the chalcone synthase gene superfamily into *Gerbera hybrida*: differential effect on the expression of family member. (1996) Molecular Breeding, vol. 2, pp. 41-50.*
Colliver et al. Differential modification of flavonoid and isoflavonoid biosynthesis with an antisense chalcon synthease construct in transgenic Lotus corniculatus. (1997) PMB; vol. 35, pp. 509-522.*
Aharoni et al., "Novel Insight into Vascular, Stress, and Auxin-dependent-Independent gene Expression Programs in Strawberry, a Non-Climacteric Fruit," Plant Physiol., Jul. 2002, pp. 1019-1031, vol. 129, American Society of Plant Biologists.
Allona et al., "Analysis of xylem formation in pine by cDNA sequencing," Proc. Nat'l Acad. Sci., Aug. 1998, pp. 9693-9698, vol. 95, The National Academy of Sciences.

(Continued)

Primary Examiner — Cathy Kingdon Worley
(74) Attorney, Agent, or Firm — Foley & Lardner LLP

(57) ABSTRACT

Novel plant polysaccharide synthesis genes and polypeptides encoded by such genes are provided. These genes and polynucleotide sequences are useful regulating polysaccharide synthesis and plant phenotype. Moreover, these genes are useful for expression profiling of plant polysaccharide synthesis genes. One aspect of the present invention therefore are polynucleotides encoding cellulose synthase from *Pinus radiata* and methods of using such a polynucleotide to regulate polysaccharides of a plant.

16 Claims, 17 Drawing Sheets

OTHER PUBLICATIONS

Altschul et al., "Basic Local Alignment Search Tool", J. Mol. Biol., Academic Press Limited, Oct. 5, 1990, vol. 215, No. 3, pp. 403-410.

Altschul, et al., "Gapped BLAST and PSI-BLAST: a new generation of protein database search programs", *Nucleic Acids Res.*, 1997, vol. 25, pp. 3389-3402.

An et al., "Organ-specific and Developmental Regulation of the Nopaline Synthase Promoter in Transgenic Tobacco Plants," Plant Physiol., 1998, vol. 88, pp. 547-552.

Aronen et al., "Seasonal changes in the transient expression of a 35S CaMV-GUS gene construct introduced into Scots pine buds," Tree Physiol., Jan. 1995, pp. 65-70, vol. 15, No. 1, Heron Publishing, Victoria, Canada.

Austin et al., "Production and field performance of transgenic alfalfa (*Medicago sativa* L.) expressing alpha-amylase abnd manganese-dependent lignin peroxidase," Euphytica, 1995, vol. 85, pp. 381-393.

Baumann et al., "The DNA Binding Site of the Dof Protein NtBBF1 is Essential for Tissue-Specific and Auxin-Regulated Expressiono f the *rolB* Oncogene in Plants," The Plant Cell, Mar. 1999, vol. 11, pp. 323-333.

Birch, R.G., "Plant Transformation: Problems and Strategies for Practical Application," Annu. Rev. Plant Physiol. Plant Mol. Biol., 1997, vol. 48, pp. 297-326.

Blanton et al., "A 1,4-β-glucan-synthase system from *Doctyostelium discoideum*," Planta, 1990, vol. 180, pp. 324-332.

Blanton et al., "Prestalk cells in monolayer cultures exhibit two distinct modes of cellulose synthesis during stalk cell differentiation in *Dictyostelium*," Development, 1993, vol. 119, pp. 703-710.

Boynton et al., "Chloroplast Transformation in *Chlamydomonas* with High Velicity Microprojectiles," Science, Jun. 10, 1998, vol. 240, pp. 1534-1538.

Brummer et al., E.C. Alfalfa (*Medicago sativa* L.), 2004, pp. 1-2.

Burn et al., "Functional Analysis of the *Cellulose synthase* Genes CesA1, CesA2, and CesA3 in Arabidopsis," *Plant Physiology*, Jun. 2002, vol. 129, pp. 797-807.

Canton et al., GenBank Accession BX255611, Feb. 25, 2003.

Carillo et al., "The multiple sequence alignment problem in biology," SIAM J. Applied Math., Oct. 1988, vol. 48, No. 5, pp. 1073-1082.

Carillo et al., SIAM J. Applied Math., 1988, 48:1073.

Chang, et al., "A Simple and Efficient Method for Isolating RNA from Pine Trees," *Plant Molecular Biology Reporter*, 1993, vol. 11, No. 2, pp. 113-116.

Cheong et al., "Transcriptional Profiling Reveals Novel Interactions between Wounding, Pathogen, Abiotic Stress, and Hormonal Responses in Arabidopsis," Plant Physiol., Jun. 2002, pp. 661-677, vol. 129, American Society of Plant Biologists.

Colliver, et al., "Differential modification of flavonoid and isflavonoid biosynthesis with an antisense chalcone synthase construct in transgenic *Lotus corniculatus*", PMB, vol. 35, pp. 509-522, (1997).

Crawley et al., "An Enzyme-Linked Immunosorbent Assay for N-Acetylglucosaminyltransferase-V$^1$," Analytical Biochemistray, 1990, vol. 185, pp. 112-117.

Doblin et al., "Pollen Tubes of *Nicotiana Alata* Express Two Genes from Different Beta-Glucan Synthase Families", Plant Physiology, vol. 125, Apr. 2001, pp. 2040-2052. (XP003010501).

Doblin et al., "Cellulose Biosynthesis in Plants: from Genes to Rosettes," Plant Cell Physiol., 2002, vol. 43, No. 12, pp. 1407-1420.

Elbashir et al., "Analysis of gene function in somatic mammalian cells using small interfering RNAs," Methods Enzymol., 2002, pp. 199-213, vol. 26, Academic Press.

Elbashir et al., "Duplexes of 21-nucleotide RNAs mediate RNA interference in cultured mammalian cells," Nature, May 2001, pp. 494-498, vol. 411, Macmillan Magazines Ltd.

Elbashir et al., "Functional analysis of siRNAs for mediating efficient RNAi in *Drosophila melanogaster* embryo lysate," EMBO J., 2001, pp. 6877-6888, vol. 20, No. 23, European Molecular Biology Organization.

Ellis et al., "Expression of inducible angiosperm promoters in a gymnosperm," *Picea glauca* (white spruce), Plant Mol. Biol., Jul. 1991, pp. 19-27, vol. 17, No. 1, Kluwer Academic Publishers.

Elomaa et al., "Transformation of antisense constructs of the Chalcone synthase gene superfamily into *Gerbera hybrida*: differential effect on the expression of family member", *Molecular Breeding*, vol. 2, pp. 41-50, (1996).

Favery et al., "KOJAK encodes a cellulose synthase-like protein required for root hair cell morphogenesis in *Arabidopsis*," Genes & Development, 2001, vol. 15, pp. 79-89.

Forester et al., "Genetic engineering of crop plants: from genome to gene," Expl. Agric., 1997, vol. 33, pp. 15-33.

Fromm et al., "An Octopine Synthase Enhancer Element Directs Tissue-Specific Expression and Binds ASF-1, a Factor from Tobacco Nuclear Extracts," The Plant Cell, Oct. 1989, vol. 1, pp. 977-984.

Gish et al., "Identification of protein coding regions by database similarity search," Nature Genetics, Mar. 1993, vol. 3, pp. 266-272.

Goubet et al., "AtCSLA7, a Cellulose Synthase-Like Putative Glycosyltransferase, Is Important for Pollen Tube Growth and Embryogenesis in *Arabidopsis*," Plant Physiology, Feb. 2003, vol. 131, pp. 547-557.

Grotkopp et al., "Evolution of genome size in pines (*Pinus*) and its life-history correlates: supertree analyses.", *Evolution*, vol. 58, 2004, pp. 1705-1729.

Guevara-Garcia et al., "A 42 bp fragment of the *pmas1* promoter containing an *ocs*-like element confers a developmental, wound- and chemically inducible expression pattern," Plant Molecular Biology, 1998, vol. 38, pp. 743-753.

Guo et al., "Protein tolerance to random amino acid change", *PNAS*, vol. 101, pp. 9205-9210, (2004).

Harborth et al., "Identification of essential genes in cultured mammalian cells using small interfering RNAs," J. Cell Sci., Oct. 2001, pp. 4557-4565, vol. 114, The Company of Biologists Ltd.

Hertzberg et al., "A transcriptional roadmap to wood formation," Proc. Nat'l Acad. Sci., Dec. 2001, pp. 14732-14737, vol. 98, No. 25.

Hertzberg et al., "cDNA microarray analysis of small plant tissue samples using a cDNA tag target amplification protocol," Plant J., 2001, pp. 585-591, vol. 25, No. 5, Blackwell Science Ltd.

Hill et al., "Functional analysis of conserved histidines in ADP-Glucose pyrophosphorylase from *Escherichia coli*", Biochem. and Biophys. Res. Comm., vol. 244, pp. 573-577, (1998).

Hinchee et al,. "Production of transgenic soybean plants using *Agrobacterium*-mediated DNA transfer," Bio/Technology, Aug. 1988, vol. 6, pp. 915-922.

Holland et al., "A Comparative Analysis of the Plant Cellulose Synthase (*CesA*) Gene Family," Plant Physiology, Aug. 2000, vol. 123, pp. 1313-1323.

Holland et al., "A Comparative Analysis of the Plant Cellulose Synthase (CESA) Gene Family", Plant Physiology, vol. 123, Aug. 2000, pp. 1313-1323 (XP000960951).

Horsch et al., "Analysis of *Agrobacterium tumefaciens* cirulence mutants in leaf discs," Proc. Natl. Acad. Sci. USA, Apr. 1986, vol. 83, pp. 2571-2575.

Horsch et al., "Rapid Assay of Foreign Gene Expression in Leaf Discs Transformed by *Agrobacterium tumefaciens*: Role of T-DNA Borders in the Transfer Process," Proc. Natl. Acad. Sci. USA, Jun. 1986, vol. 83, pp. 4428-4432.

Huang et al., "*Agrobacterium rhizogenes*-mediated genetic transformation and regeneration of a conifer: *Larix decidua*," In Vitro Cell, Oct. 1991, vol. 27P, pp. 201-207.

Huang et al., "In Vitro Cell" 27:201-207 (1991).

Huber et al., "Detection of Single Base Alterations in Genomic DNA by Solid Phase Polymeriase Chain Reaction on Oligonucleotide Microarrays," Analytical Biochemistry, 2001, vol. 299, pp. 24-30.

Hughes et al., "Expression profiling using microarrays fabricated by an ink-jet oligonucleotide synthesizer," Nature Biotechnology, Apr. 2001, vol. 19, pp. 342-347.

Hutvágner et al., "A Cellular Function for the RNA-Interference Enzyme Dicer in the Maturation of the let-7 Small Temporal RNA," Science, Aug. 2001, pp. 834-838, vol. 293.

Kane et al., "Assessment of the sensitivity and specificity of oligonucleotide (50mer) microarrays," Nucleic Acids Research, 2000, vol. 28, No. 22, pp. 4552-4557.

Kerr et al., "Statistical design and the analysis of gene expression microarray data," Genet. Res., Camb., 2001, vol. 77, pp. 123-128.

Kirst et al., "Analysis of microarray gene expression levels as quantitative traits: discovery of candidate genes, regulatory networks and mapping of gene expression qtls.," Int'l Union of Forestry Research Organizations Biennial Conference, S6.8, Jun. 2003, Umea, Sweden.

Klein et al., "Genetic Transformation of Maize Cells by Particle Bombardment," Plant Physiol., 1989, vol. 91, pp. 440-444.

Lagos-Quintana et al., "Identification of Novel Genes Coding for Small Expressed RNAs, Science," Oct. 2001, pp. 853-858, vol. 294.

Lagos-Quintana et al., "Identification of Tissue-Specific MicroRNAs from Mouse, Curr. Biol.," Apr. 2002, pp. 735-739, vol. 12, Elsevier Science Ltd.

Larson et al., "Formation and Properties of Juveline Wood in Southern Pines: A Synopsis," U.S. Dept. of Agriculture, Forest Service, Forest Products Laboratory, General Technical Report, 2001, FPL-GTR-129, pp. 1-42.

Lazar et al., "Transforming growth factor alpha: mutation of aspartic acid 47 and leucine 48 results in different biological activities", *MCB*, 1998, vol. 8, pp. 1247-1252.

Li et al., "Selection of optimal DNA oligos for gene expression arrays," Bioinformatics, 2001, vol. 17, No. 11, pp. 1067-1076.

Lloyd et al., "Commercially-feasible micropropagation of mountain laurel, *kalmia latifolia*, by use of shoot-tip culture," Combined Proceedings of the International Plant Propagators Society, 1980, vol. 30, pp. 421-427.

Lockhart et al., "Expression monitoring by hybridization to high-density oligonucleotide arrays," Nature Biotechnology, Dec. 1996, vol. 14, pp. 1675-1680.

Lyznik et al., "Stable co-transformation of maize protoplasts with *gusA* and *neo* genes," Plant Molecular Biology, 1989, vol. 13, p. 151-161.

Madden et al., "Applications of Network BLAST Server," Meth. Enzymol., 1996, vol. 266, pp. 131-141.

Marita et al., "NMR characterization of lignins from transgenic poplars with suppressed caffeic acid O-methyltransferase activity", J. Chem. Soc., Perkin Trans. 1, 2001, pp. 2939-2945, The Royal Society of Chemistry.

Martinez et al., "Single-Stranded Antisense siRNAs Guide Target RNA Cleavage in RNAi," Cell, Sep. 2002, pp. 563-574, vol. 110, Cell Press.

McGALL et al., "Light-directed synthesis of high-density oligonucleotide arrays using semiconductor photoresists," Proc. Natl. Acad. Sci. USA, Nov. 1996, vol. 93, pp. 13555-13560.

McManus et al., "Gene Silencing in Mammals by Small Interfering RNAs, Nature Rev. Genetics," Oct. 2002, pp. 737-747, vol. 3, Nature Publishing Group.

Meiyanto et al., "Application of Fluorescently Labeled Poly(dU) for Gene Expression Profiling on cDNA Microarrays," BioTechniques, Aug. 2001, vol. 31, pp. 406-413.

Odel et al., "Identification of DNA sequences required for activity of the cauliflower mosaic virus 35S promoter," Nature, Feb. 28, 1985, vol. 313, pp. 810-812.

Oomen et al., "Modulation of the cellulose content of tuber cell walls by antisense expression of different potato (*Solanum tuberosum* L.) CesA clones," *Phytochemistry*, 2004, vol. 65, pp. 535-546.

Pettersen et al., "Wood sugar Analysis by Anion Chromatography," J. Wood Chem. & Technol., 1991, pp. 495-501, vol. 11, No. 4, Marcel Dekker, Inc.

Potrykus et al., "Direct gene transfer to cells of a granimaceous monocot," Mol. Gen. Genet., 1985, vol. 199, pp. 183-188.

Ray, Curr. Topics in Plant Biochem. & Phys. 11:18-41 (1992).

Ray, Peter M., "Mechanisms of wall loosening for cell growth," Curr. Topics in Plant Biochem. & Phys., 1992, vol. 11, pp. 18-41.

Relogio et al., "Optimization of oligonucleotide-based DNA microarrays," Nucleic Acids Research, 2002, vol. 30, No. 11, e51, 10 pages.

Rhodes et al., "Genetically Transformed Maize Plants from Protoplasts," Science, 1988, vol. 240, pp. 204-207.

Richmond et al., "The Cellulose Synthase Superfamily," Plant Physiology, Oct. 2000, vol. 124, pp. 495-498.

Rogers et al., "Improved Vectors for Plant Transformation: Expression Cassette Vectors and New Selectable Markers," *Methods in Enzymology*, 1987, pp. 252-277, vol. 153, Academic Press, Inc.

Rydelius et al., "Growing *Eucalyptus* for Pulp and Energy," presented at the Mechanization in Short Rotation, Intensive Culture Forestry Conference, Mobile, AL, 1994.

Rydelius et al., "Growing *Eucalyptus* for Pulp and Energy," presented at the Mechanization in Short Rotation, Intensive Culture Forestry Conference, Mobile, AL, 1994, pp. 53-56.

Saxena et al., "Multidomain Architecture of β-Glycosyl Transferases: Implications for Mechanism of Action," Journal of Bacteriology, Mar. 1995, vol. 177, No. 6, pp. 1419-1424.

Saxena et al., "Structure-function characterization of cellulose synthase: relationship to other glycosyltransferases," *Phytochemistry*, 2001, vol. 57, pp. 1135-1148.

Schenk et al., "Coordinated plant defense responses in *Arabidopsis* revealed by microarray analysis," Proc. Nat'l Acad. Sci., Oct. 2000, pp. 11655-11660, vol. 97, No. 21.

Schmidhauser et al., "Regions of Broad-Host-Range Plasmid RK2 Involved in Replication and Stable Maintenance in Nine Species of Gram-Negative Bacteria," *Journal of Bateriology*, Oct. 1985, pp. 446-455, vol. 164, No. 1, American Society for Microbiology.

Sederoff et al., NXRV_022_D06_F NXRV (Nsf Xylem Root wood Vertical) *Pinus taeda* cDNA clone NXRV_022_D06 5' similar to *Arabidopsis thaliana* sequence At4g18780 cellulose synthase catalytic subunit (IRX1), mRNA sequence, *GenBank Accession* BM492221, pp. 1-2, (2003).

Shi et al., "Gibberellin and abscisic acid regulate *GAST1* expression at the level of transcription," Plant Molecular Biology, 1998, vol. 38, pp. 1053-1060.

Smith et al., "Antisense RNA Inhibition of Polygalacturonase Gene Expression in Transgenic Tomatoes", Nature, Aug. 1988, vol. 334, No. 25, pp. 724-726.

Smith et al., "Inheritance and Effect on Ripening of Antisense Polygalacturonase Genes in Transgenic Tomatoes", Plant Molecular Biology, International Society for Plant Molecular Biology, Kluwer Academic Publishers, Mar. 1990, vol. 14, No. 3, pp. 369-379.

Stein et al., "Differential display technology: a general guide," CMLS, Cell. Mol. Life Sci., 2002, vol. 59, pp. 1235-1240.

Sterky et al., "Gene discovery in the wood-forming tissues of poplar: Analysis of 5,692 expressed sequence tags," Proc. Natl. Acad. Sci. USA, Oct. 1998, vol. 95, pp. 13330-13335.

Stults et al., "Enzyme-Linked Immunosorbent Assay (ELISA)-Based Quantification and Identification of in Vitro Enzyme-Catalyzed Glycosphingolipid Synthesis and Degradation Products with Carbohydrate Sequence-Specific Monoclonal Antibodies," Analytical Biochemistry, 1988, vol. 174, pp. 151-156.

Stults et al., "Measurement of β-Galactosyltransferase Activity in Cell Extracts with an ELISA-Based Assay," Archives of Biochemistry and Biophysics, Jul. 1990, vol. 280, No. 1, pp. 20-26.

Stults et al., "β1-3-*N*-Acetylglucosaminyltransferase in Human Leukocytes: Properties and Role in Regulating Neolacto Glycosphingolipid Biosynthesis," Archives of Biochemistry and Biophysics, May 15, 1993, vol. 303, No. 1, pp. 125-133.

Supplemental Partial European Search Report for EP Application No. 04754589.2 mailed Jul. 24, 2007.

Svab et al., "Stable transformation of plastids in higher plants," Proc. Natl. Acad. Sci. USA, Nov. 1990, vol. 87, pp. 8526-8530.

Thibaud-Nissen et al., "Clustering of Microarray Data Reveals Transcript Patterns Associated with Somatic Embryogenesis in Soybean," Plant Physiol., May 2003, pp. 118-136, vol. 132, American Society of Plant Biologists.

Thomas et al., "Size constraints for targeting post-transcriptional gene silencing and for RNA-directed methylation in *Nicotiana benthamiana* using a potato virus X vector", *The Plant Journal*, 2001, vol. 25, pp. 417-425.

Tyschl, "Expanding small RNA interference," Nature Biotechnol., May 2002, pp. 446-448, vol. 20, Nature Publishing Group.

Tuschl, "RNA Interference and Small Interfering RNAs, Chembiochem.," 2001, pp. 239-245, vol. 2, Wiley-VCH-Verlag GmbH.

Vandesompele et al., "Accurate normalization of real-time quantitative RT-PCR data by geometric averaging of multiple internatl control genes," Genome Biol., 2002, 3: research/0034.1, 12 pages.

Wang et al., "Non-destructive Evaluations of Trees," Experimental Techniques, Nov./Dec. 2000, vol. 24, No. 6, pp. 27-29.

Whetten et al., "Functional genomics and cell wall biosynthesis in loblolly pine," Plant Mol. Biol., 2001, pp. 275-291, vol. 47, Kluwer Academic Publishers, Netherlands.

Wildt et al., "Antibody arrays for high-throughput screening of antibody-antigen interactions," Nature Biotechnology, Sep. 2000, vol. 18, pp. 989-994.

Wolfinger et al., "Assessing Gene Significance from cDNA Microarray Expression Data via Mixed Models," Journal of Computational Biology, 2001, vol. 8, No. 6, pp. 625-637.

Yan et al., "Determination of GDP-Fuc:Galβ1-4GlcNAc-R (Fuc to GlcNAc) α1,3 Fucosyltransferase Activity by a Solid-Phase Method," Analytical Biochemistry, 1994, vol. 223, pp. 111-118.

Ye et al., "Determination of $S_2$-fibril-angle and fiber-wall thickness by microscopic transmission ellipsometry," Tappi J., Jun. 1997, pp. 181-190, vol. 80, No. 6.

Zacharias et al., "Genome sizes and chromosomes in the basal metazoan Hydra", *Zoology*, vol. 107, pp. 219-227.

Zhang et al., "PowerBLAST: A New Network BLAST Application for Interactive or Automated Sequence Analysis and Annotation," Genome Research, 1997, vol. 7, pp. 649-656.

The Translation of the Notice of Reasons for Rejection received for the related Japanese Patent Application No. 2006-515258, dated Mar. 17, 2010.

Plant Biology 2002, 2002, Poster Abstract #320 [online] (http://abstracts.aspb.org/pb2002/P44/0721.html.).

Plant Biology 2002, 2002, Poster Abstract #337 [online] (http://abstracts.aspb.org/pb2002/P44/1154html.).

GeneBank Accession AF458083, 2003, [online] (http://www.ncbi.nlm.nih.gov/sviewer/viewer.fcgi?27462650:NCBI:4410999).

Holland, et al., "A Comparative Analysis of the Plant Cellulose Synthase (*CesA*) Gene Family", *Plant Physiology*, 2000, vol. 123, pp. 1313-1323.

B1 Taylor, et al., "Interactions among three distinct CesA proteins essential for cellulose synthesis", *PNAS*, 2003, vol. 100, No. 3, pp. 1450-1455.

The Translation of the Decision of Rejection (Translation) received for the related Japanese Patent Application No. 2006-515258, Nov. 8, 2010.

Plant Biology 2002, 2002, Poster Abstract #321 [online] (http://abstracts.aspb.org/pb2002/P44/0737.html.).

* cited by examiner

FIGURE 1.

MEARAGLVAGSYKRNELMVVPGHDGPKPIRLSTLQDCQVCGDKIGCNPNGELFVAC
NECGFPVCRPCYEYERKDGNRCCPQCKTRYRRHKGSPRVEGDDEEDGMDDLEQEFN
MERDRQSVVSHRGNAFDATPRAAHSIANRSINGDNYALSLPPIMDGDSLSVQRFPHA
ATVIGNGLDPVKENYGSAAWKERVENWKAKHDKKSGSIKDGIYDPDEADDIMMTE
AEARQPFSRKVPIPSSLINPYRIVIVLRLIILGFFFRYRLMNPAKDALGLWLTSIICEIWF
AFSWILDQFPKWFPITRETYLDRLSMRYEREGEPCKLAPVDFFVSTVDPLKEPPLITAN
TVLSILAADYPVDRVSCYVSDDGASMLTFDSMTETSEFARKWVPFCKKYSIEPRAPD
FYFSQKIDYLKDKVQPTFVKERRAMKREYEEFKVRINALVSTAQNTFDEGWVMQDG
TPWPGNNTRDHPGMIQVFLGSSGAHDIEGNELPRLVYVSREKRPGYQHHKKAGAMN
ALVRVSAVLTNAPFILNLDCDHYLNNSKAVREAMCFLMDPQLGKKLCYVQFPQRFD
GIDRHDRYANRNTVFFDINMKGLDGIQGPVYVGTGCVFNRQALYGYDPPVSQKKPK
MTCDCWPSWCCCCFGSRKKTKKSSKKFFGRKKSSKPTEIAAPIFSLEEIEEGLEGYEE
HEKSWLMSQKSFEKRFGQSPVFITSTLMENGGVPESVNSPALIKEAIHVISIGYEEKTE
WGKEIGWIYGSVTEYILTGFKMHCRGWRSVYCMPPRPAFKGSAPINLSDRLHQVLR
WALGSIEIFLSRHCPLWYAYGGNLKWLERLAYINTIVYPFTSIPLVAYCTLPAICLLTG
KFITPTLTSLASVWFMGLFISIIATGVLELRWSGVSIEEFWRNEQFWVIGGVSAHLFAV
FQGLLKVLGGVDTNFTVTAKGSDEEDQFGELYMFKWTTLLIPPTTLLIINLVSLVAGV
SAAVNNNYQSWGPLFGKLFFACWVILHLYPFLKGLLGRQNRTPTIVILWS

FIGURE 2.

AQEREYEEFKVQINALVAKAQKMPEEGWTMQDGTAWAGNNPRDHPGMIQVFLGH
SGGLDTDGNELPRLVYVSREKRPGFQHHKKAGAMNALIRVSAVLTNGAYLLNVDC
DHYFNNSKALKEAMCFMMDPAYGKKTCYVQFPQRFDGIDLHDRYANRNIVFFDINL
KGLDGIQGPVYVGTGCCFNRQALYGYDPVLTEEDLEPNIIVKSCCGSRKKGKGGNK
KYIDKKRAMKRTESTVPIFNMEDVEEGVEGYDDERSLLMSQKSLEKRFGQSPVFISA
TFMEQGGLPPSTNPATLLKEAIHVISCGYEDKTEWGKEIGWIYGSVTEDILTGFKMHA
RGWISIYCMPPRPAFKGSAPINLSDRLNQVLRWALGSIEILLSRHCPIWYGYNGKLRL
LERLAYINTIVYPLTSIPLIAYCILPAFCLLTNKFIIPEISNFASMWFILLFVSIFTTGILEL
RWSGVSIEDWWRNEQFWVIGGTSAHLFAVFQGLLKVLAGIDTNFTVTSKAGDEDGD
FAELYVFKWTSLLIPPTTVLIVNIIGIVAGVSYAINSGYQSWGPLFGKLFFAIWVIAHL
YPFLKGLLGRQNRTPTIVIVWSILLASIFSLLWVRIDPFTSATTASTANGQCGINC

FIGURE 3.

MEVSSGLVAGSHNRNELVVIRRENELGQKPLQKLSGQICQICGDDVGLTVDGELFVA
CNECAFPICRTCYEYERREGSQICPQCKTRFKCLRGCARVDGDEEEDGVDDLENEFN
FDGRHRQEMDRQGYGAEAMLHGHMSYGRGSDLDLSHVHPLPQVPLLTNGQMVDDI
PPEHHALVPAYMGAGGGGGGGGKRIHPLPFTDSGLPVQPRSMDPSKDLAAYGYGSV
AWKERMESWKQKQEKLQTMKNEKGGKEWDDDGDNPDLPLMDEARQPLSRKLPIS
SSQINPYRMIIVIRLVVLGFFFHYRVMHPVNDAYALWLISVICEIWFGLSWILDQFPK
WLPIDRETYLDRLSLRYEKEGQPSQLAPVDIFVSTVDPLKEPPLVTANTVLSILAVDYP
VDKVSCYVSDDGAAMLTFEALSETSEFARKWVPFCKKFNIEPRAPEFYFAQKIDYLK
DKVEASFVKERRAMKREYEEFKVRINALVAKAQKVPEEGWTMQDGTPWPGNNVR
DHPGMIQVFLGQSGGHDSDGNELPRLVYVSREKRPGYNHHKKAGAMNALVRVSAV
LTNAPYLLNLDCDHYFNNSKAIREAMCFMMDPLIGKRVCYVQFPQRFDGIDRHDRY
ANRNTVFFDINMKGLDGIQGPIYVGTGCVFRRLALYGYDAPKAKKPPTRTCNCLPK
WCCCGCCCSGTKKKKKTTKPKTELKKRFFKKKDAGTPPPLEGIEEGIEVIESENPTPQ
HKLEKKFGQSSVFVASTLLEDGGTLKGTSPASLLKEAIHVISCGYEDKTEWGKEVGW
IYGSVTEDILTGFKMHCHGWRSIYCIPARPAFKGSAPINLSDRLHQVLRWALGSIEIFL
SRHCPLWYGYGGGLKWLERLSYINATVYPWTSIPLLAYCTLPAVCLLTGKFITPELSN
VASLWFLSLFICIFATSILEMRWSGVGIEEWWRNEQFWVIGGVSAHLFAVFQGLLKV
LAGVDTNFTVTSKGGDDKEFSELYAFKWTTLLIPPTTLLIINLIGVVAGVSNAINNGY
ESW

FIGURE 4.

MAPSLDSWAKQNVHKGTPVVVKMENLNWSMLELESPSDEDIFPAGAPAAGEGAAP
ERTRNKNAKQLTWVLLLRAHRAAGCLASMAAAFLGLASAVRRRVAAGRTDNDVSE
ASRRGGGVRESPTLKARFYTCTKVFLWLSIVLLGFEVAAYFKGWHYGAHNVELQHL
LATSFSVKGVFDRLYSKWVSIRVEYLAPPLQFLANACIVLFLIQSLDRLVLCLGCFWI
KFKNIKPIPKEDASVDVESGEKGYFPMVLVQLPMCNEKEVYQQSIAAVCNLDWPKS
KLLIQVLDDSDDPTAQSLIKEEVNKWQQEGARIVYRHRVIREGYKAGNLKSAMNCS
YVKEYEFVSIFDADFQPAPDFLKRTVPHFKDNDELGLVQARWSFVNKDENLLTRLQ
HINLAFHFEVEQQVNGVFLNFFGFNGTAGVWRIKALEDSGGWLERTTVEDMDIAVR
AHLHGWKFIFLNDVEAQCELPESYEAYRKQQHRWHSGPMQLFRLCLPAIIKSKISIW
KKFNLIFLFFLLRKLILPFYSFTLFCIILPMTMFVPEAELPAWVVCYIPATMSFLNILPAP
KSFPFIVPYLLFENTMSVTKFNAMISGLFQLGSAYEWVVTKKSGRSSEGDLLSLVEKE
TKHKRGNSAPDLEALKEEISRQEKKASRKKKHNRIYTKELTLAFLLLTASARSLLSAQ
GVHFYFLLFQGISFLLVGLDLIGEQVE

FIGURE 5.

MAQISAKDLIPDSLTMSREDIAGQLGMVWELIKAPLIVPVLRLSVYVCLAMALMLFM
ERVYMGIVIVLVKLFWKKPEKRYNWEPIEEDLESGSSNFPFVLVQIPMYNEKEVYKIS
IGAACGLSWPADRLVIQVLDDSTDPVIKQMVELECQRWASKGINIVYQIRETRGGYK
AGALKEGLKRSYVKHCEFVAIFDADFRPEPDYLKRAIPYFLRNPDLALVQARWRFVN
SNECLLTRMQEMSLDYHFTVEQEVGSATHAFFGFNGTAGVWRIGAINEAGGWKDRT
TVEDMDLAVRASLRGWKFVYLGDLQVKSELPSTFKAFRFQQHRWSCGPANLFRKM
VMEIVRNKKVRFWKKVYVIYSFFFVRKIIAHMVTFFFYCVVLPLTIWVPEVHVPIWG
AVYIPSIITILNSVGTPRSIHLLFYWILFENVMSMHRTKATFIGLLEAGRANEWVVTEK
LGDTLKNKSKKLRFTFNFADRLHLLELGFGVFLFVTGCYDFLYGKNNYFVYLWLQTI
TFFIAGFGYIGTIV

FIGURE 6.

MSGFAVGSHSRNELHVTNGGAADEHRSPPRQNAARTCRVCGDEIGLKDDGAPFVAC
HECGFPVCRPCYVYERSDGTQCCPQCNARYKRHKGCPRVAGDDEDDHFEGEDFEDE
FQIRNRGENEVRPTGFDRSENGDSHAPQVHPNGQVFSSAGSVVGAELEGEGNAEWK
ERIEKWKIRQEKRGLVGKDDGGNGDGEEDDYLMAEARQPLSRKVPISSSKISPYRIVI
VLRLVVLGFFLHFRILTPATDAFPLWLISVICETWFALSWILDQFPKWNPINRETYLDR
LSIRFEREGEPSRLTPVDVFVSSVDPLKEPPIITANTVLSILAVDYPVDKVCCYVSDDG
ASMLLFDTLSETAEFARRWVPFCKKYSIEPRTPEFYFSQKIDYLKDKVEPSFVKERRA
MKREYEEFKVRVNALVAK420AQKKPEEGWVMQDGTPWPGNNTRDHPGMIQVYLG
SAGALDVEGKELPRLVYVSREKRPGYQHHKKAGAMNALVRVSAVLTNAPFLLNLD
CDHYINNSKAIREAMCFLMDPQLGKKLCYVQFPQRFDGIDRHDRYANRNIVFFDINM
RGLDGIQGPVYVGTGCVFNRQALYGYDPPVSQKRPKMTCDCWPSWCSCCCGGSRK
SKSKKKDDTSLLGPVHAKKKKMTGKNYLKKKGSGPVFDLEDIEEGLEGFDELEKSSL
MSQKNFEKRFGQSPVFIASTLMEDGGLPEGTNSTSLIKEAIHVISCGYEEKTEWGKEIG
WIYGSVTEDILTGFKMHCRGWKSVYCMPKRPAFKGSAPINLSDRLHQVLRWALGSV
EIFLSRHCPLWYAWGGKLKLLERLAYINTIVYPFTSIPLLFYCTIPAVCLLTGKFIIPTLT
NFASIWFLALFLSIIATGVLELRWSGVSIEDWWRNEQFWVIGGVSAHLFAVFQGLLK
VLAGVDTNFTVTAKAAEDSEFGELYLFKWTTLLKPPTTLIILNMVGVVAGVSDAINN
GYGSWGPLFGKLFFAFWVIVHLYPFLKGLMGKQNRTPTIVVLWSVLLASIFSLVWVR
IDPFLPKQTGPVLKPCGVEC

FIGURE 7.

MEAGAGLVAGSHNRNELVVIHGHEESKPLKNLDGQVCEICGDEVGLTVDGDLFVAC
NECGFPVCRPCYEYERREGSQLCPQCKTRYKRLKGSPRVEGDDDEEDIDDLEHEFNIE
DEQNKHKYMAEAMLHGKMSYGRGPEDDDNAQFPSVIAGGRSRPVSGEFPISSYGHG
EMPSSLHKRVHPYPISEPGSERWDEKKEGGWKERMDDWKLQQGNLGPEPDDINDPD
MAMIDEARQPLSRKVPIASSKINPYRMVIVARLAILAFFLRYRILNPVHDAFGLWLTSI
ICEIWFAFSWILDQFPKWFPIDRETYLDRLSLRYEREGEPNMLSPVDVFVSTVDPMKE
PPLVTGNTVLSILAMDYPVDKISCYVSDDGASMLTFESLSETAEFARKWVPFCKKFSI
EPRAPEMYFTLKIDYLKDKVQPTFVKERRAMKREYEEFKVRINALVAKAAKVPPEG
WIMQDGTPWPGNNTKDHPGMIQVFLGHSGGLDADGNELPRLVYVSREKRPGFQHH
KKAGAMNALVRVSGVLTNAPFMLNLDCDHYINNSKAVREAMCFLMDPQIGRKVCY
VQFPQRFDGIDTNDRYANRNTVFFDINMKGLDGIQGPVYVGTGCVFRRQALYGYEP
PKGPKRPKMVSCDCCPCFGRRKKLPKYSKHSANGDAADLQGMDDDKELLMSEMNF
EKKFGQSAIFVTSTLMEQGGVPPSSSPAALLKEAIHVISCGYEDKTEWGTELGWIYGS
ITEDILTGFKMHCRGWRSIYCMPKRPAFKGSAPINLSDRLNQVLRWALGSVEIFFSHH
SPVWYGYKGGKLKWLERFAYVNTTIYPFTSLPLLAYCTLPAICLLTDKFIMPAISTFA
SLFFIALFMSIFATGILELRWSGVSIEEWWRNEQFWVIGGVSAHLFAVVQGLLKVLAG
IDTNFTVTSKASDDEDFGELYAFKWTTLLIPPTTILIINLVGVVAGISDAINNGYQAWG
PLFGKLFFAFWVILHLYPFLKGLMGRQNRTPTIVVIWSVLLASIFSLLWVRIDPF

FIGURE 8.

MDRLSATGLLPDTFGGARDDISMQLSLIWAQIKAPLLVPLLRLAVFLCLAMSLMLFL
ERVYMAVVILLVKLFGRKPEKRYRWEPMKDDVELGNSAYPMVLVQIPMYNEREVY
QLSIGAACGLSWPSDRIIIQVLDDSTDPTIKDLVELECQRWASKGINIRYEIRDNRNGY
KAGALKEGMKRSYVKQCDYVAILDADFQPEPDFLWRTIPFLVHNPEVALVQARWKF
VNADECLMTRMQEMSLDYHFTVEQEVGSSTHAFFGFNGTAGVWRISALNEAGGWK
DRTTVEDMDLAVRASLKGWKFVYLGSLKVKNELPSTFKAYRFQQHRWSCGPANLF
RKMAMEIIRNKKVTLWKKVHVIYSFFLVRKIVAHIVTFIFYCVVLPATVFVPEVTVPK
WGAVYIPSIITVLNAVGTPRSLHLVVFWILFENVMSFHRTKATFIGLLEAGRVNEWIV
TEKLGDALKVKASNKVPKKPKFRFGDRLHVLELGVGAYLFFCGCYDIAFGRNHYFM
YLFAQAIAFFIMGFGYIGTFVPNS

FIGURE 9.

MEHRSRPLNLCHVDPKLIAVNRAHMLIHGAALLILIHYRASFFFAEEASSPGQPTTLA
WLIIFLGELTLSLTWLLHQAFRWRPVSRTAFPERLPGDGELPSIDVLVCTADPDKEPT
VAVMNTVISAMALDYPPEKLHVYLSDDGGSLLTLHGMREAYDFARRWLPFCKRFGI
KTRCPKAYFMDDEDVSASVGYESEKKEVKEKYELFEAHINGYRNRNYGESRDGRLD
HPSTIEVIHGNSSDEVVQADQQQMPLLVYVSREKRPSYPHNFKAGALNVLLRVSGVI
SNSPYVLVLDCDMYCNDPSSARRAMCFHLDPTLSPSLSFVQFPQSFHNISKNDIYDSK
IRSPFGTLLCGMDGLQGPLIAGTGFYIKRESLYSEPMQEGTTANLMDLKAIFGHSNEFI
KHLHWSDKLNKNILSEPGTVCRDTEHLASCHYENGTKW

FIGURE 10.

MNTGGRLIAGSHNRNEFVLINADESSRIKSVKELSGQICQICGDEVEIADGELFVACNE
CAFPVCRPCYEYERREGNQACPQCKTRYKRLKGSPRVEGDEEEDDIDDLDNEFDYDP

SDPQHVAEKTFSSRLNYGRGAHRNASGMPTDVESSPLSSQIPLLTYGQEDAEISPDQH
ALIVPPATGHAYRVHPMPYPDSSNPLHPRPMAPEKDITLYGYGSVAWKDKMEKWR
KKQNEKLQVVKHEGAGDGGDFGSDELDDPDLPMMDEGRQPLSRKLPIPSSKINPYRL
LIILRLVILGLFLHYRILHPVNDAYGLWLTSVICEIWFAVSWILDQFPKWYPIERETYL
DRLSLRYEREGKPSELAPVDVFVSTVDPMKEPPLITANTVLSILAVDYPVDKVACYVS
DDGAAMLTFEALSETSEFAKKWVPFCKRFNIEPRAPEWYFSQKMDYLKNKVHPEFV
RERRAIKREYEEFKVRINALVAMAQKVPEEGWTMQDGTPWPGNNVRDHPGMIQVF
LGHSGVCDDDGNELPRLVYVSREKRPGFEHHKKAGAMNALIRVSAVISNAPYLLNV
DCDHYINNSKALREAMCFMMDPTSGKKVCYVQFPQRFDGIDRHDRYSNRNVVFFDI
NMKGLDGLQGPIYVGTGCVFRRQALYGHDAPSKKKPPSKTCNCWPKWCCLCCGGR
KNKKGKTKKERSKKTKNRETSKQIHALENIEEGVSEVSNEKSSEMTQIKLEKKFGQSP
VFVASTTLEDGGVPPDASPASLLKEAIQVISCGYEDKTEWGKEVGWIYGSVTEDILTG
FKMHCHGWRSVYCIPKRPAFKGSAPINLSDRLHQVLRWALGSVEIFLSRHCPIWYGY
GGGLKWLERFSYINSVVYPWTSIPLIVYCSLPAICLLTGQFIVPEISNYASLVFMALFISI
AATGILEMQWGGVGIDDWWRNEQFWVIGGVSSHLFALVQGLLKVLGGVNTNFTVT
SKAADDGAFSELYIFKWTSLLIPPMTLLIMNIVGVVVGISDAINNGYDSWGPLF

FIGURE 11.

MDTGVHMRRMSTPGIRQVNNSRDDTDSVVSSAEFASYTVHIPPTPEYQPMYMSIETS
NAEKVEDLYASNSLFTGGYNRATRSFLKEKMTDSVSNHPQMAGMNGSMCEIPGCD
AKIMRDERGEDIVPCDCDFKICRDCFRDAVRGGDVICLGCKEPYKGLDMAEPEMND
GRRVSSGGMSKRERRMSMIKSRMSLKRSEMDDFDHRNWLFETKGSYGYGNAMWP
KEDVDGDDDGFGNPQVLHDKKWRPLTRKVNVSPKILSPYRLLIFLRIIALALLLMWRI
KHPNEDAMWLWAMSVVCEIWFGFSWLLDQLPKLCPINRTTDLGALKMKFETPSPTN
PTGKCDLPGIDIFVSTADPEKEPPLVTANTILSILAADYPVEKLACYVSDDGGALLTFE
AMAEAASFANLWVPFCRKHRIEPRNPESYFSLKRDPYKDKVRQDFVRDRRRVKREY
DEFKVRINGLSNSIRRRSDAYNACEEIKAAKLQNKNESGEGVESLKIPKATWMADGT
HWPGTWTGPAAEHSRGDHASVIQVMLKPPSDEPLRGTESTSPIDLAEVDIRLPMLVYI
SREKRPGYDHNKKAGAMNALVRASAIMSNGPFILNLDCDHYIYNSQAMREGMCFM
MDRGGDRICYVQFPQRFEGIDPSDRYANHNTVFFDVNMRALDGLQGPVYVGTGCLF
RRTALYGFDPPRVKEHGGCFSQIFKRHRSAATVASTPEVSLVENRFLGMGDSSQEEV
NLLPNKFGNSVLFVESIHIAEFQGRPLADDPSVKNGRPPGALTIPRQLLDAPTVAEAIS
VISCWYEDKTEWGQRIGWIYGSVTEDVVTGYRMHNRGWRSIYCVTKRDAFRGTAPI
NLTDRLHQVLRWATGSVEIFFSRNNALLASRRMKFLQRIAYMNVGLYPFTSIFLVVY
CFLPALSLFSGQFIVQSLDVTFLTYLLAITVTLCILAMLEIKWSGIELEEWWRNEQFWL
IGGTSAHLAAVIQGLLKVIAGIEISFTLTSKSAGDENDDEFAELYLFKWTSLMILPITI

FIGURE 12.

MEHSSGPLNLCHVLTKSIIINRTHMLVHATALSALIYYRASFFFSESKSRDRATTLACL
TMFLAELGLSFLWLLSQAFRWRPVRRTAFPKRLPEDKELPPIDVFVCTADPDKEPTV
DVMNTVVSAMALDYPPEKLHVYLSDDGGSTLTLHGTREAYDFARWWLPFCKRYGI
KTRCPKAFFKEEEDGEGIGMSSDNEFGSEKKIVKEKYELFKERVNEYRKRHRGDSSH
TGRDHPPTIEVVRGNVPDEVMQAHQDPMPKLIYVSREKRPSHHHHFKAGALNVLLR
VSGVMSNSPYILVLDCDMYCNDPSSARQAMCFHLDPRLSPSLMLVQFPQMFHNISEN
DIYDSKLRPYFWTCWYGMDGLKGPVLSGTCFYIKRESLYRKPVQEGYDLMDLKKLF
GHSNEFIKYLGQKEKPSKNTIAGDSAALMKETQLLTSCGYEYGTKWGQEVGFKYYS
VVEDYFTSFTLHCRGWTSVFYTPSKPQFLGTATTNFNDMLIQGMRWYSGLSQVGISR
FCPLIYGSLRMPILQSMCYAELSLFPLYCLPICCFATIPQICLVNGISIYPEVPSSYIMLFA
FIFLSSLCKHLYEVVASGHSVQTFLNEQRIWMIKSTTCYVYGTIDAIMTQIGMRTASF
LPTNKVDDDEQSKRYEMGIFDFQTSIMFLAPMVTLVILNMASFFGGVARVLTLGGFD
KLFMQIALSLFVLVMSYPVIKAMVLRTDKGRIPRSVTTLSAFLSLVLLLQGSSFLM

FIGURE 13.

MEANAGMVAGSYKRNELVRIRHDSDSAPKPLKHLDGHMCQICGDTVGLSASGDVF
VACNECAFPVCRPCYEYERKDGNQCCPQCKTRYKRQKGSPRVEGDDDEDGVDDLE
NEFSYTRGNARRRQWQGDDPDLSSSSRRESQHPVPLLTNGLPISGEIPCATPDNQSVR
TTSGPLGPSDRHSVHSVDPRQPVPVRIVDPSRDLNSYGLGNVDWKERVESWKLKQE
KNIPHMTSRFPEGKGDIEGTGSYGEELQMADDARLPLSRVVPISSSHLTPYRVVIILRLI
ILGFFLQYRATHPVKDAYPLWLTSVICEIWFALSWLLDQFPKWFPINRETYLDRLALR
YDREGEPSQLAPIDIFVSTVDPLKEPPLVTANTVLSILAVDYPVDKVSCYVSDDGSAM
LTFEALSETAEFAKKWVPFCKKHNIEPRAPEFYFAQIDYLKDKIQPSFVKERRAMKRE
YEEFKVRINALVAKAQKVPEEGWTMQDGTPWPGNNPRDHPGMIQVFLGHSGGLDT
DGNELPRLVYVSREKRPGFQHHKKAGAMNALIRVSAVLTNGAYLLNVDCDHYFNN
SKALKEAMCFMMDPALGKKTCYVQFPQRFDGIDLHDRYANRNIVFFDINLKGLDGI
QGPVYVGTGCCFNRQALYGYDPVLTEADLEPNIIVKSCCGPRKKGKGGDKNYIDKK
RAVKRTESNIPIFNMEDIEEGMEGYDDERSLLMSQKSLEKRFGQSPVFIAATFMEQGG
LPPSTNPASLLKEAIHVISCGYEDKTEWGKEIGWIYGSVTEDILTGFKMHARGWISIYC
MPPRPAFKGSAPINLSDRLNQVLRWALGSIEILLSRHCPIWYGYNGRLKWLERLAYIN
TIVYPLTSIPLIAYCILPAFCLLTGKFIIPEISNFASMWFILLFVSIFATGILELRWSGVSIE
DWWRNEQFWVIGGTSAHLFAVFQGLLKVLAGIDTNFTVTSKASDEDGDFAELYVFK
WTSLLIPPTTVLIVNLVGIVAGVSYAINSGYQSWGPLFGKLFFAIWVIAH

FIGURE 14.

MSRAPNREFQEWWNKQRERGLDLSSPSSADGPSTSGGGGGGGGPLLAVEIRTPRSDQ
AVEKSRARSARQLSWVCLLRFQQIASLLASAAGSFLSVLRTANRRIAASPADSSSSRL
YRIIRFFLILVLVLLGFELLAYSKGWHFSPPSVGSKEVLGFVELVYANWLEIRATYLAP
PLQSLTNVCIVLFLIQSVDRVVLVLGCIWIKIKGIKPVASADYEKKEDLESESGDEAYP
MVLVQIPMCNEREVYQQSIAAVCIQDWPRERMLVQVLDDSDDLDVQLLIKSEVQKW
QQRGIRIVYRHRLIRTGYKAGNLKSAMSCDYVKDYEFVAIFDADFQPGPDFLKKTIPY
FKGNDDLALVQTRWAFVNKDENLLTRLQNINLSFHFEVEQQVNGVFINFFGFNGTA
GVWRIKALEECGGWLERTTVEDMDIAVRAHLCGWKFIYLNDVKCLCELPESYEAYK
KQQHRWHSGPMQLFRLCFFDIIRSKVSLAKKANLIFLFFLLRKLILPFYSFTLFCIILPLT
MFLPEAQLPAWVVCYVPGVMSILNILPAPRSFPFIVPYLLFENTMSVTKFNAMISGLF
KFGSSYEWIVTKKLGRSSEADLLTFGEKGSDPLLETSNLHRSSSESGLAELNKMEMT
KKAGKLRRNRLYRKELGLAFILLTAAVRSLLSAQGIHFYFLLFQGISFLVVGLDLIGE
QVS

FIGURE 15.

MACRERRRRTRSLLSLLSPPPPPDPLASAFDLGEKEGRKRTTMEANGGMAAGSYKR
NELVRIRHDSDGGPKPLKNLNGQICQICGDTVGLTASGDVFVACNECAFPVCRPCYE
YERKDGNQSCPQCKSRYKRHKGSPRVDGDDDEDEVDDLENEFNYAQGTSAARQQW
QGEDPDLSSSSRHESRHPIPLLTNGQPMSGEIPCASIDSQSVRTTSGPLGPSDKHVHSLP
YVDPRQPVPVRIVDPSKDLNTYGLGNVDWKERVEGWKLKQEKNMTQMPNKYHEG
KNDIEGTGSNGEELQMADDARQPMSRVVPISSSHLTPYRVVIILRLIILGFFLQYRVTH
PVKDAYPLWLTSVICEIWFALSWLLDQFPKWSPINRETYLDRLALRHDREGEPSQLA
PVDVFVSTVDPLKEPPLITANTVLSILAVDYPVDKVSCYVSDDGSAMLTFEALSETAE
FARKWVPFCKKHNIEPRAPEFYFAQKIDYLKDKIQPSFVKERRAMKREYEEFKVRIN
ALVAKAQKMPEEGWTMQDGTAWPGNNPRDHPGMIQVFLGHSGGLDTDGNELPRL
VYVSREKRPGFQHHKKAGAMNALIRVSAVLTNGAYLLNVDCDHYFNNSKALKEAM
CFMMDPAYGKKTCYVQFPQRFDGIDLHDRYANRNIVFFDINLKGLDGIQGPVYVGT
GCCFNRQALYGYDPVLTEEDLEPNIIVKSCCGSRKKGKGGNKKYIDKKRAMKRTEST
VPIFNMEDVEEGVEGYDDERSLLMSQKSLEKRFGQSPVFISATFMEQGGLPPSTNPAT
LLKEAIHVISCGYEDKTEWGKEIGWIYGSVTEDILTGFKMHARGWISIYCMPPRPAFK
GSAPINLSDRLNQVLRWALGSIEILLSRHCPIWYGYNGKLRLLERLAYINTIVYPLTSIP
LIAYCILPAFCLFTNKFIIPEISNFASMWFILLFVSIFTTGILELRWSGVSIEDWWRNEQF
WVIGGTSAHLFAVFQGLLKVLAGIDTNFTVTSKAGDEDGDFAELYVFKWTSL

Figure 16.

MESEGETGGKSMKILGGQVYQICGDNVGKSVDGEPFVACNVCAFPVCRPCYEYERK
DGNQSCPQCKTRYKRHRGSPAILGDQEEDADADDSVSDFNYSENQNLNRKTEERILS
WHMQYGQNEDVSAPNYDKEVSHNHIPRLTSGQEVSGELSAASPERLSVASPDVGAG
KRIHSLPYVADANQSPNIRVVDPVREFGSSGLNNVAWKERVDGWKMKQEKNVAPM
STAQATSERGVGDIDASTDVLVDDSLLNDEARQPLSRKVSVPSSRINPYRMVIVLRLII
LSIFLHYRITNPVPNAYALWLISVICEIWFAISWILDQFPKWFPVNRETYLDRLAIRYD
REGEPSQLAAVDIFVSTVDPLKEPPLVTANTVLSILAVDYPVDKVSCYVSDDGAAML
TFEALSETSEFARKWVPFCKKYSIEPRAPEWYFALKIDYLKDKVHPSFVKDRRAMKR
EYEEFKVRINGLVAKAAKIPEEGWIMQDGTPWPGNNTRDHPGMIQVFLGQSGGLDA
EGNELPRLVYVSREKRPGFQHHKKAGAMNALVRVSAVLTNGPFLLNLDCDHYINNS
KALREAMCFLMDPNLGKHVCYVQFPQRFDGIDRNDRYANRNTVFFDINLRGLDGIQ
GPVYVGTGCVFNRTALYGYEPPHKPKQRKSGFLSSLCGGSRKKSRSSKKGSDKKKSS
KHVDPTVPIFSLEDIEEGVEGAGFDDEKSLLMSQMSLEKRFGQSAVFVASTLMENGG
VPQSATPETLLKEAIHVISCGYEDKSDWGSEIGWIYGSVTEDILTGFKMHARGWRSIY
CMPKRPAFKGSAPINLSDRLNQVLRWALGSVEILFSRHCPIWYGYGGRLKWLERFAY
VNTTIYPITAIPLLMYCTLPAVCLLTNKFIIPQISNVASIWFISLFLSIFATGILEMRWSG
VGIDEWWRNEQFWVIGGVSAHLFAVFQGLLKVLAGIDTNFTVTSKASDEDGDSAEL
YMFKWTTLLIPPTTLLIINLVGVVAGISYAINSGYQSWGPLFGKLFFAFWVIVH

FIGURE 17.

MDRLSATGLLPDTFGGARDDISMQLSLIWAQIKAPLLVPLLRLAVFLCLAMSLMLFL
ERVYMAVVILLVKLFGRKPEKRYRWEPMKDDVELGNSAYPMVLVQIPMYNEREVY
QLSIGAACGLSWPSDRIIIQVLDDSTDPTIKDLVELECQRWASKGINIRYEIRDNRNGY
KAGALKEGMKRSYVKQCDYVAILDADFQPEPDFLWRTIPFLVHNPEVALVQARWKF
VNADECLMTRMQEMSLDYHFTVEQEVGSSTHAFFGFNGTAGVWRISALNEAGGWK
DRTTVEDMDLAVRASLKGWKFVYLGSLKVKNELPSTFKAYRFQQHRWSCGPANLF
RKMAMEIIRNKKVTLWKKVHVIYSFFLVRKIVAHIVTFIFYCVVLPATVFVPEVTVPK
WGAVYIPSIITVLNAVGTPRSLHLVVFWILFENVMSFHRTKATFIGLLEAGRVNEWIV
TEKLGDALKVKASNKVPKKPKFRFGDRLHVLELGVGAYLFFCGCYDIAFGRNHYFM
YLFAQAIAFFIMGFYIGTFVPNS

FIGURE 18.

MAPSFDWWAKGGHKGTPVVVKMENPNWSMVELESPSEEDFLIGGDSAPSGRVRDK
GRNKNAKQLTWVLLLKAHKAAGCLTSIAGAAFTLASAVRRRVASGRTDADADEAE
TGESRSGREKENPTVKSRIYACIKAFLWLSILLLGFEVAAYFKGWHFGALELQYLLA
APLGVKGAFNSLYSRWVLIRVEYLAPPLQFLANVCIVLFLIQSIDRLVLCLGCFWIKFK
KIKPVPKESGAAVDPESGENGFFPMVLVQIPMCNEKEVYQQSIAAVCNLDWPKSSLLI
QVLDDSDDPTTQSLIKEEVQKWQQEGANILYRHRVIRDGYKAGNLKSAMNCSYVKD
YEFVAIFDADFQPTPDFLKRTVPHFKDNEELGLVQARWSFVNKDENLLTRLQNVNLS
FHFEVEQQVNGIFINFFGFNGTAGVWRIKALEDAGGWLERTTVEDMDIAVRAHLRG
WKFVFLNDVECQCELPESYEAYRKQQHRWHSGPMQLFRLCLLDIIRSKISVWKKFN
MIFLFFLLRKLILPFYSFTLFCIILPMTMFVPEAELPAWVVCYIPATMSFLNILPAPKSFP
FIVPYLLFENTMSVTKFNAMISGLFQLGSAYEWVVTKKSGRSSEGDLVALIDKEPKH
QRGVSVPDLEEMKEEIQKQEKLASRKKKHNRIYVKELSLAFLLLTASARSLLSAQGIH
FYFLLFQGISFLLVGLDLIGEQVE

FIGURE 19.

MESDAENGGKPLKSLGGQVCQICGENVGKTLDGEPFIACDVCAFPVCRPCYEYERK
DGNQSCPQCKTRYKRHKGSPAILGDHEEDGDAGDDYHYSSEDQTQKEKIAERMLSW
HMTYGRGENVAPANYDGEVSRNHIPLLTSRQEVSGELSAASPERLSMASPGVGRVH
RVRPLSYASDVTQSPNIRVVDPAREFGSPGIGNVAWKERVDGWKMKQEKNVGPMS
TGQAASERGAGDIDASTDVLVDDSLLNDEARQPLSRKVSIPSSRINPYRMVIMLRLVI
LCIFLHYRITNPVPNAYALWLISVICEIWFAISWILDQFPKWFPVNRETYLDRLALRYD
REGEPSQLAAVDIFVSTVDPLKEPPLVTANTVLSILAVDYPVDKVSCYVSDDGAAML
TFEALSETAEFARKWVPFCKKYNIEPRAPEWYFTKKIDYLKDKIQPSFVKDRRAMKR
EYEEFKVRINGLVAKAQKIPEEGWVMQDGTPWPGNNTRDHPGMIQVFLGQSGGLD
AEGNELPRLVYVSREKRPGFQHHKKAGAMNSLVRVSAVLTNGPFLLNLDCDHYINN
SKALREAMCFLMDPNLGKHVCYVQFPQRFDGIDKNDRYANRNTVFFDINLRGLDGI
QGPVYVGTCVFNRTALYGYEPPLKPKHKKPGVLSLLCGGSRKKSSKSSKKSSDRKR
SGKHVDTTVPIFSLEDIEEGVEGAGFDDEKSLLMSQMSLEKRFGQSAVFVASTLMEN
GGVPQSATPETLLKEAIHVISCGYEDKSEWGSEIGWIYGSVTEDILTGFKMHARGWR
SIYCMPKLPAFKGSAPINLSDRLNQVLRWALGSVEILFSRHCPIWYGYGGRLKWLER
FAYVNTTIYPVTAIPLLMYCTLPAVCLLTNKFIIPQISNIASIWFISLFLSIFATGILEMR
WSGVGIDEWWRNEQFWVIGGVSSHLFAVFQGLLKVLAGIDTNFTVTSKASDEEGDF
TELYTFKWTTLLIPPTTLLIINLVGVVAGISYAINSGYQSWGPLFGKLFFAFWVIIHL

FIGURE 20.

MEASAGLVAGSHNRNEFVVIHGHEEPKPLNTLSGHVCQICGEDVGLNTDGELFVAC
NECGFPVCRPCYEYERREGNQSCPQCNTRYKRQKGSPRVEGDDDEEDVDDIEHEFN
VETQQRNRQQITEAMLHGRMSYGRGPDDENSQIAHNPELPPQIPVLANGHSVVSGEI
PTSYYADNQLLANPAMLKRVHPSSEPGSGRIIMDPNRDIGSYGFGNVSWKERGDGY
KSKENKSGQLDMTEGRYQYNGGFAPNEPEDYIDPDMPMTDEARQPLSRKVPIPSSKI
NPYRMVIVIRLIVLGIFLRYRLLNPVKNAYGLWATSIVCEIWFALSWILDQFPKWLPIS
RETYLDRLSLRYEREGEPSMLAPVDLFVSTVDPLKEPPLVTANTVLSILSVDYPVDNV
SCYVSDDGASMLTFESLSETSEFARKWVPFCKKFDIEPRAPEIYFSQKIDYLKDKFQPT
FVKERRAMKREYEEFKVRINRLVAKASKVPKEGWTMQDGTPWPGNNTRDHPGMIQ
VFLGHSGGLDTEGNELPRLVYVSREKRPGFQHHKKAGAMNALVRVSAVLTNAPFM
LNLDCDHYINNSKAIREGMCFMMDPQVGRKVCYVQFPQRFDGIDRNDRYANRNTV
FFDINMKGLDGIQGPVYVGTGCMFRRQALYGYGPPKGPKRPKMVTCDCLPCCGPRK
KSPKKNSSKKSAGIPAPAYNLDGIEEGVEGYDDERALLMSQLDFEKKFGQSSAFVQS
TLMENGGVPQTANPAELLKEAIHVISCGYEDKTEWGKELGWIYGSVTEDILTGFKMH
TRGWRSIYCMPKRAAFKGSAPINLSDRLNQVLRWALGSVEIFMSRHCPIWYGYGGG
LKWLERFAYINTIVYPFTSLPLIAYCTLPAVSLLTGKFVIPQISTFASLFFIALFISIFATGI
LEMRWSGVSIEEWWRNEQFWVIGGVSAHFFAVIQGLLKVLAGIDTNFTVTAKASDD
GEFGELYAFKWTTLLIPPTTLLVINLVGVVVGVADAINNGFQSWGPLLGKLFFAFW

FIGURE 21.

MEARTNTAAGSNKRNVRVSVRDDGELGPKPPQHINSHICQICGEDVGLAADGEFFVA
CNECAFPVCRPCYEYEWKDGNQSCPQCKTRYKWHKGSPQVDGDKEDECADDLDH
DFNSTQGNRNEKQQIAEAMLHWQMAYGREDVGPSRSESQELPQLQVPLITNGQAI
SGELPAGSSEYRRIAAPPTGGGSGKRVHPLPFPDSTQTGQVRAEDPAKDFNSYGFGN
VAWKERVESWKNKQDKNTLQVTSDTYYASEGKDGDIDGCVADEEDLQMSDEARQ
PLSRKVPIASSKINPYRMVIVLRLVILCFFFRYRILNPVRNAYGLWFTSVICEIWFAISW
ILDQFPKWLPINRETYLDRLCLRYDREGEPSQLAAVDIFVSTVDPMKEPPLVTANTVL
SILSVDYPVDKVSCYVSDDGAAMLTFEALSETSEFARKWVPFVKKFDIEPRAPEWYF
AQKIDYLKDKVQPSFVKERRAMKREYEEFKVRINALVAKAQKVPEEGWIMQDGTP
WPGNNTRDHPGMIQVFLGHSGGLDTDGNELPRLVYVSREKRPGFEHHKKAGAMNS
LVRVSAVLTNGPYMLNLDCDHYINNSRALREAMCFMMDPTLGKKVCYVQFPQRFD
GIDRNDRYANHNTVFFDINLKGLDGIQGPVYVGTGCVFNRQALYGYEPPHKGKIHFS
SCCGPRKKSRKSNKKYNDTKKLDRPTDSTVPIFSSLEDIEGGVEGFDDEKSPLVFQKS
LEKKFGQSLVFVASTQMENGGVPQSATPADLLKEAIHVISCGYEDKSDWGKEIGWIY
GSVTEDILTGFKMHARGWRSIYCMPPRPAFKGSAPINLSDRLNQVLRWALGSVEILLS
RHCPIWYGYTGRLKWLERLAYINTTVYPITSIPLLAYCTLPAICLLTGKFIIPEISTLASL
WFISLFLSIFATGILEMRWSGVGIDEWWRNEQFWVIGGVSAHLFAVIQGLLKVLAGV
DTNFTVTSKASDEGGDFAELYIIKWTALLIPPTTLLIINIVGVVAGISYAISTGYRSW

FIGURE 22.

MASNGTMNSQVCQVCGDNVGVDANGEPFVACHDCGFPVCRPCQQYERDEASQCCL
HCKAPYRRYEGGPADEVEENGDPNFEKVEATDYEGEGYRVDSFNDSEINNAETKDG
NSKGVAWKERVESWKSKKNKKKTAASKTVNPGVEGIPEQTRDPEAEEAMMAEAGQ
PLSCIIPIPRTKLQPYRMVVIMRLIVLGLFFSYRVQNPVESAFGLWMTSVICEIWFALS
WILDQFPKWNPINRETFTDRLSLRYERPGEPCELAAVDFFVSTVDPLKEPPLVTANTV
LSILAVDYPVEKVSCYVSDDGAAMLTFETMSETAEFARKWVPFCKNFNIEPRAPEFY
FSLKVDYLKDKVQPNFVKERRAMKREYEEYKVRINALVAKAQKTPDEGWIMQDGT
AWPGNNIRDHPGMIQVFLGHTGAHDVEGNELPRLVYVSREKRPGYQHHKKAGAMN
ALVRVSAVLTNAPYLLNLDCDHYVNNSKAVREAMCFMMDPEVGRNVCYVQFPQRF
DGIDRSDRYANRNTVFFDINMKGLDGIQGPVYVGTGCCFNRQALYGYGPPAAARPK
ASRGCLPSLCCCCCCCPKSKTIDPKKSAPQEDLNAAIFNLQEMQSYDDYERQLLVSQ
RSFEKSFGQSSVFIASTLMDNGGVPESTNPASLIKEAIHVISCGYEEKTEWGKEVGWI
YGSVTEDILTGFKMHCRGWRSIYCMPKRPAFKGSAPINLSDRLHQVLRWALGSIEILF
SRHCPLWYGFGAGRLKWLERLAYTNTIVYPLTSLPLIAYCTLPAICLLTGEFIIPTLSNL
ASIYFMLLFISIIVTGVLELRWSGVSIEEWWRNEQFWVIGGVSAHFFAVFQGLLKVLA
GIDTNFTVTAKASDDNEFGELYAFKWTTLLIPPTTLLVINLVGIVAGFSDALNNGYQS
WGPLFGKLFFSVWVILHLYPFLKGLMGRQNRTPTIVVLWSILLASIFSLLWVKIDPFL
GPAETPTLQKCMAIDC

FIGURE 23.

MEANAGLVAGSHNRNEFVVIRPEGEVGPKPLHHLSVQICHICNEDVGLTVDGELFVA
CNECAFPICRTCYEYERSEGNQVCPQCKTRFKRHKGSARVEGDEDEDDVDDLENEF
NFGDRDKQDMQYIAEAMLHGHMSYGRGGDTDMPHVVQTTLPQVPLLTNGHMDPG
IPPEHHALVPSYMGGGKRIHPFPYADSNLPVQARSMDPTKDLAAYGYGSIAWKERVE
NWKMRQEKMQVMRNEGGPLGGGKDWDPDGNGPDGPDLPLMDEARQPLSRKLPIP
SSRINPYRMVIILRLVVIGFFFHYRVMHPVNDAFGIWLTSVICEIWFAFSWILDQFPKW
LPIDRETYLDRLSLRYEKEGQPSGLAPVDIFVSTVDPLKEPPLVTANTVLSILAVDYPV
DKVSCYVSDDGAAMLTFEALSETSEFARKWVPFCKKFNIEPRAPEWYFQQKIDYLK
DKVQPSFVKDRRAMKREYEEFKVRMNALVAKAQKVPEEGWTMQDGTPWPGNNVR
DHPGMIQVFLGHTGGHDTDGNELPRLVYVSREKRPGFNHHKKAGAMNSLVRVSAV
LTNAPYMLNLDCDHYINNSKAIRESMCFMMDPTVGKKVCYVQFPQRFDGIDRHDRY
ANRNVVFFDINMKGLDGIQGPIYVGTGCVFRRQALYGFDAPKAEKEPTRTCNCWPK
WCCCKSRKKNKKVKAKQEKKKKKSKRSDASLPIFNSEDIEAVEGVDSEKLAFISQIK
LEKKFGQSPVFVASTLLENGGVPQNASPASLLKEAIHVISCGYEDKTDWGKEVGWIY
GSVTEDILTGFKMHCHGWRSIYCIPPRPAFKGSAPINLSDRLHQVLRWALGSVEIFLSR
HCPVWYGYGGGLKWLERLSYINATVYPWTSIPLVAYCTLPAICLLTGKFIIPELSNIAS
LWFLALFICIFTTGILEMRWSGVPIDDWWRNEQFWVIGGVSAHLFAVFQGLLKVLAG
VDTNFTVTSKAGDDDDFSELYAFKWTTLLIPPTTLLIVNLIGVVAGVSNAINNGYESW
GPLF

FIGURE 24.

MEANAGLVAGSHNRNEFVVIRPEGEVGPKPLHHLSVQICHICNEDVGLTVDGELFVA
CNECAFPICRTCYEYERSEGNQVCPQCKTRFKRHKGSARVEGDEDEDDVDDLENEF
NFGDRDKQDMQYIAEAMLHGHMSYGRGGDTDMPHVVQTTLPQVPLLTNGHMDPG
IPPEHHALVPSYMGGGKRIHPFPYADSNLPVQARSMDPTKDLAAYGYGSIAWKERVE
NWKMRQEKMQVMRNEGGPLGGGKDWDPDGNGPDGPDLPLMDEARQPLSRKLPIP
SSRINPYRMVIILRLVVIGFFFHYRVMHPVNDAFGIWLTSVICEIWFAFSWILDQFPKW
LPIDRETYLDRLSLRYEKEGQPSGLAPVDIFVSTVDPLKEPPLVTANTVLSILAVDYPV
DKVSCYVSDDGAAMLTFEALSETSEFARKWVPFCKKFNIEPRAPEWYFQQKIDYLK
DKVQPSFVKDRRAMKREYEEFKVRMNALVAKAQKVPEEGWTMQDGTPWPGNNVR
DHPGMIQVFLGHTGGHDTDGNELPRLVYVSREKRPGFNHHKKAGAMNSLVRVSAV
LTNAPYMLNLDCDHYINNSKAIRESMCFMMDPTVGKKVCYVQFPQRFDGIDRHDRY
ANRNVVFFDINMKGLDGIQGPIYVGTGCVFRRQALYGFDAPKAEKEPTRTCNCWPK
WCCCKSRKKNKKVKAKQEKKKKKSKRSDASLPIFNSEDIEAVEGVDSEKLAFISQIK
LEKKFGQSPVFVASTLLENGGVPQNASPASLLKEAIHVISCGYEDKTDWGKEVGWIY
GSVTEDILTGFKMHCHGWRSIYCIPPRPAFKGSAPINLSDRLHQVLRWALGSVEIFLSR
HCPVWYGYGGGLKWLERLSYINATVYPWTSIPLVAYCTLPAICLLTGKFIIPEVLPLT
FMPYINIVSELACEGLSHFDILF

FIGURE 25.

MAPNFGVGQWWSKQSHKGTSVVVKMENPNYSMLELESPANGFQVDKGGRGKNAK
QLTWVLLLKAHKAAGCLAWLANGVWALFASVRRRFTAPSDESGKSSEKSKLYRVIR
CFLIASIFLLGFELLAYWKGWHFSRPNLHIPPSLSINGLLQSIYSGWLYTRANYLAPPL
QYLANVCIILFLIQSADRALLCVGCFWIKLKKIKPVPKCELGDAADLEQGDNAAYPM
VLVQMPMCNEREVYQQSIAAVCNLDWPKDHMLVQVLDDSDDVEVQFLIAAEVQK
WQQKGVHIVYRHRVVRTGYKAGNLKSAMNCDYVKDYEFVAIFDADFRPDPDFLKR
TVPHFKDNDELALVQARWSFVNRDENLLTRLQNINLSFHFEVEQQVNSVFVNFFGFN
GTAGVWRIKALEESGGWLERTTVEDMDIAVRAHLNGWKFIFLDDVKCLCELPESYE
AYRKQQHRWHSGPMQLFRLCLPDIIRSKIAFWKKANLIFLFFLLRKLILPFYSFTLFCII
LPMTMFLPEAELPAWVVCYVPAIMSLLNILPAPRSFPFIIPYLLFENTMSVTKFNAMIS
GLFQLGSAYEWVVTKKSGRASETDLLALVERESHVQLEHPKHHRGVSESGLDALSK
LDEQKHQQPPKKKLNRIYKKELALAFLLLTASARSLMSAQGIHFYFLLFQGISFLVVG
LDLIGEQTS

FIGURE 26.

MEPNDFPLYTTLEKKSLLYRAYSCTHFSAIIGLICYRLLYIPSEDSWPWILIFVAELGFS
YSWILDQALRWWPVERTVFPNRLSKRFQSKLPPVDIFICTADPFKEPPLTVINTVLSAL
AVDYPMGKLSCYVSDDGGSPLTFYALLEASRFAKIWIPFCDKYSIQDRCPEVYFSNPS
ALENVNLPFMKDWKHVNKMYSELKDRINNVMEMGSVPPDKQNEHQGFKDWASGS
SRRDHPSIVQILLEKGEDRDIDGNDLPDLIYVSREKRPGIPHHYKAGALNVLLRVSGV
MSNAPFILTLDCDMYTNNPEALRQAMCFFLDPKTGDQFGFVQFPQVFHGITKNDIYG
NNLRIFIEIDFKGQDGIDGPFYVGTGCIHRREALCRTERRQSSSNYHKVASTIVCAEET
VAKDKACPSKMLKNARELANCTYEDNTLWGKEFGMIYGCAVEDILSGFVIQCKGW
RSIYCNPRRSAFLGCAPNNLIDTLTQHKRWAVGHLQLFVSKFCPYIYGIHRMQIAQR
MCYSYCPLWSLSSMHKLCYGLIPGLCMLRGISLFPKLSSSCFFLFAFLAISAYGYSLFE
YIWNVGSLNRWCNEQRMWMIKGVSAYLFALIEFAGKMIGVSEVGFEVTNKVVDSE
AAKRYETEIFEFGVASPLFVRPATLVVINLISVVGGLARILREGYSAFECITLQLILCSFI
VITGYPILEAMFLSKAKGRIPTSITIFFTLDAVSVWSVASMAIPSR

FIGURE 27.

MATNFEFQEWWNKEKETHRGTSVVVKMENPNWSMVELQSPDDDFQHSDKQGRGK
NARQLTWVWLLKAHRAAGCVAWLAQGLWSLLSAVKRRVTLNKNQNRVTEEDKPG
KSKLYRVIRGFLLFAILMLGFEIAAYMKGWHFSRPPFDFSPSLDLQGVLHSIYSEWVF
VRATYLAPPLQTLANICIVLFLIQSADRLVLAMGCLWIHIKKIKPVPQFEFPSSAADLE
KGASADYPMVLVQIPMCNEMEVYQQSIAAVCNLDWPKERMLVQVLDDSDDVDVQ
LLIKSEVQKWQQKDINIVYKHRVVRTGYKAGNLKSAMACDYVKDYEFVAIFDADFQ
PSPDFLKKTVPHFKGNEDLALVQARWAFVNKDENLLTRLQNINLAFHFEVEQQVNG
VFINFFGFNGTAGVWRIKALEESGGWLERTTVEDMDIAVRAHLNGWKFIYLNDVQC
LCELPESYEAYRKQQHRWHSGPMQLFRLCLPDIIRSKEIGFSKKANLIFLFFLLRKLILP
FYSFTLFCIILPMTMFLPEAQLPSWVICYVPVIMSFFNILPAPRSFPFIVPYLLFENTMSV
TKFNAMISGLFQLGSAYEWVVTKKLGRSSEADLVAFMEKESHPQLEHPRHHRGVSE
SGLDVLNKLTEQQQKQPFKKKANRLYRKELALAFLLLTASARSLLSAQGIHFYFLLF
QGISFLLVGLDLIGEQVS

FIGURE 28.

MEPNGFPLYTTLEKKSFVYRAYACAHFSAIIGLLYYRIVYIPSEDYWPWIMIFVAELG
FAYGWILEQAFRWRPVERKVFPERLSKRFKSDLPPVDIFICTADPIKEPPLAVINTVLS
ALAVDYPVEKLSCYVSDDGVSSLTFYALFEASRFAKIWLPFCYNYSIQDRSPEAYFSA
RSGQEKENMSFTRECKSVKKAYLEMKDRINNAVEMGSVPDDKQKEHTGFKDWILG
STRRDHPSIVQILLENGEDKDIQGNDLPSLIYVSREKRPGIPHHYKAGALNALIRISGL
MSNAPFIITLDCDMCTNNCEALRQAMCFFLDPQTGHQFAYVQFPQGFHGITRNDLYA
NDHLRISYWQFKGMDGLEGPLYAGTGCIHRRDALCGKEGRLASSTSKAQTSPSKML
KDARHLANCACEENTLWGKEVGMIYGCAEEDALTGFVIQSRGWKSIYCTPRRKAFL
GGAPVNMNDTLIQIKRWSAGYLEFFLSKFCPYVYGIQRTSTVQCMCYGVCCLWAPS
SLYILCYGLLPALAMLNGLSLFPKASNPWFILFVSLAASTYGYSLIEFMCIGGSFKSW
WNEQRMWLIKGVSSYLFALIQVVCKMLGLSEVGFEVTSKVVDSEAAKRHEEEMLEF
GVASAMFVPPASLAITNLISLVGGLARIMREGYQTFDSMIWQLLLCSFIVLISYPILEA
MFLRKDKGRIPTSITIVSIFVAVSACSVASILIPTW

FIGURE 29.

MDRLSYSSANILPQTFQGTRDDIVEQIALLWQQIRAPLVAPLLNICIYFCLLMSVMLFI
ERVYMAVVIVLIKVFGKKPEKRYKWGAIKEDVELGNSVYPMVLVQIPMYNEREVYQ
LSIGAACALSWPSNRVIIQVLDDSTDLTIKDLVEMECQKWASKGINIKYEIRGNRNGY
KAGALKEGMKHSYVRECDYVVIFDADFQPDRDFLSRTIPFLVHNPELALVQARWKF
A

SEQUENCE LISTING

<160> NUMBER OF SEQ ID NOS: 83

<210> SEQ ID NO 1
<211> LENGTH: 1024
<212> TYPE: DNA
<213> ORGANISM: Eucalyptus grandis

<400> SEQUENCE: 1

```
ggggaaaaag caaccatata aaactattgc cattcgcaca ggaacagaac gacgagatca      60
tggaggccag ggcgggactt gttgcaggtt cctataagcg gaacgagctt atggtagtcc     120
ctggacacga tgggcccaag cccatcaggc tatccaccct ccaggattgc caagtctgcg     180
gagataaaat cggctgcaac ccgaatgggg aactattcgt ggcctgcaac gagtgtggat     240
tccctgtgtg tcgtccctgt tatgagtacg agagaaagga tgggaaccgg tgctgccctc     300
agtgcaagac tcggtacagg cgtcacaaag ggagtccccg ggttgaaggc gatgatgaag     360
aagatggcat ggacgactta gaacaagaat tcaacatgga aagagatcgc caaagcgtag     420
tcagtcacag aggaaacgcc ttcgacgcta ctcctcgggc tgcccacagt atcgctaacc     480
gctcgataaa tggagataat tatgcacttt cccttcctcc gatcatggat ggcgacagtt     540
taagtgttca gcgttttcca catgcagcta ctgtgattgg aaatggatta gatccagtca     600
aagagaacta tgggagtgct gcatggaagg agagagtgga gaattggaaa gcgaagcacg     660
ataagaaaag tggcagcatc aaggatggca tatatgatcc agacgaggcc gatgatataa     720
tgatgactga agccgaagcg agacagcctt tttcgcgtaa ggtgccaatc ccctccagtc     780
taatcaatcc ctacagaatt gttattgtgt tgcgtttgat aattctggga ttcttcttcc     840
gctaccgatt gatgaatcct gccaaggacg cacttggcct ctggttgacc tccattatct     900
gcgagatctg gttcgccttc tcctggattc ttgatcagtt ccccaagtgg tttcccatca     960
ctagagaaac ttatctcgac agattatcta tgagatacga gagggaagga gagccttgca    1020
agct                                                                 1024
```

<210> SEQ ID NO 2
<211> LENGTH: 1024
<212> TYPE: DNA
<213> ORGANISM: Eucalyptus grandis

<400> SEQUENCE: 2

```
ctgacgtgct cgttgactcc ccggagattg gtccgcagag atagccgatg ggtccggcga      60
caaggaggag cctggatcgt cggatgacgg cggggtcgac actgcgaagg ttgatggggc     120
taagggtggc ggtgaagcct atgatcctgc ttctaagaag ctcaggagag agaatatgag     180
gagttcaagg tgcaaatcaa tgctttggtt gcaaaggcac aaaagatgcc agaagaaggg     240
tggacaatgc aggatggcac tgcctgggct ggaaataacc ccagggatca ccctggaatg     300
atacaggttt tcctgggcca cagtggggga cttgatactg atggaaatga gctacctcga     360
cttgtttatg tttctcgtga aaagcgacct ggtttccaac atcacgagaa agctggagcc     420
atgattgctt tgatccgggt ctcagctgtc ctaaccaacg gaccgtatct tttgaatgtt     480
gactgtgatc attactttaa taaagtaaag cattgaaaga agcaatgtgt tcatgatgg      540
atcccgctta tggaaagaag acgtgctatg tgcagttccc acaacgtttt gatgggattg     600
acttgcacga tcgatatgct aaccgcaaca tcgtcttctt tgatatagat taacttgaaa     660
gggcttgacg tcatccaagg tcctgtctat gttggaattg gatgttgttt caacaggcaa     720
```

| | | |
|---|---|---|
| gcccttttatg gatatgaccc tgtattaacc gaggaagatc tggaaccaaa tattattgta | 780 | |
| aagagttgtg gttcaagaaa gaaggggaag ggtggcaata agtacattga caagaaaaga | 840 | |
| gcaatgaaaa gaactgaatc cactgttcca attttcaata tagaagatgt tgaggagggg | 900 | |
| gttgaaggat atgatgatga gacgtcgctc ctgatgtctc agaaaagtct agagaaaaga | 960 | |
| ttcggtcagt ctcctgtttt cattgcggct actttcatgg aacagggtgg cctacgacca | 1020 | |
| tcta | 1024 | |

<210> SEQ ID NO 3
<211> LENGTH: 1024
<212> TYPE: DNA
<213> ORGANISM: Eucalyptus grandis

<400> SEQUENCE: 3

| | | |
|---|---|---|
| ctcgacacat tgctttcttc cgagttcaca gttaacatga gatctctctg tgtgactatc | 60 | |
| ctcagtctct ttgccactta gatctgaacc gcaattctgt tgctttcttt cgtattcttt | 120 | |
| gttctttcgc taagaagggc tgaaaatcaa gaacggtagt aagagcaaag agaaatggag | 180 | |
| gtgagttctg gttagtagc gggctctcac aacaggaacg agctggttgt catccgccgc | 240 | |
| gagaatgaac tcggacaaaa gccgttgcag aagttgagcg ggcaaatttg ccagatttgc | 300 | |
| ggcgacgacg ttggattgac cgtggacggc gagctattcg tcgcctgcaa tgagtgtgcg | 360 | |
| ttccccattt gcaggacttg ctatgagtac gaacggcgcg agggaagcca aatttgtcct | 420 | |
| cagtgcaaaa ccagattcaa gtgcttaagg gggtgtgcaa gagtggatgg agatgaggaa | 480 | |
| gaggatggtg tggatgactt ggagaacgag ttcaactttg atgggaggca taggcaagag | 540 | |
| atggatcgcc aggatatgg tgcagaggca atgcttcatg gccatatgag ctatggccgt | 600 | |
| ggctcggatt tggatctgtc tcacgttcat ccactgcccc aagtcccact cctcaccaat | 660 | |
| ggtcaaatgg ttgatgatat tcctccggag caccatgctt tggtgccagc ctacatggga | 720 | |
| gctggaggcg gcggtggcgg aggtggcaaa aggattcacc cacttccttt cactgattct | 780 | |
| ggtcttccag tgcaacctcg atccatggat ccttcaaagg acttggctgc ttatggatat | 840 | |
| ggaagcgttg cttggaaaga gaggatggag agttggaaac aaaagcaaga gaaactacag | 900 | |
| acgatgaaga acgagaaagg tggcaaggaa tgggacgatg atggggacaa cccagatcta | 960 | |
| ccactaatgg atgaggcgag acagccgctg tcaagaaagt tgcctatatc ctccagccaa | 1020 | |
| atca | 1024 | |

<210> SEQ ID NO 4
<211> LENGTH: 1024
<212> TYPE: DNA
<213> ORGANISM: Eucalyptus grandis

<400> SEQUENCE: 4

| | | |
|---|---|---|
| gtcctttggc gctccgttgc ctcctcctcg ttcacggctc atgaacaccc cctctctgca | 60 | |
| cgtcgtccat cattttcttc tctaatcctc attggcatta gcattttgat ctgataaaag | 120 | |
| ccacttggtc gcaacacgtt cggtgtttct tggctcgcct tccctgaagt gaatcttcta | 180 | |
| cgaaagctga aagcttggcc tttcctgcga agtgggtgtg cttcaagaat cgagattcga | 240 | |
| gaaaatcaag acttcaaaat ggcacccttcg ctcgattcgt gggcaaaaca gaacgttcac | 300 | |
| aagggcaccc ccgtcgtcgt caagatggag aacctgaact ggtccatgct cgagctggag | 360 | |
| agcccgtcgg acgaggacat cttccccgcc ggcgcccccg ccgccggcga ggggcggcg | 420 | |
| ccggagcgga cgcgcaacaa gaacgcgaag cagctcacgt gggtcctgct cctcagggcc | 480 | |

| | |
|---|---|
| cacagggccg ccggctgcct ggcctccatg gccgccgcct tcctcggcct cgcctccgcc | 540 |
| gtcaggcgcc gcgtggccgc cggcaggacc gacaacgacg tcagcgaggc ttctcgtcgc | 600 |
| ggcgggggag tgagagagag ccccactctc aaggccaggt tctatacttg cacaaaagtg | 660 |
| ttcctttggc tgtccattgt cctgttaggg tttgaagtgg ctgcttactt caagggttgg | 720 |
| cactatggtg cgcacaatgt cgagttgcaa cacctgttgg caacttcttt ctcagttaag | 780 |
| ggtgttttcg atcggttgta ttcgaagtgg gtttcgatcc gggtggaata tcttgctcct | 840 |
| ccattgcagt tcttggccaa tgcttgcata gtgctcttcc ttatccagag cttggacagg | 900 |
| cttgtcctgt gtttgggttg tttctggatc aaattcaaaa acatcaagcc gatcccaaag | 960 |
| gaggacgcct cagtcgatgt cgaatccggc gagaagggat acttccctat ggtcctagtg | 1020 |
| caac | 1024 |

<210> SEQ ID NO 5
<211> LENGTH: 1024
<212> TYPE: DNA
<213> ORGANISM: Eucalyptus grandis

<400> SEQUENCE: 5

| | |
|---|---|
| ctctcccctc ttcatcgact ccactcgctc tctttccctc ccctctctct ctctcttccg | 60 |
| cagcaatgcg tctgttcctt tccttcctgg cttcgctcta gtcgaggaca agaacagagg | 120 |
| cattccgtcg gcacgaactc agagagagag aaagagagag agggactgaa gaagcaggtg | 180 |
| gtcttggaag ggtgcaaaag gaaagtgagg aaaaggggag agaaggaagc cgaacggagg | 240 |
| cagcatttcc cctctgcttg cctcatttgc tcgagagaga gagaaagaga gagaggggga | 300 |
| ggcagcgagt gagatctacc ttttcgtac actagcttct caaatgcct gctttgacct | 360 |
| agttaagaca cccctcgatt accattccat ctgaggaacg atttcctagt ccaaacccaa | 420 |
| cttttccaaat cctagataat aacatcccct gttttctcc tctgttttgc tttctgtgct | 480 |
| ctgctccaga aaacagagca gcgccaaaca gagcagggta gaaaacagag tctcgagcct | 540 |
| ctgtctcgaa atggcgcaaa tctcggccaa ggacctgatc ccggactcgt taaccatgtc | 600 |
| ccgggaggac atcgcgggcc agctggggat ggtgtgggag ctgatcaagg cgccgctgat | 660 |
| cgtcccggtg ctgcggctct cggtctacgt atgcctcgcg atggcgctca tgctttttcat | 720 |
| ggagagggtc tacatgggca tcgtcatcgt cctcgtcaag ctcttctgga agaagccgga | 780 |
| gaagcgctac aattgggagc ccatcgagga ggacctcgag tccggaagct ccaacttccc | 840 |
| cttcgtcctc gtccaaatcc caatgtacaa cgagaaagag gtgtacaaga tttcgatcgg | 900 |
| agcagcgtgc gggctgtcct ggccggcgga ccgcctcgtg atccaagtcc tcgacgactc | 960 |
| caccgatccc gtaattaagc aaatggtgga gctggagtgc cagaggtggg cgagcaaggg | 1020 |
| gatc | 1024 |

<210> SEQ ID NO 6
<211> LENGTH: 3438
<212> TYPE: DNA
<213> ORGANISM: Eucalyptus grandis

<400> SEQUENCE: 6

| | |
|---|---|
| ctcctcggcg cctcccctc gcgatcgctt ccgctcggc cgtggcctc cccgacacca | 60 |
| tgtccggctt cgccgtgggc tctcactccc ggaacgagct ccatgtcacg aatggtggcg | 120 |
| ctgctgacga acaccgctct cctccccgcc aaaacgcggc cagaacctgc cgcgtctgcg | 180 |
| gcgacgagat cggcctgaag gacgacggcg ctccgttcgt cgcctgccac gagtgcggct | 240 |

```
tccccgtctg ccgcccctgc tacgtctacg agcgcagcga cggcacccag tgctgccccc      300
agtgcaacgc ccgctacaag cgccacaaag ggtgccccccg ggtcgcggga gacgacgagg     360
acgaccactt cgaaggcgag gatttcgagg acgagtttca gatcaggaac cgcggcgaga      420
atgaagttcg ccccaccggt ttcgatcgtt cggaaaatgg ggacagtcac cgccgcaag      480 tccatccgaa cggtcaggtt ttctcttcgg ccggaagcgt cgtcggcgcg agttggaag      540 gagaaggcaa tgcggagtgg aaggagagga tcgagaagtg gaaaatcagg caagaaaaga     600
ggggcttagt gggcaaggac gatggcggga acggcgatgg agaggaagat gactacctga     660
tggctgaagc tcggcaacca ctttcgagaa aagtaccgat ttcttcgagc aaaataagcc     720
cataccgaat tgtcatcgtc ctgcgcctcg tagtcctagg cttttttcctc catttccgta    780 tcttaacccc tgcaactgat gcattccctc tatggcttat ctcagttata tgtgaaacat     840
ggtttgcctt gtcgtggatt cttgatcaat tccctaagtg gaacccgata aacagagaaa     900
cttatttgga tagattatcc ataaggtttg agagggaggg tgagcccagt cgcttaactc      960
ctgtggatgt gttcgtcagt tctgtggacc ctcttaagga accaccaata atcactgcaa    1020
atactgtcct ctcaatcctg gccgttgatt acccggtgga caaagtttgt tgctatgtat    1080
ctgatgatgg cgcttcgatg ctgcttttg acactctctc tgaaactgct gagtttgcga    1140
ggaggtgggt cccattctgc aagaagtata gcatcgagcc gaggactcca gagttttact   1200
tttctcaaaa gattgattac ctgaaagata aggtggagcc cagctttgtg aaggaacgta    1260
gagccatgaa aagagagtat gaagagttca aagtgagggt caatgcattg gtggcaaaag    1320
ctcagaaaaa acctgaagaa ggatgggtaa tgcaagatgg tacccctgg cctgaaaata     1380 atacgcgcga tcatcctggc atgatccagg tttatttggg aagtgctgga gcattggacg    1440
tggaaggtaa ggagttgcct cgacttgtat atgtgtcccg tgagaagcga cctggttacc    1500
agcaccacaa gaaggctggt gcaatgaatg ctctggttcg agtgtcggca gtgctaacaa    1560
acgcacccct cttgttgaac ttggattgtg accactacat caacaacagt aaggctatca    1620
gggaagctat gtgttttcta atggatcccc aacttggaaa gaagctttgc tatgttcaat    1680
ttcctcagag gttcgatggc attgatcgac atgcacagata tgctaatagg aacatagttt    1740 tcttgatat caacatgaga gggcttgatg ggatacaagg accagtgtat gttggaactg     1800
gatgtgtgtt caatcggcag gcattgtatg ggtatgatcc tccagtgtcc caaaagcggc    1860
caaagatgac atgtgattgc tggccttcat ggtgctcttg ttgctgcggt ggttcaagga    1920
agtcaaagtc aaagaagaag gatgatacga gtttgcttgg gcctgttcat gcgaagaaga    1980 aaagatgac aggaaagaac tacttgaaga agaaagggtc tggacctgtc tttgatctag    2040
aagacattga agaaggactt gagggttttg atgagctaga aaaatcatcg ctcatgtctc    2100
agaagaattt tgagaagcgg tttggacagt cacctgtatt cattgcctcc acactaatgg   2160
aagatggtgg cttgccagaa gggactaact ccacttcact tattaaggaa gctatccatg   2220
tcataagttg tggctatgaa gagaaaacag aatgggggcaa agagattgga tggatttatg   2280
gctccgttac agaagatatc ttgacaggct tcaagatgca ttgtagagga tggaagtctg    2340
tatattgcat gcccaaaaga ccagctttca agggatcagc acctataaat ctgtcagatc    2400
gactccatca agttctgaga tgggctcttg gctccgttga gatttttcctc agtcgtcatt    2460 gtcctttgtg gtatgcttgg ggaggaaaac tcaaactgct tgagaggctt gcctatatca    2520
acaccattgt ctacccttc acttccattc ctttgctttt ctactgtaca ataccctgccg   2580 tttgccttct cactgggaaa ttcattatcc ccacgctcac taactttgcg agcatatggt    2640
```

| | | |
|---|---|---|
| tcttggccct | tttcctatcc atcatagcca ctggcgtgct tgaactacgg tggagtggtg | 2700 |
| tcagcatcga | ggactggtgg cgtaatgaac aattctgggt cattggtgga gtatctgcac | 2760 |
| acctcttcgc | tgtattccaa ggcctcctca aggtgcttgc cggagttgat actaacttca | 2820 |
| ctgttacagc | aaaggcagcc gaggacagtg agtttggtga actctacctt ttcaagtgga | 2880 |
| ctacccttct | caaaccacca accactctaa taatcttgaa catggtcggt gtcgtcgccg | 2940 |
| gtgtttcgga | tgccataaac aatggatacg gatcgtgggg ccctctgttc gggaagctct | 3000 |
| tcttcgcctt | tgggtgatc gtccatctct accctttcct caaaggtctg atgggaaaac | 3060 |
| agaacaggac | acccacgatc gtggtccttt ggtccgtact tctcgcctct attttctcat | 3120 |
| tggtctgggt | ccggatcgat ccgttcctgc cgaagcaaac cggtccagtt ctcaaaccgt | 3180 |
| gtggggtgga | gtgctgattc tggcgtcgga tttcattcaa catgccgtct ctccgacccg | 3240 |
| attagatgtg | tcgctttacg gagctgtttc tttctgtctc ttacttggga catattgtaa | 3300 |
| tgcactaggg | gaaatcttcc cgattgaaat ctcttgatta gcataggttt tgcttgaaga | 3360 |
| gtgtggaact | gaaatgtgca agtcctggt tttgaacttt ttgcaatata ttctgctcaa | 3420 |
| gattaagcaa | aaaaaaaa | 3438 |

<210> SEQ ID NO 7
<211> LENGTH: 1024
<212> TYPE: DNA
<213> ORGANISM: Eucalyptus grandis

<400> SEQUENCE: 7

| | | |
|---|---|---|
| gctaagtcct | gttctagcac caccgccatc ctcctcctcc tcctcctccc atggaagccg | 60 |
| gagctggact | tgtcgccggt tctcacaacc gcaacgagct cgttgtgatt cacggccatg | 120 |
| aggagtcgaa | gcctttgaag aacttggatg gcaagtgtg tgagatctgt ggggatgagg | 180 |
| ttgggctcac | ggttgatgga gatttgttcg tggcatgcaa cgagtgcgga tttccggttt | 240 |
| gtcggccttg | ctatgagtat gagaggagag aagggagcca gttgtgccct cagtgcaaga | 300 |
| ctcgatacaa | gcgtctcaaa gggagcccaa gagtggaggg tgatgatgat gaagaagaca | 360 |
| ttgatgatct | cgagcacgaa ttcaacattg aagatgagca gaacaagcac aagtacatgg | 420 |
| cagaagctat | gcttcatggg aagatgagct atggaagagg tcctgaggat gacgataacg | 480 |
| ctcaatttcc | atcagttata gctggtggca gatcccgacc tgttagtggc gagttcccaa | 540 |
| tatcatctta | tggtcacgga gagatgccct cttcccttca caaacgagtt catccatatc | 600 |
| caatttctga | acccggaagt gaaagatggg atgaaaagaa agaggagggg tggaaagaaa | 660 |
| gaatggacga | ctggaagctg cagcagggca acctcggccc tgaacctgat gacatcaatg | 720 |
| acccggacat | ggcaatgata gatgaggcaa ggcagccact ctccaggaaa gtaccaattg | 780 |
| catcgagcaa | gatcaaccca taccggatgg tgatagttgc tcggcttgcc atattggctt | 840 |
| tcttccttcg | atacaggata ttgaacccag tacatgatgc atttggtctt tggttaacat | 900 |
| ccatcatctg | tgagatatgg ttcgctttct cctggatcct ggatcagttt cccaaatggt | 960 |
| tccctattga | tcgtgagacc tatcttgatc gcctctctct cagatatgaa agggaaggtg | 1020 |
| aacc | | 1024 |

<210> SEQ ID NO 8
<211> LENGTH: 1024
<212> TYPE: DNA
<213> ORGANISM: Eucalyptus grandis

<400> SEQUENCE: 8

```
agagagagag agagagagag agagagagct ttcgtcttcg ttctcatttc ctctctcctc    60
cccccttgtt cattcgtttc tcgtttctgc ttccgtcttc gtttgagggc agcggcagag   120
aaaaagcttc cattttcttt cgatagagtt cgtccgtccg tcttcatcga taagtaattg   180
tcttattttg ctcagctgtt ggattcgtga tcaggccctt cttttccatg tcgtttttt    240 cagtgggtct ctctgcaatg catcaagagg agtgaccttt gagcgagcga ttcactgaca   300
tttccagctc tgccttcctt tttttcccac ttctgctttg cttgacccag aagcaatatt   360
gcaaagcaaa tattctctct ccaactctct gcttttttca gataattcaa ttgccagatc   420
acagagatct acttgctctc atcagctctg gtccctagca tcacattctc cctctctcgc   480
attgctctgt ttcgcgatcg aaaaacagag caaacgagtc tctgccgaaa tggaccggct   540
ctctgcaact ggtctccttc ccgacacgtt cggaggagca agagacgaca tctccatgca   600
actttcgctg atttgggctc agatcaaggc gccgttgctc gtcccgttgc tccggctcgc   660
ggtgttcctt tgcctggcca tgtcgctgat gctgttcctc gagagggtgt acatggccgt   720
cgtgatcctc ttggtgaagc tcttcggccg gaagccggag aagcggtaca ggtgggagcc   780
catgaaggac gacgtcgagc tgggcaactc ggcctacccc atggtcctgg ttcaaatccc   840
aatgtacaac gagcgagagg tttatcagct ctcgatcgga gccgcatgcg gtctctcgtg   900
gccgtccgac cgcatcatca ttcaagtcct cgacgattcc accgacccga cgatcaagga   960
cctggtggag ctggagtgcc agaggtgggc gagcaaaggg atcaacatca ggtacgagat  1020
ccgg                                                               1024

<210> SEQ ID NO 9
<211> LENGTH: 1024
<212> TYPE: DNA
<213> ORGANISM: Eucalyptus grandis

<400> SEQUENCE: 9
gtccctagtt ccttacttgc tcttctttct ctccacataa agctggcctc ttgttcctct    60
ctcctcctcc tcctcctcct ctattaacca ccgtcgacga gcatcgatca gaaaggctag   120
tggcatcgcc tcaaggacag agaacgaaag aactatggag catcggttcg cgccctctaa   180
acctttgcca tgtagacccg aaattgatcg ccgtcaaccg tgcacacatg ctcatccatg   240
gagcagctct acttatcctt atacactata gagcttcctt tttcttcgcc gaagaagcta   300
gctcaccggg ccaacccacc actttggctt ggctcattat tttcctgggc gagctaacgc   360
tgtccctcac gtggcttctc caccaggcct tccgatggcg gccgtgtcg cggaccgcct    420 ttcccgagag gttgcccggc gatggggagc tcccatcgat agacgtgctg gtgtgcacag   480
cggaccccga taaggagccc accgtggcag tgatgaacac agtgatatcg gcaatggcgc   540
tcgactatcc accggagaag ctccacgtgt acctctcaga cgacggcggc tcgctgctca   600
cgctgcacgg gatgagggag gcgtacgatt tcgcgagacg gtggttgccg ttttgcaaga   660
ggtttggaat aaagacgagg tgccccaagg cttacttcat cgaagacgag gatgtgagcg   720
ctagcgtggg gtacgaatcc gagaagaagg aggtcaagga gaagtatgaa ttgttcgagg   780
cgtatataaa tggatataga aacaggaact atggtgaatc acgggatggg aggctggatc   840
atccgtctac cattgaggtg atccatggaa attcctcaga cgaagttgtg caagctgacc   900
aacagcaaat gcctctgctt gtttacgtct ccagggaaaa aaggccttct taccctcata   960
acttcaaagc tggagctctc aatgttctgc ttcgcgtgtc gggggtgatg agcaactcgc  1020
cgta                                                              1024
```

<210> SEQ ID NO 10
<211> LENGTH: 1024
<212> TYPE: DNA
<213> ORGANISM: Eucalyptus grandis

<400> SEQUENCE: 10

| | | | | | |
|---|---|---|---|---|---|
| cccttccctt | cccttccctg | tcacgcctct | ccctctctc | tctctctaga | cgctcgcgaa | 60 |
| tacgcaggcg | agacccattt | cctcccttcc | tttctctctc | tgtgaatcta | cccgtctaaa | 120 |
| aaaggctgtc | cgcagcacat | tgatcgagat | cgagagcgca | gcagagcatc | ccccgctcga | 180 |
| caagcattct | ccccgccag | atcggccgct | gcattcctcg | tcgtagaggg | ggaggcagcc | 240 |
| tttcttggtg | ggtggctccg | gcggcaatg | cggagatccg | ggtctgttct | gaagagctga | 300 |
| gactgctgct | gggtttctct | tctttctttc | cttcttgtg | ccgttcgctt | ccttgcgttc | 360 |
| ttgtcggtgg | tgggtgagtc | gggtcctctc | gttctggtcc | cgccatgaac | actggaggga | 420 |
| ggctcatcgc | cgggtcgcac | aaccggaacg | agttcgtgct | catcaatgcc | gatgagagtt | 480 |
| cacggatcaa | atctgtgaaa | gaactgagcg | ggcaaatatg | tcagatatgt | ggggatgaag | 540 |
| tggagatagc | agatggcgag | ctcttcgttg | cctgtaatga | atgtgctttt | ccagtgtgtc | 600 |
| ggccttgcta | tgagtatgag | agaagagaag | gaaatcaggc | ctgcccgcaa | tgtaaaacta | 660 |
| gatacaagcg | cctcaaaggc | agtccgaggg | tcgaaggcga | tgaggaagaa | gatgacattg | 720 |
| atgatttgga | caatgagttc | gattatgacc | cttcggatcc | tcagcatgtc | gctgagaaaa | 780 |
| cgttctcttc | acggcttaat | tatggccgtg | gtgcccatcg | gaacgcatct | ggaatgccca | 840 |
| ctgacgttga | atcctctccg | cttagttcac | aaattcctct | cttgacatat | ggccaagagg | 900 |
| atgctgagat | ttctcctgat | caacacgctc | ttattgttcc | ccctgccacg | ggtcatgcat | 960 |
| atagagttca | tccgatgcca | tatccggatt | cttctaatcc | tcttcatccc | agaccaatgg | 1020 |
| cccc | | | | | | 1024 |

<210> SEQ ID NO 11
<211> LENGTH: 1024
<212> TYPE: DNA
<213> ORGANISM: Eucalyptus grandis

<400> SEQUENCE: 11

| | | | | | |
|---|---|---|---|---|---|
| tgccgcttgt | ttcttcttct | tcttcttctt | cttccacgcg | atgttgttca | gctcgagcca | 60 |
| ggggtagcgc | tcggtccggg | tcgttagccc | tccgagtttt | cagctgctgc | tgctttcact | 120 |
| tcagcgggtg | ttgctctgag | ctgagggctc | ttgtagtggg | accaagatgg | ataccggagt | 180 |
| tcacatgaga | agaatgagca | cgcccgggat | ccgacaagtg | aataactcca | gggacgatac | 240 |
| tgacagcgtg | gtcagcagcg | ccgagttcgc | tagctacacg | gtccacatac | cccccacgcc | 300 |
| ggagtaccaa | ccgatgtaca | tgtcgattga | gacttcgaat | gccgagaaag | tcgaggacct | 360 |
| gtacgcgtcg | aactcgctct | tcacaggagg | gtacaaccgc | gccacccgct | cctttctgaa | 420 |
| ggagaagatg | accgactctg | tgtcgaacca | ccctcagatg | gcgggcatga | atgggtcgat | 480 |
| gtgcgaaatt | cccgggtgtg | atgcgaagat | catgagggac | gagcgaggag | aagacatcgt | 540 |
| ccctgcgac | tgtgacttca | agatatgcag | ggactgtttc | agggacgcgg | tgagaggggg | 600 |
| agatgtgatt | tgcttggggt | gcaaggagcc | ttacaagggg | ctggacatgg | ccgagcctga | 660 |
| gatgaatgat | gggcggcggg | tatcttctgg | cgggatgtcg | aagagggagc | ggaggatgtc | 720 |
| catgatcaaa | tcgaggatgt | cactgaagag | gtcggaaatg | gacgacttcg | accataggaa | 780 |
| ctggctcttc | gaaaccaagg | ggagctacgg | atatgggaac | gcgatgtggc | ctaaagagga | 840 |

| | |
|---|---|
| cgtcgatggg gatgacgatg gattcggtaa ccctcaagtg ctccatgaca aaaagtggag | 900 |
| gcccctact cgcaaggtca atgtctcccc aaaaatcctt agtccctaca ggctcttgat | 960 |
| tttcctccga attattgctc tggcactact tttgatgtgg cggattaagc atcctaatga | 1020 |
| agat | 1024 |

<210> SEQ ID NO 12
<211> LENGTH: 1024
<212> TYPE: DNA
<213> ORGANISM: Eucalyptus grandis

<400> SEQUENCE: 12

| | |
|---|---|
| gtataaccct atgtgctaaa atcttggaga acttcctatt catatcagaa gaagaaccga | 60 |
| tcctgtcata tggagcatag ctcaggccct ctcaatctct gtcatgtcct cacaaaatca | 120 |
| atcatcatca accgcaccca catgctcgtt cacgccacag ctctatccgc tctcatatac | 180 |
| tatagagctt cgttttcctt cagtgagagt aaatcgagag acagagccac aactttggca | 240 |
| tgtctcacca tgttccttgc cgagctaggg ctatctttcc tgtggctgct cagccaagcc | 300 |
| ttccggtggc ggcccgtcag acggactgcc ttccccaagc ggctgccaga ggacaaggag | 360 |
| ctgccaccca tcgatgtgtt tgtgtgcacg gcggacccag ataaggagcc gactgttgac | 420 |
| gtgatgaaca cggtggtgtc ggcaatggcg cttgactatc ccccggagaa gctccatgtg | 480 |
| tacctctcgg acgatggcgg ctcgacactg accttgcatg ggacgaggga ggcctacgat | 540 |
| ttcgcaagat ggtggctgcc cttctgcaag aggtatggga taaagacgag gtgtccgaag | 600 |
| gcattttta aggaggaaga ggatggtgag gggattggca tgagttctga taatgagttt | 660 |
| ggctctgaga agaagatagt caaggagaaa tatgagttgt tcaaagaacg agtaaatgag | 720 |
| taccgaaaga ggcaccgagg tgactccagc cacactggcc gagaccatcc gcctaccatc | 780 |
| gaggtggtcc gagggaatgt ccctgatgaa gttatgcaag cacaccaaga ccccatgcct | 840 |
| aagcttatat acgtctcaag agaaaagaga ccttctcatc accatcactt caaagctgga | 900 |
| gctctcaacg ttcttctccg ggtatcagga gtgatgagca actcgcctta cattttagtg | 960 |
| ttggattgcg acatgtactg caacgaccct tcttcggctc ggcaggcgat gtgttttcat | 1020 |
| ttgg | 1024 |

<210> SEQ ID NO 13
<211> LENGTH: 1024
<212> TYPE: DNA
<213> ORGANISM: Eucalyptus grandis

<400> SEQUENCE: 13

| | |
|---|---|
| aaagcactga gtgagagctg gaactgaagt gactgactga tgttagagag agagagaatt | 60 |
| gagatagaga tggagtgacg aggaagcctc ccctcccttc ttcaccaaac gttcgctctc | 120 |
| tcccgctcca cacctccttc gctgctgccc cctccattgc gtagcaccgt cgccgccgct | 180 |
| cgccgccgat ctcctcttct ccgagacccg gaatcgcgaa ccgcttgtcg agcaccgcga | 240 |
| tcgcccccga gcgagcgaga gcgagagcga gaggggagga catggaagcg aatgccggga | 300 |
| tggtggccgg atcctacaag cggaacgagc tggtccggat acgccacgac tccgacagcg | 360 |
| cgcccaagcc cctgaagcac ttggatggcc acatgtgtca gatttgtggt gataccgttg | 420 |
| gactttcggc cagtggtgat gtgtttgttg cgtgtaatga gtgcgcattc ccagtgtgcc | 480 |
| gtccctgtta tgagtatgag aggaaagatg gaaaccagtg ttgtcctcag tgtaagactc | 540 |
| gctacaaaag gcaaaaaggg agtcctcgag tggaaggaga tgatgacgaa gatggtgtcg | 600 |

```
atgatttaga gaacgagttc agctacaccc gaggaaatgc caggaggcgc caatggcagg      660
gagacgatcc tgacctctcg tcttcttcta gacgtgaatc tcaacatcca gtccccttc       720 tcactaatgg actgccaata tctggtgaaa tccctgtgc tacacctgac aaccaatctg       780
ttcggacaac atctggacct tgggccctt ctgataggca ttcagttcat tctgttgatc      840
ctagacagcc agttcctgtg cgaattgtgg acccctccag ggacttgaac tcttatggcc      900
ttggaaatgt tgattggaaa gaagggttg aaagttggaa actcaagcag gaaaagaaca      960 tccccccacat gaccagtaga ttcccggaag gaaaaggaga catagaagga actggctctt     1020
atgg                                                                   1024
```

<210> SEQ ID NO 14
<211> LENGTH: 1024
<212> TYPE: DNA
<213> ORGANISM: Eucalyptus grandis

<400> SEQUENCE: 14

```
cccacaccgc cacccgctga cgtcatcgcc gtcgcctcgt tcgtcatctt cttcttcttc      60
ttcttcgtcg tcgtcgtcgt cgtcgtcgtc ggcgtcgtcc tcgccgcgtc gttctccgga      120
tccctcgcac tgacgatgcc cgcgctccat cggggcgaat ccgcgctgtg atccttctcg      180 ctcccccgc ccgcaccgcc attgatgtct cgagcgccga accgcgagtt ccaggaatgg       240
tggaacaagc agcgcgagcg cggcctcgac ctctcctccc cctcctccgc cgacggcccc      300
tccaccagcg gcggcggcgg cggcggcggc ggccgctcc tcgccgtcga gatccggacc      360
ccgcggtccg atcaggccgt cgagaagtcc cgcgcacgca gcgcccgtca gctctcctgg      420
gtctgcctcc tccggttcca gcagatcgcc tccctcctcg cctccgccgc ggggtcattc      480
ctctccgtcc tccgcaccgc caaccggagg atcgccgcct ccccgcgga ctcctcctcg       540 tcgcggctgt accggatcat caggttcttc ctgatcctcg tcctggtgct gctagggttc      600
gagctgctgg cgtattccaa ggggtggcat ttcagccccc cctccgtcgg gtccaaggag      660
gtgctgggat tcgtggagct ggtgtacgcg aattggctcg agattagggc tacgtacctg      720
gcgccgccgc tgcagagctt gaccaacgtg tgcattgtgc tgttccttat acagtccgtg      780
gatcgagtgg tgttggtgtt gggctgcatt tggatcaaga tcaaggggat aaagccggtg      840
gcgtcggcta ttatgagaa gaaggaagat ttggagagcg aaagtgggga tgaggcgtat       900
cccatggtgt tggtgcagat tccgatgtgc aacgagaggg aggtttatca acagtctatt      960
gcagcagtat gcattcaaga ctggccgagg gaaagaatgc ttgtgcaggt tcttgatgat     1020
tctg                                                                   1024
```

<210> SEQ ID NO 15
<211> LENGTH: 1024
<212> TYPE: DNA
<213> ORGANISM: Eucalyptus grandis

<400> SEQUENCE: 15

```
ggcttattac agatccagaa gccgagcgac agtgagcgtg tttcagaggc aagtaccatg      60
gcgtgccgag aaaggcgaag aagaactcgg tctctcctct ctctcctctc tcctcctcct      120
ccgccagatc ctctcgcttc cgccttcgat ctcggggaga aggaaggaag gaagaggacg      180
acgatggagg ccaatggcgg catggccgcc ggatcttaca agaggaacga gctggtccgg      240
attcgccacg actcggacgg cggacccaaa ccctgaaga atttgaatgg ccagatttgt      300
cagatatgtg gcgatactgt tggacttacg gccagcggcg atgttttgt tgcttgcaat      360
```

```
gagtgtgcat tccctgtgtg ccgtccctgt tatgagtacg agaggaaaga tggtaaccaa      420
tcatgtcctc agtgcaagtc tcgatataag aggcacaaag gtagtcctcg agttgacgga      480
gatgatgatg aggatgaggt tgatgacctg gagaatgagt tcaattatgc ccagggaacc      540
agtgctgcaa ggcaacagtg gcagggagaa gatccagatc tttcttcttc ttctagacat      600
gaatctcgac atccaatccc tcttctaacc aatgggcagc cgatgtctgg tgaaatccct      660
tgtgctagta ttgacagcca atctgtgagg actacatctg gacctctggg tccttctgat      720
aaacatgtgc actcgcttcc ctatgttgat cccagacagc cagttcctgt gcggattgtg      780
gatccatcaa aggatttgaa tacttatggc ctcggaaatg ttgactggaa ggaaagggtt      840
gaaggatgga aacttaaaca agagaaaaac atgacgcaga tgccaaacaa atatcatgaa      900
gggaagaacg acatagaggg cactggctct aatggagaag aacttcaaat ggctgatgat      960
gcacgtcaac ctatgagtcg tgtggtgcct atatcgtcgt ctcacctcac tccgtaccgt     1020
gttg                                                                 1024

<210> SEQ ID NO 16
<211> LENGTH: 1024
<212> TYPE: DNA
<213> ORGANISM: Eucalyptus grandis

<400> SEQUENCE: 16
gagagaacca gaggagcgac agctagcgtt tccccgcaca ccgctctctc tctctctctc       60
tctctctgct catcctcttc tctctctcag ctctggtcag tttcgatctg catttttca      120 tgctctccct ctgggttcgg ttcggttctg ttggattcga ttcgatggag agttgaagaa      180
agtgctcttc tttgtgcagg aactgagcgt ttcgcctccc gtcctccgtc gttctatccg      240
gtcaagatcg gattttgagg aatttactca cggatctgtg tttttactgg aaaacaagtt      300
gcttctgaat gcaacactag agatctctac agcttctgct aatgccacat caagttcgga      360
atcagtgaag tcatcctctc ttagcatccg agccaggagg agctattgcg atggagtcgg      420
aaggagaaac tggggggaaag tcaatgaaaa ttctgggtgg tcaagtctac cagatttgtg      480
gtgataacgt tggcaaaagt gttgatggcg agccgtttgt tgcttgcaat gtctgtgcat      540
ttcctgtctg taggccatgc tatgagtatg agaggaaaga cgggaatcag tcatgtcctc      600
aatgcaaaac cagatacaag aggcacagag gaagtccggc tattcttggt gaccaagaag      660
aagatgctga tgctgatgat agtgtgagtg atttcaatta ctcagaaaat caaaatctaa      720
accggaagac tgaagagcgc atcttgagtt ggcacatgca gtatgacag aatgaggatg      780 tgagtgcacc aaactacgat aaggaggttt ctcacaacca tattcctcga cttacaagtg      840
gccaagaggt ttctggggag ttatctgctg cttcgcctga acgcctctct gtggcatctc      900
ctgatgttgg tgctgggaag cgcatccatt ctctacctta tgtagccgat gctaatcaat      960
cacctaacat cagggtggtg gacccagtgc gggaatttgg ttcatcagga ctgaacaacg     1020
ttgc                                                                 1024

<210> SEQ ID NO 17
<211> LENGTH: 1024
<212> TYPE: DNA
<213> ORGANISM: Eucalyptus grandis

<400> SEQUENCE: 17
agagagagag agagagagag agagagagct ttcgtcttcg ttctcatttc ctctctcctc       60
cccccttgtt cattcgtttc tcgtttctgc ttccgtcttc gtttgagggc agcggcagag      120
```

| | |
|---|---|
| aaaaagcttc catttttctt cgatagagtt cgtccgtccg tcttcatcga taagtaattg | 180 |
| tcttattttg ctcagctgtt ggattcgtga tcaggccctt cttttccatg tcgttttttt | 240 |
| cagtgggtct ctctgcaatg catcaagagg agtgaccttt gagcgagcga ttcactgaca | 300 |
| tttccagctc tgccttcctt ttttttccac ttctgctttg cttgacccag aagcaatatt | 360 |
| gcaaagcaaa tattctctct ccaactctct gcttttttca gataattcaa ttgccagatc | 420 |
| acagagatct acttgctctc atcagctctg gtccctagca tcacattctc cctctctcgc | 480 |
| attgctctgt ttcgcgatcg aaaaacagag caaacgagtc tctgccgaaa tggaccggct | 540 |
| ctctgcaact ggtctccttc ccgacacgtt cggaggagca agagacgaca tctccatgca | 600 |
| actttcgctg atttgggctc agatcaaggc gccgttgctc gtcccgttgc tccggctcgc | 660 |
| ggtgttcctt tgcctggcca tgtcgctgat gctgttcctc gagagggtgt acatggccgt | 720 |
| cgtgatcctc ttggtgaagc tcttcggccg gaagccggag aagcggtaca ggtgggagcc | 780 |
| catgaaggac gacgtcgagc tgggcaactc ggcctacccc atggtcctgg ttcaaatccc | 840 |
| aatgtacaac gagcgagagg tttatcagct ctcgatcgga gccgcatgcg gtctctcgtg | 900 |
| gccgtccgac cgcatcatca ttcaagtcct gacgattcc accgacccga cgatcaagga | 960 |
| cctggtggag ctggagtgcc agaggtgggc gagcaaaggg atcaacatca ggtacgagat | 1020 |
| ccgg | 1024 |

<210> SEQ ID NO 18
<211> LENGTH: 1024
<212> TYPE: DNA
<213> ORGANISM: Eucalyptus grandis

<400> SEQUENCE: 18

| | |
|---|---|
| gctctccaga acgctctctg ttccttcttc ttcttcttct tctcattagc ccccgtatca | 60 |
| ctcatctccc aatgtcgcca tgatctagag acgccttgct ccggtgctcc ttccacgcgt | 120 |
| ccctctccct ctgcctgtcc ctctctctct ctctctcttc ctctgaagca gttggtttat | 180 |
| ctgaatccac acaagcgctc tctttctctc tctctccctt tcgccgcggc tggtgtgtct | 240 |
| ctcccatact aggacaagaa tgaggctaaa ttcctagctc cttttggctt ttcctctttct | 300 |
| gggactcggc taaatcttgc gaaaattgga aaagctccaa tctttatccc gtggaaccaa | 360 |
| attgtacgaa gtgggtgttt tttctagatc aaggttgacg aagaccaaga ccaagaatgg | 420 |
| cgccctcgtt tgattggtgg gcgaaaggag gccacaaggg caccccggtc gtcgtcaaga | 480 |
| tggagaaccc caactggtcc atggtcgagc tcgagtcgcc gtccgaggag gacttcctca | 540 |
| tcggcggcga ctccgcgccg tcggggcggg tccgcgacaa gggccggaac aagaacgcca | 600 |
| agcagctcac ttgggtcctc ctcctcaagg cccacaaagc cgccggctgc ctcacctcca | 660 |
| ttgccggcgc ggcgttcact ctcgcctccg cggtgcggcg ccgcgtcgcc tccggaagga | 720 |
| ctgacgctga tgccgacgaa gccgagaccg gcgaatctcg cagcggcaga gagaaggaga | 780 |
| accccactgt gaagtccagg atctatgcgt gtataaaagc gtttctttgg ttgtcgattt | 840 |
| tgttgctagg atttgaggtt gctgcatact ttaaggttg gcatttcgga gctctcgaat | 900 |
| tgcaatactt gttagctgca cctttagggg ttaagggtgc cttcaattcc ttgtattcga | 960 |
| ggtgggtttt gattcgggtg gagtatctcg ctccgccgtt gcagttcttg gccaatgtgt | 1020 |
| gcat | 1024 |

<210> SEQ ID NO 19
<211> LENGTH: 1024
<212> TYPE: DNA

<213> ORGANISM: Eucalyptus grandis

<400> SEQUENCE: 19

| | | | | | |
|---|---|---|---|---|---|
| gtcatatcca | gctatccagt | ggctttggca | tgggaggctg | acgcatcgac | atcgaccccg | 60 |
| cgctttgatg | atcccccatcg | tcgctgtcct | tcgttctcca | tttcccctc | ttcgattcga | 120 |
| tcacccccc | gaccttccgc | tcgatttcag | atcagtttcg | gatttcgagg | cttttgcaga | 180 |
| agtatagaag | ctgccttgga | agtggaagga | ctccgataaa | gcagattccg | attgcctctt | 240 |
| tagcacgtgc | gaaggtgcat | gtgagcctct | acatatgcac | cgatcttgtt | gacgccgagt | 300 |
| cagttttgcg | ttcttctctt | gacgtctcgg | caaagaggtg | ctccagcgat | ggaatccgat | 360 |
| gctgaaaatg | ggggaaagcc | cttgaaaagt | ctgggggggcc | aagtctgcca | gatatgtggt | 420 |
| gaaaatgtcg | gcaaaactct | tgatgggggaa | cccttcattg | cttgcgatgt | ctgtgcattt | 480 |
| cctgtctgtc | ggccctgcta | cgaatacgag | aggaaggatg | gaaatcagtc | gtgcccacaa | 540 |
| tgcaagacca | gatacaagag | gcacaaagga | agtcctgcca | ttcttggtga | ccatgaagag | 600 |
| gatggagatg | ctggcgatga | ctaccattac | tcttctgaag | atcaaactca | aaggagaaa | 660 |
| attgcagaac | gcatgttgag | ctggcatatg | acatatggac | gaggggaaaa | tgttgctccg | 720 |
| gccaactatg | atggagaggt | ttctcgtaac | catattcctc | tgcttactag | tagacaagag | 780 |
| gtttctggag | agttatctgc | tgcttcacct | gagcgacttt | ctatggcatc | tcctggagtt | 840 |
| ggtagagtgc | atcgcgttcg | tccacttct | tatgcatctg | atgttactca | atcacctaac | 900 |
| ataagggttg | tggatccagc | gagggaattt | ggttcacctg | gaattggcaa | tgttgcttgg | 960 |
| aaggagagag | tagatggctg | gaagatgaaa | caagagaaaa | atgttggacc | aatgagcact | 1020 |
| ggcc | | | | | 1024 |

<210> SEQ ID NO 20
<211> LENGTH: 1024
<212> TYPE: DNA
<213> ORGANISM: Pinus radiata

<400> SEQUENCE: 20

| | | | | | |
|---|---|---|---|---|---|
| gatggctcgc | accttgagcg | tcatggatga | atttctgtat | atggatctga | tctgatagaa | 60 |
| attcagtgtc | tgaatcttgt | ctttttttat | cacaggggcg | aagctttcat | gcaggacttt | 120 |
| ttagcttaaa | ttttttgaat | ttggcagaga | attgaactta | acaatggaag | ccagcgccgg | 180 |
| cttggttgcc | ggttctcata | acagaaacga | gttcgtggtc | atccatggac | atgaggagcc | 240 |
| gaagcctttg | aacacgttga | gtggccacgt | ctgccagatt | tgtggcgagg | acgtcgggct | 300 |
| taacacagac | ggcgagctgt | tcgttgcctg | taatgagtgc | gggtttcctg | tctgtcggcc | 360 |
| gtgctatgag | tacgagagac | gagaaggaaa | tcagtcgtgc | ccgcagtgca | atactcgtta | 420 |
| caagcgtcaa | aagggagtc | cacgggtgga | aggtgacgat | gatgaagaag | acgttgatga | 480 |
| catagaacat | gaatttaatg | tggagactca | gcaaagaaac | aggcagcaga | tcaccgaggc | 540 |
| gatgctccac | ggacgcatga | gctatggccg | aggtcccgac | gacgaaaatt | cgcagattgc | 600 |
| tcataatcca | gagcttcctc | cgcagattcc | tgtacttgca | acggccact | cggttgtgag | 660 |
| tggggagatt | ccaacgtcat | actacgcaga | caaccaattg | cttgccaacc | ctgcaatgct | 720 |
| gaagcgtgtg | catccaagct | ccgagccggg | gagtggaagg | atcatcatgg | atccaaacag | 780 |
| ggatattggt | tcttatggct | ttgggaacgt | gtcttggaag | gagcgaggcg | atggttataa | 840 |
| atcgaaggaa | aacaaatcag | gccagttgga | tatgacggaa | gggagatatc | aatataatgg | 900 |
| ggggtttgca | ccaaatgagc | ctgaagatta | tattgatccc | gatatgccaa | tgaccgatga | 960 |

| | |
|---|---|
| agcaaggcag ccactgtccc gaaaagtgcc aattccttca agcaaaataa atccataccg | 1020 |
| aatg | 1024 |

<210> SEQ ID NO 21
<211> LENGTH: 1024
<212> TYPE: DNA
<213> ORGANISM: Pinus radiata

<400> SEQUENCE: 21

| | |
|---|---|
| cgatacacta agaaaagtag tcgtgcaagt attagatggc tggctgggat agttggaaaa | 60 |
| ggaatagtag aaatgggaca gaagtttcat tctgtaagct ttttcatgga ctgttagtct | 120 |
| tctctttgct ttcagcttaa gcagctttag tgctggcatt ttgatgctca gtaatcacaa | 180 |
| gttggagctt tggtctggat tagaaggatt tgagcctgtt ttagtgcatt acagaccgtt | 240 |
| ttaaggttgc tttttgcagt tttgataagg ctgggattga agtggggagt ttaatgatgg | 300 |
| ctaggatgaa ggagaggctg agatactggg cattttgatg tgggttaagc tggatttcag | 360 |
| ctgatttcaa tacctttttg ttctggggag cagaaatcag tgaacgggac tttagcagga | 420 |
| agaacccatt ttgacgtgga gctaagtgtt gttaggattc aaaggtgatc aattagtgcg | 480 |
| cgggaggttc agtggcaatg gaggctagaa caaacacagc agcaggttct aacaaaagga | 540 |
| atgtgcgtgt ttcggttcga gatgatggag aacttgggcc taagcctcca caacacataa | 600 |
| atagccacat ttgccagata tgtggagaag atgttggctt agcagcagat ggggagttct | 660 |
| ttgtagcttg caatgagtgt gcatttccag tatgcaggcc ttgctatgaa atgagtgga | 720 |
| aggatggaaa tcaatcttgt ccacaatgca agactagata caagtggcat aaaggtagcc | 780 |
| ctcaagtgga tggtgacaag gaagatgaat gtgcagatga tttggatcat gacttcaact | 840 |
| ccactcaggg taacaggaat gaaaaacagc agattgcaga ggccatgttg cattggcaaa | 900 |
| tggcctatgg acgaggggag gatgttggtc catcacgctc agaaagtcag gagcttcctc | 960 |
| agcttcaagt tcccttatt accaatggac aagcgatttc tggtgagttg ccagcaggat | 1020 |
| cctc | 1024 |

<210> SEQ ID NO 22
<211> LENGTH: 1024
<212> TYPE: DNA
<213> ORGANISM: Pinus radiata

<400> SEQUENCE: 22

| | |
|---|---|
| gtcatggctt ccaacgggac tatgaactct caagtttgtc aagtttgcgg ggacaacgtt | 60 |
| ggggttgatg caaacagtga gcccttcgtt gcctgccatg actgtggctt tcctgtttgt | 120 |
| cgtccctgcc agcagtacga gagagacgaa gcaagtcagt gctgcctgca ttgcaaagct | 180 |
| ccgtatcggc gctacgaagg cggcccagct gatgaggttg aagagaacgg agatcccaac | 240 |
| tttgaaaaag tagaagcaac tgactatgaa ggggaaggct atcgtgttga ttcatttaat | 300 |
| gatagtgaga ttaataatgc tgaaacaaag gatggcaaca gcaagggcgt ggcgtggaag | 360 |
| gaaagagttg agagctggaa gtccaaaaaa aataagaaaa aaactgccgc cagcaaaaca | 420 |
| gttaatcccg gcgtggaagg aatcccagag cagacaaggg atccagaggc ggaggaagca | 480 |
| atgatggctc aggccgggca gccgctatcg tgtataatac ccattccacg caccaaactc | 540 |
| caaccgtata ggatggttgt tattatgcgg ctgatcgttc tagggttatt cttcagctac | 600 |
| cgagtacaga atcctgtgga gagcgcattt ggcctgtgga tgacctcagt tatttgtgag | 660 |
| atctggttcg ctttatcctg gattcttgat cagtttccca gtggaatcc gatcaatcgc | 720 |

```
gaaacattca cagacagatt gtctttaagg tacgagagac cgggcgagcc ctgtgagctt      780
gcggccgtgg acttcttcgt gagtaccgtg gacccactga aagagcctcc tttagttacg      840
gccaacaccg ttctgtccat tctggctgtg gattaccctg tggagaaagt tcttgctat       900 gtctctgacg atggtgcggc catgctcacg ttcgagacca tgtcggagac agctgagttc      960
gctaggaagt gggttccttt ctgcaagaac tttaacatcg agcctcgagc tcctgaattc     1020
tact                                                                  1024

<210> SEQ ID NO 23
<211> LENGTH: 1024
<212> TYPE: DNA
<213> ORGANISM: Pinus radiata

<400> SEQUENCE: 23
gagatggtgg ctatctttaa ctgaagaaaa gagggcctta ggtatacaag aagctggaga       60
gaggagaagc caaggtgcca gccagtcctt cagcttttgg gactctgcct gcccatagcc      120
ggaggcctga acatatgatt ctaggttcat ttttggcgta tgctcacaag tttcctcgtg      180
gagaaaacac cagggaactt gataaaattc atgttttttc tattgcagaa gtaccccaaa      240
atggattttg agctgataat ggtatgagga ttcgacaagg acgagtttgt tgggttgtgc      300
tgaaaagcaa agcagatctg ctgcgcaatc tggaattcag cttatatcca ctctgcgatc      360
aggaatccac ttttctctaa agactgatag caatggaggc caatgctgga ctggttgctg      420
gttctcacaa caggaatgaa tttgtagtca tcaggcctga aggcgaagtg ggtcctaagc      480
ctctacatca tttaagtgta caaatttgcc atatctgtaa tgaagacgtt ggtctcacag      540
tggatgggga actgtttgtt gcctgcaacg aatgtgcatt cccaatctgc aggacttgct      600
acgagtacga gcggagtgag ggtaaccagg tctgccctca tgcaaaacg agattcaaac       660 gacataaggg aagtgccaga gttgaaggag atgaagatga agatgatgtt gatgaccttg      720
aaaatgagtt caattttggg gaccgagaca aacaagatat gcagtacatt gcagaagcga      780
tgcttcatgg gcatatgagc tatggccgag gtggtgatac agatatgcct catgtagttc      840
agacaactct tccacaagtg ccactactta ccaatggcca catggatccc gggatccctc      900
cagaacacca tgctctagtc ccttcatata tgggtggggg aaaaagaatt catccattcc      960
cttatgccga ttctaatctt ccagtccaag ccaggtcaat ggatccaacc aaggacttgg     1020
cagc                                                                  1024

<210> SEQ ID NO 24
<211> LENGTH: 1024
<212> TYPE: DNA
<213> ORGANISM: Pinus radiata

<400> SEQUENCE: 24
agatgtgaga tggtggctat ctttaactga agaaagagg gccttaggta tacaagaagc        60
tggagagagg agaagccaag gtgccagcca gtccttcagc ttttgggact ctgcctgccc      120
atagccggag gcctgaacat atgattctag gttcattttt ggcgtatgct cacaagtttc      180
ctcgtggaga aaacaccagg gaacttgata aaattcatgt tttttctatt gcagaagtac      240
cccaaaatgg attttgagct gataatggta tgaggattcg acaaggacga gtttgttggg      300
ttgtgctgaa aagcaaagca gatctgctgc gcaatctgga attcagctta tatccactct      360
gcgatcagga tccacttttt ctctaaagac tgatagcaat ggaggccaat gctggactgg      420
ttgctggttc tcacaacagg aatgaatttg tagtcatcag gcctgaaggc gaagtgggtc      480
```

```
ctaagcctct acatcattta agtgtacaaa tttgccatat ctgtaatgaa gacgttggtc      540
tcacagtgga tggggaactg tttgttgcct gcaacgaatg tgcattccca atctgcagga      600
cttgctacga gtacgagcgg agtgagggta accaggtctg ccctcaatgc aaaacgagat      660
tcaaacgaca taagggaagt gccagagttg aaggagatga agatgaagat gatgttgatg      720
accttgaaaa tgagttcaat tttggggacc gagacaaaca agatatgcag tacattgcag      780
aagcgatgct tcatgggcat atgagctatg gccgaggtgg tgatacagat atgcctcatg      840
tagttcagac aactcttcca caagtgccac tacttaccaa tggccacatg gatcccggga      900
tccctccaga acaccatgct ctagtccctt catatatggg tgggggaaaa agaattcatc      960 cattcccttta tgccgattct aatcttccag tccaagccag gtcaatggat ccaaccaagg     1020
actt                                                                  1024

<210> SEQ ID NO 25
<211> LENGTH: 1024
<212> TYPE: DNA
<213> ORGANISM: Pinus radiata

<400> SEQUENCE: 25
ggttcacgtt cattcattca ctcatcgtga gcagcagtac atcaacagtt cttgaagaac       60
attgataggt tggctatttc aatcctttca tggggaatat ttaagtctgg atccgagcct      120
gaactcaatg gattttcagc gatccttgtg cttgggaagc ctggatctcc ttaatcatag      180
gatctgctag ttctgtatca aatgcatttt gagttcacgg agctgtattt acaacatttt      240
aggttgctgt tttgctatct taaaagtcat taggagtagt gacataaact gtagttttta      300
ggccataggt tgcaattcag agtaactaga acgttgatt ttcattgtac tgatttttt       360 gatggcaccc aatttcggtg ttgggcaatg gtggagtaag cagagccaca agggaacctc      420
tgttgttgtg aaaatggaga acccaaatta ctcaatgcta gaattagaga gccctgcaaa      480
tggttttcag gtcgataagg ggggtcgagg caagaatgct aagcagctca catgggttct      540
tctgctgaag gctcataagg cagcaggatg cctggcttgg cttgccaatg gagtttgggc      600
actttttgct tcagtcagaa gacgtttcac tgcgccttct gatgaatcag ggaagtcttc      660
tgagaaaagc aagctttaca gagttatcag gtgtttcctt atagcttcca ttttcttgtt      720
agggtttgag ctattggctt attggaaggg gtggcatttc agccggccaa atctgcatat      780 tccccccatct ctaagcataa atggccttct gcaatctata tattcaggat ggctttatac      840
cagagcgaat tacctagctc ctcctcttca gtatttggcc aatgtgtgca tcatattgtt      900
ccttatccag tcggcggatc gagccctgtt atgcgttggt tgtttttgga ttaaactgaa      960
gaagatcaag ccagttccca aatgtgagtt gggagatgca gctgatttgg agcagggaga     1020
caat                                                                  1024

<210> SEQ ID NO 26
<211> LENGTH: 1024
<212> TYPE: DNA
<213> ORGANISM: Pinus radiata

<400> SEQUENCE: 26
gacaacatac gtgtgcttgc ttcgccttg gtgattgaag caagctgctg atggagccta       60
acgactttcc tttgtatact acactggaaa agaaatcact cttatacaga gcttattcgt      120
gcacccactt ttctgcaata atcggtctca tatgttatcg cttgttgtat atcccaagtg      180
aggattcttg gccatggatt ctgatatttg tcgcagaact aggcttctcg tacagctgga      240
```

| | | | | | |
|---|---|---|---|---|---|
| ttctggatca | ggccctaaga | tggtggccag | ttgaacgaac | agtcttccca | aacagacttt | 300 |
| ctaagaggtt | tcagagcaag | ttaccgcctg | tggatatctt | tatttgcact | gctgatcctt | 360 |
| tcaaagaacc | tccactgact | gttataaaca | cagtattgtc | cgctctcgcc | gtagattatc | 420 |
| ccatgggaaa | attgtcatgt | tatgtttctg | acgacggagg | atcacctctg | acattttatg | 480 |
| ctctcttgga | agcttcacgt | tttgcaaaga | tctggattcc | attttgtgat | aaatactcca | 540 |
| ttcaagacag | atgtccggag | gtttacttct | caaatcccag | tgctctggaa | aacgtaaatc | 600 |
| tgcccttcat | gaaagactgg | aagcatgtaa | ataaaatgta | ttctgaattg | aaggatcgaa | 660 |
| tcaacaacgt | catggagatg | ggcagtgttc | caccagataa | acagaatgaa | caccaaggat | 720 |
| tcaaggactg | ggcttctgga | agcagtaggc | gagatcatcc | aagtatagtt | cagattttac | 780 |
| tggagaaggg | agaggacagg | gacattgacg | gaaatgatct | gcccgatctt | atatatgtct | 840 |
| cccgtgagaa | gcgacctgga | attccccacc | attataaggc | tggtgctctt | aatgttctgc | 900 |
| taagagtctc | tggcgtaatg | agcaatgctc | ccttcattct | cactcttgat | tgcgacatgt | 960 |
| acaccaacaa | tcctgaggcc | cttcggcaag | ccatgtgctt | tttcttggac | cctaaaacag | 1020 |
| gtga | | | | | | 1024 |

<210> SEQ ID NO 27
<211> LENGTH: 1024
<212> TYPE: DNA
<213> ORGANISM: Pinus radiata

<400> SEQUENCE: 27

| | | | | | |
|---|---|---|---|---|---|
| ctggtgtgct | gttgcaggag | aatgtgggat | cgcgggttcg | aacttcgtgg | agtgtagggt | 60 |
| tttggcttgg | aatgaggata | gaagggcgaa | cgagaagagt | agggaagggc | agttattgat | 120 |
| tgcgtgcgcg | cctggcttat | cgcatctcga | cattcgcgga | tcgaatctca | caaactccag | 180 |
| gcggcctccg | cattgtgaga | tcggcgcagc | ttctatgtag | gcggggctgc | cgatgggttc | 240 |
| gttttctatc | agttagaaga | cggaggaagc | ggaggaggac | aacgtactta | ctattattgt | 300 |
| tatcgttgtc | aaaagtcttt | ccaacttatg | ccaaagatcc | attcttgcat | tcactgaagt | 360 |
| gaaaagatcc | aggtttgggc | agagtgcttt | ttccattttt | tgttcatgtg | actccccggg | 420 |
| gggtggggcg | tcgtttggtt | cttatgtatg | gcaaccaatt | ttgagtttca | agaatggtgg | 480 |
| aacaaggaga | agaaacccca | caggggcact | tccgtggtag | tgaaaatgga | gaatccaaat | 540 |
| tggtccatgg | tggaattgca | aagccccgac | gacgatttcc | agcattcaga | taagcagggc | 600 |
| cgaggcaaaa | atgccaggca | acttacctgg | gtttggctgc | tgaaagccca | tcgcgccgcg | 660 |
| ggctgtgtcg | cctggctcgc | gcaggggcta | tggagccttc | tctccgccgt | aaaaagaagg | 720 |
| gtcactttga | acaagaatca | aaatcgtgtg | acagaggagg | acaaaccagg | aaaagtaaa | 780 |
| ctgtatagag | tcattagagg | gtttctgtta | tttgccattt | tgatgctagg | gtttgagatt | 840 |
| gcggcttata | tgaaaggctg | gcactttagc | cgccctcctt | tcgactttc | tccgtcgctg | 900 |
| gacttgcagg | gcgttttgca | ttccatttat | tctgaatggg | tatttgttag | ggccactat | 960 |
| cttgcccctc | ctcttcagac | attggccaac | atctgtattg | tgctgttct | tatccagtcg | 1020 |
| gcag | | | | | | 1024 |

<210> SEQ ID NO 28
<211> LENGTH: 1024
<212> TYPE: DNA
<213> ORGANISM: Pinus radiata

<400> SEQUENCE: 28

```
aagtagagaa gccaaaaaga tatgaggtct ttgtgtgcct ttgatcattg gtaactgaag      60
caagttgcca atggagccta atggctttcc tctgtatacg acactggaaa agaaatcctt     120
cgtatacaga gcttatgcct gtgcccactt ttctgcaata attggtctcc tatattatcg     180
cattgtgtat atcccaagtg aagattattg gccatggatt atgatatttg tggcagaact     240
aggcttcgcc tacggttgga ttttggagca ggccttcagg tggcggcctg ttgagcgaaa     300
agtcttccca gaaagacttt ctaagaggtt aagagcgat  ctaccgcctg ttgatatatt     360
tatatgcact gctgatccta tcaaagaacc tccactcgct gtcataaaca cagtactgtc     420
ggctttggct gtagactatc ccgtagaaaa actgtcatgt tatgtttctg atgatggagt     480
atcctcgctt acattttatg ctctcttcga agcttcacgt tttgcaaaga tttggcttcc     540
attttgttat aactactcga ttcaagacag atcaccagag gcatatttct cggcaagatc     600
tggtcaggaa aaggaaaata tgtcctttac tagagaatgt aagagtgtaa agaaagcgta     660
tttggaaatg aaggatcgta tcaataacgc gtgtggagatg ggaagtgttc cggatgacaa     720
acagaaagaa cacacgggct tcaaagactg gattttggga agcactaggc gagatcatcc     780
gagtattgtt cagattctac tggagaacgg agaggacaag gacattcagg gtaatgatct     840
gcccagtctt atttatgtct cccgtgaaaa gcgaccggga attcctcacc attacaaggc     900
cggcgctctt aatgctctga ttagaatctc cggcttaatg agcaatgctc ccttcattat     960
cactcttgat tgcgacatgt gcaccaacaa ttgtgaagca cttcgtcaag ccatgtgctt    1020
tttc                                                                1024

<210> SEQ ID NO 29
<211> LENGTH: 1024
<212> TYPE: DNA
<213> ORGANISM: Pinus radiata

<400> SEQUENCE: 29
gctgctgcca attgcataga tctgctcaag gcaccaccat ggatcggttg tcttattcca      60
gtgccaacat attgccacag acatttcaag gcacaaggga tgacatagtt gagcagattg     120
cgttgctttg gcagcagatt cgggctcctc tggttgcccc attgctgaat atctgtattt     180
acttctgcct gctcatgtct gtcatgctct tcattgaaag agtttatatg gcagtagtca     240
ttgtgttgat taaggtgttt ggaaagaagc cagagaagga atacaagtgg ggggccatta     300
aggaggacgt ggagcttggc aacagtgttt atcccatggt cttagtgcag ataccaatgt     360
acaatgagag ggaggtttat cagctctcaa ttggagcagc atgtgcattg tcatggcctt     420
caaatcgggt tatcattcaa gtgctcgatg attccactga ccttacaatc aaggatttgg     480
tggagatgga atgtcagaaa tgggcgagta aaggcataaa tatcaagtac gaaatcagag     540
gcaacagaaa tgggtacaaa gctggtgccc tgaaagaggg aatgaagcat agctacgtaa     600
gggaatgcga ttacgttgta atatttgatg cagattttca gcccgatcga gactttctga     660
gcagaacgat tccattctta gtgcacaatc cagaattggc cttagttcaa gctcgttgga     720
agtttgcatg aatgaatggt ggattgattg attgattagc ctatcaacca caacacacac     780
agaaaaggct gaaggccgtc aggactcagg ggggcctccc tccggtctcc gttggtcctg     840 ttttttccact ccccccaccca tctcattcca agtgtttggc ctgcagcagg ctggccaacc     900
tggcagccgc gccagtggta acagcgatgt gtacttttca ccttcagtct attcgtccag     960
gactgtaaca cgtaaagttt tacgaagttc attatcagct ctgttgtatc aatcaatgaa    1020
caaa                                                                1024
```

```
<210> SEQ ID NO 30
<211> LENGTH: 1024
<212> TYPE: PRT
<213> ORGANISM: Eucalyptus grandis

<400> SEQUENCE: 30
```

| | | | | | | | | | | | | | | |
|---|---|---|---|---|---|---|---|---|---|---|---|---|---|---|
| Met | Glu | Ala | Arg | Ala | Gly | Leu | Val | Ala | Gly | Ser | Tyr | Lys | Arg | Asn | Glu |
| 1 | | | | 5 | | | | | 10 | | | | | 15 | |
| Leu | Met | Val | Val | Pro | Gly | His | Asp | Gly | Pro | Lys | Pro | Ile | Arg | Leu | Ser |
| | | | 20 | | | | | 25 | | | | | 30 | | |
| Thr | Leu | Gln | Asp | Cys | Gln | Val | Cys | Gly | Asp | Lys | Ile | Gly | Cys | Asn | Pro |
| | | | 35 | | | | 40 | | | | | 45 | | | |
| Asn | Gly | Glu | Leu | Phe | Val | Ala | Cys | Asn | Glu | Cys | Gly | Phe | Pro | Val | Cys |
| | 50 | | | | | 55 | | | | | 60 | | | | |
| Arg | Pro | Cys | Tyr | Glu | Tyr | Glu | Arg | Lys | Asp | Gly | Asn | Arg | Cys | Cys | Pro |
| 65 | | | | | 70 | | | | | 75 | | | | | 80 |
| Gln | Cys | Lys | Thr | Arg | Tyr | Arg | Arg | His | Lys | Gly | Ser | Pro | Arg | Val | Glu |
| | | | | 85 | | | | | 90 | | | | | 95 | |
| Gly | Asp | Asp | Glu | Glu | Asp | Gly | Met | Asp | Asp | Leu | Glu | Gln | Glu | Phe | Asn |
| | | | 100 | | | | | 105 | | | | | 110 | | |
| Met | Glu | Arg | Asp | Arg | Gln | Ser | Val | Val | Ser | His | Arg | Gly | Asn | Ala | Phe |
| | | 115 | | | | | 120 | | | | | 125 | | | |
| Asp | Ala | Thr | Pro | Arg | Ala | Ala | His | Ser | Ile | Ala | Asn | Arg | Ser | Ile | Asn |
| | 130 | | | | | 135 | | | | | 140 | | | | |
| Gly | Asp | Asn | Tyr | Ala | Leu | Ser | Leu | Pro | Pro | Ile | Met | Asp | Gly | Asp | Ser |
| 145 | | | | | 150 | | | | | 155 | | | | | 160 |
| Leu | Ser | Val | Gln | Arg | Phe | Pro | His | Ala | Ala | Thr | Val | Ile | Gly | Asn | Gly |
| | | | | 165 | | | | | 170 | | | | | 175 | |
| Leu | Asp | Pro | Val | Lys | Glu | Asn | Tyr | Gly | Ser | Ala | Ala | Trp | Lys | Glu | Arg |
| | | | 180 | | | | | 185 | | | | | 190 | | |
| Val | Glu | Asn | Trp | Lys | Ala | Lys | His | Asp | Lys | Ser | Gly | Ser | Ile | Lys |
| | | 195 | | | | | 200 | | | | | 205 | | | |
| Asp | Gly | Ile | Tyr | Asp | Pro | Asp | Glu | Ala | Asp | Asp | Ile | Met | Met | Thr | Glu |
| | 210 | | | | | 215 | | | | | 220 | | | | |
| Ala | Glu | Ala | Arg | Gln | Pro | Phe | Ser | Arg | Lys | Val | Pro | Ile | Pro | Ser | Ser |
| 225 | | | | | 230 | | | | | 235 | | | | | 240 |
| Leu | Ile | Asn | Pro | Tyr | Arg | Ile | Val | Ile | Leu | Arg | Leu | Ile | Ile | Leu |
| | | | | 245 | | | | | 250 | | | | | 255 | |
| Gly | Phe | Phe | Arg | Tyr | Arg | Leu | Met | Asn | Pro | Ala | Lys | Asp | Ala | Leu |
| | | | 260 | | | | | 265 | | | | | 270 | | |
| Gly | Leu | Trp | Leu | Thr | Ser | Ile | Ile | Cys | Glu | Ile | Trp | Phe | Ala | Phe | Ser |
| | | 275 | | | | | 280 | | | | | 285 | | | |
| Trp | Ile | Leu | Asp | Gln | Phe | Pro | Lys | Trp | Phe | Pro | Ile | Thr | Arg | Glu | Thr |
| | 290 | | | | | 295 | | | | | 300 | | | | |
| Tyr | Leu | Asp | Arg | Leu | Ser | Met | Arg | Tyr | Glu | Arg | Glu | Gly | Glu | Pro | Cys |
| 305 | | | | | 310 | | | | | 315 | | | | | 320 |
| Lys | Leu | Ala | Pro | Val | Asp | Phe | Phe | Val | Ser | Thr | Val | Asp | Pro | Leu | Lys |
| | | | | 325 | | | | | 330 | | | | | 335 | |
| Glu | Pro | Pro | Leu | Ile | Thr | Ala | Asn | Thr | Val | Leu | Ser | Ile | Leu | Ala | Ala |
| | | | 340 | | | | | 345 | | | | | 350 | | |
| Asp | Tyr | Pro | Val | Asp | Arg | Val | Ser | Cys | Tyr | Val | Ser | Asp | Asp | Gly | Ala |
| | | 355 | | | | | 360 | | | | | 365 | | | |
| Ser | Met | Leu | Thr | Phe | Asp | Ser | Met | Thr | Glu | Thr | Ser | Glu | Phe | Ala | Arg |
| | 370 | | | | | 375 | | | | | 380 | | | | |

-continued

```
Lys Trp Val Pro Phe Cys Lys Lys Tyr Ser Ile Glu Pro Arg Ala Pro
385                 390                 395                 400

Asp Phe Tyr Phe Ser Gln Lys Ile Asp Tyr Leu Lys Asp Lys Val Gln
                405                 410                 415

Pro Thr Phe Val Lys Glu Arg Arg Ala Met Lys Arg Glu Tyr Glu Glu
            420                 425                 430

Phe Lys Val Arg Ile Asn Ala Leu Val Ser Thr Ala Gln Asn Thr Phe
        435                 440                 445

Asp Glu Gly Trp Val Met Gln Asp Gly Thr Pro Trp Pro Gly Asn Asn
    450                 455                 460

Thr Arg Asp His Pro Gly Met Ile Gln Val Phe Leu Gly Ser Ser Gly
465                 470                 475                 480

Ala His Asp Ile Glu Gly Asn Glu Leu Pro Arg Leu Val Tyr Val Ser
                485                 490                 495

Arg Glu Lys Arg Pro Gly Tyr Gln His His Lys Lys Ala Gly Ala Met
            500                 505                 510

Asn Ala Leu Val Arg Val Ser Ala Val Leu Thr Asn Ala Pro Phe Ile
        515                 520                 525

Leu Asn Leu Asp Cys Asp His Tyr Leu Asn Asn Ser Lys Ala Val Arg
    530                 535                 540

Glu Ala Met Cys Phe Leu Met Asp Pro Gln Leu Gly Lys Lys Leu Cys
545                 550                 555                 560

Tyr Val Gln Phe Pro Gln Arg Phe Asp Gly Ile Asp Arg His Asp Arg
                565                 570                 575

Tyr Ala Asn Arg Asn Thr Val Phe Phe Asp Ile Asn Met Lys Gly Leu
            580                 585                 590

Asp Gly Ile Gln Gly Pro Val Tyr Val Gly Thr Gly Cys Val Phe Asn
        595                 600                 605

Arg Gln Ala Leu Tyr Gly Tyr Asp Pro Pro Val Ser Gln Lys Lys Pro
    610                 615                 620

Lys Met Thr Cys Asp Cys Trp Pro Ser Trp Cys Cys Cys Cys Phe Gly
625                 630                 635                 640

Ser Arg Lys Lys Thr Lys Lys Ser Ser Lys Lys Phe Phe Gly Arg Lys
                645                 650                 655

Lys Ser Ser Lys Pro Thr Glu Ile Ala Ala Pro Ile Phe Ser Leu Glu
            660                 665                 670

Glu Ile Glu Glu Gly Leu Glu Gly Tyr Glu Glu His Glu Lys Ser Trp
        675                 680                 685

Leu Met Ser Gln Lys Ser Phe Glu Lys Arg Phe Gly Gln Ser Pro Val
    690                 695                 700

Phe Ile Thr Ser Thr Leu Met Glu Asn Gly Gly Val Pro Glu Ser Val
705                 710                 715                 720

Asn Ser Pro Ala Leu Ile Lys Glu Ala Ile His Val Ile Ser Ile Gly
                725                 730                 735

Tyr Glu Glu Lys Thr Glu Trp Gly Lys Glu Ile Gly Trp Ile Tyr Gly
            740                 745                 750

Ser Val Thr Glu Tyr Ile Leu Thr Gly Phe Lys Met His Cys Arg Gly
        755                 760                 765

Trp Arg Ser Val Tyr Cys Met Pro Pro Arg Pro Ala Phe Lys Gly Ser
    770                 775                 780

Ala Pro Ile Asn Leu Ser Asp Arg Leu His Gln Val Leu Arg Trp Ala
785                 790                 795                 800

Leu Gly Ser Ile Glu Ile Phe Leu Ser Arg His Cys Pro Leu Trp Tyr
                805                 810                 815
```

-continued

```
Ala Tyr Gly Gly Asn Leu Lys Trp Leu Glu Arg Leu Ala Tyr Ile Asn
            820                 825                 830

Thr Ile Val Tyr Pro Phe Thr Ser Ile Pro Leu Val Ala Tyr Cys Thr
        835                 840                 845

Leu Pro Ala Ile Cys Leu Leu Thr Gly Lys Phe Ile Thr Pro Thr Leu
850                 855                 860

Thr Ser Leu Ala Ser Val Trp Phe Met Gly Leu Phe Ile Ser Ile Ile
865                 870                 875                 880

Ala Thr Gly Val Leu Glu Leu Arg Trp Ser Gly Val Ser Ile Glu Glu
            885                 890                 895

Phe Trp Arg Asn Glu Gln Phe Trp Val Ile Gly Gly Val Ser Ala His
        900                 905                 910

Leu Phe Ala Val Phe Gln Gly Leu Leu Lys Val Leu Gly Gly Val Asp
    915                 920                 925

Thr Asn Phe Thr Val Thr Ala Lys Gly Ser Asp Glu Glu Asp Gln Phe
930                 935                 940

Gly Glu Leu Tyr Met Phe Lys Trp Thr Thr Leu Leu Ile Pro Pro Thr
945                 950                 955                 960

Thr Leu Leu Ile Ile Asn Leu Val Ser Leu Val Ala Gly Val Ser Ala
            965                 970                 975

Ala Val Asn Asn Asn Tyr Gln Ser Trp Gly Pro Leu Phe Gly Lys Leu
        980                 985                 990

Phe Phe Ala Cys Trp Val Ile Leu His Leu Tyr Pro Phe Leu Lys Gly
    995                 1000                1005

Leu Leu Gly Arg Gln Asn Arg Thr Pro Thr Ile Val Ile Leu Trp Ser
1010                1015                1020

<210> SEQ ID NO 31
<211> LENGTH: 628
<212> TYPE: PRT
<213> ORGANISM: Eucalyptus grandis

<400> SEQUENCE: 31

Ala Gln Glu Arg Glu Tyr Glu Glu Phe Lys Val Gln Ile Asn Ala Leu
1               5                   10                  15

Val Ala Lys Ala Gln Lys Met Pro Glu Glu Gly Trp Thr Met Gln Asp
            20                  25                  30

Gly Thr Ala Trp Ala Gly Asn Asn Pro Arg Asp His Pro Gly Met Ile
        35                  40                  45

Gln Val Phe Leu Gly His Ser Gly Gly Leu Asp Thr Asp Gly Asn Glu
    50                  55                  60

Leu Pro Arg Leu Val Tyr Val Ser Arg Glu Lys Arg Pro Gly Phe Gln
65                  70                  75                  80

His His Lys Lys Ala Gly Ala Met Asn Ala Leu Ile Arg Val Ser Ala
                85                  90                  95

Val Leu Thr Asn Gly Ala Tyr Leu Leu Asn Val Asp Cys Asp His Tyr
            100                 105                 110

Phe Asn Asn Ser Lys Ala Leu Lys Glu Ala Met Cys Phe Met Met Asp
        115                 120                 125

Pro Ala Tyr Gly Lys Lys Thr Cys Tyr Val Gln Phe Pro Gln Arg Phe
    130                 135                 140

Asp Gly Ile Asp Leu His Asp Arg Tyr Ala Asn Arg Asn Ile Val Phe
145                 150                 155                 160

Phe Asp Ile Asn Leu Lys Gly Leu Asp Gly Ile Gln Gly Pro Val Tyr
                165                 170                 175
```

Val Gly Thr Gly Cys Cys Phe Asn Arg Gln Ala Leu Tyr Gly Tyr Asp
            180                 185                 190

Pro Val Leu Thr Glu Glu Asp Leu Glu Pro Asn Ile Ile Val Lys Ser
            195                 200                 205

Cys Cys Gly Ser Arg Lys Gly Lys Gly Gly Asn Lys Lys Tyr Ile
210                 215                 220

Asp Lys Lys Arg Ala Met Lys Arg Thr Glu Ser Thr Val Pro Ile Phe
225                 230                 235                 240

Asn Met Glu Asp Val Glu Gly Val Glu Gly Tyr Asp Asp Glu Arg
            245                 250                 255

Ser Leu Leu Met Ser Gln Lys Ser Leu Glu Lys Arg Phe Gly Gln Ser
            260                 265                 270

Pro Val Phe Ile Ser Ala Thr Phe Met Glu Gln Gly Gly Leu Pro Pro
            275                 280                 285

Ser Thr Asn Pro Ala Thr Leu Leu Lys Glu Ala Ile His Val Ile Ser
            290                 295                 300

Cys Gly Tyr Glu Asp Lys Thr Glu Trp Gly Lys Glu Ile Gly Trp Ile
305                 310                 315                 320

Tyr Gly Ser Val Thr Glu Asp Ile Leu Thr Gly Phe Lys Met His Ala
            325                 330                 335

Arg Gly Trp Ile Ser Ile Tyr Cys Met Pro Pro Arg Pro Ala Phe Lys
            340                 345                 350

Gly Ser Ala Pro Ile Asn Leu Ser Asp Arg Leu Asn Gln Val Leu Arg
            355                 360                 365

Trp Ala Leu Gly Ser Ile Glu Ile Leu Leu Ser Arg His Cys Pro Ile
            370                 375                 380

Trp Tyr Gly Tyr Asn Gly Lys Leu Arg Leu Leu Glu Arg Leu Ala Tyr
385                 390                 395                 400

Ile Asn Thr Ile Val Tyr Pro Leu Thr Ser Ile Pro Leu Ile Ala Tyr
            405                 410                 415

Cys Ile Leu Pro Ala Phe Cys Leu Leu Thr Asn Lys Phe Ile Ile Pro
            420                 425                 430

Glu Ile Ser Asn Phe Ala Ser Met Trp Phe Ile Leu Leu Phe Val Ser
            435                 440                 445

Ile Phe Thr Thr Gly Ile Leu Glu Leu Arg Trp Ser Gly Val Ser Ile
            450                 455                 460

Glu Asp Trp Trp Arg Asn Glu Gln Phe Trp Val Ile Gly Gly Thr Ser
465                 470                 475                 480

Ala His Leu Phe Ala Val Phe Gln Gly Leu Leu Lys Val Leu Ala Gly
            485                 490                 495

Ile Asp Thr Asn Phe Thr Val Thr Ser Lys Ala Gly Asp Glu Asp Gly
            500                 505                 510

Asp Phe Ala Glu Leu Tyr Val Phe Lys Trp Thr Ser Leu Leu Ile Pro
            515                 520                 525

Pro Thr Thr Val Leu Ile Val Asn Ile Ile Gly Ile Val Ala Gly Val
            530                 535                 540

Ser Tyr Ala Ile Asn Ser Gly Tyr Gln Ser Trp Gly Pro Leu Phe Gly
545                 550                 555                 560

Lys Leu Phe Phe Ala Ile Trp Val Ile Ala His Leu Tyr Pro Phe Leu
            565                 570                 575

Lys Gly Leu Leu Gly Arg Gln Asn Arg Thr Pro Thr Ile Val Ile Val
            580                 585                 590

Trp Ser Ile Leu Leu Ala Ser Ile Phe Ser Leu Leu Trp Val Arg Ile

```
                      595                 600                 605
Asp Pro Phe Thr Ser Ala Thr Thr Ala Ser Thr Ala Asn Gly Gln Cys
            610                 615                 620

Gly Ile Asn Cys
625

<210> SEQ ID NO 32
<211> LENGTH: 1024
<212> TYPE: PRT
<213> ORGANISM: Eucalyptus grandis

<400> SEQUENCE: 32

Met Glu Val Ser Ser Gly Leu Val Ala Gly Ser His Asn Arg Asn Glu
  1               5                  10                  15

Leu Val Val Ile Arg Arg Glu Asn Glu Leu Gly Gln Lys Pro Leu Gln
             20                  25                  30

Lys Leu Ser Gly Gln Ile Cys Gln Ile Cys Gly Asp Asp Val Gly Leu
         35                  40                  45

Thr Val Asp Gly Glu Leu Phe Val Ala Cys Asn Glu Cys Ala Phe Pro
     50                  55                  60

Ile Cys Arg Thr Cys Tyr Glu Tyr Glu Arg Arg Glu Gly Ser Gln Ile
 65                  70                  75                  80

Cys Pro Gln Cys Lys Thr Arg Phe Lys Cys Leu Arg Gly Cys Ala Arg
                 85                  90                  95

Val Asp Gly Asp Glu Glu Asp Gly Val Asp Asp Leu Glu Asn Glu
            100                 105                 110

Phe Asn Phe Asp Gly Arg His Arg Gln Glu Met Asp Arg Gln Gly Tyr
        115                 120                 125

Gly Ala Glu Ala Met Leu His Gly His Met Ser Tyr Gly Arg Gly Ser
    130                 135                 140

Asp Leu Asp Leu Ser His Val His Pro Leu Pro Gln Val Pro Leu Leu
145                 150                 155                 160

Thr Asn Gly Gln Met Val Asp Asp Ile Pro Pro Glu His His Ala Leu
                165                 170                 175

Val Pro Ala Tyr Met Gly Ala Gly Gly Gly Gly Gly Gly Gly Gly Lys
            180                 185                 190

Arg Ile His Pro Leu Pro Phe Thr Asp Ser Gly Leu Pro Val Gln Pro
        195                 200                 205

Arg Ser Met Asp Pro Ser Lys Asp Leu Ala Ala Tyr Gly Tyr Gly Ser
    210                 215                 220

Val Ala Trp Lys Glu Arg Met Glu Ser Trp Lys Gln Lys Gln Glu Lys
225                 230                 235                 240

Leu Gln Thr Met Lys Asn Glu Lys Gly Gly Lys Glu Trp Asp Asp Asp
                245                 250                 255

Gly Asp Asn Pro Asp Leu Pro Leu Met Asp Glu Ala Arg Gln Pro Leu
            260                 265                 270

Ser Arg Lys Leu Pro Ile Ser Ser Gln Ile Asn Pro Tyr Arg Met
        275                 280                 285

Ile Ile Val Ile Arg Leu Val Val Leu Gly Phe Phe His Tyr Arg
    290                 295                 300

Val Met His Pro Val Asn Asp Ala Tyr Ala Leu Trp Leu Ile Ser Val
305                 310                 315                 320

Ile Cys Glu Ile Trp Phe Gly Leu Ser Trp Ile Leu Asp Gln Phe Pro
                325                 330                 335

Lys Trp Leu Pro Ile Asp Arg Glu Thr Tyr Leu Asp Arg Leu Ser Leu
```

-continued

```
                340                 345                 350
Arg Tyr Glu Lys Glu Gly Gln Pro Ser Gln Leu Ala Pro Val Asp Ile
            355                 360                 365

Phe Val Ser Thr Val Asp Pro Leu Lys Glu Pro Pro Leu Val Thr Ala
        370                 375                 380

Asn Thr Val Leu Ser Ile Leu Ala Val Asp Tyr Pro Val Asp Lys Val
385                 390                 395                 400

Ser Cys Tyr Val Ser Asp Gly Ala Ala Met Leu Thr Phe Glu Ala
                405                 410                 415

Leu Ser Glu Thr Ser Glu Phe Ala Arg Lys Trp Val Pro Phe Cys Lys
            420                 425                 430

Lys Phe Asn Ile Glu Pro Arg Ala Pro Glu Phe Tyr Phe Ala Gln Lys
        435                 440                 445

Ile Asp Tyr Leu Lys Asp Lys Val Glu Ala Ser Phe Val Lys Glu Arg
        450                 455                 460

Arg Ala Met Lys Arg Glu Tyr Glu Glu Phe Lys Val Arg Ile Asn Ala
465                 470                 475                 480

Leu Val Ala Lys Ala Gln Lys Val Pro Glu Glu Gly Trp Thr Met Gln
                485                 490                 495

Asp Gly Thr Pro Trp Pro Gly Asn Asn Val Arg Asp His Pro Gly Met
            500                 505                 510

Ile Gln Val Phe Leu Gly Gln Ser Gly Gly His Asp Ser Asp Gly Asn
        515                 520                 525

Glu Leu Pro Arg Leu Val Tyr Val Ser Arg Lys Arg Pro Gly Tyr
        530                 535                 540

Asn His His Lys Lys Ala Gly Ala Met Asn Ala Leu Val Arg Val Ser
545                 550                 555                 560

Ala Val Leu Thr Asn Ala Pro Tyr Leu Leu Asn Leu Asp Cys Asp His
                565                 570                 575

Tyr Phe Asn Asn Ser Lys Ala Ile Arg Glu Ala Met Cys Phe Met Met
            580                 585                 590

Asp Pro Leu Ile Gly Lys Arg Val Cys Tyr Val Gln Phe Pro Gln Arg
        595                 600                 605

Phe Asp Gly Ile Asp Arg His Asp Arg Tyr Ala Asn Arg Asn Thr Val
        610                 615                 620

Phe Phe Asp Ile Asn Met Lys Gly Leu Asp Gly Ile Gln Gly Pro Ile
625                 630                 635                 640

Tyr Val Gly Thr Gly Cys Val Phe Arg Arg Leu Ala Leu Tyr Gly Tyr
                645                 650                 655

Asp Ala Pro Lys Ala Lys Lys Pro Pro Thr Arg Thr Cys Asn Cys Leu
            660                 665                 670

Pro Lys Trp Cys Cys Cys Gly Cys Cys Cys Ser Gly Thr Lys Lys Lys
        675                 680                 685

Lys Lys Thr Thr Lys Pro Lys Thr Glu Leu Lys Lys Arg Phe Phe Lys
        690                 695                 700

Lys Lys Asp Ala Gly Thr Pro Pro Leu Glu Gly Ile Glu Glu Gly
705                 710                 715                 720

Ile Glu Val Ile Glu Ser Glu Asn Pro Thr Pro Gln His Lys Leu Glu
                725                 730                 735

Lys Lys Phe Gly Gln Ser Ser Val Phe Val Ala Ser Thr Leu Leu Glu
            740                 745                 750

Asp Gly Gly Thr Leu Lys Gly Thr Ser Pro Ala Ser Leu Leu Lys Glu
        755                 760                 765
```

```
Ala Ile His Val Ile Ser Cys Gly Tyr Glu Asp Lys Thr Glu Trp Gly
                770             775                 780

Lys Glu Val Gly Trp Ile Tyr Gly Ser Val Thr Glu Asp Ile Leu Thr
785                 790                 795                 800

Gly Phe Lys Met His Cys His Gly Trp Arg Ser Ile Tyr Cys Ile Pro
                805                 810                 815

Ala Arg Pro Ala Phe Lys Gly Ser Ala Pro Ile Asn Leu Ser Asp Arg
                820                 825                 830

Leu His Gln Val Leu Arg Trp Ala Leu Gly Ser Ile Glu Ile Phe Leu
                835                 840                 845

Ser Arg His Cys Pro Leu Trp Tyr Gly Tyr Gly Gly Leu Lys Trp
850                 855                 860

Leu Glu Arg Leu Ser Tyr Ile Asn Ala Thr Val Tyr Pro Trp Thr Ser
865                 870                 875                 880

Ile Pro Leu Leu Ala Tyr Cys Thr Leu Pro Ala Val Cys Leu Leu Thr
                885                 890                 895

Gly Lys Phe Ile Thr Pro Glu Leu Ser Asn Val Ala Ser Leu Trp Phe
                900                 905                 910

Leu Ser Leu Phe Ile Cys Ile Phe Ala Thr Ser Ile Leu Glu Met Arg
                915                 920                 925

Trp Ser Gly Val Gly Ile Glu Glu Trp Trp Arg Asn Glu Gln Phe Trp
930                 935                 940

Val Ile Gly Gly Val Ser Ala His Leu Phe Ala Val Phe Gln Gly Leu
945                 950                 955                 960

Leu Lys Val Leu Ala Gly Val Asp Thr Asn Phe Thr Val Thr Ser Lys
                965                 970                 975

Gly Gly Asp Asp Lys Glu Phe Ser Glu Leu Tyr Ala Phe Lys Trp Thr
                980                 985                 990

Thr Leu Leu Ile Pro Pro Thr Thr Leu Leu Ile Ile Asn Leu Ile Gly
                995                 1000                1005

Val Val Ala Gly Val Ser Asn Ala Ile Asn Asn Gly Tyr Glu Ser Trp
    1010                1015                1020

<210> SEQ ID NO 33
<211> LENGTH: 709
<212> TYPE: PRT
<213> ORGANISM: Eucalyptus grandis

<400> SEQUENCE: 33

Met Ala Pro Ser Leu Asp Ser Trp Ala Lys Gln Asn Val His Lys Gly
1               5                   10                  15

Thr Pro Val Val Val Lys Met Glu Asn Leu Asn Trp Ser Met Leu Glu
                20                  25                  30

Leu Glu Ser Pro Ser Asp Glu Asp Ile Phe Pro Ala Gly Ala Pro Ala
                35                  40                  45

Ala Gly Glu Gly Ala Ala Pro Gly Arg Thr Arg Asn Lys Asn Ala Lys
                50                  55                  60

Gln Leu Thr Trp Val Leu Leu Arg Ala His Arg Ala Ala Gly Cys
65                  70                  75                  80

Leu Ala Ser Met Ala Ala Ala Phe Leu Gly Leu Ala Ser Ala Val Arg
                85                  90                  95

Arg Arg Val Ala Ala Gly Arg Thr Asp Asn Asp Val Ser Glu Ala Ser
                100                 105                 110

Arg Arg Gly Gly Gly Val Arg Glu Ser Pro Thr Leu Lys Ala Arg Phe
                115                 120                 125
```

-continued

Tyr Thr Cys Thr Lys Val Phe Leu Trp Leu Ser Ile Val Leu Leu Gly
    130                 135                 140

Phe Glu Val Ala Ala Tyr Phe Lys Gly Trp His Tyr Gly Ala His Asn
145                 150                 155                 160

Val Glu Leu Gln His Leu Leu Ala Thr Ser Phe Ser Val Lys Gly Val
                165                 170                 175

Phe Asp Arg Leu Tyr Ser Lys Trp Val Ser Ile Arg Val Glu Tyr Leu
            180                 185                 190

Ala Pro Pro Leu Gln Phe Leu Ala Asn Ala Cys Ile Val Leu Phe Leu
        195                 200                 205

Ile Gln Ser Leu Asp Arg Leu Val Leu Cys Leu Gly Cys Phe Trp Ile
    210                 215                 220

Lys Phe Lys Asn Ile Lys Pro Ile Pro Lys Glu Asp Ala Ser Val Asp
225                 230                 235                 240

Val Glu Ser Gly Glu Lys Gly Tyr Phe Pro Met Val Leu Val Gln Leu
                245                 250                 255

Pro Met Cys Asn Glu Lys Glu Val Tyr Gln Gln Ser Ile Ala Ala Val
            260                 265                 270

Cys Asn Leu Asp Trp Pro Lys Ser Lys Leu Leu Ile Gln Val Leu Asp
        275                 280                 285

Asp Ser Asp Asp Pro Thr Ala Gln Ser Leu Ile Lys Glu Val Asn
    290                 295                 300

Lys Trp Gln Gln Glu Gly Ala Arg Ile Val Tyr Arg His Arg Val Ile
305                 310                 315                 320

Arg Glu Gly Tyr Lys Ala Gly Asn Leu Lys Ser Ala Met Asn Cys Ser
                325                 330                 335

Tyr Val Lys Glu Tyr Glu Phe Val Ser Ile Phe Asp Ala Asp Phe Gln
            340                 345                 350

Pro Ala Pro Asp Phe Leu Lys Arg Thr Val Pro His Phe Lys Asp Asn
        355                 360                 365

Asp Glu Leu Gly Leu Val Gln Ala Arg Trp Ser Phe Val Asn Lys Asp
    370                 375                 380

Glu Asn Leu Leu Thr Arg Leu Gln His Ile Asn Leu Ala Phe His Phe
385                 390                 395                 400

Glu Val Glu Gln Gln Val Asn Gly Val Phe Leu Asn Phe Phe Gly Phe
                405                 410                 415

Asn Gly Thr Ala Gly Val Trp Arg Ile Lys Ala Leu Glu Asp Ser Gly
            420                 425                 430

Gly Trp Leu Glu Arg Thr Thr Val Glu Asp Met Asp Ile Ala Val Arg
        435                 440                 445

Ala His Leu His Gly Trp Lys Phe Ile Phe Leu Asn Asp Val Glu Ala
    450                 455                 460

Gln Cys Glu Leu Pro Glu Ser Tyr Glu Ala Tyr Arg Lys Gln Gln His
465                 470                 475                 480

Arg Trp His Ser Gly Pro Met Gln Leu Phe Arg Leu Cys Leu Pro Ala
                485                 490                 495

Ile Ile Lys Ser Lys Ile Ser Ile Trp Lys Lys Phe Asn Leu Ile Phe
            500                 505                 510

Leu Phe Phe Leu Leu Arg Lys Leu Ile Leu Pro Phe Tyr Ser Phe Thr
        515                 520                 525

Leu Phe Cys Ile Ile Leu Pro Met Thr Met Phe Val Pro Glu Ala Glu
    530                 535                 540

Leu Pro Ala Trp Val Val Cys Tyr Ile Pro Ala Thr Met Ser Phe Leu
545                 550                 555                 560

```
Asn Ile Leu Pro Ala Pro Lys Ser Phe Pro Phe Ile Val Pro Tyr Leu
            565                 570                 575
Leu Phe Glu Asn Thr Met Ser Val Thr Lys Phe Asn Ala Met Ile Ser
        580                 585                 590
Gly Leu Phe Gln Leu Gly Ser Ala Tyr Glu Trp Val Val Thr Lys Lys
    595                 600                 605
Ser Gly Arg Ser Ser Glu Gly Asp Leu Leu Ser Leu Val Glu Lys Glu
610                 615                 620
Thr Lys His Lys Arg Gly Asn Ser Ala Pro Asp Leu Glu Ala Leu Lys
625                 630                 635                 640
Glu Glu Ile Ser Arg Gln Lys Lys Ala Ser Arg Lys Lys His
                645                 650                 655
Asn Arg Ile Tyr Thr Lys Glu Leu Thr Leu Ala Phe Leu Leu Leu Thr
            660                 665                 670
Ala Ser Ala Arg Ser Leu Leu Ser Ala Gln Gly Val His Phe Tyr Phe
        675                 680                 685
Leu Leu Phe Gln Gly Ile Ser Phe Leu Leu Val Gly Leu Asp Leu Ile
    690                 695                 700
Gly Glu Gln Val Glu
705

<210> SEQ ID NO 34
<211> LENGTH: 527
<212> TYPE: PRT
<213> ORGANISM: Eucalyptus grandis

<400> SEQUENCE: 34

Met Ala Gln Ile Ser Ala Lys Asp Leu Ile Pro Asp Ser Leu Thr Met
 1               5                  10                  15
Ser Arg Glu Asp Ile Ala Gly Gln Leu Gly Met Val Trp Glu Leu Ile
                20                  25                  30
Lys Ala Pro Leu Ile Val Pro Val Leu Arg Leu Ser Val Tyr Val Cys
            35                  40                  45
Leu Ala Met Ala Leu Met Leu Phe Met Glu Arg Val Tyr Met Gly Ile
        50                  55                  60
Val Ile Val Leu Val Lys Leu Phe Trp Lys Lys Pro Glu Lys Arg Tyr
 65                  70                  75                  80
Asn Trp Glu Pro Ile Glu Glu Asp Leu Glu Ser Gly Ser Ser Asn Phe
                85                  90                  95
Pro Phe Val Leu Val Gln Ile Pro Met Tyr Asn Glu Lys Glu Val Tyr
            100                 105                 110
Lys Ile Ser Ile Gly Ala Ala Cys Gly Leu Ser Trp Pro Ala Asp Arg
        115                 120                 125
Leu Val Ile Gln Val Leu Asp Asp Ser Thr Asp Pro Val Ile Lys Gln
    130                 135                 140
Met Val Glu Leu Glu Cys Gln Arg Trp Ala Ser Lys Gly Ile Asn Ile
145                 150                 155                 160
Val Tyr Gln Ile Arg Glu Thr Arg Gly Gly Tyr Lys Ala Gly Ala Leu
                165                 170                 175
Lys Glu Gly Leu Lys Arg Ser Tyr Val Lys His Cys Glu Phe Val Ala
            180                 185                 190
Ile Phe Asp Ala Asp Phe Arg Pro Glu Pro Asp Tyr Leu Lys Arg Ala
        195                 200                 205
Ile Pro Tyr Phe Leu Arg Asn Pro Asp Leu Ala Leu Val Gln Ala Arg
    210                 215                 220
```

Trp Arg Phe Val Asn Ser Asn Glu Cys Leu Leu Thr Arg Met Gln Glu
225                 230                 235                 240

Met Ser Leu Asp Tyr His Phe Thr Val Glu Gln Val Gly Ser Ala
            245                 250                 255

Thr His Ala Phe Phe Gly Phe Asn Gly Thr Ala Gly Val Trp Arg Ile
            260                 265                 270

Gly Ala Ile Asn Glu Ala Gly Gly Trp Lys Asp Arg Thr Thr Val Glu
            275                 280                 285

Asp Met Asp Leu Ala Val Arg Ala Ser Leu Arg Gly Trp Lys Phe Val
290                 295                 300

Tyr Leu Gly Asp Leu Gln Val Lys Ser Glu Leu Pro Ser Thr Phe Lys
305                 310                 315                 320

Ala Phe Arg Phe Gln Gln His Arg Trp Ser Cys Gly Pro Ala Asn Leu
            325                 330                 335

Phe Arg Lys Met Val Met Glu Ile Val Arg Asn Lys Val Arg Phe
            340                 345                 350

Trp Lys Lys Val Tyr Val Ile Tyr Ser Phe Phe Val Arg Lys Ile
            355                 360                 365

Ile Ala His Met Val Thr Phe Phe Tyr Cys Val Val Leu Pro Leu
370                 375                 380

Thr Ile Trp Val Pro Glu Val His Val Pro Ile Trp Gly Ala Val Tyr
385                 390                 395                 400

Ile Pro Ser Ile Ile Thr Ile Leu Asn Ser Val Gly Thr Pro Arg Ser
            405                 410                 415

Ile His Leu Leu Phe Tyr Trp Ile Leu Phe Glu Asn Val Met Ser Met
            420                 425                 430

His Arg Thr Lys Ala Thr Phe Ile Gly Leu Leu Glu Ala Gly Arg Ala
            435                 440                 445

Asn Glu Trp Val Val Thr Glu Lys Leu Gly Asp Thr Leu Lys Asn Lys
450                 455                 460

Ser Lys Lys Leu Arg Phe Thr Phe Asn Phe Ala Asp Arg Leu His Leu
465                 470                 475                 480

Leu Glu Leu Gly Phe Gly Val Phe Leu Phe Val Thr Gly Cys Tyr Asp
            485                 490                 495

Phe Leu Tyr Gly Lys Asn Asn Tyr Phe Val Tyr Leu Trp Leu Gln Thr
            500                 505                 510

Ile Thr Phe Phe Ile Ala Gly Phe Gly Tyr Ile Gly Thr Ile Val
            515                 520                 525

<210> SEQ ID NO 35
<211> LENGTH: 1045
<212> TYPE: PRT
<213> ORGANISM: Eucalyptus grandis

<400> SEQUENCE: 35

Met Ser Gly Phe Ala Val Gly Ser His Ser Arg Asn Glu Leu His Val
1               5                   10                  15

Thr Asn Gly Gly Ala Ala Asp Glu His Arg Ser Pro Arg Gln Asn
            20                  25                  30

Ala Ala Arg Thr Cys Arg Val Cys Gly Asp Glu Ile Gly Leu Lys Asp
            35                  40                  45

Asp Gly Ala Pro Phe Val Ala Cys His Glu Cys Gly Phe Pro Val Cys
    50                  55                  60

Arg Pro Cys Tyr Val Tyr Glu Arg Ser Asp Gly Thr Gln Cys Cys Pro
65                  70                  75                  80

```
Gln Cys Asn Ala Arg Tyr Lys Arg His Lys Gly Cys Pro Arg Val Ala
                85                  90                  95
Gly Asp Asp Glu Asp Asp His Phe Glu Gly Glu Asp Phe Glu Asp Glu
            100                 105                 110
Phe Gln Ile Arg Asn Arg Gly Glu Asn Glu Val Arg Pro Thr Gly Phe
            115                 120                 125
Asp Arg Ser Glu Asn Gly Asp Ser His Ala Pro Gln Val His Pro Asn
        130                 135                 140
Gly Gln Val Phe Ser Ser Ala Gly Ser Val Val Gly Ala Glu Leu Glu
145                 150                 155                 160
Gly Glu Gly Asn Ala Glu Trp Lys Glu Arg Ile Glu Lys Trp Lys Ile
                165                 170                 175
Arg Gln Glu Lys Arg Gly Leu Val Gly Lys Asp Asp Gly Gly Asn Gly
            180                 185                 190
Asp Gly Glu Glu Asp Asp Tyr Leu Met Ala Glu Ala Arg Gln Pro Leu
        195                 200                 205
Ser Arg Lys Val Pro Ile Ser Ser Lys Ile Ser Pro Tyr Arg Ile
    210                 215                 220
Val Ile Val Leu Arg Leu Val Val Leu Gly Phe Leu His Phe Arg
225                 230                 235                 240
Ile Leu Thr Pro Ala Thr Asp Ala Phe Pro Leu Trp Leu Ile Ser Val
                245                 250                 255
Ile Cys Glu Thr Trp Phe Ala Leu Ser Trp Ile Leu Asp Gln Phe Pro
            260                 265                 270
Lys Trp Asn Pro Ile Asn Arg Glu Thr Tyr Leu Asp Arg Leu Ser Ile
        275                 280                 285
Arg Phe Glu Arg Glu Gly Glu Pro Ser Arg Leu Thr Pro Val Asp Val
        290                 295                 300
Phe Val Ser Ser Val Asp Pro Leu Lys Glu Pro Pro Ile Ile Thr Ala
305                 310                 315                 320
Asn Thr Val Leu Ser Ile Leu Ala Val Asp Tyr Pro Val Asp Lys Val
                325                 330                 335
Cys Cys Tyr Val Ser Asp Asp Gly Ala Ser Met Leu Leu Phe Asp Thr
            340                 345                 350
Leu Ser Glu Thr Ala Glu Phe Ala Arg Arg Trp Val Pro Phe Cys Lys
        355                 360                 365
Lys Tyr Ser Ile Glu Pro Arg Thr Pro Glu Phe Tyr Phe Ser Gln Lys
    370                 375                 380
Ile Asp Tyr Leu Lys Asp Lys Val Glu Pro Ser Phe Val Lys Glu Arg
385                 390                 395                 400
Arg Ala Met Lys Arg Glu Tyr Glu Glu Phe Lys Val Arg Val Asn Ala
                405                 410                 415
Leu Val Ala Lys Ala Gln Lys Lys Pro Glu Glu Gly Trp Val Met Gln
            420                 425                 430
Asp Gly Thr Pro Trp Pro Gly Asn Asn Thr Arg Asp His Pro Gly Met
        435                 440                 445
Ile Gln Val Tyr Leu Gly Ser Ala Gly Ala Leu Asp Val Glu Gly Lys
    450                 455                 460
Glu Leu Pro Arg Leu Val Tyr Val Ser Arg Glu Lys Arg Pro Gly Tyr
465                 470                 475                 480
Gln His His Lys Lys Ala Gly Ala Met Asn Ala Leu Val Arg Val Ser
                485                 490                 495
Ala Val Leu Thr Asn Ala Pro Phe Leu Leu Asn Leu Asp Cys Asp His
```

```
                    500             505             510
Tyr Ile Asn Asn Ser Lys Ala Ile Arg Glu Ala Met Cys Phe Leu Met
            515                 520                 525

Asp Pro Gln Leu Gly Lys Lys Leu Cys Tyr Val Gln Phe Pro Gln Arg
        530                 535                 540

Phe Asp Gly Ile Asp Arg His Asp Arg Tyr Ala Asn Arg Asn Ile Val
545                 550                 555                 560

Phe Phe Asp Ile Asn Met Arg Gly Leu Asp Gly Ile Gln Gly Pro Val
                565                 570                 575

Tyr Val Gly Thr Gly Cys Val Phe Asn Arg Gln Ala Leu Tyr Gly Tyr
            580                 585                 590

Asp Pro Pro Val Ser Gln Lys Arg Pro Lys Met Thr Cys Asp Cys Trp
        595                 600                 605

Pro Ser Trp Cys Ser Cys Cys Gly Gly Ser Arg Lys Ser Lys Ser
    610                 615                 620

Lys Lys Lys Asp Asp Thr Ser Leu Leu Gly Pro Val His Ala Lys Lys
625                 630                 635                 640

Lys Lys Met Thr Gly Lys Asn Tyr Leu Lys Lys Gly Ser Gly Pro
            645                 650                 655

Val Phe Asp Leu Glu Asp Ile Glu Glu Gly Leu Glu Gly Phe Asp Glu
                660                 665                 670

Leu Glu Lys Ser Ser Leu Met Ser Gln Lys Asn Phe Glu Lys Arg Phe
            675                 680                 685

Gly Gln Ser Pro Val Phe Ile Ala Ser Thr Leu Met Glu Asp Gly Gly
        690                 695                 700

Leu Pro Glu Gly Thr Asn Ser Thr Ser Leu Ile Lys Glu Ala Ile His
705                 710                 715                 720

Val Ile Ser Cys Gly Tyr Glu Glu Lys Thr Glu Trp Gly Lys Glu Ile
                725                 730                 735

Gly Trp Ile Tyr Gly Ser Val Thr Glu Asp Ile Leu Thr Gly Phe Lys
            740                 745                 750

Met His Cys Arg Gly Trp Lys Ser Val Tyr Cys Met Pro Lys Arg Pro
        755                 760                 765

Ala Phe Lys Gly Ser Ala Pro Ile Asn Leu Ser Asp Arg Leu His Gln
770                 775                 780

Val Leu Arg Trp Ala Leu Gly Ser Val Glu Ile Phe Leu Ser Arg His
785                 790                 795                 800

Cys Pro Leu Trp Tyr Ala Trp Gly Gly Lys Leu Lys Leu Leu Glu Arg
            805                 810                 815

Leu Ala Tyr Ile Asn Thr Ile Val Tyr Pro Phe Thr Ser Ile Pro Leu
            820                 825                 830

Leu Phe Tyr Cys Thr Ile Pro Ala Val Cys Leu Leu Thr Gly Lys Phe
            835                 840                 845

Ile Ile Pro Thr Leu Thr Asn Phe Ala Ser Ile Trp Phe Leu Ala Leu
        850                 855                 860

Phe Leu Ser Ile Ile Ala Thr Gly Val Leu Glu Leu Arg Trp Ser Gly
865                 870                 875                 880

Val Ser Ile Glu Asp Trp Trp Arg Asn Glu Gln Phe Trp Val Ile Gly
                885                 890                 895

Gly Val Ser Ala His Leu Phe Ala Val Phe Gln Gly Leu Leu Lys Val
            900                 905                 910

Leu Ala Gly Val Asp Thr Asn Phe Thr Val Thr Ala Lys Ala Ala Glu
            915                 920                 925
```

```
Asp Ser Glu Phe Gly Glu Leu Tyr Leu Phe Lys Trp Thr Thr Leu Leu
        930                 935                 940
Lys Pro Pro Thr Thr Leu Ile Ile Leu Asn Met Val Gly Val Val Ala
945                 950                 955                 960
Gly Val Ser Asp Ala Ile Asn Asn Gly Tyr Gly Ser Trp Gly Pro Leu
            965                 970                 975
Phe Gly Lys Leu Phe Ala Phe Trp Val Ile Val His Leu Tyr Pro
            980                 985                 990
Phe Leu Lys Gly Leu Met Gly Lys Gln Asn Arg Thr Pro Thr Ile Val
            995                1000                1005
Val Leu Trp Ser Val Leu Leu Ala Ser Ile Phe Ser Leu Val Trp Val
        1010                1015                1020
Arg Ile Asp Pro Phe Leu Pro Lys Gln Thr Gly Pro Val Leu Lys Pro
1025                1030                1035                1040
Cys Gly Val Glu Cys
            1045

<210> SEQ ID NO 36
<211> LENGTH: 1024
<212> TYPE: PRT
<213> ORGANISM: Eucalyptus grandis

<400> SEQUENCE: 36

Met Glu Ala Gly Ala Gly Leu Val Ala Gly Ser His Asn Arg Asn Glu
  1                 5                  10                  15
Leu Val Val Ile His Gly His Glu Glu Ser Lys Pro Leu Lys Asn Leu
             20                  25                  30
Asp Gly Gln Val Cys Glu Ile Cys Gly Asp Glu Val Gly Leu Thr Val
         35                  40                  45
Asp Gly Asp Leu Phe Val Ala Cys Asn Glu Cys Gly Phe Pro Val Cys
     50                  55                  60
Arg Pro Cys Tyr Glu Tyr Glu Arg Arg Glu Gly Ser Gln Leu Cys Pro
 65                  70                  75                  80
Gln Cys Lys Thr Arg Tyr Lys Arg Leu Lys Gly Ser Pro Arg Val Glu
                 85                  90                  95
Gly Asp Asp Asp Glu Glu Asp Ile Asp Leu Glu His Glu Phe Asn
            100                 105                 110
Ile Glu Asp Glu Gln Asn Lys His Lys Tyr Met Ala Glu Ala Met Leu
        115                 120                 125
His Gly Lys Met Ser Tyr Gly Arg Gly Pro Gly Asp Asp Asn Ala
    130                 135                 140
Gln Phe Pro Ser Val Ile Ala Gly Gly Arg Ser Arg Pro Val Ser Gly
145                 150                 155                 160
Glu Phe Pro Ile Ser Ser Tyr Gly His Gly Glu Met Pro Ser Ser Leu
                165                 170                 175
His Lys Arg Val His Pro Tyr Pro Ile Ser Glu Pro Gly Ser Glu Arg
            180                 185                 190
Trp Asp Glu Lys Lys Glu Gly Gly Trp Lys Glu Arg Met Asp Asp Trp
        195                 200                 205
Lys Leu Gln Gln Gly Asn Leu Gly Pro Glu Pro Asp Asp Ile Asn Asp
    210                 215                 220
Pro Asp Met Ala Met Ile Asp Glu Ala Arg Gln Pro Leu Ser Arg Lys
225                 230                 235                 240
Val Pro Ile Ala Ser Ser Lys Ile Asn Pro Tyr Arg Met Val Ile Val
                245                 250                 255
```

```
Ala Arg Leu Ala Ile Leu Ala Phe Phe Leu Arg Tyr Arg Ile Leu Asn
        260                 265                 270

Pro Val His Asp Ala Phe Gly Leu Trp Leu Thr Ser Ile Ile Cys Glu
            275                 280                 285

Ile Trp Phe Ala Phe Ser Trp Ile Leu Asp Gln Phe Pro Lys Trp Phe
290                 295                 300

Pro Ile Asp Arg Glu Thr Tyr Leu Asp Arg Leu Ser Leu Arg Tyr Glu
305                 310                 315                 320

Arg Glu Gly Glu Pro Asn Met Leu Ser Pro Val Asp Val Phe Val Ser
                325                 330                 335

Thr Val Asp Pro Met Lys Glu Pro Pro Leu Val Thr Gly Asn Thr Val
            340                 345                 350

Leu Ser Ile Leu Ala Met Asp Tyr Pro Val Asp Lys Ile Ser Cys Tyr
        355                 360                 365

Val Ser Asp Asp Gly Ala Ser Met Leu Thr Phe Glu Ser Leu Ser Glu
    370                 375                 380

Thr Ala Glu Phe Ala Arg Lys Trp Val Pro Phe Cys Lys Lys Phe Ser
385                 390                 395                 400

Ile Glu Pro Arg Ala Pro Glu Met Tyr Phe Thr Leu Lys Ile Asp Tyr
                405                 410                 415

Leu Lys Asp Lys Val Gln Pro Thr Phe Val Lys Glu Arg Arg Ala Met
            420                 425                 430

Lys Arg Glu Tyr Glu Glu Phe Lys Val Arg Ile Asn Ala Leu Val Ala
        435                 440                 445

Lys Ala Ala Lys Val Pro Pro Glu Gly Trp Ile Met Gln Asp Gly Thr
    450                 455                 460

Pro Trp Pro Gly Asn Asn Thr Lys Asp His Pro Gly Met Ile Gln Val
465                 470                 475                 480

Phe Leu Gly His Ser Gly Leu Asp Ala Asp Gly Asn Glu Leu Pro
                485                 490                 495

Arg Leu Val Tyr Val Ser Arg Glu Lys Arg Pro Gly Phe Gln His His
            500                 505                 510

Lys Lys Ala Gly Ala Met Asn Ala Leu Val Arg Val Ser Gly Val Leu
        515                 520                 525

Thr Asn Ala Pro Phe Met Leu Asn Leu Asp Cys Asp His Tyr Ile Asn
    530                 535                 540

Asn Ser Lys Ala Val Arg Glu Ala Met Cys Phe Leu Met Asp Pro Gln
545                 550                 555                 560

Ile Gly Arg Lys Val Cys Tyr Val Gln Phe Pro Gln Arg Phe Asp Gly
                565                 570                 575

Ile Asp Thr Asn Asp Arg Tyr Ala Asn Arg Asn Thr Val Phe Phe Asp
            580                 585                 590

Ile Asn Met Lys Gly Leu Asp Gly Ile Gln Gly Pro Val Tyr Val Gly
        595                 600                 605

Thr Gly Cys Val Phe Arg Arg Gln Ala Leu Tyr Gly Tyr Glu Pro Pro
    610                 615                 620

Lys Gly Pro Lys Arg Pro Lys Met Val Ser Cys Asp Cys Cys Pro Cys
625                 630                 635                 640

Phe Gly Arg Arg Lys Lys Leu Pro Lys Tyr Ser Lys His Ser Ala Asn
                645                 650                 655

Gly Asp Ala Ala Asp Leu Gln Gly Met Asp Asp Lys Glu Leu Leu
            660                 665                 670

Met Ser Glu Met Asn Phe Glu Lys Lys Phe Gly Gln Ser Ala Ile Phe
    675                 680                 685
```

```
Val Thr Ser Thr Leu Met Glu Gln Gly Gly Val Pro Pro Ser Ser Ser
    690                 695                 700

Pro Ala Ala Leu Leu Lys Glu Ala Ile His Val Ile Ser Cys Gly Tyr
705                 710                 715                 720

Glu Asp Lys Thr Glu Trp Gly Thr Glu Leu Gly Trp Ile Tyr Gly Ser
                725                 730                 735

Ile Thr Glu Asp Ile Leu Thr Gly Phe Lys Met His Cys Arg Gly Trp
            740                 745                 750

Arg Ser Ile Tyr Cys Met Pro Lys Arg Pro Ala Phe Lys Gly Ser Ala
        755                 760                 765

Pro Ile Asn Leu Ser Asp Arg Leu Asn Gln Val Leu Arg Trp Ala Leu
770                 775                 780

Gly Ser Val Glu Ile Phe Phe Ser His His Ser Pro Val Trp Tyr Gly
785                 790                 795                 800

Tyr Lys Gly Gly Lys Leu Lys Trp Leu Glu Arg Phe Ala Tyr Val Asn
                805                 810                 815

Thr Thr Ile Tyr Pro Phe Thr Ser Leu Pro Leu Leu Ala Tyr Cys Thr
            820                 825                 830

Leu Pro Ala Ile Cys Leu Leu Thr Asp Lys Phe Ile Met Pro Ala Ile
        835                 840                 845

Ser Thr Phe Ala Ser Leu Phe Phe Ile Ala Leu Phe Met Ser Ile Phe
850                 855                 860

Ala Thr Gly Ile Leu Glu Leu Arg Trp Ser Gly Val Ser Ile Glu Glu
865                 870                 875                 880

Trp Trp Arg Asn Glu Gln Phe Trp Val Ile Gly Gly Val Ser Ala His
                885                 890                 895

Leu Phe Ala Val Val Gln Gly Leu Leu Lys Val Leu Ala Gly Ile Asp
            900                 905                 910

Thr Asn Phe Thr Val Thr Ser Lys Ala Ser Asp Asp Glu Asp Phe Gly
        915                 920                 925

Glu Leu Tyr Ala Phe Lys Trp Thr Thr Leu Leu Ile Pro Pro Thr Thr
930                 935                 940

Ile Leu Ile Ile Asn Leu Val Gly Val Val Ala Gly Ile Ser Asp Ala
945                 950                 955                 960

Ile Asn Asn Gly Tyr Gln Ala Trp Gly Pro Leu Phe Gly Lys Leu Phe
                965                 970                 975

Phe Ala Phe Trp Val Ile Leu His Leu Tyr Pro Phe Leu Lys Gly Leu
            980                 985                 990

Met Gly Arg Gln Asn Arg Thr Pro Thr Ile Val Val Ile Trp Ser Val
        995                 1000                1005

Leu Leu Ala Ser Ile Phe Ser Leu Leu Trp Val Arg Ile Asp Pro Phe
    1010                1015                1020

<210> SEQ ID NO 37
<211> LENGTH: 533
<212> TYPE: PRT
<213> ORGANISM: Eucalyptus grandis

<400> SEQUENCE: 37

Met Asp Arg Leu Ser Ala Thr Gly Leu Leu Pro Asp Thr Phe Gly Gly
1               5                   10                  15

Ala Arg Asp Asp Ile Ser Met Gln Leu Ser Leu Ile Trp Ala Gln Ile
            20                  25                  30

Lys Ala Pro Leu Leu Val Pro Leu Leu Arg Leu Ala Val Phe Leu Cys
        35                  40                  45
```

-continued

```
Leu Ala Met Ser Leu Met Leu Phe Leu Glu Arg Val Tyr Met Ala Val
         50                  55                  60
Val Ile Leu Leu Val Lys Leu Phe Gly Arg Lys Pro Glu Lys Arg Tyr
 65                  70                  75                  80
Arg Trp Glu Pro Met Lys Asp Asp Val Glu Leu Gly Asn Ser Ala Tyr
                 85                  90                  95
Pro Met Val Leu Val Gln Ile Pro Met Tyr Asn Glu Arg Glu Val Tyr
             100                 105                 110
Gln Leu Ser Ile Gly Ala Ala Cys Gly Leu Ser Trp Pro Ser Asp Arg
             115                 120                 125
Ile Ile Ile Gln Val Leu Asp Asp Ser Thr Asp Pro Thr Ile Lys Asp
130                 135                 140
Leu Val Glu Leu Glu Cys Gln Arg Trp Ala Ser Lys Gly Ile Asn Ile
145                 150                 155                 160
Arg Tyr Glu Ile Arg Asp Asn Arg Asn Gly Tyr Lys Ala Gly Ala Leu
                 165                 170                 175
Lys Glu Gly Met Lys Arg Ser Tyr Val Lys Gln Cys Asp Tyr Val Ala
             180                 185                 190
Ile Leu Asp Ala Asp Phe Gln Pro Glu Pro Asp Phe Leu Trp Arg Thr
             195                 200                 205
Ile Pro Phe Leu Val His Asn Pro Glu Val Ala Leu Val Gln Ala Arg
210                 215                 220
Trp Lys Phe Val Asn Ala Asp Glu Cys Leu Met Thr Arg Met Gln Glu
225                 230                 235                 240
Met Ser Leu Asp Tyr His Phe Thr Val Glu Gln Glu Val Gly Ser Ser
                 245                 250                 255
Thr His Ala Phe Phe Gly Phe Asn Gly Thr Ala Gly Val Trp Arg Ile
             260                 265                 270
Ser Ala Leu Asn Glu Ala Gly Gly Trp Lys Asp Arg Thr Thr Val Glu
             275                 280                 285
Asp Met Asp Leu Ala Val Arg Ala Ser Leu Lys Gly Trp Lys Phe Val
290                 295                 300
Tyr Leu Gly Ser Leu Lys Val Lys Asn Glu Leu Pro Ser Thr Phe Lys
305                 310                 315                 320
Ala Tyr Arg Phe Gln Gln His Arg Trp Ser Cys Gly Pro Ala Asn Leu
                 325                 330                 335
Phe Arg Lys Met Ala Met Glu Ile Ile Arg Asn Lys Lys Val Thr Leu
             340                 345                 350
Trp Lys Lys Val His Val Ile Tyr Ser Phe Phe Leu Val Arg Lys Ile
             355                 360                 365
Val Ala His Ile Val Thr Phe Ile Phe Tyr Cys Val Val Leu Pro Ala
370                 375                 380
Thr Val Phe Val Pro Glu Val Thr Val Pro Lys Trp Gly Ala Val Tyr
385                 390                 395                 400
Ile Pro Ser Ile Ile Thr Val Leu Asn Ala Val Gly Thr Pro Arg Ser
                 405                 410                 415
Leu His Leu Val Val Phe Trp Ile Leu Phe Glu Asn Val Met Ser Phe
             420                 425                 430
His Arg Thr Lys Ala Thr Phe Ile Gly Leu Leu Glu Ala Gly Arg Val
             435                 440                 445
Asn Glu Trp Ile Val Thr Glu Lys Leu Gly Asp Ala Leu Lys Val Lys
450                 455                 460
Ala Ser Asn Lys Val Pro Lys Lys Pro Lys Phe Arg Phe Gly Asp Arg
```

```
                465                 470                 475                 480
Leu His Val Leu Glu Leu Gly Val Gly Ala Tyr Leu Phe Phe Cys Gly
                    485                 490                 495

Cys Tyr Asp Ile Ala Phe Gly Arg Asn His Tyr Phe Met Tyr Leu Phe
            500                 505                 510

Ala Gln Ala Ile Ala Phe Phe Ile Met Gly Phe Gly Tyr Ile Gly Thr
        515                 520                 525

Phe Val Pro Asn Ser
        530

<210> SEQ ID NO 38
<211> LENGTH: 440
<212> TYPE: PRT
<213> ORGANISM: Eucalyptus grandis

<400> SEQUENCE: 38

Met Glu His Arg Ser Arg Pro Leu Asn Leu Cys His Val Asp Pro Lys
1               5                   10                  15

Leu Ile Ala Val Asn Arg Ala His Met Leu Ile His Gly Ala Ala Leu
            20                  25                  30

Leu Ile Leu Ile His Tyr Arg Ala Ser Phe Phe Ala Glu Glu Ala
        35                  40                  45

Ser Ser Pro Gly Gln Pro Thr Thr Leu Ala Trp Leu Ile Ile Phe Leu
    50                  55                  60

Gly Glu Leu Thr Leu Ser Leu Thr Trp Leu Leu His Gln Ala Phe Arg
65                  70                  75                  80

Trp Arg Pro Val Ser Arg Thr Ala Phe Pro Glu Arg Leu Pro Gly Asp
                85                  90                  95

Gly Glu Leu Pro Ser Ile Asp Val Leu Val Cys Thr Ala Asp Pro Asp
            100                 105                 110

Lys Glu Pro Thr Val Ala Val Met Asn Thr Val Ile Ser Ala Met Ala
        115                 120                 125

Leu Asp Tyr Pro Pro Glu Lys Leu His Val Tyr Leu Ser Asp Asp Gly
    130                 135                 140

Gly Ser Leu Leu Thr Leu His Gly Met Arg Glu Ala Tyr Asp Phe Ala
145                 150                 155                 160

Arg Arg Trp Leu Pro Phe Cys Lys Arg Phe Gly Ile Lys Thr Arg Cys
                165                 170                 175

Pro Lys Ala Tyr Phe Met Asp Asp Glu Asp Val Ser Ala Ser Val Gly
            180                 185                 190

Tyr Glu Ser Glu Lys Lys Glu Val Lys Glu Lys Tyr Glu Leu Phe Glu
        195                 200                 205

Ala His Ile Asn Gly Tyr Arg Asn Arg Asn Tyr Gly Glu Ser Arg Asp
    210                 215                 220

Gly Arg Leu Asp His Pro Ser Thr Ile Glu Val Ile His Gly Asn Ser
225                 230                 235                 240

Ser Asp Glu Val Val Gln Ala Asp Gln Gln Met Pro Leu Leu Val
                245                 250                 255

Tyr Val Ser Arg Glu Lys Arg Pro Ser Tyr Pro His Asn Phe Lys Ala
            260                 265                 270

Gly Ala Leu Asn Val Leu Leu Arg Val Ser Gly Val Ile Ser Asn Ser
        275                 280                 285

Pro Tyr Val Leu Val Leu Asp Cys Asp Met Tyr Cys Asn Asp Pro Ser
    290                 295                 300

Ser Ala Arg Arg Ala Met Cys Phe His Leu Asp Pro Thr Leu Ser Pro
```

```
                305                 310                 315                 320
Ser Leu Ser Phe Val Gln Phe Pro Gln Ser Phe His Asn Ile Ser Lys
                    325                 330                 335

Asn Asp Ile Tyr Asp Ser Lys Ile Arg Ser Pro Phe Gly Thr Leu Leu
                340                 345                 350

Cys Gly Met Asp Gly Leu Gln Gly Pro Leu Ile Ala Gly Thr Gly Phe
            355                 360                 365

Tyr Ile Lys Arg Glu Ser Leu Tyr Ser Glu Pro Met Gln Glu Gly Thr
        370                 375                 380

Thr Ala Asn Leu Met Asp Leu Lys Ala Ile Phe Gly His Ser Asn Glu
385                 390                 395                 400

Phe Ile Lys His Leu His Trp Ser Asp Lys Leu Asn Lys Asn Ile Leu
                405                 410                 415

Ser Glu Pro Gly Thr Val Cys Arg Asp Thr Glu His Leu Ala Ser Cys
            420                 425                 430

His Tyr Glu Asn Gly Thr Lys Trp
        435                 440

<210> SEQ ID NO 39
<211> LENGTH: 1024
<212> TYPE: PRT
<213> ORGANISM: Eucalyptus grandis

<400> SEQUENCE: 39

Met Asn Thr Gly Gly Arg Leu Ile Ala Gly Ser His Asn Arg Asn Glu
 1               5                  10                  15

Phe Val Leu Ile Asn Ala Asp Glu Ser Ser Arg Ile Lys Ser Val Lys
                20                  25                  30

Glu Leu Ser Gly Gln Ile Cys Gln Ile Cys Gly Asp Glu Val Glu Ile
            35                  40                  45

Ala Asp Gly Glu Leu Phe Val Ala Cys Asn Glu Cys Ala Phe Pro Val
        50                  55                  60

Cys Arg Pro Cys Tyr Glu Tyr Glu Arg Arg Glu Gly Asn Gln Ala Cys
65                  70                  75                  80

Pro Gln Cys Lys Thr Arg Tyr Lys Arg Leu Lys Gly Ser Pro Arg Val
                85                  90                  95

Glu Gly Asp Glu Glu Asp Asp Ile Asp Asp Leu Asp Asn Glu Phe
            100                 105                 110

Asp Tyr Asp Pro Ser Asp Pro Gln His Val Ala Glu Lys Thr Phe Ser
        115                 120                 125

Ser Arg Leu Asn Tyr Gly Arg Gly Ala His Arg Asn Ala Ser Gly Met
130                 135                 140

Pro Thr Asp Val Glu Ser Ser Pro Leu Ser Ser Gln Ile Pro Leu Leu
145                 150                 155                 160

Thr Tyr Gly Gln Glu Asp Ala Glu Ile Ser Pro Asp Gln His Ala Leu
                165                 170                 175

Ile Val Pro Pro Ala Thr Gly His Ala Tyr Arg Val His Pro Met Pro
            180                 185                 190

Tyr Pro Asp Ser Ser Asn Pro Leu His Pro Arg Pro Met Ala Pro Glu
        195                 200                 205

Lys Asp Ile Thr Leu Tyr Gly Tyr Gly Ser Val Ala Trp Lys Asp Lys
    210                 215                 220

Met Glu Lys Trp Arg Lys Lys Gln Asn Glu Lys Leu Gln Val Val Lys
225                 230                 235                 240

His Glu Gly Ala Gly Asp Gly Gly Asp Phe Gly Ser Asp Glu Leu Asp
```

```
                    245                 250                 255
Asp Pro Asp Leu Pro Met Met Asp Glu Gly Arg Gln Pro Leu Ser Arg
                260                 265                 270

Lys Leu Pro Ile Pro Ser Ser Lys Ile Asn Pro Tyr Arg Leu Leu Ile
            275                 280                 285

Ile Leu Arg Leu Val Ile Leu Gly Leu Phe Leu His Tyr Arg Ile Leu
        290                 295                 300

His Pro Val Asn Asp Ala Tyr Gly Leu Trp Leu Thr Ser Val Ile Cys
305                 310                 315                 320

Glu Ile Trp Phe Ala Val Ser Trp Ile Leu Asp Gln Phe Pro Lys Trp
                325                 330                 335

Tyr Pro Ile Glu Arg Glu Thr Tyr Leu Asp Arg Leu Ser Leu Arg Tyr
            340                 345                 350

Glu Arg Glu Gly Lys Pro Ser Glu Leu Ala Pro Val Asp Val Phe Val
        355                 360                 365

Ser Thr Val Asp Pro Met Lys Glu Pro Pro Leu Ile Thr Ala Asn Thr
    370                 375                 380

Val Leu Ser Ile Leu Ala Val Asp Tyr Pro Val Asp Lys Val Ala Cys
385                 390                 395                 400

Tyr Val Ser Asp Asp Gly Ala Ala Met Leu Thr Phe Glu Ala Leu Ser
                405                 410                 415

Glu Thr Ser Glu Phe Ala Lys Lys Trp Val Pro Phe Cys Lys Arg Phe
            420                 425                 430

Asn Ile Glu Pro Arg Ala Pro Glu Trp Tyr Phe Ser Gln Lys Met Asp
        435                 440                 445

Tyr Leu Lys Asn Lys Val His Pro Glu Phe Val Arg Glu Arg Arg Ala
    450                 455                 460

Ile Lys Arg Glu Tyr Glu Glu Phe Lys Val Arg Ile Asn Ala Leu Val
465                 470                 475                 480

Ala Met Ala Gln Lys Val Pro Glu Glu Gly Trp Thr Met Gln Asp Gly
                485                 490                 495

Thr Pro Trp Pro Gly Asn Asn Val Arg Asp His Pro Gly Met Ile Gln
            500                 505                 510

Val Phe Leu Gly His Ser Gly Val Cys Asp Asp Gly Asn Glu Leu
        515                 520                 525

Pro Arg Leu Val Tyr Val Ser Arg Glu Lys Arg Pro Gly Phe Glu His
    530                 535                 540

His Lys Lys Ala Gly Ala Met Asn Ala Leu Ile Arg Val Ser Ala Val
545                 550                 555                 560

Ile Ser Asn Ala Pro Tyr Leu Leu Asn Val Asp Cys Asp His Tyr Ile
                565                 570                 575

Asn Asn Ser Lys Ala Leu Arg Glu Ala Met Cys Phe Met Met Asp Pro
            580                 585                 590

Thr Ser Gly Lys Lys Val Cys Tyr Val Gln Phe Pro Gln Arg Phe Asp
        595                 600                 605

Gly Ile Asp Arg His Asp Arg Tyr Ser Asn Arg Asn Val Val Phe Phe
    610                 615                 620

Asp Ile Asn Met Lys Gly Leu Asp Gly Leu Gln Gly Pro Ile Tyr Val
625                 630                 635                 640

Gly Thr Gly Cys Val Phe Arg Arg Gln Ala Leu Tyr Gly His Asp Ala
                645                 650                 655

Pro Ser Lys Lys Lys Pro Pro Ser Lys Thr Cys Asn Cys Trp Pro Lys
            660                 665                 670
```

```
Trp Cys Cys Leu Cys Cys Gly Gly Arg Lys Asn Lys Lys Gly Lys Thr
            675                 680                 685
Lys Lys Glu Arg Ser Lys Lys Thr Lys Asn Arg Glu Thr Ser Lys Gln
690                 695                 700
Ile His Ala Leu Glu Asn Ile Glu Glu Gly Val Ser Glu Val Ser Asn
705                 710                 715                 720
Glu Lys Ser Ser Glu Met Thr Gln Ile Lys Leu Glu Lys Lys Phe Gly
            725                 730                 735
Gln Ser Pro Val Phe Val Ala Ser Thr Thr Leu Glu Asp Gly Gly Val
            740                 745                 750
Pro Pro Asp Ala Ser Pro Ala Ser Leu Leu Lys Glu Ala Ile Gln Val
            755                 760                 765
Ile Ser Cys Gly Tyr Glu Asp Lys Thr Glu Trp Gly Lys Glu Val Gly
770                 775                 780
Trp Ile Tyr Gly Ser Val Thr Glu Asp Ile Leu Thr Gly Phe Lys Met
785                 790                 795                 800
His Cys His Gly Trp Arg Ser Val Tyr Cys Ile Pro Lys Arg Pro Ala
            805                 810                 815
Phe Lys Gly Ser Ala Pro Ile Asn Leu Ser Asp Arg Leu His Gln Val
            820                 825                 830
Leu Arg Trp Ala Leu Gly Ser Val Glu Ile Phe Leu Ser Arg His Cys
            835                 840                 845
Pro Ile Trp Tyr Gly Tyr Gly Gly Gly Leu Lys Trp Leu Glu Arg Phe
850                 855                 860
Ser Tyr Ile Asn Ser Val Val Tyr Pro Trp Thr Ser Ile Pro Leu Ile
865                 870                 875                 880
Val Tyr Cys Ser Leu Pro Ala Ile Cys Leu Leu Thr Gly Gln Phe Ile
            885                 890                 895
Val Pro Glu Ile Ser Asn Tyr Ala Ser Leu Val Phe Met Ala Leu Phe
            900                 905                 910
Ile Ser Ile Ala Ala Thr Gly Ile Leu Glu Met Gln Trp Gly Gly Val
            915                 920                 925
Gly Ile Asp Asp Trp Trp Arg Asn Glu Gln Phe Trp Val Ile Gly Gly
930                 935                 940
Val Ser Ser His Leu Phe Ala Leu Val Gln Gly Leu Leu Lys Val Leu
945                 950                 955                 960
Gly Gly Val Asn Thr Asn Phe Thr Val Thr Ser Lys Ala Ala Asp Asp
            965                 970                 975
Gly Ala Phe Ser Glu Leu Tyr Ile Phe Lys Trp Thr Ser Leu Leu Ile
            980                 985                 990
Pro Pro Met Thr Leu Leu Ile Met Asn Ile Val Gly Val Val Val Gly
            995                 1000                1005
Ile Ser Asp Ala Ile Asn Asn Gly Tyr Asp Ser Trp Gly Pro Leu Phe
   1010                1015                1020

<210> SEQ ID NO 40
<211> LENGTH: 1024
<212> TYPE: PRT
<213> ORGANISM: Eucalyptus grandis

<400> SEQUENCE: 40

Met Asp Thr Gly Val His Met Arg Arg Met Ser Thr Pro Gly Ile Arg
1               5                   10                  15
Gln Val Asn Asn Ser Arg Asp Asp Thr Asp Ser Val Val Ser Ser Ala
            20                  25                  30
```

-continued

```
Glu Phe Ala Ser Tyr Thr Val His Ile Pro Pro Thr Pro Glu Tyr Gln
         35                  40                  45

Pro Met Tyr Met Ser Ile Glu Thr Ser Asn Ala Glu Lys Val Glu Asp
 50                  55                  60

Leu Tyr Ala Ser Asn Ser Leu Phe Thr Gly Gly Tyr Asn Arg Ala Thr
 65                  70                  75                  80

Arg Ser Phe Leu Lys Glu Lys Met Thr Asp Ser Val Ser Asn His Pro
                 85                  90                  95

Gln Met Ala Gly Met Asn Gly Ser Met Cys Glu Ile Pro Gly Cys Asp
                100                 105                 110

Ala Lys Ile Met Arg Asp Glu Arg Gly Glu Asp Ile Val Pro Cys Asp
                115                 120                 125

Cys Asp Phe Lys Ile Cys Arg Asp Cys Phe Arg Asp Ala Val Arg Gly
        130                 135                 140

Gly Asp Val Ile Cys Leu Gly Cys Lys Glu Pro Tyr Lys Gly Leu Asp
145                 150                 155                 160

Met Ala Glu Pro Glu Met Asn Asp Gly Arg Val Ser Ser Gly Gly
                165                 170                 175

Met Ser Lys Arg Glu Arg Arg Met Ser Met Ile Lys Ser Arg Met Ser
                180                 185                 190

Leu Lys Arg Ser Glu Met Asp Asp Phe Asp His Arg Asn Trp Leu Phe
        195                 200                 205

Glu Thr Lys Gly Ser Tyr Gly Tyr Gly Asn Ala Met Trp Pro Lys Glu
210                 215                 220

Asp Val Asp Gly Asp Asp Gly Phe Gly Asn Pro Gln Val Leu His
225                 230                 235                 240

Asp Lys Lys Trp Arg Pro Leu Thr Arg Lys Val Asn Val Ser Pro Lys
                245                 250                 255

Ile Leu Ser Pro Tyr Arg Leu Leu Ile Phe Leu Arg Ile Ile Ala Leu
                260                 265                 270

Ala Leu Leu Leu Met Trp Arg Ile Lys His Pro Asn Glu Asp Ala Met
        275                 280                 285

Trp Leu Trp Ala Met Ser Val Val Cys Glu Ile Trp Phe Gly Phe Ser
290                 295                 300

Trp Leu Leu Asp Gln Leu Pro Lys Leu Cys Pro Ile Asn Arg Thr Thr
305                 310                 315                 320

Asp Leu Gly Ala Leu Lys Met Lys Phe Glu Thr Pro Ser Pro Thr Asn
                325                 330                 335

Pro Thr Gly Lys Cys Asp Leu Pro Gly Ile Asp Ile Phe Val Ser Thr
                340                 345                 350

Ala Asp Pro Glu Lys Glu Pro Pro Leu Val Thr Ala Asn Thr Ile Leu
        355                 360                 365

Ser Ile Leu Ala Ala Asp Tyr Pro Val Glu Lys Leu Ala Cys Tyr Val
370                 375                 380

Ser Asp Asp Gly Gly Ala Leu Leu Thr Phe Glu Ala Met Ala Glu Ala
385                 390                 395                 400

Ala Ser Phe Ala Asn Leu Trp Val Pro Phe Cys Arg Lys His Arg Ile
                405                 410                 415

Glu Pro Arg Asn Pro Glu Ser Tyr Phe Ser Leu Lys Arg Asp Pro Tyr
                420                 425                 430

Lys Asp Lys Val Arg Gln Asp Phe Val Arg Asp Arg Arg Val Lys
        435                 440                 445

Arg Glu Tyr Asp Glu Phe Lys Val Arg Ile Asn Gly Leu Ser Asn Ser
450                 455                 460
```

-continued

```
Ile Arg Arg Arg Ser Asp Ala Tyr Asn Ala Cys Glu Ile Lys Ala
465                 470                 475                 480

Ala Lys Leu Gln Asn Lys Asn Glu Ser Gly Glu Gly Val Glu Ser Leu
                485                 490                 495

Lys Ile Pro Lys Ala Thr Trp Met Ala Asp Gly Thr His Trp Pro Gly
                500                 505                 510

Thr Trp Thr Gly Pro Ala Ala Glu His Ser Arg Gly Asp His Ala Ser
            515                 520                 525

Val Ile Gln Val Met Leu Lys Pro Pro Ser Asp Glu Pro Leu Arg Gly
        530                 535                 540

Thr Glu Ser Thr Ser Pro Ile Asp Leu Ala Glu Val Asp Ile Arg Leu
545                 550                 555                 560

Pro Met Leu Val Tyr Ile Ser Arg Glu Lys Arg Pro Gly Tyr Asp His
                565                 570                 575

Asn Lys Lys Ala Gly Ala Met Asn Ala Leu Val Arg Ala Ser Ala Ile
                580                 585                 590

Met Ser Asn Gly Pro Phe Ile Leu Asn Leu Asp Cys Asp His Tyr Ile
        595                 600                 605

Tyr Asn Ser Gln Ala Met Arg Glu Gly Met Cys Phe Met Met Asp Arg
    610                 615                 620

Gly Gly Asp Arg Ile Cys Tyr Val Gln Phe Pro Gln Arg Phe Glu Gly
625                 630                 635                 640

Ile Asp Pro Ser Asp Arg Tyr Ala Asn His Asn Thr Val Phe Phe Asp
                645                 650                 655

Val Asn Met Arg Ala Leu Asp Gly Leu Gln Gly Pro Val Tyr Val Gly
                660                 665                 670

Thr Gly Cys Leu Phe Arg Arg Thr Ala Leu Tyr Gly Phe Asp Pro Pro
            675                 680                 685

Arg Val Lys Glu His Gly Gly Cys Phe Ser Gln Ile Phe Lys Arg His
        690                 695                 700

Arg Ser Ala Ala Thr Val Ala Ser Thr Pro Glu Val Ser Leu Val Glu
705                 710                 715                 720

Asn Arg Phe Leu Gly Met Gly Asp Ser Ser Gln Glu Val Asn Leu
                725                 730                 735

Leu Pro Asn Lys Phe Gly Asn Ser Val Leu Phe Val Glu Ser Ile His
                740                 745                 750

Ile Ala Glu Phe Gln Gly Arg Pro Leu Ala Asp Asp Pro Ser Val Lys
                755                 760                 765

Asn Gly Arg Pro Pro Gly Ala Leu Thr Ile Pro Arg Gln Leu Leu Asp
                770                 775                 780

Ala Pro Thr Val Ala Glu Ala Ile Ser Val Ile Ser Cys Trp Tyr Glu
785                 790                 795                 800

Asp Lys Thr Glu Trp Gly Gln Arg Ile Gly Trp Ile Tyr Gly Ser Val
                805                 810                 815

Thr Glu Asp Val Val Thr Gly Tyr Arg Met His Asn Arg Gly Trp Arg
            820                 825                 830

Ser Ile Tyr Cys Val Thr Lys Arg Asp Ala Phe Arg Gly Thr Ala Pro
        835                 840                 845

Ile Asn Leu Thr Asp Arg Leu His Gln Val Leu Arg Trp Ala Thr Gly
        850                 855                 860

Ser Val Glu Ile Phe Phe Ser Arg Asn Asn Ala Leu Leu Ala Ser Arg
865                 870                 875                 880

Arg Met Lys Phe Leu Gln Arg Ile Ala Tyr Met Asn Val Gly Leu Tyr
```

```
                    885                 890                 895
Pro Phe Thr Ser Ile Phe Leu Val Val Tyr Cys Phe Leu Pro Ala Leu
                900                 905                 910

Ser Leu Phe Ser Gly Gln Phe Ile Val Gln Ser Leu Asp Val Thr Phe
                915                 920                 925

Leu Thr Tyr Leu Leu Ala Ile Thr Val Thr Leu Cys Ile Leu Ala Met
                930                 935                 940

Leu Glu Ile Lys Trp Ser Gly Ile Glu Leu Glu Trp Trp Arg Asn
945                 950                 955                 960

Glu Gln Phe Trp Leu Ile Gly Gly Thr Ser Ala His Leu Ala Ala Val
                965                 970                 975

Ile Gln Gly Leu Leu Lys Val Ile Ala Gly Ile Glu Ile Ser Phe Thr
                980                 985                 990

Leu Thr Ser Lys Ser Ala Gly Asp Glu Asn Asp Asp Glu Phe Ala Glu
                995                 1000                1005

Leu Tyr Leu Phe Lys Trp Thr Ser Leu Met Ile Leu Pro Ile Thr Ile
                1010                1015                1020

<210> SEQ ID NO 41
<211> LENGTH: 743
<212> TYPE: PRT
<213> ORGANISM: Eucalyptus grandis

<400> SEQUENCE: 41

Met Glu His Ser Ser Gly Pro Leu Asn Leu Cys His Val Leu Thr Lys
  1               5                  10                  15

Ser Ile Ile Ile Asn Arg Thr His Met Leu Val His Ala Thr Ala Leu
                 20                  25                  30

Ser Ala Leu Ile Tyr Tyr Arg Ala Ser Phe Phe Phe Ser Glu Ser Lys
             35                  40                  45

Ser Arg Asp Arg Ala Thr Thr Leu Ala Cys Leu Thr Met Phe Leu Ala
         50                  55                  60

Glu Leu Gly Leu Ser Phe Leu Trp Leu Leu Ser Gln Ala Phe Arg Trp
 65                  70                  75                  80

Arg Pro Val Arg Arg Thr Ala Phe Pro Lys Arg Leu Pro Glu Asp Lys
                 85                  90                  95

Glu Leu Pro Pro Ile Asp Val Phe Val Cys Thr Ala Asp Pro Asp Lys
            100                 105                 110

Glu Pro Thr Val Asp Val Met Asn Thr Val Val Ser Ala Met Ala Leu
            115                 120                 125

Asp Tyr Pro Pro Glu Lys Leu His Val Tyr Leu Ser Asp Asp Gly Gly
        130                 135                 140

Ser Thr Leu Thr Leu His Gly Thr Arg Glu Ala Tyr Asp Phe Ala Arg
145                 150                 155                 160

Trp Trp Leu Pro Phe Cys Lys Arg Tyr Gly Ile Lys Thr Arg Cys Pro
                165                 170                 175

Lys Ala Phe Phe Lys Glu Glu Asp Gly Glu Gly Ile Gly Met Ser
            180                 185                 190

Ser Asp Asn Glu Phe Gly Ser Glu Lys Lys Ile Val Lys Glu Lys Tyr
        195                 200                 205

Glu Leu Phe Lys Glu Arg Val Asn Glu Tyr Arg Lys Arg His Arg Gly
    210                 215                 220

Asp Ser Ser His Thr Gly Arg Asp His Pro Thr Ile Glu Val Val
225                 230                 235                 240

Arg Gly Asn Val Pro Asp Glu Val Met Gln Ala His Gln Asp Pro Met
```

-continued

```
                245                 250                 255
Pro Lys Leu Ile Tyr Val Ser Arg Glu Lys Arg Pro Ser His His His
                260                 265                 270

His Phe Lys Ala Gly Ala Leu Asn Val Leu Leu Arg Val Ser Gly Val
                275                 280                 285

Met Ser Asn Ser Pro Tyr Ile Leu Val Leu Asp Cys Asp Met Tyr Cys
                290                 295                 300

Asn Asp Pro Ser Ser Ala Arg Gln Ala Met Cys Phe His Leu Asp Pro
305                 310                 315                 320

Arg Leu Ser Pro Ser Leu Met Leu Val Gln Phe Pro Gln Met Phe His
                325                 330                 335

Asn Ile Ser Glu Asn Asp Ile Tyr Asp Ser Lys Leu Arg Pro Tyr Phe
                340                 345                 350

Trp Thr Cys Trp Tyr Gly Met Asp Gly Leu Lys Gly Pro Val Leu Ser
                355                 360                 365

Gly Thr Cys Phe Tyr Ile Lys Arg Glu Ser Leu Tyr Arg Lys Pro Val
                370                 375                 380

Gln Glu Gly Tyr Asp Leu Met Asp Leu Lys Lys Leu Phe Gly His Ser
385                 390                 395                 400

Asn Glu Phe Ile Lys Tyr Leu Gly Gln Lys Glu Lys Pro Ser Lys Asn
                405                 410                 415

Thr Ile Ala Gly Asp Ser Ala Ala Leu Met Lys Glu Thr Gln Leu Leu
                420                 425                 430

Thr Ser Cys Gly Tyr Glu Tyr Gly Thr Lys Trp Gly Gln Glu Val Gly
                435                 440                 445

Phe Lys Tyr Tyr Ser Val Val Glu Asp Tyr Phe Thr Ser Phe Thr Leu
                450                 455                 460

His Cys Arg Gly Trp Thr Ser Val Phe Tyr Thr Pro Ser Lys Pro Gln
465                 470                 475                 480

Phe Leu Gly Thr Ala Thr Thr Asn Phe Asn Asp Met Leu Ile Gln Gly
                485                 490                 495

Met Arg Trp Tyr Ser Gly Leu Ser Gln Val Gly Ile Ser Arg Phe Cys
                500                 505                 510

Pro Leu Ile Tyr Gly Ser Leu Arg Met Pro Ile Leu Gln Ser Met Cys
                515                 520                 525

Tyr Ala Glu Leu Ser Leu Phe Pro Leu Tyr Cys Leu Pro Ile Cys Cys
                530                 535                 540

Phe Ala Thr Ile Pro Gln Ile Cys Leu Val Asn Gly Ile Ser Ile Tyr
545                 550                 555                 560

Pro Glu Val Pro Ser Ser Tyr Ile Met Leu Phe Ala Phe Ile Phe Leu
                565                 570                 575

Ser Ser Leu Cys Lys His Leu Tyr Glu Val Val Ala Ser Gly His Ser
                580                 585                 590

Val Gln Thr Phe Leu Asn Glu Gln Arg Ile Trp Met Ile Lys Ser Thr
                595                 600                 605

Thr Cys Tyr Val Tyr Gly Thr Ile Asp Ala Ile Met Thr Gln Ile Gly
                610                 615                 620

Met Arg Thr Ala Ser Phe Leu Pro Thr Asn Lys Val Asp Asp Asp Glu
625                 630                 635                 640

Gln Ser Lys Arg Tyr Glu Met Gly Ile Phe Asp Phe Gln Thr Ser Ile
                645                 650                 655

Met Phe Leu Ala Pro Met Val Thr Leu Val Ile Leu Asn Met Ala Ser
                660                 665                 670
```

-continued

```
Phe Phe Gly Gly Val Ala Arg Val Leu Thr Leu Gly Gly Phe Asp Lys
            675                 680                 685

Leu Phe Met Gln Ile Ala Leu Ser Leu Phe Val Leu Val Met Ser Tyr
        690                 695                 700

Pro Val Ile Lys Ala Met Val Leu Arg Thr Asp Lys Gly Arg Ile Pro
705                 710                 715                 720

Arg Ser Val Thr Thr Leu Ser Ala Phe Leu Ser Leu Val Leu Leu Leu
                725                 730                 735

Gln Gly Ser Ser Phe Leu Met
            740

<210> SEQ ID NO 42
<211> LENGTH: 1024
<212> TYPE: PRT
<213> ORGANISM: Eucalyptus grandis

<400> SEQUENCE: 42

Met Glu Ala Asn Ala Gly Met Val Ala Gly Ser Tyr Lys Arg Asn Glu
 1               5                  10                  15

Leu Val Arg Ile Arg His Asp Ser Asp Ser Ala Pro Lys Pro Leu Lys
            20                  25                  30

His Leu Asp Gly His Met Cys Gln Ile Cys Gly Asp Thr Val Gly Leu
        35                  40                  45

Ser Ala Ser Gly Asp Val Phe Val Ala Cys Asn Glu Cys Ala Phe Pro
    50                  55                  60

Val Cys Arg Pro Cys Tyr Glu Tyr Glu Arg Lys Asp Gly Asn Gln Cys
65                  70                  75                  80

Cys Pro Gln Cys Lys Thr Arg Tyr Lys Arg Gln Lys Gly Ser Pro Arg
                85                  90                  95

Val Glu Gly Asp Asp Asp Glu Asp Gly Val Asp Asp Leu Glu Asn Glu
            100                 105                 110

Phe Ser Tyr Thr Arg Gly Asn Ala Arg Arg Gln Trp Gln Gly Asp
        115                 120                 125

Asp Pro Asp Leu Ser Ser Ser Arg Arg Glu Ser Gln His Pro Val
    130                 135                 140

Pro Leu Leu Thr Asn Gly Leu Pro Ile Ser Gly Glu Ile Pro Cys Ala
145                 150                 155                 160

Thr Pro Asp Asn Gln Ser Val Arg Thr Thr Ser Gly Pro Leu Gly Pro
                165                 170                 175

Ser Asp Arg His Ser Val His Ser Val Asp Pro Arg Gln Pro Val Pro
            180                 185                 190

Val Arg Ile Val Asp Pro Ser Arg Asp Leu Asn Ser Tyr Gly Leu Gly
        195                 200                 205

Asn Val Asp Trp Lys Glu Arg Val Glu Ser Trp Lys Leu Lys Gln Glu
    210                 215                 220

Lys Asn Ile Pro His Met Thr Ser Arg Phe Pro Glu Gly Lys Gly Asp
225                 230                 235                 240

Ile Glu Gly Thr Gly Ser Tyr Gly Glu Glu Leu Gln Met Ala Asp Asp
                245                 250                 255

Ala Arg Leu Pro Leu Ser Arg Val Val Pro Ile Ser Ser Ser His Leu
            260                 265                 270

Thr Pro Tyr Arg Val Val Ile Ile Leu Arg Leu Ile Ile Leu Gly Phe
        275                 280                 285

Phe Leu Gln Tyr Arg Ala Thr His Pro Val Lys Asp Ala Tyr Pro Leu
    290                 295                 300
```

-continued

```
Trp Leu Thr Ser Val Ile Cys Glu Ile Trp Phe Ala Leu Ser Trp Leu
305                 310                 315                 320

Leu Asp Gln Phe Pro Lys Trp Phe Pro Ile Asn Arg Glu Thr Tyr Leu
            325                 330                 335

Asp Arg Leu Ala Leu Arg Tyr Asp Arg Glu Gly Glu Pro Ser Gln Leu
        340                 345                 350

Ala Pro Ile Asp Ile Phe Val Ser Thr Val Asp Pro Leu Lys Glu Pro
    355                 360                 365

Pro Leu Val Thr Ala Asn Thr Val Leu Ser Ile Leu Ala Val Asp Tyr
370                 375                 380

Pro Val Asp Lys Val Ser Cys Tyr Val Ser Asp Gly Ser Ala Met
385                 390                 395                 400

Leu Thr Phe Glu Ala Leu Ser Glu Thr Ala Glu Phe Ala Lys Lys Trp
            405                 410                 415

Val Pro Phe Cys Lys Lys His Asn Ile Glu Pro Arg Ala Pro Glu Phe
        420                 425                 430

Tyr Phe Ala Gln Ile Asp Tyr Leu Lys Asp Lys Ile Gln Pro Ser Phe
    435                 440                 445

Val Lys Glu Arg Arg Ala Met Lys Arg Glu Tyr Glu Glu Phe Lys Val
450                 455                 460

Arg Ile Asn Ala Leu Val Ala Lys Ala Gln Lys Val Pro Glu Glu Gly
465                 470                 475                 480

Trp Thr Met Gln Asp Gly Thr Pro Trp Pro Gly Asn Asn Pro Arg Asp
            485                 490                 495

His Pro Gly Met Ile Gln Val Phe Leu Gly Ser Gly Gly Leu Asp
        500                 505                 510

Thr Asp Gly Asn Glu Leu Pro Arg Leu Val Tyr Val Ser Arg Glu Lys
    515                 520                 525

Arg Pro Gly Phe Gln His His Lys Lys Ala Gly Ala Met Asn Ala Leu
530                 535                 540

Ile Arg Val Ser Ala Val Leu Thr Asn Gly Ala Tyr Leu Leu Asn Val
545                 550                 555                 560

Asp Cys Asp His Tyr Phe Asn Asn Ser Lys Ala Leu Lys Glu Ala Met
            565                 570                 575

Cys Phe Met Met Asp Pro Ala Leu Gly Lys Lys Thr Cys Tyr Val Gln
        580                 585                 590

Phe Pro Gln Arg Phe Asp Gly Ile Asp Leu His Asp Arg Tyr Ala Asn
    595                 600                 605

Arg Asn Ile Val Phe Phe Asp Ile Asn Leu Lys Gly Leu Asp Gly Ile
610                 615                 620

Gln Gly Pro Val Tyr Val Gly Thr Gly Cys Cys Phe Asn Arg Gln Ala
625                 630                 635                 640

Leu Tyr Gly Tyr Asp Pro Val Leu Thr Glu Ala Asp Leu Glu Pro Asn
            645                 650                 655

Ile Ile Val Lys Ser Cys Cys Gly Pro Arg Lys Lys Gly Lys Gly Gly
        660                 665                 670

Asp Lys Asn Tyr Ile Asp Lys Lys Arg Ala Val Lys Arg Thr Glu Ser
    675                 680                 685

Asn Ile Pro Ile Phe Asn Met Glu Asp Ile Glu Glu Gly Met Glu Gly
690                 695                 700

Tyr Asp Asp Glu Arg Ser Leu Leu Met Ser Gln Lys Ser Leu Glu Lys
705                 710                 715                 720

Arg Phe Gly Gln Ser Pro Val Phe Ile Ala Ala Thr Phe Met Glu Gln
            725                 730                 735
```

```
Gly Gly Leu Pro Pro Ser Thr Asn Pro Ala Ser Leu Leu Lys Glu Ala
            740                 745                 750

Ile His Val Ile Ser Cys Gly Tyr Glu Asp Lys Thr Glu Trp Gly Lys
            755                 760                 765

Glu Ile Gly Trp Ile Tyr Gly Ser Val Thr Glu Asp Ile Leu Thr Gly
            770                 775                 780

Phe Lys Met His Ala Arg Gly Trp Ile Ser Ile Tyr Cys Met Pro Pro
785                 790                 795                 800

Arg Pro Ala Phe Lys Gly Ser Ala Pro Ile Asn Leu Ser Asp Arg Leu
            805                 810                 815

Asn Gln Val Leu Arg Trp Ala Leu Gly Ser Ile Glu Ile Leu Leu Ser
            820                 825                 830

Arg His Cys Pro Ile Trp Tyr Gly Tyr Asn Gly Arg Leu Lys Trp Leu
            835                 840                 845

Glu Arg Leu Ala Tyr Ile Asn Thr Ile Val Tyr Pro Leu Thr Ser Ile
            850                 855                 860

Pro Leu Ile Ala Tyr Cys Ile Leu Pro Ala Phe Cys Leu Leu Thr Gly
865                 870                 875                 880

Lys Phe Ile Ile Pro Glu Ile Ser Asn Phe Ala Ser Met Trp Phe Ile
            885                 890                 895

Leu Leu Phe Val Ser Ile Phe Ala Thr Gly Ile Leu Glu Leu Arg Trp
            900                 905                 910

Ser Gly Val Ser Ile Glu Asp Trp Trp Arg Asn Glu Gln Phe Trp Val
            915                 920                 925

Ile Gly Gly Thr Ser Ala His Leu Phe Ala Val Phe Gln Gly Leu Leu
            930                 935                 940

Lys Val Leu Ala Gly Ile Asp Thr Asn Phe Thr Val Thr Ser Lys Ala
945                 950                 955                 960

Ser Asp Glu Asp Gly Asp Phe Ala Glu Leu Tyr Val Phe Lys Trp Thr
            965                 970                 975

Ser Leu Leu Ile Pro Pro Thr Thr Val Leu Ile Val Asn Leu Val Gly
            980                 985                 990

Ile Val Ala Gly Val Ser Tyr Ala Ile Asn Ser Gly Tyr Gln Ser Trp
            995                 1000                1005

Gly Pro Leu Phe Gly Lys Leu Phe Phe Ala Ile Trp Val Ile Ala His
    1010                1015                1020

<210> SEQ ID NO 43
<211> LENGTH: 696
<212> TYPE: PRT
<213> ORGANISM: Eucalyptus grandis

<400> SEQUENCE: 43

Met Ser Arg Ala Pro Asn Arg Glu Phe Gln Glu Trp Trp Asn Lys Gln
1               5                   10                  15

Arg Glu Arg Gly Leu Asp Leu Ser Ser Pro Ser Ser Ala Asp Gly Pro
            20                  25                  30

Ser Thr Ser Gly Gly Gly Gly Gly Gly Pro Leu Leu Ala Val
            35                  40                  45

Glu Ile Arg Thr Pro Arg Ser Asp Gln Ala Val Glu Lys Ser Arg Ala
        50                  55                  60

Arg Ser Ala Arg Gln Leu Ser Trp Val Cys Leu Leu Arg Phe Gln Gln
65                  70                  75                  80

Ile Ala Ser Leu Leu Ala Ser Ala Ala Gly Ser Phe Leu Ser Val Leu
            85                  90                  95
```

```
Arg Thr Ala Asn Arg Arg Ile Ala Ala Ser Pro Ala Asp Ser Ser Ser
                100                 105                 110

Ser Arg Leu Tyr Arg Ile Ile Arg Phe Phe Leu Ile Leu Val Leu Val
        115                 120                 125

Leu Leu Gly Phe Glu Leu Leu Ala Tyr Ser Lys Gly Trp His Phe Ser
    130                 135                 140

Pro Pro Ser Val Gly Ser Lys Glu Val Leu Gly Phe Val Glu Leu Val
145                 150                 155                 160

Tyr Ala Asn Trp Leu Glu Ile Arg Ala Thr Tyr Leu Ala Pro Pro Leu
                165                 170                 175

Gln Ser Leu Thr Asn Val Cys Ile Val Leu Phe Leu Ile Gln Ser Val
            180                 185                 190

Asp Arg Val Val Leu Val Leu Gly Cys Ile Trp Ile Lys Ile Lys Gly
        195                 200                 205

Ile Lys Pro Val Ala Ser Ala Asp Tyr Glu Lys Lys Glu Asp Leu Glu
    210                 215                 220

Ser Glu Ser Gly Asp Glu Ala Tyr Pro Met Val Leu Val Gln Ile Pro
225                 230                 235                 240

Met Cys Asn Glu Arg Glu Val Tyr Gln Gln Ser Ile Ala Ala Val Cys
                245                 250                 255

Ile Gln Asp Trp Pro Arg Glu Arg Met Leu Val Gln Val Leu Asp Asp
            260                 265                 270

Ser Asp Asp Leu Asp Val Gln Leu Leu Ile Lys Ser Glu Val Gln Lys
        275                 280                 285

Trp Gln Gln Arg Gly Ile Arg Ile Val Tyr Arg His Arg Leu Ile Arg
    290                 295                 300

Thr Gly Tyr Lys Ala Gly Asn Leu Lys Ser Ala Met Ser Cys Asp Tyr
305                 310                 315                 320

Val Lys Asp Tyr Glu Phe Val Ala Ile Phe Asp Ala Asp Phe Gln Pro
                325                 330                 335

Gly Pro Asp Phe Leu Lys Lys Thr Ile Pro Tyr Phe Lys Gly Asn Asp
            340                 345                 350

Asp Leu Ala Leu Val Gln Thr Arg Trp Ala Phe Val Asn Lys Asp Glu
        355                 360                 365

Asn Leu Leu Thr Arg Leu Gln Asn Ile Asn Leu Ser Phe His Phe Glu
    370                 375                 380

Val Glu Gln Gln Val Asn Gly Val Phe Ile Asn Phe Phe Gly Phe Asn
385                 390                 395                 400

Gly Thr Ala Gly Val Trp Arg Ile Lys Ala Leu Glu Glu Cys Gly Gly
                405                 410                 415

Trp Leu Glu Arg Thr Thr Val Glu Asp Met Asp Ile Ala Val Arg Ala
            420                 425                 430

His Leu Cys Gly Trp Lys Phe Ile Tyr Leu Asn Asp Val Lys Cys Leu
        435                 440                 445

Cys Glu Leu Pro Glu Ser Tyr Glu Ala Tyr Lys Lys Gln Gln His Arg
    450                 455                 460

Trp His Ser Gly Pro Met Gln Leu Phe Arg Leu Cys Phe Phe Asp Ile
465                 470                 475                 480

Ile Arg Ser Lys Val Ser Leu Ala Lys Lys Ala Asn Leu Ile Phe Leu
                485                 490                 495

Phe Phe Leu Leu Arg Lys Leu Ile Leu Pro Phe Tyr Ser Phe Thr Leu
            500                 505                 510

Phe Cys Ile Ile Leu Pro Leu Thr Met Phe Leu Pro Glu Ala Gln Leu
```

```
                515                 520                 525
Pro Ala Trp Val Val Cys Tyr Val Pro Gly Val Met Ser Ile Leu Asn
    530                 535                 540
Ile Leu Pro Ala Pro Arg Ser Phe Pro Phe Ile Val Pro Tyr Leu Leu
545                 550                 555                 560
Phe Glu Asn Thr Met Ser Val Thr Lys Phe Asn Ala Met Ile Ser Gly
                565                 570                 575
Leu Phe Lys Phe Gly Ser Ser Tyr Glu Trp Ile Val Thr Lys Lys Leu
            580                 585                 590
Gly Arg Ser Ser Glu Ala Asp Leu Leu Thr Phe Gly Glu Lys Gly Ser
        595                 600                 605
Asp Pro Leu Leu Glu Thr Ser Asn Leu His Arg Ser Ser Glu Ser
    610                 615                 620
Gly Leu Ala Glu Leu Asn Lys Met Glu Met Thr Lys Lys Ala Gly Lys
625                 630                 635                 640
Leu Arg Arg Asn Arg Leu Tyr Arg Lys Glu Leu Gly Leu Ala Phe Ile
                645                 650                 655
Leu Leu Thr Ala Ala Val Arg Ser Leu Leu Ser Ala Gln Gly Ile His
            660                 665                 670
Phe Tyr Phe Leu Leu Phe Gln Gly Ile Ser Phe Leu Val Val Gly Leu
        675                 680                 685
Asp Leu Ile Gly Glu Gln Val Ser
    690                 695

<210> SEQ ID NO 44
<211> LENGTH: 1024
<212> TYPE: PRT
<213> ORGANISM: Eucalyptus grandis

<400> SEQUENCE: 44

Met Ala Cys Arg Glu Arg Arg Arg Thr Arg Ser Leu Leu Ser Leu
1               5                   10                  15
Leu Ser Pro Pro Pro Pro Asp Pro Leu Ala Ser Ala Phe Asp Leu
            20                  25                  30
Gly Glu Lys Glu Gly Arg Lys Arg Thr Thr Met Glu Ala Asn Gly Gly
        35                  40                  45
Met Ala Ala Gly Ser Tyr Lys Arg Asn Glu Leu Val Arg Ile Arg His
    50                  55                  60
Asp Ser Asp Gly Gly Pro Lys Pro Leu Lys Asn Leu Asn Gly Gln Ile
65                  70                  75                  80
Cys Gln Ile Cys Gly Asp Thr Val Gly Leu Thr Ala Ser Gly Asp Val
                85                  90                  95
Phe Val Ala Cys Asn Glu Cys Ala Phe Pro Val Cys Arg Pro Cys Tyr
            100                 105                 110
Glu Tyr Glu Arg Lys Asp Gly Asn Gln Ser Cys Pro Gln Cys Lys Ser
        115                 120                 125
Arg Tyr Lys Arg His Lys Gly Ser Pro Arg Val Asp Gly Asp Asp
    130                 135                 140
Glu Asp Glu Val Asp Asp Leu Glu Asn Glu Phe Asn Tyr Ala Gln Gly
145                 150                 155                 160
Thr Ser Ala Ala Arg Gln Gln Trp Gln Gly Glu Asp Pro Asp Leu Ser
                165                 170                 175
Ser Ser Ser Arg His Glu Ser Arg His Pro Ile Pro Leu Leu Thr Asn
            180                 185                 190
Gly Gln Pro Met Ser Gly Glu Ile Pro Cys Ala Ser Ile Asp Ser Gln
```

```
                    195                 200                 205
Ser Val Arg Thr Thr Ser Gly Pro Leu Gly Pro Ser Asp Lys His Val
210                 215                 220
His Ser Leu Pro Tyr Val Asp Pro Arg Gln Pro Val Pro Val Arg Ile
225                 230                 235                 240
Val Asp Pro Ser Lys Asp Leu Asn Thr Tyr Gly Leu Gly Asn Val Asp
                    245                 250                 255
Trp Lys Glu Arg Val Glu Gly Trp Lys Leu Lys Gln Glu Lys Asn Met
                260                 265                 270
Thr Gln Met Pro Asn Lys Tyr His Glu Gly Lys Asn Asp Ile Glu Gly
            275                 280                 285
Thr Gly Ser Asn Gly Glu Glu Leu Gln Met Ala Asp Asp Ala Arg Gln
        290                 295                 300
Pro Met Ser Arg Val Val Pro Ile Ser Ser Ser His Leu Thr Pro Tyr
305                 310                 315                 320
Arg Val Val Ile Ile Leu Arg Leu Ile Ile Leu Gly Phe Phe Leu Gln
                    325                 330                 335
Tyr Arg Val Thr His Pro Val Lys Asp Ala Tyr Pro Leu Trp Leu Thr
                340                 345                 350
Ser Val Ile Cys Glu Ile Trp Phe Ala Leu Ser Trp Leu Leu Asp Gln
            355                 360                 365
Phe Pro Lys Trp Ser Pro Ile Asn Arg Glu Thr Tyr Leu Asp Arg Leu
        370                 375                 380
Ala Leu Arg His Asp Arg Glu Gly Gly Pro Ser Gln Leu Ala Pro Val
385                 390                 395                 400
Asp Val Phe Val Ser Thr Val Asp Pro Leu Lys Glu Pro Pro Leu Ile
                    405                 410                 415
Thr Ala Asn Thr Val Leu Ser Ile Leu Ala Val Asp Tyr Pro Val Asp
                420                 425                 430
Lys Val Ser Cys Tyr Val Ser Asp Asp Gly Ser Ala Met Leu Thr Phe
            435                 440                 445
Glu Ala Leu Ser Glu Thr Ala Glu Phe Ala Arg Lys Trp Val Pro Phe
        450                 455                 460
Cys Lys Lys His Asn Ile Glu Pro Arg Ala Pro Glu Phe Tyr Phe Ala
465                 470                 475                 480
Gln Lys Ile Asp Tyr Leu Lys Asp Lys Ile Gln Pro Ser Phe Val Lys
                    485                 490                 495
Glu Arg Arg Ala Met Lys Arg Asp Tyr Glu Glu Phe Lys Val Arg Ile
                500                 505                 510
Asn Ala Leu Val Ala Lys Ala Gln Lys Met Pro Glu Glu Gly Trp Thr
            515                 520                 525
Met Gln Asp Gly Thr Ala Trp Pro Gly Asn Asn Pro Arg Asp His Pro
        530                 535                 540
Gly Met Ile Gln Val Phe Leu Gly His Ser Gly Gly Leu Asp Thr Asp
545                 550                 555                 560
Gly Asn Glu Leu Pro Arg Leu Val Tyr Val Ser Arg Glu Lys Arg Pro
                    565                 570                 575
Gly Phe Gln His His Lys Lys Ala Gly Ala Met Asn Ala Leu Ile Arg
                580                 585                 590
Val Ser Ala Val Leu Thr Asn Gly Ala Tyr Leu Leu Asn Val Asp Cys
            595                 600                 605
Asp His Tyr Phe Asn Asn Ser Lys Ala Leu Lys Glu Ala Met Cys Phe
        610                 615                 620
```

```
Met Met Asp Pro Ala Tyr Gly Lys Lys Thr Cys Tyr Val Gln Phe Pro
625                 630                 635                 640

Gln Arg Phe Asp Gly Ile Asp Leu His Asp Arg Tyr Ala Asn Arg Asn
            645                 650                 655

Ile Val Phe Phe Asp Ile Asn Leu Lys Gly Leu Asp Gly Ile Gln Gly
                660                 665                 670

Pro Val Tyr Val Gly Thr Gly Cys Cys Phe Asn Arg Gln Ala Leu Tyr
            675                 680                 685

Gly Tyr Asp Pro Val Leu Thr Glu Glu Asp Leu Glu Pro Asn Ile Ile
                690                 695                 700

Val Lys Ser Cys Cys Gly Ser Arg Lys Gly Lys Gly Gly Asn Lys
705                 710                 715                 720

Lys Tyr Ile Asp Lys Arg Ala Met Lys Arg Thr Glu Ser Thr Val
                725                 730                 735

Pro Ile Phe Asn Met Glu Asp Val Glu Glu Gly Val Glu Gly Tyr Asp
                740                 745                 750

Asp Glu Arg Ser Leu Leu Met Ser Gln Lys Ser Leu Glu Lys Arg Phe
            755                 760                 765

Gly Gln Ser Pro Val Phe Ile Ser Ala Thr Phe Met Glu Gln Gly Gly
770                 775                 780

Leu Pro Pro Ser Thr Asn Pro Ala Thr Leu Leu Lys Glu Ala Ile His
785                 790                 795                 800

Val Ile Ser Cys Gly Tyr Glu Asp Lys Thr Glu Trp Gly Lys Glu Ile
                805                 810                 815

Gly Trp Ile Tyr Gly Ser Val Thr Glu Asp Ile Leu Thr Gly Phe Lys
                820                 825                 830

Met His Ala Arg Gly Trp Ile Ser Ile Tyr Cys Met Pro Pro Arg Pro
            835                 840                 845

Ala Phe Lys Gly Ser Ala Pro Ile Asn Leu Ser Asp Arg Leu Asn Gln
            850                 855                 860

Val Leu Arg Trp Ala Leu Gly Ser Ile Glu Ile Leu Ser Arg His
865                 870                 875                 880

Cys Pro Ile Trp Tyr Gly Tyr Asn Gly Lys Leu Arg Leu Leu Glu Arg
                885                 890                 895

Leu Ala Tyr Ile Asn Thr Ile Val Tyr Pro Leu Thr Ser Ile Pro Leu
            900                 905                 910

Ile Ala Tyr Cys Ile Leu Pro Ala Phe Cys Leu Phe Thr Asn Lys Phe
            915                 920                 925

Ile Ile Pro Glu Ile Ser Asn Phe Ala Ser Met Trp Phe Ile Leu Leu
            930                 935                 940

Phe Val Ser Ile Phe Thr Thr Gly Ile Leu Glu Leu Arg Trp Ser Gly
945                 950                 955                 960

Val Ser Ile Glu Asp Trp Trp Arg Asn Glu Gln Phe Trp Val Ile Gly
                965                 970                 975

Gly Thr Ser Ala His Leu Phe Ala Val Phe Gln Gly Leu Leu Lys Val
            980                 985                 990

Leu Ala Gly Ile Asp Thr Asn Phe Thr Val Thr Ser Lys Ala Gly Asp
            995                 1000                1005

Glu Asp Gly Asp Phe Ala Glu Leu Tyr Val Phe Lys Trp Thr Ser Leu
    1010                1015                1020

<210> SEQ ID NO 45
<211> LENGTH: 1024
<212> TYPE: PRT
<213> ORGANISM: Eucalyptus grandis
```

<400> SEQUENCE: 45

```
Met Glu Ser Glu Gly Glu Thr Gly Gly Lys Ser Met Lys Ile Leu Gly
 1               5                  10                  15

Gly Gln Val Tyr Gln Ile Cys Gly Asp Asn Val Gly Lys Ser Val Asp
             20                  25                  30

Gly Glu Pro Phe Val Ala Cys Asn Val Cys Ala Phe Pro Val Cys Arg
         35                  40                  45

Pro Cys Tyr Glu Tyr Glu Arg Lys Asp Gly Asn Gln Ser Cys Pro Gln
     50                  55                  60

Cys Lys Thr Arg Tyr Lys Arg His Arg Gly Ser Pro Ala Ile Leu Gly
 65                  70                  75                  80

Asp Gln Glu Asp Ala Asp Ala Asp Ser Val Ser Asp Phe Asn
                 85                  90                  95

Tyr Ser Glu Asn Gln Asn Leu Asn Arg Lys Thr Glu Arg Ile Leu
                100                 105                 110

Ser Trp His Met Gln Tyr Gly Gln Asn Glu Asp Val Ser Ala Pro Asn
            115                 120                 125

Tyr Asp Lys Glu Val Ser His Asn His Ile Pro Arg Leu Thr Ser Gly
        130                 135                 140

Gln Glu Val Ser Gly Glu Leu Ser Ala Ala Ser Pro Glu Arg Leu Ser
145                 150                 155                 160

Val Ala Ser Pro Asp Val Gly Ala Gly Lys Arg Ile His Ser Leu Pro
                165                 170                 175

Tyr Val Ala Asp Ala Asn Gln Ser Pro Asn Ile Arg Val Val Asp Pro
            180                 185                 190

Val Arg Glu Phe Gly Ser Ser Gly Leu Asn Asn Val Ala Trp Lys Glu
        195                 200                 205

Arg Val Asp Gly Trp Lys Met Lys Gln Glu Lys Asn Val Ala Pro Met
    210                 215                 220

Ser Thr Ala Gln Ala Thr Ser Glu Arg Gly Val Gly Asp Ile Asp Ala
225                 230                 235                 240

Ser Thr Asp Val Leu Val Asp Asp Ser Leu Leu Asn Asp Glu Ala Arg
                245                 250                 255

Gln Pro Leu Ser Arg Lys Val Ser Val Pro Ser Ser Arg Ile Asn Pro
            260                 265                 270

Tyr Arg Met Val Ile Val Leu Arg Leu Ile Ile Leu Ser Ile Phe Leu
        275                 280                 285

His Tyr Arg Ile Thr Asn Pro Val Pro Asn Ala Tyr Ala Leu Trp Leu
    290                 295                 300

Ile Ser Val Ile Cys Glu Ile Trp Phe Ala Ile Ser Trp Ile Leu Asp
305                 310                 315                 320

Gln Phe Pro Lys Trp Phe Pro Val Asn Arg Glu Thr Tyr Leu Asp Arg
                325                 330                 335

Leu Ala Ile Arg Tyr Asp Arg Glu Gly Glu Pro Ser Gln Leu Ala Ala
            340                 345                 350

Val Asp Ile Phe Val Ser Thr Val Asp Pro Leu Lys Glu Pro Pro Leu
        355                 360                 365

Val Thr Ala Asn Thr Val Leu Ser Ile Leu Ala Val Asp Tyr Pro Val
    370                 375                 380

Asp Lys Val Ser Cys Tyr Val Ser Asp Gly Ala Ala Met Leu Thr
385                 390                 395                 400

Phe Glu Ala Leu Ser Glu Thr Ser Glu Phe Ala Arg Lys Trp Val Pro
                405                 410                 415
```

-continued

Phe Cys Lys Lys Tyr Ser Ile Glu Pro Arg Ala Pro Glu Trp Tyr Phe
            420                 425                 430

Ala Leu Lys Ile Asp Tyr Leu Lys Asp Lys Val His Pro Ser Phe Val
            435                 440                 445

Lys Asp Arg Arg Ala Met Lys Arg Glu Tyr Glu Phe Lys Val Arg
450                 455                 460

Ile Asn Gly Leu Val Ala Lys Ala Lys Ile Pro Glu Glu Gly Trp
465                 470                 475                 480

Ile Met Gln Asp Gly Thr Pro Trp Pro Gly Asn Asn Thr Arg Asp His
            485                 490                 495

Pro Gly Met Ile Gln Val Phe Leu Gly Gln Ser Gly Gly Leu Asp Ala
            500                 505                 510

Glu Gly Asn Glu Leu Pro Arg Leu Val Tyr Val Ser Arg Glu Lys Arg
            515                 520                 525

Pro Gly Phe Gln His His Lys Lys Ala Gly Ala Met Asn Ala Leu Val
            530                 535                 540

Arg Val Ser Ala Val Leu Thr Asn Gly Pro Phe Leu Leu Asn Leu Asp
545                 550                 555                 560

Cys Asp His Tyr Ile Asn Asn Ser Lys Ala Leu Arg Glu Ala Met Cys
            565                 570                 575

Phe Leu Met Asp Pro Asn Leu Gly Lys His Val Cys Tyr Val Gln Phe
            580                 585                 590

Pro Gln Arg Phe Asp Gly Ile Asp Arg Asn Asp Arg Tyr Ala Asn Arg
            595                 600                 605

Asn Thr Val Phe Phe Asp Ile Asn Leu Arg Gly Leu Asp Gly Ile Gln
            610                 615                 620

Gly Pro Val Tyr Val Gly Thr Gly Cys Val Phe Asn Arg Thr Ala Leu
625                 630                 635                 640

Tyr Gly Tyr Glu Pro Pro His Lys Pro Lys Gln Arg Lys Ser Gly Phe
            645                 650                 655

Leu Ser Ser Leu Cys Gly Gly Ser Arg Lys Lys Ser Arg Ser Ser Lys
            660                 665                 670

Lys Gly Ser Asp Lys Lys Lys Ser Ser Lys His Val Asp Pro Thr Val
            675                 680                 685

Pro Ile Phe Ser Leu Glu Asp Ile Glu Glu Gly Val Glu Gly Ala Gly
            690                 695                 700

Phe Asp Asp Glu Lys Ser Leu Leu Met Ser Gln Met Ser Leu Glu Lys
705                 710                 715                 720

Arg Phe Gly Gln Ser Ala Val Phe Val Ala Ser Thr Leu Met Glu Asn
            725                 730                 735

Gly Gly Val Pro Gln Ser Ala Thr Pro Glu Thr Leu Leu Lys Glu Ala
            740                 745                 750

Ile His Val Ile Ser Cys Gly Tyr Glu Asp Lys Ser Asp Trp Gly Ser
            755                 760                 765

Glu Ile Gly Trp Ile Tyr Gly Ser Val Thr Glu Asp Ile Leu Thr Gly
            770                 775                 780

Phe Lys Met His Ala Arg Gly Trp Arg Ser Ile Tyr Cys Met Pro Lys
785                 790                 795                 800

Arg Pro Ala Phe Lys Gly Ser Ala Pro Ile Asn Leu Ser Asp Arg Leu
            805                 810                 815

Asn Gln Val Leu Arg Trp Ala Leu Gly Ser Val Glu Ile Leu Phe Ser
            820                 825                 830

Arg His Cys Pro Ile Trp Tyr Gly Tyr Gly Gly Arg Leu Lys Trp Leu

```
                835                 840                 845
Glu Arg Phe Ala Tyr Val Asn Thr Thr Ile Tyr Pro Ile Thr Ala Ile
850                 855                 860

Pro Leu Leu Met Tyr Cys Thr Leu Pro Ala Val Cys Leu Leu Thr Asn
865                 870                 875                 880

Lys Phe Ile Ile Pro Gln Ile Ser Asn Val Ala Ser Ile Trp Phe Ile
                885                 890                 895

Ser Leu Phe Leu Ser Ile Phe Ala Thr Gly Ile Leu Glu Met Arg Trp
                900                 905                 910

Ser Gly Val Gly Ile Asp Glu Trp Trp Arg Asn Glu Gln Phe Trp Val
                915                 920                 925

Ile Gly Gly Val Ser Ala His Leu Phe Ala Val Phe Gln Gly Leu Leu
                930                 935                 940

Lys Val Leu Ala Gly Ile Asp Thr Asn Phe Thr Val Thr Ser Lys Ala
945                 950                 955                 960

Ser Asp Glu Asp Gly Asp Ser Ala Glu Leu Tyr Met Phe Lys Trp Thr
                965                 970                 975

Thr Leu Leu Ile Pro Pro Thr Thr Leu Leu Ile Ile Asn Leu Val Gly
                980                 985                 990

Val Val Ala Gly Ile Ser Tyr Ala Ile Asn Ser Gly Tyr Gln Ser Trp
                995                 1000                1005

Gly Pro Leu Phe Gly Lys Leu Phe Phe Ala Phe Trp Val Ile Val His
    1010                1015                1020

<210> SEQ ID NO 46
<211> LENGTH: 533
<212> TYPE: PRT
<213> ORGANISM: Eucalyptus grandis

<400> SEQUENCE: 46

Met Asp Arg Leu Ser Ala Thr Gly Leu Leu Pro Asp Thr Phe Gly Gly
1               5                   10                  15

Ala Arg Asp Asp Ile Ser Met Gln Leu Ser Leu Ile Trp Ala Gln Ile
                20                  25                  30

Lys Ala Pro Leu Leu Val Pro Leu Leu Arg Leu Ala Val Phe Leu Cys
            35                  40                  45

Leu Ala Met Ser Leu Met Leu Phe Leu Glu Arg Val Tyr Met Ala Val
    50                  55                  60

Val Ile Leu Leu Val Lys Leu Phe Gly Arg Lys Pro Glu Lys Arg Tyr
65                  70                  75                  80

Arg Trp Glu Pro Met Lys Asp Asp Val Glu Leu Gly Asn Ser Ala Tyr
                85                  90                  95

Pro Met Val Leu Val Gln Ile Pro Met Tyr Asn Glu Arg Glu Val Tyr
            100                 105                 110

Gln Leu Ser Ile Gly Ala Ala Cys Gly Leu Ser Trp Pro Ser Asp Arg
        115                 120                 125

Ile Ile Ile Gln Val Leu Asp Asp Ser Thr Asp Pro Thr Ile Lys Asp
    130                 135                 140

Leu Val Glu Leu Glu Cys Gln Arg Trp Ala Ser Lys Gly Ile Asn Ile
145                 150                 155                 160

Arg Tyr Glu Ile Arg Asp Asn Arg Asn Gly Tyr Lys Ala Gly Ala Leu
                165                 170                 175

Lys Glu Gly Met Lys Arg Ser Tyr Val Lys Gln Cys Asp Tyr Val Ala
            180                 185                 190

Ile Leu Asp Ala Asp Phe Gln Pro Glu Pro Asp Phe Leu Trp Arg Thr
```

```
              195                 200                 205
Ile Pro Phe Leu Val His Asn Pro Glu Val Ala Leu Val Gln Ala Arg
    210                 215                 220

Trp Lys Phe Val Asn Ala Asp Glu Cys Leu Met Thr Arg Met Gln Glu
225                 230                 235                 240

Met Ser Leu Asp Tyr His Phe Thr Val Glu Gln Val Gly Ser Ser
                245                 250                 255

Thr His Ala Phe Phe Gly Phe Asn Gly Thr Ala Gly Val Trp Arg Ile
                260                 265                 270

Ser Ala Leu Asn Glu Ala Gly Gly Trp Lys Asp Arg Thr Thr Val Glu
            275                 280                 285

Asp Met Asp Leu Ala Val Arg Ala Ser Leu Lys Gly Trp Lys Phe Val
        290                 295                 300

Tyr Leu Gly Ser Leu Lys Val Lys Asn Glu Leu Pro Ser Thr Phe Lys
305                 310                 315                 320

Ala Tyr Arg Phe Gln Gln His Arg Trp Ser Cys Gly Pro Ala Asn Leu
                325                 330                 335

Phe Arg Lys Met Ala Met Glu Ile Ile Arg Asn Lys Lys Val Thr Leu
                340                 345                 350

Trp Lys Lys Val His Val Ile Tyr Ser Phe Phe Leu Val Arg Lys Ile
            355                 360                 365

Val Ala His Ile Val Thr Phe Ile Phe Tyr Cys Val Val Leu Pro Ala
        370                 375                 380

Thr Val Phe Val Pro Glu Val Thr Val Pro Lys Trp Gly Ala Val Tyr
385                 390                 395                 400

Ile Pro Ser Ile Ile Thr Val Leu Asn Ala Val Gly Thr Pro Arg Ser
                405                 410                 415

Leu His Leu Val Val Phe Trp Ile Leu Phe Glu Asn Val Met Ser Phe
                420                 425                 430

His Arg Thr Lys Ala Thr Phe Ile Gly Leu Leu Glu Ala Gly Arg Val
            435                 440                 445

Asn Glu Trp Ile Val Thr Glu Lys Leu Gly Asp Ala Leu Lys Val Lys
        450                 455                 460

Ala Ser Asn Lys Val Pro Lys Lys Pro Lys Phe Arg Phe Gly Asp Arg
465                 470                 475                 480

Leu His Val Leu Glu Leu Gly Val Gly Ala Tyr Leu Phe Phe Cys Gly
                485                 490                 495

Cys Tyr Asp Ile Ala Phe Gly Arg Asn His Tyr Phe Met Tyr Leu Phe
                500                 505                 510

Ala Gln Ala Ile Ala Phe Phe Ile Met Gly Phe Gly Tyr Ile Gly Thr
            515                 520                 525

Phe Val Pro Asn Ser
    530

<210> SEQ ID NO 47
<211> LENGTH: 709
<212> TYPE: PRT
<213> ORGANISM: Eucalyptus grandis

<400> SEQUENCE: 47

Met Ala Pro Ser Phe Asp Trp Trp Ala Lys Gly Gly His Lys Gly Thr
1               5                   10                  15

Pro Val Val Val Lys Met Glu Asn Pro Asn Trp Ser Met Val Glu Leu
                20                  25                  30

Glu Ser Pro Ser Glu Glu Asp Phe Leu Ile Gly Gly Asp Ser Ala Pro
```

```
                    35                  40                  45
Ser Gly Arg Val Arg Asp Lys Gly Arg Asn Lys Asn Ala Lys Gln Leu
        50                  55                  60
Thr Trp Val Leu Leu Lys Ala His Lys Ala Ala Gly Cys Leu Thr
 65                  70                  75                  80
Ser Ile Ala Gly Ala Ala Phe Thr Leu Ala Ser Ala Val Arg Arg Arg
                85                  90                  95
Val Ala Ser Gly Arg Thr Asp Ala Asp Ala Asp Glu Ala Glu Thr Gly
                100                 105                 110
Glu Ser Arg Ser Gly Arg Glu Lys Glu Asn Pro Thr Val Lys Ser Arg
                115                 120                 125
Ile Tyr Ala Cys Ile Lys Ala Phe Leu Trp Leu Ser Ile Leu Leu Leu
                130                 135                 140
Gly Phe Glu Val Ala Ala Tyr Phe Lys Gly Trp His Phe Gly Ala Leu
145                 150                 155                 160
Glu Leu Gln Tyr Leu Leu Ala Ala Pro Leu Gly Val Lys Gly Ala Phe
                165                 170                 175
Asn Ser Leu Tyr Ser Arg Trp Val Leu Ile Arg Val Glu Tyr Leu Ala
                180                 185                 190
Pro Pro Leu Gln Phe Leu Ala Asn Val Cys Ile Val Leu Phe Leu Ile
                195                 200                 205
Gln Ser Ile Asp Arg Leu Val Leu Cys Leu Gly Cys Phe Trp Ile Lys
                210                 215                 220
Phe Lys Lys Ile Lys Pro Val Pro Lys Glu Ser Gly Ala Ala Val Asp
225                 230                 235                 240
Pro Glu Ser Gly Glu Asn Gly Phe Phe Pro Met Val Leu Val Gln Ile
                245                 250                 255
Pro Met Cys Asn Glu Lys Glu Val Tyr Gln Gln Ser Ile Ala Ala Val
                260                 265                 270
Cys Asn Leu Asp Trp Pro Lys Ser Ser Leu Leu Ile Gln Val Leu Asp
                275                 280                 285
Asp Ser Asp Asp Pro Thr Thr Gln Ser Leu Ile Lys Glu Glu Val Gln
290                 295                 300
Lys Trp Gln Gln Glu Gly Ala Asn Ile Leu Tyr Arg His Arg Val Ile
305                 310                 315                 320
Arg Asp Gly Tyr Lys Ala Gly Asn Leu Lys Ser Ala Met Asn Cys Ser
                325                 330                 335
Tyr Val Lys Asp Tyr Glu Phe Val Ala Ile Phe Asp Ala Asp Phe Gln
                340                 345                 350
Pro Thr Pro Asp Phe Leu Lys Arg Thr Val Pro His Phe Lys Asp Asn
                355                 360                 365
Glu Glu Leu Gly Leu Val Gln Ala Arg Trp Ser Phe Val Asn Lys Asp
                370                 375                 380
Glu Asn Leu Leu Thr Arg Leu Gln Asn Val Asn Leu Ser Phe His Phe
385                 390                 395                 400
Glu Val Glu Gln Gln Val Asn Gly Ile Phe Ile Asn Phe Phe Gly Phe
                405                 410                 415
Asn Gly Thr Ala Gly Val Trp Arg Ile Lys Ala Leu Glu Asp Ala Gly
                420                 425                 430
Gly Trp Leu Glu Arg Thr Thr Val Glu Asp Met Asp Ile Ala Val Arg
            435                 440                 445
Ala His Leu Arg Gly Trp Lys Phe Val Phe Leu Asn Asp Val Glu Cys
450                 455                 460
```

```
Gln Cys Glu Leu Pro Glu Ser Tyr Glu Ala Tyr Arg Lys Gln Gln His
465                 470                 475                 480

Arg Trp His Ser Gly Pro Met Gln Leu Phe Arg Leu Cys Leu Leu Asp
            485                 490                 495

Ile Ile Arg Ser Lys Ile Ser Val Trp Lys Lys Phe Asn Met Ile Phe
                500                 505                 510

Leu Phe Phe Leu Leu Arg Lys Leu Ile Leu Pro Phe Tyr Ser Phe Thr
        515                 520                 525

Leu Phe Cys Ile Ile Leu Pro Met Thr Met Phe Val Pro Glu Ala Glu
    530                 535                 540

Leu Pro Ala Trp Val Val Cys Tyr Ile Pro Ala Thr Met Ser Phe Leu
545                 550                 555                 560

Asn Ile Leu Pro Ala Pro Lys Ser Phe Pro Phe Ile Val Pro Tyr Leu
                565                 570                 575

Leu Phe Glu Asn Thr Met Ser Val Thr Lys Phe Asn Ala Met Ile Ser
        580                 585                 590

Gly Leu Phe Gln Leu Gly Ser Ala Tyr Glu Trp Val Thr Lys Lys
    595                 600                 605

Ser Gly Arg Ser Ser Glu Gly Asp Leu Val Ala Leu Ile Asp Lys Glu
610                 615                 620

Pro Lys His Gln Arg Gly Val Ser Val Pro Asp Leu Glu Glu Met Lys
625                 630                 635                 640

Glu Glu Ile Gln Lys Gln Glu Lys Leu Ala Ser Arg Lys Lys Lys His
                645                 650                 655

Asn Arg Ile Tyr Val Lys Glu Leu Ser Leu Ala Phe Leu Leu Leu Thr
                660                 665                 670

Ala Ser Ala Arg Ser Leu Leu Ser Ala Gln Gly Ile His Phe Tyr Phe
            675                 680                 685

Leu Leu Phe Gln Gly Ile Ser Phe Leu Leu Val Gly Leu Asp Leu Ile
        690                 695                 700

Gly Glu Gln Val Glu
705

<210> SEQ ID NO 48
<211> LENGTH: 1024
<212> TYPE: PRT
<213> ORGANISM: Eucalyptus grandis

<400> SEQUENCE: 48

Met Glu Ser Asp Ala Glu Asn Gly Gly Lys Pro Leu Lys Ser Leu Gly
1               5                   10                  15

Gly Gln Val Cys Gln Ile Cys Gly Glu Asn Val Gly Lys Thr Leu Asp
            20                  25                  30

Gly Glu Pro Phe Ile Ala Cys Asp Val Cys Ala Phe Pro Val Cys Arg
        35                  40                  45

Pro Cys Tyr Glu Tyr Glu Arg Lys Asp Gly Asn Gln Ser Cys Pro Gln
    50                  55                  60

Cys Lys Thr Arg Tyr Lys Arg His Lys Gly Ser Pro Ala Ile Leu Gly
65                  70                  75                  80

Asp His Glu Glu Asp Gly Asp Ala Gly Asp Asp Tyr His Tyr Ser Ser
                85                  90                  95

Glu Asp Gln Thr Gln Lys Glu Lys Ile Ala Glu Arg Met Leu Ser Trp
            100                 105                 110

His Met Thr Tyr Gly Arg Gly Glu Asn Val Ala Pro Ala Asn Tyr Asp
        115                 120                 125
```

-continued

Gly Glu Val Ser Arg Asn His Ile Pro Leu Leu Thr Ser Arg Gln Glu
130                 135                 140

Val Ser Gly Glu Leu Ser Ala Ala Ser Pro Glu Arg Leu Ser Met Ala
145                 150                 155                 160

Ser Pro Gly Val Gly Arg Val His Arg Val Arg Pro Leu Ser Tyr Ala
            165                 170                 175

Ser Asp Val Thr Gln Ser Pro Asn Ile Arg Val Val Asp Pro Ala Arg
            180                 185                 190

Glu Phe Gly Ser Pro Gly Ile Gly Asn Val Ala Trp Lys Glu Arg Val
        195                 200                 205

Asp Gly Trp Lys Met Lys Gln Glu Lys Asn Val Gly Pro Met Ser Thr
    210                 215                 220

Gly Gln Ala Ala Ser Glu Arg Gly Ala Gly Asp Ile Asp Ala Ser Thr
225                 230                 235                 240

Asp Val Leu Val Asp Asp Ser Leu Leu Asn Asp Glu Ala Arg Gln Pro
            245                 250                 255

Leu Ser Arg Lys Val Ser Ile Pro Ser Ser Arg Ile Asn Pro Tyr Arg
            260                 265                 270

Met Val Ile Met Leu Arg Leu Val Ile Leu Cys Ile Phe Leu His Tyr
        275                 280                 285

Arg Ile Thr Asn Pro Val Pro Asn Ala Tyr Ala Leu Trp Leu Ile Ser
    290                 295                 300

Val Ile Cys Glu Ile Trp Phe Ala Ile Ser Trp Ile Leu Asp Gln Phe
305                 310                 315                 320

Pro Lys Trp Phe Pro Val Asn Arg Glu Thr Tyr Leu Asp Arg Leu Ala
            325                 330                 335

Leu Arg Tyr Asp Arg Glu Gly Glu Pro Ser Gln Leu Ala Ala Val Asp
            340                 345                 350

Ile Phe Val Ser Thr Val Asp Pro Leu Lys Glu Pro Pro Leu Val Thr
        355                 360                 365

Ala Asn Thr Val Leu Ser Ile Leu Ala Val Asp Tyr Pro Val Asp Lys
    370                 375                 380

Val Ser Cys Tyr Val Ser Asp Asp Gly Ala Ala Met Leu Thr Phe Glu
385                 390                 395                 400

Ala Leu Ser Glu Thr Ala Glu Phe Ala Arg Lys Trp Val Pro Phe Cys
            405                 410                 415

Lys Lys Tyr Asn Ile Glu Pro Arg Ala Pro Glu Trp Tyr Phe Thr Lys
            420                 425                 430

Lys Ile Asp Tyr Leu Lys Asp Lys Ile Gln Pro Ser Phe Val Lys Asp
        435                 440                 445

Arg Arg Ala Met Lys Arg Glu Tyr Glu Glu Phe Lys Val Arg Ile Asn
    450                 455                 460

Gly Leu Val Ala Lys Ala Gln Lys Ile Pro Glu Glu Gly Trp Val Met
465                 470                 475                 480

Gln Asp Gly Thr Pro Trp Pro Gly Asn Asn Thr Arg Asp His Pro Gly
            485                 490                 495

Met Ile Gln Val Phe Leu Gly Ser Gly Gly Leu Asp Ala Glu Gly
            500                 505                 510

Asn Glu Leu Pro Arg Leu Val Tyr Val Ser Arg Glu Lys Arg Pro Gly
        515                 520                 525

Phe Gln His His Lys Lys Ala Gly Ala Met Asn Ser Leu Val Arg Val
    530                 535                 540

Ser Ala Val Leu Thr Asn Gly Pro Phe Leu Leu Asn Leu Asp Cys Asp
545                 550                 555                 560

```
His Tyr Ile Asn Asn Ser Lys Ala Leu Arg Glu Ala Met Cys Phe Leu
            565                 570                 575

Met Asp Pro Asn Leu Gly Lys His Val Cys Tyr Val Gln Phe Pro Gln
            580                 585                 590

Arg Phe Asp Gly Ile Asp Lys Asn Asp Arg Tyr Ala Asn Arg Asn Thr
            595                 600                 605

Val Phe Phe Asp Ile Asn Leu Arg Gly Leu Asp Gly Ile Gln Gly Pro
            610                 615                 620

Val Tyr Val Gly Thr Gly Cys Val Phe Asn Arg Thr Ala Leu Tyr Gly
625                 630                 635                 640

Tyr Glu Pro Pro Leu Lys Pro Lys His Lys Lys Pro Gly Val Leu Ser
            645                 650                 655

Leu Leu Cys Gly Gly Ser Arg Lys Lys Ser Ser Lys Ser Ser Lys Lys
            660                 665                 670

Ser Ser Asp Arg Lys Arg Ser Gly Lys His Val Asp Thr Thr Val Pro
            675                 680                 685

Ile Phe Ser Leu Glu Asp Ile Glu Glu Gly Val Glu Gly Ala Gly Phe
            690                 695                 700

Asp Asp Glu Lys Ser Leu Leu Met Ser Gln Met Ser Leu Glu Lys Arg
705                 710                 715                 720

Phe Gly Gln Ser Ala Val Phe Ala Ser Thr Leu Met Glu Asn Gly
            725                 730                 735

Gly Val Pro Gln Ser Ala Thr Pro Glu Thr Leu Leu Lys Glu Ala Ile
            740                 745                 750

His Val Ile Ser Cys Gly Tyr Glu Asp Lys Ser Glu Trp Gly Ser Glu
            755                 760                 765

Ile Gly Trp Ile Tyr Gly Ser Val Thr Glu Asp Ile Leu Thr Gly Phe
            770                 775                 780

Lys Met His Ala Arg Gly Trp Arg Ser Ile Tyr Cys Met Pro Lys Leu
785                 790                 795                 800

Pro Ala Phe Lys Gly Ser Ala Pro Ile Asn Leu Ser Asp Arg Leu Asn
            805                 810                 815

Gln Val Leu Arg Trp Ala Leu Gly Ser Val Glu Ile Leu Phe Ser Arg
            820                 825                 830

His Cys Pro Ile Trp Tyr Gly Tyr Gly Gly Arg Leu Lys Trp Leu Glu
            835                 840                 845

Arg Phe Ala Tyr Val Asn Thr Thr Ile Tyr Pro Val Thr Ala Ile Pro
850                 855                 860

Leu Leu Met Tyr Cys Thr Leu Pro Ala Val Cys Leu Leu Thr Asn Lys
865                 870                 875                 880

Phe Ile Ile Pro Gln Ile Ser Asn Ile Ala Ser Ile Trp Phe Ile Ser
            885                 890                 895

Leu Phe Leu Ser Ile Phe Ala Thr Gly Ile Leu Glu Met Arg Trp Ser
            900                 905                 910

Gly Val Gly Ile Asp Glu Trp Trp Arg Asn Glu Gln Phe Trp Val Ile
            915                 920                 925

Gly Gly Val Ser Ser His Leu Phe Ala Val Phe Gln Gly Leu Leu Lys
            930                 935                 940

Val Leu Ala Gly Ile Asp Thr Asn Phe Thr Val Thr Ser Lys Ala Ser
945                 950                 955                 960

Asp Glu Glu Gly Asp Phe Thr Glu Leu Tyr Thr Phe Lys Trp Thr Thr
            965                 970                 975

Leu Leu Ile Pro Pro Thr Thr Leu Leu Ile Ile Asn Leu Val Gly Val
```

-continued

```
            980                 985                 990
Val Ala Gly Ile Ser Tyr Ala Ile Asn Ser Gly Tyr Gln Ser Trp Gly
        995                1000               1005

Pro Leu Phe Gly Lys Leu Phe Phe Ala Phe Trp Val Ile Ile His Leu
   1010               1015               1020

<210> SEQ ID NO 49
<211> LENGTH: 1024
<212> TYPE: PRT
<213> ORGANISM: Pinus radiata

<400> SEQUENCE: 49

Met Glu Ala Ser Ala Gly Leu Val Ala Gly Ser His Asn Arg Asn Glu
  1               5                  10                  15

Phe Val Val Ile His Gly His Glu Glu Pro Lys Pro Leu Asn Thr Leu
                 20                  25                  30

Ser Gly His Val Cys Gln Ile Cys Gly Glu Asp Val Gly Leu Asn Thr
             35                  40                  45

Asp Gly Glu Leu Phe Val Ala Cys Asn Glu Cys Gly Phe Pro Val Cys
         50                  55                  60

Arg Pro Cys Tyr Glu Tyr Glu Arg Glu Gly Asn Gln Ser Cys Pro
 65                  70                  75                  80

Gln Cys Asn Thr Arg Tyr Lys Arg Gln Lys Gly Ser Pro Arg Val Glu
                 85                  90                  95

Gly Asp Asp Asp Glu Glu Asp Val Asp Ile Glu His Glu Phe Asn
            100                 105                 110

Val Glu Thr Gln Gln Arg Asn Arg Gln Gln Ile Thr Glu Ala Met Leu
            115                 120                 125

His Gly Arg Met Ser Tyr Gly Arg Gly Pro Asp Asp Glu Asn Ser Gln
        130                 135                 140

Ile Ala His Asn Pro Glu Leu Pro Pro Gln Ile Pro Val Leu Ala Asn
145                 150                 155                 160

Gly His Ser Val Val Ser Gly Glu Ile Pro Thr Ser Tyr Tyr Ala Asp
                165                 170                 175

Asn Gln Leu Leu Ala Asn Pro Ala Met Leu Lys Arg Val His Pro Ser
            180                 185                 190

Ser Glu Pro Gly Ser Gly Arg Ile Met Asp Pro Asn Arg Asp Ile
            195                 200                 205

Gly Ser Tyr Gly Phe Gly Asn Val Ser Trp Lys Glu Arg Gly Asp Gly
        210                 215                 220

Tyr Lys Ser Lys Glu Asn Lys Ser Gly Gln Leu Asp Met Thr Glu Gly
225                 230                 235                 240

Arg Tyr Gln Tyr Asn Gly Gly Phe Ala Pro Asn Glu Pro Glu Asp Tyr
                245                 250                 255

Ile Asp Pro Asp Met Pro Met Thr Asp Glu Ala Arg Gln Pro Leu Ser
            260                 265                 270

Arg Lys Val Pro Ile Pro Ser Ser Lys Ile Asn Pro Tyr Arg Met Val
            275                 280                 285

Ile Val Ile Arg Leu Ile Val Leu Gly Ile Phe Leu Arg Tyr Arg Leu
        290                 295                 300

Leu Asn Pro Val Lys Asn Ala Tyr Gly Leu Trp Ala Thr Ser Ile Val
305                 310                 315                 320

Cys Glu Ile Trp Phe Ala Leu Ser Trp Ile Leu Asp Gln Phe Pro Lys
                325                 330                 335

Trp Leu Pro Ile Ser Arg Glu Thr Tyr Leu Asp Arg Leu Ser Leu Arg
```

-continued

```
                340                 345                 350
Tyr Glu Arg Glu Gly Glu Pro Ser Met Leu Ala Pro Val Asp Leu Phe
            355                 360                 365
Val Ser Thr Val Asp Pro Leu Lys Glu Pro Leu Val Thr Ala Asn
    370                 375                 380
Thr Val Leu Ser Ile Leu Ser Val Asp Tyr Pro Val Asp Asn Val Ser
385                 390                 395                 400
Cys Tyr Val Ser Asp Asp Gly Ala Ser Met Leu Thr Phe Glu Ser Leu
                405                 410                 415
Ser Glu Thr Ser Glu Phe Ala Arg Lys Trp Val Pro Phe Cys Lys Lys
            420                 425                 430
Phe Asp Ile Glu Pro Arg Ala Pro Glu Ile Tyr Phe Ser Gln Lys Ile
            435                 440                 445
Asp Tyr Leu Lys Asp Lys Phe Gln Pro Thr Phe Val Lys Glu Arg Arg
        450                 455                 460
Ala Met Lys Arg Glu Tyr Glu Glu Phe Lys Val Arg Ile Asn Arg Leu
465                 470                 475                 480
Val Ala Lys Ala Ser Lys Val Pro Lys Glu Gly Trp Thr Met Gln Asp
                485                 490                 495
Gly Thr Pro Trp Pro Gly Asn Asn Thr Arg Asp His Pro Gly Met Ile
                500                 505                 510
Gln Val Phe Leu Gly His Ser Gly Gly Leu Asp Thr Glu Gly Asn Glu
            515                 520                 525
Leu Pro Arg Leu Val Tyr Val Ser Arg Glu Lys Arg Pro Gly Phe Gln
        530                 535                 540
His His Lys Lys Ala Gly Ala Met Asn Ala Leu Val Arg Val Ser Ala
545                 550                 555                 560
Val Leu Thr Asn Ala Pro Phe Met Leu Asn Leu Asp Cys Asp His Tyr
                565                 570                 575
Ile Asn Asn Ser Lys Ala Ile Arg Glu Gly Met Cys Phe Met Met Asp
                580                 585                 590
Pro Gln Val Gly Arg Lys Val Cys Tyr Val Gln Phe Pro Gln Arg Phe
        595                 600                 605
Asp Gly Ile Asp Arg Asn Asp Arg Tyr Ala Asn Arg Asn Thr Val Phe
        610                 615                 620
Phe Asp Ile Asn Met Lys Gly Leu Asp Gly Ile Gln Gly Pro Val Tyr
625                 630                 635                 640
Val Gly Thr Gly Cys Met Phe Arg Arg Gln Ala Leu Tyr Gly Tyr Gly
                645                 650                 655
Pro Pro Lys Gly Pro Lys Arg Pro Lys Met Val Thr Cys Asp Cys Leu
            660                 665                 670
Pro Cys Cys Gly Pro Arg Lys Lys Ser Pro Lys Lys Asn Ser Ser Lys
        675                 680                 685
Lys Ser Ala Gly Ile Pro Ala Pro Ala Tyr Asn Leu Asp Gly Ile Glu
    690                 695                 700
Glu Gly Val Glu Gly Tyr Asp Asp Glu Arg Ala Leu Leu Met Ser Gln
705                 710                 715                 720
Leu Asp Phe Glu Lys Lys Phe Gly Gln Ser Ser Ala Phe Val Gln Ser
                725                 730                 735
Thr Leu Met Glu Asn Gly Gly Val Pro Gln Thr Ala Asn Pro Ala Glu
            740                 745                 750
Leu Leu Lys Glu Ala Ile His Val Ile Ser Cys Gly Tyr Glu Asp Lys
            755                 760                 765
```

-continued

```
Thr Glu Trp Gly Lys Glu Leu Gly Trp Ile Tyr Gly Ser Val Thr Glu
        770                 775                 780

Asp Ile Leu Thr Gly Phe Lys Met His Thr Arg Gly Trp Arg Ser Ile
785                 790                 795                 800

Tyr Cys Met Pro Lys Arg Ala Ala Phe Lys Gly Ser Ala Pro Ile Asn
                805                 810                 815

Leu Ser Asp Arg Leu Asn Gln Val Leu Arg Trp Ala Leu Gly Ser Val
                820                 825                 830

Glu Ile Phe Met Ser Arg His Cys Pro Ile Trp Tyr Gly Tyr Gly Gly
                835                 840                 845

Gly Leu Lys Trp Leu Glu Arg Phe Ala Tyr Ile Asn Thr Ile Val Tyr
        850                 855                 860

Pro Phe Thr Ser Leu Pro Leu Ile Ala Tyr Cys Thr Leu Pro Ala Val
865                 870                 875                 880

Ser Leu Leu Thr Gly Lys Phe Val Ile Pro Gln Ile Ser Thr Phe Ala
                885                 890                 895

Ser Leu Phe Phe Ile Ala Leu Phe Ile Ser Ile Phe Ala Thr Gly Ile
                900                 905                 910

Leu Glu Met Arg Trp Ser Gly Val Ser Ile Glu Glu Trp Trp Arg Asn
                915                 920                 925

Glu Gln Phe Trp Val Ile Gly Gly Val Ser Ala His Phe Phe Ala Val
        930                 935                 940

Ile Gln Gly Leu Leu Lys Val Leu Ala Gly Ile Asp Thr Asn Phe Thr
945                 950                 955                 960

Val Thr Ala Lys Ala Ser Asp Asp Gly Glu Phe Gly Glu Leu Tyr Ala
                965                 970                 975

Phe Lys Trp Thr Thr Leu Leu Ile Pro Pro Thr Thr Leu Leu Val Ile
                980                 985                 990

Asn Leu Val Gly Val Val Val Gly Val Ala Asp Ala Ile Asn Asn Gly
                995                 1000                1005

Phe Gln Ser Trp Gly Pro Leu Leu Gly Lys Leu Phe Phe Ala Phe Trp
        1010                1015                1020

<210> SEQ ID NO 50
<211> LENGTH: 1024
<212> TYPE: PRT
<213> ORGANISM: Pinus radiata

<400> SEQUENCE: 50

Met Glu Ala Arg Thr Asn Thr Ala Gly Ser Asn Lys Arg Asn Val
 1               5                  10                  15

Arg Val Ser Val Arg Asp Asp Gly Glu Leu Gly Pro Lys Pro Pro Gln
                20                  25                  30

His Ile Asn Ser His Ile Cys Gln Ile Cys Gly Glu Asp Val Gly Leu
        35                  40                  45

Ala Ala Asp Gly Glu Phe Phe Val Ala Cys Asn Glu Cys Ala Phe Pro
    50                  55                  60

Val Cys Arg Pro Cys Tyr Glu Tyr Glu Trp Lys Asp Gly Asn Gln Ser
65                  70                  75                  80

Cys Pro Gln Cys Lys Thr Arg Tyr Lys Trp His Lys Gly Ser Pro Gln
                85                  90                  95

Val Asp Gly Asp Lys Glu Asp Glu Cys Ala Asp Asp Leu Asp His Asp
                100                 105                 110

Phe Asn Ser Thr Gln Gly Asn Arg Asn Glu Lys Gln Gln Ile Ala Glu
        115                 120                 125
```

```
Ala Met Leu His Trp Gln Met Ala Tyr Gly Arg Gly Glu Asp Val Gly
            130                 135                 140

Pro Ser Arg Ser Glu Ser Gln Glu Leu Pro Gln Leu Gln Val Pro Leu
145                 150                 155                 160

Ile Thr Asn Gly Gln Ala Ile Ser Gly Glu Leu Pro Ala Gly Ser Ser
                165                 170                 175

Glu Tyr Arg Arg Ile Ala Ala Pro Pro Thr Gly Gly Ser Gly Lys
                180                 185                 190

Arg Val His Pro Leu Pro Phe Pro Asp Ser Thr Gln Thr Gly Gln Val
                195                 200                 205

Arg Ala Glu Asp Pro Ala Lys Asp Phe Asn Ser Tyr Gly Phe Gly Asn
210                 215                 220

Val Ala Trp Lys Glu Arg Val Glu Ser Trp Lys Asn Lys Gln Asp Lys
225                 230                 235                 240

Asn Thr Leu Gln Val Thr Ser Asp Thr Tyr Ala Ser Glu Gly Lys
                245                 250                 255

Asp Gly Asp Ile Asp Gly Cys Val Ala Asp Glu Asp Leu Gln Met
                260                 265                 270

Ser Asp Glu Ala Arg Gln Pro Leu Ser Arg Lys Val Pro Ile Ala Ser
                275                 280                 285

Ser Lys Ile Asn Pro Tyr Arg Met Val Ile Val Leu Arg Leu Val Ile
                290                 295                 300

Leu Cys Phe Phe Phe Arg Tyr Arg Ile Leu Asn Pro Val Arg Asn Ala
305                 310                 315                 320

Tyr Gly Leu Trp Phe Thr Ser Val Ile Cys Glu Ile Trp Phe Ala Ile
                325                 330                 335

Ser Trp Ile Leu Asp Gln Phe Pro Lys Trp Leu Pro Ile Asn Arg Glu
                340                 345                 350

Thr Tyr Leu Asp Arg Leu Cys Leu Arg Tyr Asp Arg Glu Gly Glu Pro
                355                 360                 365

Ser Gln Leu Ala Ala Val Asp Ile Phe Val Ser Thr Val Asp Pro Met
                370                 375                 380

Lys Glu Pro Pro Leu Val Thr Ala Asn Thr Val Leu Ser Ile Leu Ser
385                 390                 395                 400

Val Asp Tyr Pro Val Asp Lys Val Ser Cys Tyr Val Ser Asp Asp Gly
                405                 410                 415

Ala Ala Met Leu Thr Phe Glu Ala Leu Ser Glu Thr Ser Glu Phe Ala
                420                 425                 430

Arg Lys Trp Val Pro Phe Val Lys Lys Phe Asp Ile Glu Pro Arg Ala
                435                 440                 445

Pro Glu Trp Tyr Phe Ala Gln Lys Ile Asp Tyr Leu Lys Asp Lys Val
                450                 455                 460

Gln Pro Ser Phe Val Lys Glu Arg Arg Ala Met Lys Arg Glu Tyr Glu
465                 470                 475                 480

Glu Phe Lys Val Arg Ile Asn Ala Leu Val Ala Lys Ala Gln Lys Val
                485                 490                 495

Pro Glu Glu Gly Trp Ile Met Gln Asp Gly Thr Pro Trp Pro Gly Asn
                500                 505                 510

Asn Thr Arg Asp His Pro Gly Met Ile Gln Val Phe Leu Gly His Ser
                515                 520                 525

Gly Gly Leu Asp Thr Asp Gly Asn Glu Leu Pro Arg Leu Val Tyr Val
                530                 535                 540

Ser Arg Glu Lys Arg Pro Gly Phe Glu His His Lys Lys Ala Gly Ala
545                 550                 555                 560
```

Met Asn Ser Leu Val Arg Val Ser Ala Val Leu Thr Asn Gly Pro Tyr
                565                 570                 575

Met Leu Asn Leu Asp Cys Asp His Tyr Ile Asn Asn Ser Arg Ala Leu
            580                 585                 590

Arg Glu Ala Met Cys Phe Met Met Asp Pro Thr Leu Gly Lys Lys Val
        595                 600                 605

Cys Tyr Val Gln Phe Pro Gln Arg Phe Asp Gly Ile Asp Arg Asn Asp
    610                 615                 620

Arg Tyr Ala Asn His Asn Thr Val Phe Phe Asp Ile Asn Leu Lys Gly
625                 630                 635                 640

Leu Asp Gly Ile Gln Gly Pro Val Tyr Val Gly Thr Gly Cys Val Phe
                645                 650                 655

Asn Arg Gln Ala Leu Tyr Gly Tyr Glu Pro Pro His Lys Gly Lys Ile
            660                 665                 670

His Phe Ser Ser Cys Cys Gly Pro Arg Lys Lys Ser Arg Lys Ser Asn
        675                 680                 685

Lys Lys Tyr Asn Asp Thr Lys Lys Leu Asp Arg Pro Thr Asp Ser Thr
    690                 695                 700

Val Pro Ile Phe Ser Ser Leu Glu Asp Ile Glu Gly Gly Val Glu Gly
705                 710                 715                 720

Phe Asp Asp Glu Lys Ser Pro Leu Val Phe Gln Lys Ser Leu Glu Lys
                725                 730                 735

Lys Phe Gly Gln Ser Leu Val Phe Val Ala Ser Thr Gln Met Glu Asn
            740                 745                 750

Gly Gly Val Pro Gln Ser Ala Thr Pro Ala Asp Leu Leu Lys Glu Ala
        755                 760                 765

Ile His Val Ile Ser Cys Gly Tyr Glu Asp Lys Ser Asp Trp Gly Lys
    770                 775                 780

Glu Ile Gly Trp Ile Tyr Gly Ser Val Thr Glu Asp Ile Leu Thr Gly
785                 790                 795                 800

Phe Lys Met His Ala Arg Gly Trp Arg Ser Ile Tyr Cys Met Pro Pro
                805                 810                 815

Arg Pro Ala Phe Lys Gly Ser Ala Pro Ile Asn Leu Ser Asp Arg Leu
            820                 825                 830

Asn Gln Val Leu Arg Trp Ala Leu Gly Ser Val Glu Ile Leu Leu Ser
        835                 840                 845

Arg His Cys Pro Ile Trp Tyr Gly Tyr Thr Gly Arg Leu Lys Trp Leu
    850                 855                 860

Glu Arg Leu Ala Tyr Ile Asn Thr Thr Val Tyr Pro Ile Thr Ser Ile
865                 870                 875                 880

Pro Leu Leu Ala Tyr Cys Thr Leu Pro Ala Ile Cys Leu Leu Thr Gly
                885                 890                 895

Lys Phe Ile Ile Pro Glu Ile Ser Thr Leu Ala Ser Leu Trp Phe Ile
            900                 905                 910

Ser Leu Phe Leu Ser Ile Phe Ala Thr Gly Ile Leu Glu Met Arg Trp
        915                 920                 925

Ser Gly Val Gly Ile Asp Glu Trp Trp Arg Asn Glu Gln Phe Trp Val
    930                 935                 940

Ile Gly Gly Val Ser Ala His Leu Phe Ala Val Ile Gln Gly Leu Leu
945                 950                 955                 960

Lys Val Leu Ala Gly Val Asp Thr Asn Phe Thr Val Thr Ser Lys Ala
                965                 970                 975

Ser Asp Glu Gly Gly Asp Phe Ala Glu Leu Tyr Ile Ile Lys Trp Thr

```
                  980               985               990
Ala Leu Leu Ile Pro Pro Thr Thr Leu Leu Ile Ile Asn Ile Val Gly
         995              1000              1005

Val Val Ala Gly Ile Ser Tyr Ala Ile Ser Thr Gly Tyr Arg Ser Trp
    1010              1015              1020

<210> SEQ ID NO 51
<211> LENGTH: 984
<212> TYPE: PRT
<213> ORGANISM: Pinus radiata

<400> SEQUENCE: 51

Met Ala Ser Asn Gly Thr Met Asn Ser Gln Val Cys Gln Val Cys Gly
  1               5                  10                  15

Asp Asn Val Gly Val Asp Ala Asn Gly Glu Pro Phe Val Ala Cys His
             20                  25                  30

Asp Cys Gly Phe Pro Val Cys Arg Pro Cys Gln Gln Tyr Glu Arg Asp
         35                  40                  45

Glu Ala Ser Gln Cys Cys Leu His Cys Lys Ala Pro Tyr Arg Arg Tyr
     50                  55                  60

Glu Gly Gly Pro Ala Asp Glu Val Glu Asn Gly Asp Pro Asn Phe
 65                  70                  75                  80

Glu Lys Val Glu Ala Thr Asp Tyr Glu Gly Glu Gly Tyr Arg Val Asp
                 85                  90                  95

Ser Phe Asn Asp Ser Glu Ile Asn Asn Ala Glu Thr Lys Asp Gly Asn
            100                 105                 110

Ser Lys Gly Val Ala Trp Lys Glu Arg Val Glu Ser Trp Lys Ser Lys
        115                 120                 125

Lys Asn Lys Lys Lys Thr Ala Ala Ser Lys Thr Val Asn Pro Gly Val
    130                 135                 140

Glu Gly Ile Pro Glu Gln Thr Arg Asp Pro Glu Ala Glu Glu Ala Met
145                 150                 155                 160

Met Ala Glu Ala Gly Gln Pro Leu Ser Cys Ile Ile Pro Ile Pro Arg
                165                 170                 175

Thr Lys Leu Gln Pro Tyr Arg Met Val Val Ile Met Arg Leu Ile Val
            180                 185                 190

Leu Gly Leu Phe Phe Ser Tyr Arg Val Gln Asn Pro Val Glu Ser Ala
        195                 200                 205

Phe Gly Leu Trp Met Thr Ser Val Ile Cys Glu Ile Trp Phe Ala Leu
    210                 215                 220

Ser Trp Ile Leu Asp Gln Phe Pro Lys Trp Asn Pro Ile Asn Arg Glu
225                 230                 235                 240

Thr Phe Thr Asp Arg Leu Ser Leu Arg Tyr Glu Arg Pro Gly Glu Pro
                245                 250                 255

Cys Glu Leu Ala Ala Val Asp Phe Phe Val Ser Thr Val Asp Pro Leu
            260                 265                 270

Lys Glu Pro Pro Leu Val Thr Ala Asn Thr Val Leu Ser Ile Leu Ala
        275                 280                 285

Val Asp Tyr Pro Val Glu Lys Val Ser Cys Tyr Val Ser Asp Asp Gly
    290                 295                 300

Ala Ala Met Leu Thr Phe Glu Thr Met Ser Glu Thr Ala Glu Phe Ala
305                 310                 315                 320

Arg Lys Trp Val Pro Phe Cys Lys Asn Phe Asn Ile Glu Pro Arg Ala
                325                 330                 335

Pro Glu Phe Tyr Phe Ser Leu Lys Val Asp Tyr Leu Lys Asp Lys Val
```

```
                340             345             350
Gln Pro Asn Phe Val Lys Glu Arg Arg Ala Met Lys Arg Glu Tyr Glu
            355                 360                 365
Glu Tyr Lys Val Arg Ile Asn Ala Leu Val Ala Lys Ala Gln Lys Thr
        370                 375                 380
Pro Asp Glu Gly Trp Ile Met Gln Asp Gly Thr Ala Trp Pro Gly Asn
385                 390                 395                 400
Asn Ile Arg Asp His Pro Gly Met Ile Gln Val Phe Leu Gly His Thr
                405                 410                 415
Gly Ala His Asp Val Glu Gly Asn Glu Leu Pro Arg Leu Val Tyr Val
                420                 425                 430
Ser Arg Glu Lys Arg Pro Gly Tyr Gln His His Lys Lys Ala Gly Ala
            435                 440                 445
Met Asn Ala Leu Val Arg Val Ser Ala Val Leu Thr Asn Ala Pro Tyr
        450                 455                 460
Leu Leu Asn Leu Asp Cys Asp His Tyr Val Asn Asn Ser Lys Ala Val
465                 470                 475                 480
Arg Glu Ala Met Cys Phe Met Met Asp Pro Glu Val Gly Arg Asn Val
                485                 490                 495
Cys Tyr Val Gln Phe Pro Gln Arg Phe Asp Gly Ile Asp Arg Ser Asp
            500                 505                 510
Arg Tyr Ala Asn Arg Asn Thr Val Phe Phe Asp Ile Asn Met Lys Gly
        515                 520                 525
Leu Asp Gly Ile Gln Gly Pro Val Tyr Val Gly Thr Gly Cys Cys Phe
    530                 535                 540
Asn Arg Gln Ala Leu Tyr Gly Tyr Gly Pro Ala Ala Ala Arg Pro
545                 550                 555                 560
Lys Ala Ser Arg Gly Cys Leu Pro Ser Leu Cys Cys Cys Cys Cys Cys
                565                 570                 575
Cys Pro Lys Ser Lys Thr Ile Asp Pro Lys Lys Ser Ala Pro Gln Glu
            580                 585                 590
Asp Leu Asn Ala Ala Ile Phe Asn Leu Gln Glu Met Gln Ser Tyr Asp
        595                 600                 605
Asp Tyr Glu Arg Gln Leu Leu Val Ser Gln Arg Ser Phe Glu Lys Ser
    610                 615                 620
Phe Gly Gln Ser Ser Val Phe Ile Ala Ser Thr Leu Met Asp Asn Gly
625                 630                 635                 640
Gly Val Pro Glu Ser Thr Asn Pro Ala Ser Leu Ile Lys Glu Ala Ile
                645                 650                 655
His Val Ile Ser Cys Gly Tyr Glu Glu Lys Thr Glu Trp Gly Lys Glu
            660                 665                 670
Val Gly Trp Ile Tyr Gly Ser Val Thr Glu Asp Ile Leu Thr Gly Phe
        675                 680                 685
Lys Met His Cys Arg Gly Trp Arg Ser Ile Tyr Cys Met Pro Lys Arg
    690                 695                 700
Pro Ala Phe Lys Gly Ser Ala Pro Ile Asn Leu Ser Asp Arg Leu His
705                 710                 715                 720
Gln Val Leu Arg Trp Ala Leu Gly Ser Ile Glu Ile Leu Phe Ser Arg
                725                 730                 735
His Cys Pro Leu Trp Tyr Gly Phe Gly Ala Gly Arg Leu Lys Trp Leu
            740                 745                 750
Glu Arg Leu Ala Tyr Thr Asn Thr Ile Val Tyr Pro Leu Thr Ser Leu
        755                 760                 765
```

```
Pro Leu Ile Ala Tyr Cys Thr Leu Pro Ala Ile Cys Leu Leu Thr Gly
            770                 775                 780

Glu Phe Ile Ile Pro Thr Leu Ser Asn Leu Ala Ser Ile Tyr Phe Met
785                 790                 795                 800

Leu Leu Phe Ile Ser Ile Ile Val Thr Gly Val Leu Glu Leu Arg Trp
                805                 810                 815

Ser Gly Val Ser Ile Glu Glu Trp Trp Arg Asn Glu Gln Phe Trp Val
            820                 825                 830

Ile Gly Gly Val Ser Ala His Phe Phe Ala Val Phe Gln Gly Leu Leu
            835                 840                 845

Lys Val Leu Ala Gly Ile Asp Thr Asn Phe Thr Val Thr Ala Lys Ala
850                 855                 860

Ser Asp Asn Glu Phe Gly Glu Leu Tyr Ala Phe Lys Trp Thr Thr
865                 870                 875                 880

Leu Leu Ile Pro Pro Thr Thr Leu Leu Val Ile Asn Leu Val Gly Ile
                885                 890                 895

Val Ala Gly Phe Ser Asp Ala Leu Asn Asn Gly Tyr Gln Ser Trp Gly
            900                 905                 910

Pro Leu Phe Gly Lys Leu Phe Phe Ser Val Trp Val Ile Leu His Leu
            915                 920                 925

Tyr Pro Phe Leu Lys Gly Leu Met Gly Arg Gln Asn Arg Thr Pro Thr
930                 935                 940

Ile Val Val Leu Trp Ser Ile Leu Leu Ala Ser Ile Phe Ser Leu Leu
945                 950                 955                 960

Trp Val Lys Ile Asp Pro Phe Leu Gly Pro Ala Glu Thr Pro Thr Leu
                965                 970                 975

Gln Lys Cys Met Ala Ile Asp Cys
                980

<210> SEQ ID NO 52
<211> LENGTH: 1024
<212> TYPE: PRT
<213> ORGANISM: Pinus radiata

<400> SEQUENCE: 52

Met Glu Ala Asn Ala Gly Leu Val Ala Gly Ser His Asn Arg Asn Glu
1               5                   10                  15

Phe Val Val Ile Arg Pro Glu Gly Val Gly Pro Lys Pro Leu His
                20                  25                  30

His Leu Ser Val Gln Ile Cys His Ile Cys Asn Glu Asp Val Gly Leu
            35                  40                  45

Thr Val Asp Gly Glu Leu Phe Val Ala Cys Asn Glu Cys Ala Phe Pro
50                  55                  60

Ile Cys Arg Thr Cys Tyr Glu Tyr Glu Arg Ser Glu Gly Asn Gln Val
65                  70                  75                  80

Cys Pro Gln Cys Lys Thr Arg Phe Lys Arg His Lys Gly Ser Ala Arg
                85                  90                  95

Val Glu Gly Asp Glu Asp Glu Asp Val Asp Asp Leu Glu Asn Glu
            100                 105                 110

Phe Asn Phe Gly Asp Arg Asp Lys Gln Asp Met Gln Tyr Ile Ala Glu
            115                 120                 125

Ala Met Leu His Gly His Met Ser Tyr Gly Arg Gly Asp Thr Asp
            130                 135                 140

Met Pro His Val Val Gln Thr Thr Leu Pro Gln Val Pro Leu Leu Thr
145                 150                 155                 160
```

```
Asn Gly His Met Asp Pro Gly Ile Pro Pro Glu His His Ala Leu Val
            165                 170                 175

Pro Ser Tyr Met Gly Gly Lys Arg Ile His Pro Phe Pro Tyr Ala
            180                 185                 190

Asp Ser Asn Leu Pro Val Gln Ala Arg Ser Met Asp Pro Thr Lys Asp
            195                 200                 205

Leu Ala Ala Tyr Gly Tyr Gly Ser Ile Ala Trp Lys Glu Arg Val Glu
            210                 215                 220

Asn Trp Lys Met Arg Gln Glu Lys Met Gln Val Met Arg Asn Glu Gly
225                 230                 235                 240

Gly Pro Leu Gly Gly Lys Asp Trp Asp Pro Asp Gly Asn Gly Pro
            245                 250                 255

Asp Gly Pro Asp Leu Pro Leu Met Asp Glu Ala Arg Gln Pro Leu Ser
            260                 265                 270

Arg Lys Leu Pro Ile Pro Ser Ser Arg Ile Asn Pro Tyr Arg Met Val
            275                 280                 285

Ile Ile Leu Arg Leu Val Val Ile Gly Phe Phe His Tyr Arg Val
            290                 295                 300

Met His Pro Val Asn Asp Ala Phe Gly Ile Trp Leu Thr Ser Val Ile
305                 310                 315                 320

Cys Glu Ile Trp Phe Ala Phe Ser Trp Ile Leu Asp Gln Phe Pro Lys
            325                 330                 335

Trp Leu Pro Ile Asp Arg Glu Thr Tyr Leu Asp Arg Leu Ser Leu Arg
            340                 345                 350

Tyr Glu Lys Glu Gly Gln Pro Ser Gly Leu Ala Pro Val Asp Ile Phe
            355                 360                 365

Val Ser Thr Val Asp Pro Leu Lys Glu Pro Pro Leu Val Thr Ala Asn
            370                 375                 380

Thr Val Leu Ser Ile Leu Ala Val Asp Tyr Pro Val Asp Lys Val Ser
385                 390                 395                 400

Cys Tyr Val Ser Asp Asp Gly Ala Ala Met Leu Thr Phe Glu Ala Leu
            405                 410                 415

Ser Glu Thr Ser Glu Phe Ala Arg Lys Trp Val Pro Phe Cys Lys Lys
            420                 425                 430

Phe Asn Ile Glu Pro Arg Ala Pro Glu Trp Tyr Phe Gln Gln Lys Ile
            435                 440                 445

Asp Tyr Leu Lys Asp Lys Val Gln Pro Ser Phe Val Lys Asp Arg Arg
            450                 455                 460

Ala Met Lys Arg Glu Tyr Glu Glu Phe Lys Val Arg Met Asn Ala Leu
465                 470                 475                 480

Val Ala Lys Ala Gln Lys Val Pro Glu Glu Gly Trp Thr Met Gln Asp
            485                 490                 495

Gly Thr Pro Trp Pro Gly Asn Asn Val Arg Asp His Pro Gly Met Ile
            500                 505                 510

Gln Val Phe Leu Gly His Thr Gly Gly His Asp Thr Asp Gly Asn Glu
            515                 520                 525

Leu Pro Arg Leu Val Tyr Val Ser Arg Glu Lys Arg Pro Gly Phe Asn
            530                 535                 540

His His Lys Lys Ala Gly Ala Met Asn Ser Leu Val Arg Val Ser Ala
545                 550                 555                 560

Val Leu Thr Asn Ala Pro Tyr Met Leu Asn Leu Asp Cys Asp His Tyr
            565                 570                 575

Ile Asn Asn Ser Lys Ala Ile Arg Glu Ser Met Cys Phe Met Met Asp
            580                 585                 590
```

```
Pro Thr Val Gly Lys Lys Val Cys Tyr Val Gln Phe Pro Gln Arg Phe
            595                 600                 605

Asp Gly Ile Asp Arg His Asp Arg Tyr Ala Asn Arg Asn Val Val Phe
            610                 615                 620

Phe Asp Ile Asn Met Lys Gly Leu Asp Gly Ile Gln Gly Pro Ile Tyr
625                 630                 635                 640

Val Gly Thr Gly Cys Val Phe Arg Arg Gln Ala Leu Tyr Gly Phe Asp
            645                 650                 655

Ala Pro Lys Ala Glu Lys Glu Pro Thr Arg Thr Cys Asn Cys Trp Pro
            660                 665                 670

Lys Trp Cys Cys Cys Lys Ser Arg Lys Asn Lys Lys Val Lys Ala
            675                 680                 685

Lys Gln Glu Lys Lys Lys Lys Ser Lys Arg Ser Asp Ala Ser Leu
            690                 695                 700

Pro Ile Phe Asn Ser Glu Asp Ile Glu Ala Val Glu Gly Val Asp Ser
705                 710                 715                 720

Glu Lys Leu Ala Phe Ile Ser Gln Ile Lys Leu Glu Lys Lys Phe Gly
            725                 730                 735

Gln Ser Pro Val Phe Val Ala Ser Thr Leu Leu Glu Asn Gly Gly Val
            740                 745                 750

Pro Gln Asn Ala Ser Pro Ala Ser Leu Leu Lys Glu Ala Ile His Val
            755                 760                 765

Ile Ser Cys Gly Tyr Glu Asp Lys Thr Asp Trp Gly Lys Glu Val Gly
            770                 775                 780

Trp Ile Tyr Gly Ser Val Thr Glu Asp Ile Leu Thr Gly Phe Lys Met
785                 790                 795                 800

His Cys His Gly Trp Arg Ser Ile Tyr Cys Ile Pro Pro Arg Pro Ala
            805                 810                 815

Phe Lys Gly Ser Ala Pro Ile Asn Leu Ser Asp Arg Leu His Gln Val
            820                 825                 830

Leu Arg Trp Ala Leu Gly Ser Val Glu Ile Phe Leu Ser Arg His Cys
            835                 840                 845

Pro Val Trp Tyr Gly Tyr Gly Gly Leu Lys Trp Leu Glu Arg Leu
            850                 855                 860

Ser Tyr Ile Asn Ala Thr Val Tyr Pro Trp Thr Ser Ile Pro Leu Val
865                 870                 875                 880

Ala Tyr Cys Thr Leu Pro Ala Ile Cys Leu Leu Thr Gly Lys Phe Ile
            885                 890                 895

Ile Pro Glu Leu Ser Asn Ile Ala Ser Leu Trp Phe Leu Ala Leu Phe
            900                 905                 910

Ile Cys Ile Phe Thr Thr Gly Ile Leu Glu Met Arg Trp Ser Gly Val
            915                 920                 925

Pro Ile Asp Asp Trp Trp Arg Asn Glu Gln Phe Trp Val Ile Gly Gly
            930                 935                 940

Val Ser Ala His Leu Phe Ala Val Phe Gln Gly Leu Leu Lys Val Leu
945                 950                 955                 960

Ala Gly Val Asp Thr Asn Phe Thr Val Thr Ser Lys Ala Gly Asp Asp
            965                 970                 975

Asp Asp Phe Ser Glu Leu Tyr Ala Phe Lys Trp Thr Thr Leu Leu Ile
            980                 985                 990

Pro Pro Thr Thr Leu Leu Ile Val Asn Leu Ile Gly Val Val Ala Gly
            995                1000                1005

Val Ser Asn Ala Ile Asn Asn Gly Tyr Glu Ser Trp Gly Pro Leu Phe
```

-continued

```
           1010              1015              1020

<210> SEQ ID NO 53
<211> LENGTH: 927
<212> TYPE: PRT
<213> ORGANISM: Pinus radiata

<400> SEQUENCE: 53
```

| | | | | | | | | | | | | | | |
|---|---|---|---|---|---|---|---|---|---|---|---|---|---|---|
| Met | Glu | Ala | Asn | Ala | Gly | Leu | Val | Ala | Gly | Ser | His | Asn | Arg | Asn | Glu |
| 1 | | | | 5 | | | | | 10 | | | | | 15 | |
| Phe | Val | Val | Ile | Arg | Pro | Glu | Gly | Val | Gly | Pro | Lys | Pro | Leu | His |
| | | | 20 | | | | | 25 | | | | | 30 | |
| His | Leu | Ser | Val | Gln | Ile | Cys | His | Ile | Cys | Asn | Glu | Asp | Val | Gly | Leu |
| | | 35 | | | | | 40 | | | | | 45 | | | |
| Thr | Val | Asp | Gly | Glu | Leu | Phe | Val | Ala | Cys | Asn | Glu | Cys | Ala | Phe | Pro |
| 50 | | | | | 55 | | | | | 60 | | | | | |
| Ile | Cys | Arg | Thr | Cys | Tyr | Glu | Tyr | Glu | Arg | Ser | Glu | Gly | Asn | Gln | Val |
| 65 | | | | 70 | | | | | 75 | | | | | 80 | |
| Cys | Pro | Gln | Cys | Lys | Thr | Arg | Phe | Lys | Arg | His | Lys | Gly | Ser | Ala | Arg |
| | | | | 85 | | | | | 90 | | | | | 95 | |
| Val | Glu | Gly | Asp | Glu | Asp | Glu | Asp | Val | Asp | Asp | Leu | Glu | Asn | Glu |
| | | | 100 | | | | | 105 | | | | | 110 | |
| Phe | Asn | Phe | Gly | Asp | Arg | Asp | Lys | Gln | Asp | Met | Gln | Tyr | Ile | Ala | Glu |
| | | 115 | | | | | 120 | | | | | 125 | | | |
| Ala | Met | Leu | His | Gly | His | Met | Ser | Tyr | Gly | Arg | Gly | Gly | Asp | Thr | Asp |
| 130 | | | | | 135 | | | | | 140 | | | | | |
| Met | Pro | His | Val | Val | Gln | Thr | Thr | Leu | Pro | Gln | Val | Pro | Leu | Leu | Thr |
| 145 | | | | | 150 | | | | | 155 | | | | | 160 |
| Asn | Gly | His | Met | Asp | Pro | Gly | Ile | Pro | Pro | Glu | His | His | Ala | Leu | Val |
| | | | | 165 | | | | | 170 | | | | | 175 | |
| Pro | Ser | Tyr | Met | Gly | Gly | Gly | Lys | Arg | Ile | His | Pro | Phe | Pro | Tyr | Ala |
| | | | 180 | | | | | 185 | | | | | 190 | | |
| Asp | Ser | Asn | Leu | Pro | Val | Gln | Ala | Arg | Ser | Met | Asp | Pro | Thr | Lys | Asp |
| | | | 195 | | | | | 200 | | | | | 205 | | |
| Leu | Ala | Ala | Tyr | Gly | Tyr | Gly | Ser | Ile | Ala | Trp | Lys | Glu | Arg | Val | Glu |
| | 210 | | | | | 215 | | | | | 220 | | | | |
| Asn | Trp | Lys | Met | Arg | Gln | Glu | Lys | Met | Gln | Val | Met | Arg | Asn | Glu | Gly |
| 225 | | | | | 230 | | | | | 235 | | | | | 240 |
| Gly | Pro | Leu | Gly | Gly | Gly | Lys | Asp | Trp | Asp | Pro | Asp | Gly | Asn | Gly | Pro |
| | | | | 245 | | | | | 250 | | | | | 255 | |
| Asp | Gly | Pro | Asp | Leu | Pro | Leu | Met | Asp | Glu | Ala | Arg | Gln | Pro | Leu | Ser |
| | | | 260 | | | | | 265 | | | | | 270 | | |
| Arg | Lys | Leu | Pro | Ile | Pro | Ser | Ser | Arg | Ile | Asn | Pro | Tyr | Arg | Met | Val |
| | | | 275 | | | | | 280 | | | | | 285 | | |
| Ile | Ile | Leu | Arg | Leu | Val | Val | Ile | Gly | Phe | Phe | Phe | His | Tyr | Arg | Val |
| | 290 | | | | | 295 | | | | | 300 | | | | |
| Met | His | Pro | Val | Asn | Asp | Ala | Phe | Gly | Ile | Trp | Leu | Thr | Ser | Val | Ile |
| 305 | | | | | 310 | | | | | 315 | | | | | 320 |
| Cys | Glu | Ile | Trp | Phe | Ala | Phe | Ser | Trp | Ile | Leu | Asp | Gln | Phe | Pro | Lys |
| | | | | 325 | | | | | 330 | | | | | 335 | |
| Trp | Leu | Pro | Ile | Asp | Arg | Glu | Thr | Tyr | Leu | Asp | Arg | Leu | Ser | Leu | Arg |
| | | | 340 | | | | | 345 | | | | | 350 | | |
| Tyr | Glu | Lys | Glu | Gly | Gln | Pro | Ser | Gly | Leu | Ala | Pro | Val | Asp | Ile | Phe |
| | | | 355 | | | | | 360 | | | | | 365 | | |
| Val | Ser | Thr | Val | Asp | Pro | Leu | Lys | Glu | Pro | Pro | Leu | Val | Thr | Ala | Asn |

```
                    370                 375                 380
Thr Val Leu Ser Ile Leu Ala Val Asp Tyr Pro Val Asp Lys Val Ser
385                 390                 395                 400

Cys Tyr Val Ser Asp Asp Gly Ala Ala Met Leu Thr Phe Glu Ala Leu
                405                 410                 415

Ser Glu Thr Ser Glu Phe Ala Arg Lys Trp Val Pro Phe Cys Lys Lys
                420                 425                 430

Phe Asn Ile Glu Pro Arg Ala Pro Glu Trp Tyr Phe Gln Gln Lys Ile
                435                 440                 445

Asp Tyr Leu Lys Asp Lys Val Gln Pro Ser Phe Val Lys Asp Arg Arg
450                 455                 460

Ala Met Lys Arg Glu Tyr Glu Glu Phe Lys Val Arg Met Asn Ala Leu
465                 470                 475                 480

Val Ala Lys Ala Gln Lys Val Pro Glu Glu Gly Trp Thr Met Gln Asp
                485                 490                 495

Gly Thr Pro Trp Pro Gly Asn Asn Val Arg Asp His Pro Gly Met Ile
                500                 505                 510

Gln Val Phe Leu Gly His Thr Gly Gly His Asp Thr Asp Gly Asn Glu
                515                 520                 525

Leu Pro Arg Leu Val Tyr Val Ser Arg Glu Lys Arg Pro Gly Phe Asn
530                 535                 540

His His Lys Lys Ala Gly Ala Met Asn Ser Leu Val Arg Val Ser Ala
545                 550                 555                 560

Val Leu Thr Asn Ala Pro Tyr Met Leu Asn Leu Asp Cys Asp His Tyr
                565                 570                 575

Ile Asn Asn Ser Lys Ala Ile Arg Glu Ser Met Cys Phe Met Met Asp
                580                 585                 590

Pro Thr Val Gly Lys Lys Val Cys Tyr Val Gln Phe Pro Gln Arg Phe
                595                 600                 605

Asp Gly Ile Asp Arg His Asp Arg Tyr Ala Asn Arg Asn Val Val Phe
                610                 615                 620

Phe Asp Ile Asn Met Lys Gly Leu Asp Gly Ile Gln Gly Pro Ile Tyr
625                 630                 635                 640

Val Gly Thr Gly Cys Val Phe Arg Arg Gln Ala Leu Tyr Gly Phe Asp
                645                 650                 655

Ala Pro Lys Ala Glu Lys Pro Thr Arg Thr Cys Asn Cys Trp Pro
                660                 665                 670

Lys Trp Cys Cys Cys Lys Ser Arg Lys Lys Asn Lys Lys Val Lys Ala
                675                 680                 685

Lys Gln Glu Lys Lys Lys Lys Ser Lys Arg Ser Asp Ala Ser Leu
690                 695                 700

Pro Ile Phe Asn Ser Glu Asp Ile Glu Ala Val Glu Gly Val Asp Ser
705                 710                 715                 720

Glu Lys Leu Ala Phe Ile Ser Gln Ile Lys Leu Glu Lys Lys Phe Gly
                725                 730                 735

Gln Ser Pro Val Phe Val Ala Ser Thr Leu Leu Glu Asn Gly Gly Val
                740                 745                 750

Pro Gln Asn Ala Ser Pro Ala Ser Leu Leu Lys Glu Ala Ile His Val
                755                 760                 765

Ile Ser Cys Gly Tyr Glu Asp Lys Thr Asp Trp Gly Lys Glu Val Gly
                770                 775                 780

Trp Ile Tyr Gly Ser Val Thr Glu Asp Ile Leu Thr Gly Phe Lys Met
785                 790                 795                 800
```

```
His Cys His Gly Trp Arg Ser Ile Tyr Cys Ile Pro Pro Arg Pro Ala
                805                 810                 815

Phe Lys Gly Ser Ala Pro Ile Asn Leu Ser Asp Arg Leu His Gln Val
            820                 825                 830

Leu Arg Trp Ala Leu Gly Ser Val Glu Ile Phe Leu Ser Arg His Cys
        835                 840                 845

Pro Val Trp Tyr Gly Tyr Gly Gly Leu Lys Trp Leu Glu Arg Leu
    850                 855                 860

Ser Tyr Ile Asn Ala Thr Val Tyr Pro Trp Thr Ser Ile Pro Leu Val
865                 870                 875                 880

Ala Tyr Cys Thr Leu Pro Ala Ile Cys Leu Leu Thr Gly Lys Phe Ile
                885                 890                 895

Ile Pro Glu Val Leu Pro Leu Thr Phe Met Pro Tyr Ile Asn Ile Val
            900                 905                 910

Ser Glu Leu Ala Cys Glu Gly Leu Ser His Phe Asp Ile Leu Phe
        915                 920                 925

<210> SEQ ID NO 54
<211> LENGTH: 690
<212> TYPE: PRT
<213> ORGANISM: Pinus radiata

<400> SEQUENCE: 54

Met Ala Pro Asn Phe Gly Val Gly Gln Trp Trp Ser Lys Gln Ser His
 1               5                  10                  15

Lys Gly Thr Ser Val Val Lys Met Glu Asn Pro Asn Tyr Ser Met
            20                  25                  30

Leu Glu Leu Glu Ser Pro Ala Asn Gly Phe Gln Val Asp Lys Gly Gly
        35                  40                  45

Arg Gly Lys Asn Ala Lys Gln Leu Thr Trp Val Leu Leu Lys Ala
    50                  55                  60

His Lys Ala Ala Gly Cys Leu Ala Trp Leu Ala Asn Gly Val Trp Ala
65                  70                  75                  80

Leu Phe Ala Ser Val Arg Arg Arg Phe Thr Ala Pro Ser Asp Glu Ser
                85                  90                  95

Gly Lys Ser Ser Glu Lys Ser Lys Leu Tyr Arg Val Ile Arg Cys Phe
            100                 105                 110

Leu Ile Ala Ser Ile Phe Leu Leu Gly Phe Glu Leu Leu Ala Tyr Trp
        115                 120                 125

Lys Gly Trp His Phe Ser Arg Pro Asn Leu His Ile Pro Pro Ser Leu
    130                 135                 140

Ser Ile Asn Gly Leu Leu Gln Ser Ile Tyr Ser Gly Trp Leu Tyr Thr
145                 150                 155                 160

Arg Ala Asn Tyr Leu Ala Pro Pro Leu Gln Tyr Leu Ala Asn Val Cys
                165                 170                 175

Ile Ile Leu Phe Leu Ile Gln Ser Ala Asp Arg Ala Leu Leu Cys Val
            180                 185                 190

Gly Cys Phe Trp Ile Lys Leu Lys Lys Ile Lys Pro Val Pro Lys Cys
        195                 200                 205

Glu Leu Gly Asp Ala Ala Asp Leu Glu Gln Gly Asp Asn Ala Ala Tyr
    210                 215                 220

Pro Met Val Leu Val Gln Met Pro Met Cys Asn Glu Arg Glu Val Tyr
225                 230                 235                 240

Gln Gln Ser Ile Ala Ala Val Cys Asn Leu Asp Trp Pro Lys Asp His
                245                 250                 255
```

```
Met Leu Val Gln Val Leu Asp Ser Asp Val Glu Val Gln Phe
            260                 265                 270

Leu Ile Ala Ala Glu Val Gln Lys Trp Gln Lys Gly Val His Ile
            275                 280                 285

Val Tyr Arg His Arg Val Arg Thr Gly Tyr Lys Ala Gly Asn Leu
            290                 295                 300

Lys Ser Ala Met Asn Cys Asp Tyr Val Lys Asp Tyr Glu Phe Val Ala
305                 310                 315                 320

Ile Phe Asp Ala Asp Phe Arg Pro Asp Pro Asp Phe Leu Lys Arg Thr
                325                 330                 335

Val Pro His Phe Lys Asp Asn Asp Glu Leu Ala Leu Val Gln Ala Arg
                340                 345                 350

Trp Ser Phe Val Asn Arg Asp Glu Asn Leu Leu Thr Arg Leu Gln Asn
                355                 360                 365

Ile Asn Leu Ser Phe His Phe Glu Val Glu Gln Val Asn Ser Val
            370                 375                 380

Phe Val Asn Phe Phe Gly Phe Asn Gly Thr Ala Gly Val Trp Arg Ile
385                 390                 395                 400

Lys Ala Leu Glu Glu Ser Gly Gly Trp Leu Glu Arg Thr Thr Val Glu
                405                 410                 415

Asp Met Asp Ile Ala Val Arg Ala His Leu Asn Gly Trp Lys Phe Ile
                420                 425                 430

Phe Leu Asp Asp Val Lys Cys Leu Cys Glu Leu Pro Glu Ser Tyr Glu
                435                 440                 445

Ala Tyr Arg Lys Gln Gln His Arg Trp His Ser Gly Pro Met Gln Leu
            450                 455                 460

Phe Arg Leu Cys Leu Pro Asp Ile Ile Arg Ser Lys Ile Ala Phe Trp
465                 470                 475                 480

Lys Lys Ala Asn Leu Ile Phe Leu Phe Phe Leu Leu Arg Lys Leu Ile
                485                 490                 495

Leu Pro Phe Tyr Ser Phe Thr Leu Phe Cys Ile Ile Leu Pro Met Thr
                500                 505                 510

Met Phe Leu Pro Glu Ala Glu Leu Pro Ala Trp Val Val Cys Tyr Val
            515                 520                 525

Pro Ala Ile Met Ser Leu Leu Asn Ile Leu Pro Ala Pro Arg Ser Phe
            530                 535                 540

Pro Phe Ile Ile Pro Tyr Leu Leu Phe Glu Asn Thr Met Ser Val Thr
545                 550                 555                 560

Lys Phe Asn Ala Met Ile Ser Gly Leu Phe Gln Leu Gly Ser Ala Tyr
                565                 570                 575

Glu Trp Val Val Thr Lys Lys Ser Gly Arg Ala Ser Glu Thr Asp Leu
            580                 585                 590

Leu Ala Leu Val Glu Arg Glu Ser His Val Gln Leu Glu His Pro Lys
            595                 600                 605

His His Arg Gly Val Ser Glu Ser Gly Leu Asp Ala Leu Ser Lys Leu
            610                 615                 620

Asp Glu Gln Lys His Gln Gln Pro Pro Lys Lys Lys Leu Asn Arg Ile
625                 630                 635                 640

Tyr Lys Lys Glu Leu Ala Leu Ala Phe Leu Leu Leu Thr Ala Ser Ala
                645                 650                 655

Arg Ser Leu Met Ser Ala Gln Gly Ile His Phe Tyr Phe Leu Leu Phe
                660                 665                 670

Gln Gly Ile Ser Phe Leu Val Val Gly Leu Asp Leu Ile Gly Glu Gln
                675                 680                 685
```

Thr Ser
    690

<210> SEQ ID NO 55
<211> LENGTH: 738
<212> TYPE: PRT
<213> ORGANISM: Pinus radiata

<400> SEQUENCE: 55

Met Glu Pro Asn Asp Phe Pro Leu Tyr Thr Thr Leu Glu Lys Lys Ser
 1               5                  10                  15

Leu Leu Tyr Arg Ala Tyr Ser Cys Thr His Phe Ser Ala Ile Ile Gly
            20                  25                  30

Leu Ile Cys Tyr Arg Leu Leu Tyr Ile Pro Ser Glu Asp Ser Trp Pro
        35                  40                  45

Trp Ile Leu Ile Phe Val Ala Glu Leu Gly Phe Ser Tyr Ser Trp Ile
    50                  55                  60

Leu Asp Gln Ala Leu Arg Trp Trp Pro Val Glu Arg Thr Val Phe Pro
65                  70                  75                  80

Asn Arg Leu Ser Lys Arg Phe Gln Ser Lys Leu Pro Pro Val Asp Ile
                85                  90                  95

Phe Ile Cys Thr Ala Asp Pro Phe Lys Glu Pro Pro Leu Thr Val Ile
            100                 105                 110

Asn Thr Val Leu Ser Ala Leu Ala Val Asp Tyr Pro Met Gly Lys Leu
        115                 120                 125

Ser Cys Tyr Val Ser Asp Asp Gly Gly Ser Pro Leu Thr Phe Tyr Ala
    130                 135                 140

Leu Leu Glu Ala Ser Arg Phe Ala Lys Ile Trp Ile Pro Phe Cys Asp
145                 150                 155                 160

Lys Tyr Ser Ile Gln Asp Arg Cys Pro Glu Val Tyr Phe Ser Asn Pro
                165                 170                 175

Ser Ala Leu Glu Asn Val Asn Leu Pro Phe Met Lys Asp Trp Lys His
            180                 185                 190

Val Asn Lys Met Tyr Ser Glu Leu Lys Asp Arg Ile Asn Asn Val Met
        195                 200                 205

Glu Met Gly Ser Val Pro Pro Asp Lys Gln Asn Glu His Gln Gly Phe
    210                 215                 220

Lys Asp Trp Ala Ser Gly Ser Ser Arg Arg Asp His Pro Ser Ile Val
225                 230                 235                 240

Gln Ile Leu Leu Glu Lys Gly Glu Asp Arg Asp Ile Asp Gly Asn Asp
                245                 250                 255

Leu Pro Asp Leu Ile Tyr Val Ser Arg Glu Lys Arg Pro Gly Ile Pro
            260                 265                 270

His His Tyr Lys Ala Gly Ala Leu Asn Val Leu Leu Arg Val Ser Gly
        275                 280                 285

Val Met Ser Asn Ala Pro Phe Ile Leu Thr Leu Asp Cys Asp Met Tyr
    290                 295                 300

Thr Asn Asn Pro Glu Ala Leu Arg Gln Ala Met Cys Phe Phe Leu Asp
305                 310                 315                 320

Pro Lys Thr Gly Asp Gln Phe Gly Phe Val Gln Phe Pro Gln Val Phe
                325                 330                 335

His Gly Ile Thr Lys Asn Asp Ile Tyr Gly Asn Asn Leu Arg Ile Phe
            340                 345                 350

Ile Glu Ile Asp Phe Lys Gly Gln Asp Gly Ile Asp Gly Pro Phe Tyr
        355                 360                 365

Val Gly Thr Gly Cys Ile His Arg Arg Glu Ala Leu Cys Arg Thr Glu
            370                 375                 380

Arg Arg Gln Ser Ser Ser Asn Tyr His Lys Val Ala Ser Thr Ile Val
385                 390                 395                 400

Cys Ala Glu Glu Thr Val Ala Lys Asp Lys Ala Cys Pro Ser Lys Met
                405                 410                 415

Leu Lys Asn Ala Arg Glu Leu Ala Asn Cys Thr Tyr Glu Asp Asn Thr
            420                 425                 430

Leu Trp Gly Lys Glu Phe Gly Met Ile Tyr Gly Cys Ala Val Glu Asp
            435                 440                 445

Ile Leu Ser Gly Phe Val Ile Gln Cys Lys Gly Trp Arg Ser Ile Tyr
            450                 455                 460

Cys Asn Pro Arg Ser Ala Phe Leu Gly Cys Ala Pro Asn Asn Leu
465                 470                 475                 480

Ile Asp Thr Leu Thr Gln His Lys Arg Trp Ala Val Gly His Leu Gln
            485                 490                 495

Leu Phe Val Ser Lys Phe Cys Pro Tyr Ile Tyr Gly Ile His Arg Met
            500                 505                 510

Gln Ile Ala Gln Arg Met Cys Tyr Ser Tyr Cys Pro Leu Trp Ser Leu
            515                 520                 525

Ser Ser Met His Lys Leu Cys Tyr Gly Leu Ile Pro Gly Leu Cys Met
530                 535                 540

Leu Arg Gly Ile Ser Leu Phe Pro Lys Leu Ser Ser Cys Phe Phe
545                 550                 555                 560

Leu Phe Ala Phe Leu Ala Ile Ser Ala Tyr Gly Tyr Ser Leu Phe Glu
            565                 570                 575

Tyr Ile Trp Asn Val Gly Ser Leu Asn Arg Trp Cys Asn Glu Gln Arg
            580                 585                 590

Met Trp Met Ile Lys Gly Val Ser Ala Tyr Leu Phe Ala Leu Ile Glu
            595                 600                 605

Phe Ala Gly Lys Met Ile Gly Val Ser Glu Val Gly Phe Glu Val Thr
            610                 615                 620

Asn Lys Val Val Asp Ser Glu Ala Ala Lys Arg Tyr Glu Thr Glu Ile
625                 630                 635                 640

Phe Glu Phe Gly Val Ala Ser Pro Leu Phe Val Arg Pro Ala Thr Leu
                645                 650                 655

Val Val Ile Asn Leu Ile Ser Val Val Gly Gly Leu Ala Arg Ile Leu
            660                 665                 670

Arg Glu Gly Tyr Ser Ala Phe Glu Cys Ile Thr Leu Gln Leu Ile Leu
            675                 680                 685

Cys Ser Phe Ile Val Ile Thr Gly Tyr Pro Ile Leu Glu Ala Met Phe
            690                 695                 700

Leu Ser Lys Ala Lys Gly Arg Ile Pro Thr Ser Ile Thr Ile Phe Phe
705                 710                 715                 720

Thr Leu Asp Ala Val Ser Val Trp Ser Val Ala Ser Met Ala Ile Pro
                725                 730                 735

Ser Arg

<210> SEQ ID NO 56
<211> LENGTH: 699
<212> TYPE: PRT
<213> ORGANISM: Pinus radiata

<400> SEQUENCE: 56

```
Met Ala Thr Asn Phe Glu Phe Gln Glu Trp Trp Asn Lys Glu Lys Glu
  1               5                  10                  15

Thr His Arg Gly Thr Ser Val Val Lys Met Glu Asn Pro Asn Trp
         20                  25                  30

Ser Met Val Glu Leu Gln Ser Pro Asp Asp Phe Gln His Ser Asp
             35                  40                  45

Lys Gln Gly Arg Gly Lys Asn Ala Arg Gln Leu Thr Trp Val Trp Leu
 50                  55                  60

Leu Lys Ala His Arg Ala Ala Gly Cys Val Ala Trp Leu Ala Gln Gly
 65                  70                  75                  80

Leu Trp Ser Leu Leu Ser Ala Val Lys Arg Arg Val Thr Leu Asn Lys
             85                  90                  95

Asn Gln Asn Arg Val Thr Glu Glu Asp Lys Pro Gly Lys Ser Lys Leu
            100                 105                 110

Tyr Arg Val Ile Arg Gly Phe Leu Leu Phe Ala Ile Leu Met Leu Gly
            115                 120                 125

Phe Glu Ile Ala Ala Tyr Met Lys Gly Trp His Phe Ser Arg Pro Pro
    130                 135                 140

Phe Asp Phe Ser Pro Ser Leu Asp Leu Gln Gly Val Leu His Ser Ile
145                 150                 155                 160

Tyr Ser Glu Trp Val Phe Val Arg Ala Thr Tyr Leu Ala Pro Pro Leu
                165                 170                 175

Gln Thr Leu Ala Asn Ile Cys Ile Val Leu Phe Leu Ile Gln Ser Ala
                180                 185                 190

Asp Arg Leu Val Leu Ala Met Gly Cys Leu Trp Ile His Ile Lys Lys
            195                 200                 205

Ile Lys Pro Val Pro Gln Phe Glu Phe Pro Ser Ser Ala Ala Asp Leu
210                 215                 220

Glu Lys Gly Ala Ser Ala Asp Tyr Pro Met Val Leu Gln Ile Pro
225                 230                 235                 240

Met Cys Asn Glu Met Glu Val Tyr Gln Gln Ser Ile Ala Ala Val Cys
                245                 250                 255

Asn Leu Asp Trp Pro Lys Glu Arg Met Leu Val Gln Val Leu Asp Asp
            260                 265                 270

Ser Asp Asp Val Asp Val Gln Leu Leu Ile Lys Ser Glu Val Gln Lys
275                 280                 285

Trp Gln Gln Lys Asp Ile Asn Ile Val Tyr Lys His Arg Val Val Arg
290                 295                 300

Thr Gly Tyr Lys Ala Gly Asn Leu Lys Ser Ala Met Ala Cys Asp Tyr
305                 310                 315                 320

Val Lys Asp Tyr Glu Phe Val Ala Ile Phe Asp Ala Asp Phe Gln Pro
                325                 330                 335

Ser Pro Asp Phe Leu Lys Lys Thr Val Pro His Phe Lys Gly Asn Glu
                340                 345                 350

Asp Leu Ala Leu Val Gln Ala Arg Trp Ala Phe Val Asn Lys Asp Glu
            355                 360                 365

Asn Leu Leu Thr Arg Leu Gln Asn Ile Asn Leu Ala Phe His Phe Glu
            370                 375                 380

Val Glu Gln Gln Val Asn Gly Val Phe Ile Asn Phe Gly Phe Asn
385                 390                 395                 400

Gly Thr Ala Gly Val Trp Arg Ile Lys Ala Leu Glu Glu Ser Gly Gly
                405                 410                 415

Trp Leu Glu Arg Thr Thr Val Glu Asp Met Asp Ile Ala Val Arg Ala
            420                 425                 430
```

```
His Leu Asn Gly Trp Lys Phe Ile Tyr Leu Asn Asp Val Gln Cys Leu
            435                 440                 445

Cys Glu Leu Pro Glu Ser Tyr Glu Ala Tyr Arg Lys Gln Gln His Arg
        450                 455                 460

Trp His Ser Gly Pro Met Gln Leu Phe Arg Leu Cys Leu Pro Asp Ile
465                 470                 475                 480

Ile Arg Ser Lys Glu Ile Gly Phe Ser Lys Lys Ala Asn Leu Ile Phe
                485                 490                 495

Leu Phe Phe Leu Leu Arg Lys Leu Ile Leu Pro Phe Tyr Ser Phe Thr
            500                 505                 510

Leu Phe Cys Ile Ile Leu Pro Met Thr Met Phe Leu Pro Glu Ala Gln
            515                 520                 525

Leu Pro Ser Trp Val Ile Cys Tyr Val Pro Val Ile Met Ser Phe Phe
        530                 535                 540

Asn Ile Leu Pro Ala Pro Arg Ser Phe Pro Phe Ile Val Pro Tyr Leu
545                 550                 555                 560

Leu Phe Glu Asn Thr Met Ser Val Thr Lys Phe Asn Ala Met Ile Ser
                565                 570                 575

Gly Leu Phe Gln Leu Gly Ser Ala Tyr Glu Trp Val Val Thr Lys Lys
            580                 585                 590

Leu Gly Arg Ser Ser Glu Ala Asp Leu Val Ala Phe Met Glu Lys Glu
            595                 600                 605

Ser His Pro Gln Leu Glu His Pro Arg His Arg Gly Val Ser Glu
        610                 615                 620

Ser Gly Leu Asp Val Leu Asn Lys Leu Thr Glu Gln Gln Lys Gln
625                 630                 635                 640

Pro Phe Lys Lys Lys Ala Asn Arg Leu Tyr Arg Lys Glu Leu Ala Leu
                645                 650                 655

Ala Phe Leu Leu Leu Thr Ala Ser Ala Arg Ser Leu Leu Ser Ala Gln
            660                 665                 670

Gly Ile His Phe Tyr Phe Leu Leu Phe Gln Gly Ile Ser Phe Leu Leu
            675                 680                 685

Val Gly Leu Asp Leu Ile Gly Glu Gln Val Ser
        690                 695
```

<210> SEQ ID NO 57
<211> LENGTH: 723
<212> TYPE: PRT
<213> ORGANISM: Pinus radiata

<400> SEQUENCE: 57

```
Met Glu Pro Asn Gly Phe Pro Leu Tyr Thr Thr Leu Glu Lys Lys Ser
1               5                   10                  15

Phe Val Tyr Arg Ala Tyr Ala Cys Ala His Phe Ser Ala Ile Ile Gly
            20                  25                  30

Leu Leu Tyr Tyr Arg Ile Val Tyr Ile Pro Ser Glu Asp Tyr Trp Pro
        35                  40                  45

Trp Ile Met Ile Phe Val Ala Glu Leu Gly Phe Ala Tyr Gly Trp Ile
    50                  55                  60

Leu Glu Gln Ala Phe Arg Trp Arg Pro Val Glu Arg Lys Val Phe Pro
65                  70                  75                  80

Glu Arg Leu Ser Lys Arg Phe Lys Ser Asp Leu Pro Val Asp Ile
                85                  90                  95

Phe Ile Cys Thr Ala Asp Pro Ile Lys Glu Pro Pro Leu Ala Val Ile
            100                 105                 110
```

```
Asn Thr Val Leu Ser Ala Leu Ala Val Asp Tyr Pro Val Glu Lys Leu
        115                 120                 125

Ser Cys Tyr Val Ser Asp Asp Gly Val Ser Ser Leu Thr Phe Tyr Ala
        130                 135                 140

Leu Phe Glu Ala Ser Arg Phe Ala Lys Ile Trp Leu Pro Phe Cys Tyr
145                 150                 155                 160

Asn Tyr Ser Ile Gln Asp Arg Ser Pro Glu Ala Tyr Phe Ser Ala Arg
        165                 170                 175

Ser Gly Gln Glu Lys Glu Asn Met Ser Phe Thr Arg Glu Cys Lys Ser
        180                 185                 190

Val Lys Lys Ala Tyr Leu Glu Met Lys Asp Arg Ile Asn Asn Ala Val
        195                 200                 205

Glu Met Gly Ser Val Pro Asp Lys Gln Lys Glu His Thr Gly Phe
        210                 215                 220

Lys Asp Trp Ile Leu Gly Ser Thr Arg Arg Asp His Pro Ser Ile Val
225                 230                 235                 240

Gln Ile Leu Leu Glu Asn Gly Glu Asp Lys Asp Ile Gln Gly Asn Asp
        245                 250                 255

Leu Pro Ser Leu Ile Tyr Val Ser Arg Glu Lys Arg Pro Gly Ile Pro
        260                 265                 270

His His Tyr Lys Ala Gly Ala Leu Asn Ala Leu Ile Arg Ile Ser Gly
        275                 280                 285

Leu Met Ser Asn Ala Pro Phe Ile Ile Thr Leu Asp Cys Asp Met Cys
        290                 295                 300

Thr Asn Asn Cys Glu Ala Leu Arg Gln Ala Met Cys Phe Phe Leu Asp
305                 310                 315                 320

Pro Gln Thr Gly His Gln Phe Ala Tyr Val Gln Phe Pro Gln Gly Phe
        325                 330                 335

His Gly Ile Thr Arg Asn Asp Leu Tyr Ala Asn Asp His Leu Arg Ile
        340                 345                 350

Ser Tyr Trp Gln Phe Lys Gly Met Asp Gly Leu Glu Gly Pro Leu Tyr
        355                 360                 365

Ala Gly Thr Gly Cys Ile His Arg Arg Asp Ala Leu Cys Gly Lys Glu
        370                 375                 380

Gly Arg Leu Ala Ser Ser Thr Ser Lys Ala Gln Thr Ser Pro Ser Lys
385                 390                 395                 400

Met Leu Lys Asp Ala Arg His Leu Ala Asn Cys Ala Cys Glu Glu Asn
        405                 410                 415

Thr Leu Trp Gly Lys Glu Val Gly Met Ile Tyr Gly Cys Ala Glu Glu
        420                 425                 430

Asp Ala Leu Thr Gly Phe Val Ile Gln Ser Arg Gly Trp Lys Ser Ile
        435                 440                 445

Tyr Cys Thr Pro Arg Arg Lys Ala Phe Leu Gly Gly Ala Pro Val Asn
450                 455                 460

Met Asn Asp Thr Leu Ile Gln Ile Lys Arg Trp Ser Ala Gly Tyr Leu
465                 470                 475                 480

Glu Phe Phe Leu Ser Lys Phe Cys Pro Tyr Val Tyr Gly Ile Gln Arg
        485                 490                 495

Thr Ser Thr Val Gln Cys Met Cys Tyr Gly Val Cys Cys Leu Trp Ala
        500                 505                 510

Pro Ser Ser Leu Tyr Ile Leu Cys Tyr Gly Leu Leu Pro Ala Leu Ala
        515                 520                 525

Met Leu Asn Gly Leu Ser Leu Phe Pro Lys Ala Ser Asn Pro Trp Phe
```

```
                530                 535                 540
Ile Leu Phe Val Ser Leu Ala Ala Ser Thr Tyr Gly Tyr Ser Leu Ile
545                 550                 555                 560

Glu Phe Met Cys Ile Gly Gly Ser Phe Lys Ser Trp Trp Asn Glu Gln
                565                 570                 575

Arg Met Trp Leu Ile Lys Gly Val Ser Ser Tyr Leu Phe Ala Leu Ile
                580                 585                 590

Gln Val Val Cys Lys Met Leu Gly Leu Ser Glu Val Gly Phe Glu Val
                595                 600                 605

Thr Ser Lys Val Val Asp Ser Glu Ala Ala Lys Arg His Glu Glu Glu
                610                 615                 620

Met Leu Glu Phe Gly Val Ala Ser Ala Met Phe Val Pro Pro Ala Ser
625                 630                 635                 640

Leu Ala Ile Thr Asn Leu Ile Ser Leu Val Gly Gly Leu Ala Arg Ile
                645                 650                 655

Met Arg Glu Gly Tyr Gln Thr Phe Asp Ser Met Ile Trp Gln Leu Leu
                660                 665                 670

Leu Cys Ser Phe Ile Val Leu Ile Ser Tyr Pro Ile Leu Glu Ala Met
                675                 680                 685

Phe Leu Arg Lys Asp Lys Gly Arg Ile Pro Thr Ser Ile Thr Ile Val
690                 695                 700

Ser Ile Phe Val Ala Val Ser Ala Cys Ser Val Ala Ser Ile Leu Ile
705                 710                 715                 720

Pro Thr Trp

<210> SEQ ID NO 58
<211> LENGTH: 230
<212> TYPE: PRT
<213> ORGANISM: Pinus radiata

<400> SEQUENCE: 58

Met Asp Arg Leu Ser Tyr Ser Ser Ala Asn Ile Leu Pro Gln Thr Phe
  1               5                  10                  15

Gln Gly Thr Arg Asp Asp Ile Val Glu Gln Ile Ala Leu Leu Trp Gln
                20                  25                  30

Gln Ile Arg Ala Pro Leu Val Ala Pro Leu Leu Asn Ile Cys Ile Tyr
            35                  40                  45

Phe Cys Leu Leu Met Ser Val Met Leu Phe Ile Glu Arg Val Tyr Met
        50                  55                  60

Ala Val Val Ile Val Leu Ile Lys Val Phe Gly Lys Lys Pro Glu Lys
 65                  70                  75                  80

Arg Tyr Lys Trp Gly Ala Ile Lys Glu Asp Val Glu Leu Gly Asn Ser
                85                  90                  95

Val Tyr Pro Met Val Leu Val Gln Ile Pro Met Tyr Asn Glu Arg Glu
            100                 105                 110

Val Tyr Gln Leu Ser Ile Gly Ala Ala Cys Ala Leu Ser Trp Pro Ser
        115                 120                 125

Asn Arg Val Ile Ile Gln Val Leu Asp Asp Ser Thr Asp Leu Thr Ile
130                 135                 140

Lys Asp Leu Val Glu Met Glu Cys Gln Lys Trp Ala Ser Lys Gly Ile
145                 150                 155                 160

Asn Ile Lys Tyr Glu Ile Arg Gly Asn Arg Asn Gly Tyr Lys Ala Gly
                165                 170                 175

Ala Leu Lys Glu Gly Met Lys His Ser Tyr Val Arg Glu Cys Asp Tyr
            180                 185                 190
```

```
Val Val Ile Phe Asp Ala Asp Phe Gln Pro Asp Arg Asp Phe Leu Ser
        195                 200                 205

Arg Thr Ile Pro Phe Leu Val His Asn Pro Glu Leu Ala Leu Val Gln
    210                 215                 220

Ala Arg Trp Lys Phe Ala
225                 230

<210> SEQ ID NO 59
<211> LENGTH: 60
<212> TYPE: DNA
<213> ORGANISM: Eucalyptus grandis

<400> SEQUENCE: 59
aggcggtttg aaatggttag agcgattatc ttacataaac gccacagtat acccctggac      60

<210> SEQ ID NO 60
<211> LENGTH: 60
<212> TYPE: DNA
<213> ORGANISM: Eucalyptus grandis

<400> SEQUENCE: 60
gtgagagaga gccccactct caaggccagg ttctatactt gcacaaaagt gttcctttgg      60

<210> SEQ ID NO 61
<211> LENGTH: 60
<212> TYPE: DNA
<213> ORGANISM: Eucalyptus grandis

<400> SEQUENCE: 61
tcatgctttt catggagagg gtctacatgg gcatcgtcat cgtcctcgtc aagctcttct      60

<210> SEQ ID NO 62
<211> LENGTH: 60
<212> TYPE: DNA
<213> ORGANISM: Eucalyptus grandis

<400> SEQUENCE: 62
acacagttct gtcaatattg gctatggact atccagtcga taagatttcc tgctacgttt      60

<210> SEQ ID NO 63
<211> LENGTH: 60
<212> TYPE: DNA
<213> ORGANISM: Eucalyptus grandis

<400> SEQUENCE: 63
cgtccgtctt catcgataag taattgtctt attttgctca gctgttggat tcgtgatcag      60

<210> SEQ ID NO 64
<211> LENGTH: 60
<212> TYPE: DNA
<213> ORGANISM: Eucalyptus grandis

<400> SEQUENCE: 64
gagagtcctt gtacagcgaa cccatgcaag aaggtactac agctaatctc atggatttga      60

<210> SEQ ID NO 65
<211> LENGTH: 60
<212> TYPE: DNA
<213> ORGANISM: Eucalyptus grandis

<400> SEQUENCE: 65
gatgggattg atcgtcacga tcgatactct aacaggaatg tcgtattctt cgatatcaac      60
```

<210> SEQ ID NO 66
<211> LENGTH: 60
<212> TYPE: DNA
<213> ORGANISM: Eucalyptus grandis

<400> SEQUENCE: 66
ttttgatgtc cctacggtga caatggtaca tgctcgttac ttggtgtagt tattcttgtt    60

<210> SEQ ID NO 67
<211> LENGTH: 60
<212> TYPE: DNA
<213> ORGANISM: Eucalyptus grandis

<400> SEQUENCE: 67
caagtcaacg acttgttatg tatacggaac catagacgcg attatgacac aaatcggcat    60

<210> SEQ ID NO 68
<211> LENGTH: 60
<212> TYPE: DNA
<213> ORGANISM: Eucalyptus grandis

<400> SEQUENCE: 68
aaaaagacca ttccttattt taagggaaac gatgatctag cattggtcca gacgagatgg    60

<210> SEQ ID NO 69
<211> LENGTH: 60
<212> TYPE: DNA
<213> ORGANISM: Eucalyptus grandis

<400> SEQUENCE: 69
aatccctctt ctaaccaatg ggcagccgat gtctggtgaa atcccttgtg ctagtattga    60

<210> SEQ ID NO 70
<211> LENGTH: 60
<212> TYPE: DNA
<213> ORGANISM: Eucalyptus grandis

<400> SEQUENCE: 70
tccgaagtgg tttccagtaa atcgtgaaac gtatctcgac agactagcca ttaggtatga    60

<210> SEQ ID NO 71
<211> LENGTH: 60
<212> TYPE: DNA
<213> ORGANISM: Eucalyptus grandis

<400> SEQUENCE: 71
aaaataaaca cgtttgagtg aaatttgttt gttgtgagga gcatttgtat atttgtgccc    60

<210> SEQ ID NO 72
<211> LENGTH: 60
<212> TYPE: DNA
<213> ORGANISM: Eucalyptus grandis

<400> SEQUENCE: 72
gttcggttcc aggtaattca tgagtataat ttagtccatt agggttgtag gaccccttgtc    60

<210> SEQ ID NO 73
<211> LENGTH: 60
<212> TYPE: DNA
<213> ORGANISM: Eucalyptus grandis

<400> SEQUENCE: 73
attccgattg cctctttagc acgtgcgaag gtgcatgtga gcctctacat atgcaccgat    60

<210> SEQ ID NO 74
<211> LENGTH: 60
<212> TYPE: DNA
<213> ORGANISM: Pinus radiata

<400> SEQUENCE: 74
tttatatccg tggaatgtaa ttcattaacg cgtgcccata attaggcagc ttttacgagt     60

<210> SEQ ID NO 75
<211> LENGTH: 60
<212> TYPE: DNA
<213> ORGANISM: Pinus radiata

<400> SEQUENCE: 75
tcaaacatcc atttgctggt caaccatgtc tattccaaaa ttaatttgcc attcggaaag     60

<210> SEQ ID NO 76
<211> LENGTH: 60
<212> TYPE: DNA
<213> ORGANISM: Pinus radiata

<400> SEQUENCE: 76
gaatttgatg tttttaacgg ctgtgattgc ctatattttg tttcattctg tactacggat     60

<210> SEQ ID NO 77
<211> LENGTH: 60
<212> TYPE: DNA
<213> ORGANISM: Pinus radiata

<400> SEQUENCE: 77
tctgtatctc agatgttgtc tagctttaat gtattcagca agcggtgtga gataaagttt     60

<210> SEQ ID NO 78
<211> LENGTH: 60
<212> TYPE: DNA
<213> ORGANISM: Pinus radiata

<400> SEQUENCE: 78
tattccagag gtactaccct tgacattcat gccctatatt aacattgtat ctgagttggc     60

<210> SEQ ID NO 79
<211> LENGTH: 60
<212> TYPE: DNA
<213> ORGANISM: Pinus radiata

<400> SEQUENCE: 79
tgatgatgtc acataatcca caggaatgat ccgtcaacaa ttcagatact ttgcaattga     60

<210> SEQ ID NO 80
<211> LENGTH: 60
<212> TYPE: DNA
<213> ORGANISM: Pinus radiata

<400> SEQUENCE: 80
gaacaaggtt ccgttgtaaa ctcatggtcc ctgattagaa gtttgtttat gtgatagttt     60

<210> SEQ ID NO 81
<211> LENGTH: 60
<212> TYPE: DNA
<213> ORGANISM: Pinus radiata

<400> SEQUENCE: 81
ttgcccttgt aatgttcttt gacactaact ggagacctga ttttaggcca agattcaagt     60

```
<210> SEQ ID NO 82
<211> LENGTH: 60
<212> TYPE: DNA
<213> ORGANISM: Pinus radiata

<400> SEQUENCE: 82
aaattgccaa agtcgcgaca tatatagata gtacaactgt tctaatttac cgcgtttttc    60

<210> SEQ ID NO 83
<211> LENGTH: 60
<212> TYPE: DNA
<213> ORGANISM: Pinus radiata

<400> SEQUENCE: 83
ggggttttaa tatgatttcc acgaaaccaa gtggtctaag tggtataagg acaagtcaat    60
```

POLYNUCLEOTIDES ENCODING CELLULOSE SYNTHASE FROM PINUS RADIATA AND METHODS OF USE FOR REGULATING POLYSACCHARIDES OF A PLANT

CROSS-REFERENCE TO RELATED PATENT APPLICATIONS

This application is a Divisional of U.S. patent application Ser. No. 10/861,910, filed Jun. 7, 2004, and it claims the benefit under 35 USC §119(e) of U.S. Application No. 60/476,239, filed Jun. 6, 2003, incorporated herein by reference in its entirety.

SUMMARY OF THE INVENTION

The present invention relates generally to the field of plant polysaccharide synthesis genes and polypeptides encoded by such genes, and the use of such polynucleotide and polypeptide sequences for controlling plant phenotype. The invention specifically provides cell cycle polynucleotide and polypeptide sequences isolated from *Eucalyptus* and *Pinus* and sequences related thereto.

BACKGROUND OF THE INVENTION

Plant cells walls are composed mainly of cellulose, pectin, and hemicellulose. Cellulose is comprised of crystalline β-1, 4-glucan microfibrils, which are extremely strong and resist enzymatic and mechanical degradation. Cellulose content has a profound effect on the structural properties of plant fibers and wood products, as well as, nutritional quantity, digestibility and palatability of animal and human foodstuffs. Additionally, cellulose is the major structural component of industrially-important plant fibers, such as cotton, flax, hemp, jute and forestry species, such as *Eucalyptus* ssp. and *Pinus* ssp.

Cellulose is also commonly used in a variety industrial applications. Some biodegradable plastics and digestible medicine capsules, as well as medical fillers and fiber additives for food can be made from plant polysaccharides. Moreover, certain plastics, such as cellulose acetate, and synthetic textiles, such as rayon, are derived from cellulose.

Polysaccharides have a profound impact on food quality. Cell walls contribute to crispness in carrots, while degradation of cell walls is required for softening of fruits such as peaches and tomatoes. In maize, increased amylose is desirable for cattle feed, but not for human consumption, and increased cell wall strength reduces digestibility. In fiber crops, such as timber, cellulose is the primary polymer of interest. Wood density, a fundamental measure of structural timber quality, is essentially a measure of cellulose content. In the paper pulping industry, efficiency is measured in terms of yield of cellulose and thus a high cellulose content is desirable.

The ability to alter expression of polysaccharide synthesis genes is extremely powerful because polysaccharide synthesis affects plant phenotype as well as growth rates. Control of polysaccharide synthesis has applications for, inter alia, alteration of wood properties and, in particular, lumber and wood pulp properties. For example, improvements to wood pulp that can be effected by altering polysaccharide synthesis gene expression include increased or decreased lignin and cellulose content. Manipulating the polysaccharide synthesis in a plant can also engineer better lumber having increased dimensional stability, increased tensile strength, increased shear strength, increased compression strength, decreased reaction wood, increased stiffness, increased or decreased hardness, decreased spirality, decreased shrinkage, and desirable characteristics with respect to weight, density, and specific gravity.

A. Polysaccharides Genes and Proteins

Cellulose synthesis is catalyzed, in part, by cellulose synthase. Cellulose synthases are members of the large family of inverting processive β-glycosyltransferases. The cellulose synthase (Ces) genes encode cellulose synthases and are responsible, in part, for regulating cellulose biosynthesis. CesA, a cellulose synthase, belongs to the cellulose synthase superfamily, which is characterized by four conserved domains, U1-U4. U1-U3 each have a conserved aspartate as well as an N' zinc finger domain. The U4 domain possesses a putative substrate binding site, Q-x-x-R—W. Saxena et al., *J. Bacteriol.* 177: 1419 (1995).

CesA proteins are predicted be an eight transmembrane domain protein having about 1100 amino acids. The CesA proteins function as part of a large membrane-bound complex that polymerizes activated glucose into a cellulose polymer. The substrate for Ces in higher plants is UDP-Glucose (UDPG) and most, if not all evidence supports the hypothesis that cellulose synthase genes encode a glycosyltransferase that is integral to the cellulose biosynthetic pathway (See, Holland et al., Plant Physiol., 123: 1313 (2000)).

In silico analysis identified the cellulose synthase-like proteins (Csl), a large family of proteins in plants believed to be processive polysaccharide β-glycosyltransferases. See, e.g., Goubet et al., *Plant Physiol.* 131:547 (1993). The cellulose synthase-like proteins possess the conserved U1-U4 domains, like the cellulose synthases, but lack the N' zinc finger domain. Doblin et al., *Plant Cell Physiol.* 43:1407 (2002). It is believed that cellulose synthase-like enzymes control the production of non-cellulosic plant polysaccharides.

B. Expression Profiling and Microarray Analysis in Polysaccharide Synthesis

The multigenic control of polysaccharide synthesis presents difficulties in determining the genes responsible for phenotypic determination. One major obstacle to identifying genes and gene expression differences that contribute to phenotype in plants is the difficulty with which the expression of more than a handful of genes can be studied concurrently. Another difficulty in identifying and understanding gene expression and the interrelationship of the genes that contribute to plant phenotype is the high degree of sensitivity to environmental factors that plants demonstrate.

There have been recent advances using genome-wide expression profiling. In particular, the use of DNA microarrays has been useful to examine the expression of a large number of genes in a single experiment. Several studies of plant gene responses to developmental and environmental stimuli have been conducted using expression profiling. For example, microarray analysis was employed to study gene expression during fruit ripening in strawberry, Aharoni et al., *Plant Physiol.* 129:1019-1031 (2002), wound response in Arabodopsis, Cheong et al., *Plant Physiol.* 129:661-7 (2002), pathogen response in Arabodopsis, Schenk et al., *Proc. Nat'l Acad. Sci.* 97:11655-60 (2000), and auxin response in soybean, Thibaud-Nissen et al., *Plant Physiol.* 132:118. Whetten et al., *Plant Mol. Biol.* 47:275-91 (2001) discloses expression profiling of cell wall biosynthetic genes in *Pinus taeda* L. using cDNA probes. Whetten et al. examined genes which were differentially expressed between differentiating juvenile and mature secondary xylem. Additionally, to determine the effect of certain environmental stimuli on gene expression, gene expression in compression wood was compared to normal wood. 156 of the 2300 elements examined showed differential expression. Whetten, supra at 285. Comparison of juvenile wood to mature wood showed 188 elements as differentially expressed. Id. at 286.

Although expression profiling and, in particular, DNA microarrays provide a convenient tool for genome-wide expression analysis, their use has been limited to organisms for which the complete genome sequence or a large cDNA collection is available. See Hertzberg et al., *Proc. Nat'l Acad. Sci.* 98:14732-7 (2001a), Hertzberg et al., *Plant J.,* 25:585 (2001b). For example, Whetten, supra, states, "A more complete analysis of this interesting question awaits the completion of a larger set of both pine and poplar ESTs." Whetten et al. at 286. Furthermore, microarrays comprising cDNA or EST probes may not be able to distinguish genes of the same family because of sequence similarities among the genes. That is, cDNAs or ESTs, when used as microarray probes, may bind to more than one gene of the same family.

Methods of manipulating gene expression to yield a plant with a more desirable phenotype would be facilitated by a better understanding of polysaccharide synthetic gene expression in various types of plant tissue, at different stages of plant development, and upon stimulation by different environmental cues. The ability to control plant architecture and agronomically important traits would be improved by a better understanding of how polysaccharide synthesis gene expression effects formation of plant tissues and how plant growth and the polysaccharide synthesis are connected. Among the large number of genes, the expression of which can change during development of a plant, only a fraction are likely to effect phenotypic changes during any given stage of the plant development.

SUMMARY OF THE INVENTION

Accordingly, there is a need for tools and methods useful in determining the changes in the expression of polysaccharide synthesis genes that result in desirable phenotypes. There is also a need for polynucleotides useful in such methods. There is a further need for methods which can correlate changes in polysaccharide synthesis gene expression to a phenotype. There is a further need for methods of identifying polysaccharide synthesis genes and gene products that impact plant phenotype, and that can be manipulated to obtain a desired phenotype.

In one aspect, the present invention provides isolated polynucleotide comprising a nucleic acid sequence selected from the group consisting of SEQ ID NOs: 1-29 and conservative variants thereof.

In another aspect, the present invention provides a plant cell transformed with an isolated polynucleotide comprising a nucleic acid sequence selected from the group consisting of SEQ ID NOs: 1-29 and conservative variants thereof.

In a further aspect, the present invention provides a transgenic plant comprising a polynucleotide comprising a nucleic acid sequence selected from the group consisting of SEQ ID NOs: 1-29 and conservative variants thereof.

In another aspect, the present invention provides a DNA construct comprising at least one polynucleotide having the sequence of any one of SEQ ID NOs: 1-29 and conservative variants thereof.

In an aspect, the present invention provides method of making a transformed plant comprising transforming a plant cell with a DNA construct, culturing the transformed plant cell under conditions that promote growth of a plant.

In another aspect, the present invention provides an isolated polynucleotide comprising a sequence encoding the catalytic or substrate-binding domain of a polypeptide selected from of any one of SEQ ID NOs: 30-58, wherein the polynucleotide encodes a polypeptide having the activity of said polypeptide selected from any one of SEQ ID NOs: 30-58.

In an additional aspect, the invention provides a method of making a transformed plant comprising transforming a plant cell with a DNA construct comprising at least one polynucleotide having the sequence of any of SEQ ID NOs: 1-29 and culturing the transformed plant cell under conditions that promote growth of a plant.

In a further aspect, the invention provides wood obtained from a transgenic tree which has been transformed with a DNA construct of the present invention.

In an additional aspect, the invention provides wood pulp obtained from a transgenic tree which has been transformed with a DNA construct of the present invention.

In a further aspect, the invention provides a method of making wood, comprising transforming a plant with a DNA construct comprising a polynucleotide having a nucleic acid sequence selected from the group consisting of SEQ ID NOs: 1-29 and conservative variants thereof, culturing the transformed plant under conditions that promote growth of a plant; and obtaining wood from the plant.

The invention also provides a method of making wood pulp, comprising transforming a plant with a DNA construct comprising a polynucleotide having a nucleic acid sequence selected from the group consisting of SEQ ID NOs: 1-29 and conservative variants thereof, culturing the transformed plant under conditions that promote growth of a plant, and obtaining wood pulp from the plant.

Another aspect of the present invention provides an isolated polypeptide comprising an amino acid sequence encoded by an isolated polynucleotide of the present invention.

In a further aspect, the present invention provides an isolated polypeptide comprising an amino acid sequence selected from the group consisting of SEQ ID NOs: 30-58.

In an additional aspect, the present invention provides a method of altering a plant phenotype of a plant, comprising altering expression in the plant of a polypeptide encoded by any one of SEQ ID NOs: 1-29.

In one aspect, the present invention provides a polynucleotide comprising a nucleic acid sequence selected from the group consisting of SEQ ID NOs: 59-83.

In another aspect, the present invention provides method of correlating gene expression in two different samples, comprising detecting a level of expression of one or more genes encoding a product encoded by a nucleic acid sequence selected from the group consisting of SEQ ID NOs: 1-29 and conservative variants thereof in a first sample, detecting a level of expression of the one or more genes in a second sample, comparing the level of expression of the one or more genes in the first sample to the level of expression of the one or more genes in the second sample, and correlating a difference in expression level of the one or more genes between the first and second samples.

In a further aspect, the present invention provides a method of correlating the possession of a plant phenotype to the level of gene expression in the plant of one or more genes comprising detecting a level of expression of one or more genes encoding a product encoded by a nucleic acid sequence selected from the group consisting of SEQ ID NOs: 1-29 and conservative variants thereof in a first plant possessing a phenotype, detecting a level of expression of the one or more genes in a second plant lacking the phenotype, comparing the level of expression of the one or more genes in the first plant to the level of expression of the one or more genes in the second plant, and correlating a difference in expression level of the one or more genes between the first and second plants to possession of the phenotype.

In an additional aspect, the invention provides a method of correlating gene expression to propensity to form reaction wood, comprising detecting a level of expression of one or more genes encoding a product encoded by a nucleic acid sequence selected from the group consisting of SEQ ID NOs: 1-29 and conservative variants thereof in a first plant cell in xylem displaying a normal wood phenotype, detecting a level of expression of the one or more genes in a second plant cell in xylem displaying a reaction wood phenotype, comparing the level of the expression of the one or more genes in the first plant cells to the level of expression of the one or more genes in the second plants cells, and correlating a difference in expression level of the one or more genes between the first and second samples to the propensity to form reaction wood.

In one aspect, the present invention provides a combination for detecting expression of one or more genes, comprising two or more oligonucleotides, wherein each oligonucleotide is capable of hybridizing to a nucleic acid sequence selected from the group consisting of SEQ ID NOs: 1-29.

In another aspect, the present invention provides a combination for detecting expression of one or more genes, comprising two or more oligonucleotides, wherein each oligonucleotide is capable of hybridizing to gene product encoded by a nucleic acid sequence selected from the group consisting of SEQ ID NOs: 1-29.

In a further aspect, the present invention provides a microarray comprising a combination of the present invention on a solid support, wherein each of said two or more oligonucleotides occupies a unique location on said solid support.

In an additional aspect, the present invention provides a method for detecting one or more genes in a sample, comprising contacting the sample with two or more oligonucleotides, wherein each oligonucleotide is capable of hybridizing to a gene comprising a nucleic acid sequence selected from the group consisting of SEQ ID NOs: 1-29 under standard hybridization conditions and detecting the one or more genes of interest which are hybridized to the one or more oligonucleotides.

In one aspect, the present invention provides a method for detecting one or more nucleic acid sequences encoded by one or more genes in a sample, comprising contacting the sample with two or more oligonucleotides, wherein each oligonucleotide is capable of hybridizing to a nucleic acid sequence encoded by a gene comprising a nucleic acid sequence selected from the group consisting of SEQ ID NOs: 1-29 under standard hybridization conditions and detecting the one or more nucleic acid sequences which are hybridized to the one or more oligonucleotides.

In one aspect, the present invention provides a kit for detecting gene expression comprising a microarray together with one or more buffers or reagents for a nucleotide hybridization reaction.

Other features, objects, and advantages of the present invention are apparent from the detailed description that follows. It should be understood, however, that the detailed description, while indicating preferred embodiments of the invention, are given by way of illustration only, not limitation. Various changes and modifications within the spirit and scope of the invention will be apparent to those skilled in the art from the detailed description.

BRIEF DESCRIPTION OF THE DRAWINGS

FIG. 1. Amino acid sequence of SEQ ID NO: 30. The conserved cellulose synthase domain is underlined.

FIG. 2. Amino acid sequence of SEQ ID NO: 31. The conserved cellulose synthase domain is underlined.

FIG. 3. Amino acid sequence of SEQ ID NO: 32. The conserved cellulose synthase domain is underlined.

FIG. 4. Amino acid sequence of SEQ ID NO: 33. The conserved family 2 glycosyl transferase domain is underlined.

FIG. 5. Amino acid sequence of SEQ ID NO: 34. The conserved glycosyl transferase, family 2, family domain is underlined.

FIG. 6. Amino acid sequence of SEQ ID NO: 35. The conserved cellulose synthase domain is underlined.

FIG. 7. Amino acid sequence of SEQ ID NO: 36. The conserved cellulose synthase domain is underlined.

FIG. 8. Amino acid sequence of SEQ ID NO: 37. The conserved family 2 glycosyl transferase domain is underlined.

FIG. 9. Amino acid sequence of SEQ ID NO: 38. The conserved nucleotide-diphospho-sugar transferase domain is underlined.

FIG. 10. Amino acid sequence of SEQ ID NO: 39. The conserved cellulose synthase domain is underlined.

FIG. 11. Amino acid sequence of SEQ ID NO: 40. The conserved cellulose synthase domain is underlined.

FIG. 12. Amino acid sequence of SEQ ID NO: 41. The conserved cellulose synthase domain is underlined.

FIG. 13. Amino acid sequence of SEQ ID NO: 42. The conserved cellulose synthase domain is underlined.

FIG. 14. Amino acid sequence of SEQ ID NO: 43. The conserved glycosyl transferase, family 2 domain is underlined.

FIG. 15. Amino acid sequence of SEQ ID NO: 44. The conserved cellulose synthase domain is underlined.

FIG. 16. Amino acid sequence of SEQ ID NO: 45. The conserved cellulose synthase domain is underlined.

FIG. 17. Amino acid sequence of SEQ ID NO: 46. The conserved Glycoside hydrolase, family 2, domain is underlined.

FIG. 18. Amino acid sequence of SEQ ID NO: 47. The conserved Glycosyl transferase, family 2 domain is underlined.

FIG. 19. Amino acid sequence of SEQ ID NO: 48. The conserved cellulose synthase domain is underlined.

FIG. 20. Amino acid sequence of SEQ ID NO: 49. The conserved cellulose synthase domain is underlined.

FIG. 21. Amino acid sequence of SEQ ID NO: 50. The conserved cellulose synthase domain is underlined.

FIG. 22. Amino acid sequence of SEQ ID NO: 51. The conserved cellulose synthase domain is underlined.

FIG. 23. Amino acid sequence of SEQ ID NO: 52. The conserved cellulose synthase domain is underlined.

FIG. 24. Amino acid sequence of SEQ ID NO: 53. The conserved cellulose synthase domain is underlined.

FIG. 25. Amino acid sequence of SEQ ID NO: 54. The conserved glycosyl transferase, family 2 domain is conserved.

FIG. 26. Amino acid sequence of SEQ ID NO: 55. The conserved cellulose synthase domain is underlined.

FIG. 27. Amino acid sequence of SEQ ID NO: 56. The conserved glycolsyl transferase, family 2 domain is underlined.

FIG. 28. Amino acid sequence of SEQ ID NO: 57. The conserved cellulose synthase domain is underlined.

FIG. 29. Amino acid sequence of SEQ ID NO: 58. The conserved glycolsyl transferase, family 2 domain is underlined.

DETAILED DESCRIPTION OF THE PREFERRED EMBODIMENTS

Figure 30:
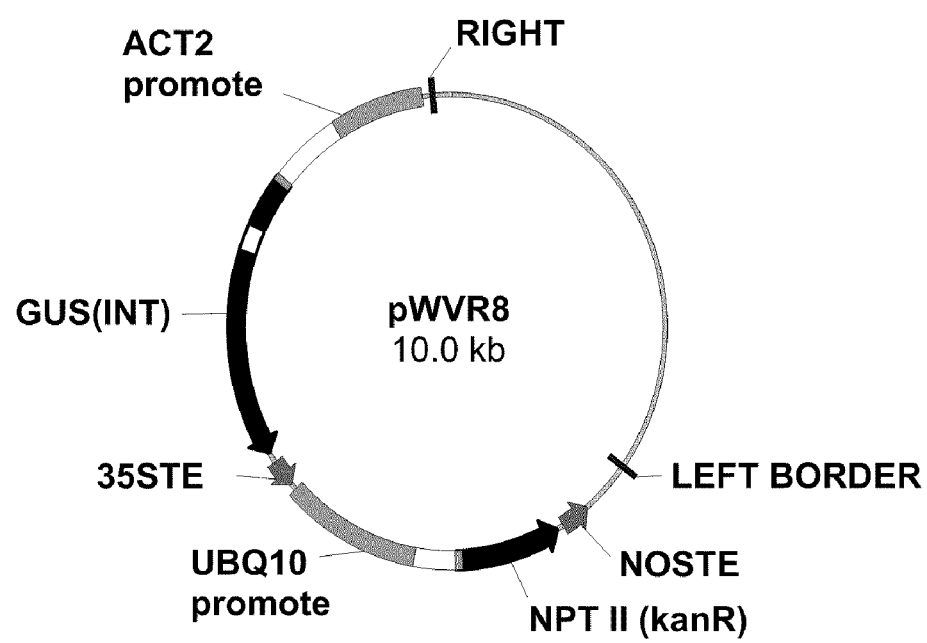
FIG. 30. Vector map of pWVR 8.

The inventors have discovered novel isolated polysaccharide synthesis genes and polynucleotides useful for altering the phenotypic properties of plants. The inventors has also discovered methods of identifying the multigenic factors that contribute to a phenotype and for manipulating gene expression to affect a plant phenotype. These genes, which are derived from plants of commercially important forestry genera, pine and eucalyptus, are involved in the plant polysaccharide synthesis and are, at least in part, responsible for expression of phenotypic characteristics important in commercial wood, such as stiffness, strength, density, fiber dimensions, coarseness, cellulose and lignin content, and extractives content. Generally speaking, the genes and polynucleotides encode a protein which can be a cellulose synthase, a cellulose synthase-like protein, a glycosyltransferase or a polypeptide having the same function, and the invention further includes such proteins and polypeptides.

The methods of the present invention for selecting polysaccharide synthesis gene sequences to target for manipulation will permit better design and control of transgenic plants with more highly engineered phenotypes. The ability to control plant architecture and agronomically important traits in commercially important forestry species will be improved by the information obtained from the methods.

Unless indicated otherwise, all technical and scientific terms are used herein in a manner that conforms to common technical usage. Generally, the nomenclature of this description and the described laboratory procedures, including cell culture, molecular genetics, and nucleic acid chemistry and hybridization, respectively, are well known and commonly employed in the art. Standard techniques are used for recombinant nucleic acid methods, oligonucleotide synthesis, cell culture, tissue culture, transformation, transfection, transduction, analytical chemistry, organic synthetic chemistry, chemical syntheses, chemical analysis, and pharmaceutical formulation and delivery. Generally, enzymatic reactions and purification and/or isolation steps are performed according to the manufacturers' specifications. Absent an indication to the contrary, the techniques and procedures in question are performed according to conventional methodology disclosed, for example, in Sambrook et al., MOLECULAR CLONING A LABORATORY MANUAL, 2d ed. (Cold Spring Harbor Laboratory Press, 1989), and Current Protocols in Molecular Biology, John Wiley & Sons, 1989). Specific scientific methods relevant to the present invention are discussed in more detail below. However, this discussion is provided as an example only, and does not limit the manner in which the methods of the invention can be carried out.

A. Plant Polysaccharide Synthesis Genes and Proteins

1. Polysaccharide Synthesis Genes, Polynucleotide and Polypeptide Sequences

One aspect of the present invention relates to novel polysaccharide synthesis genes and polypeptides encoded by such genes.

The present invention provides novel plant polysaccharide synthesis genes and polynucleotides and novel polysaccharide synthesis proteins and polypeptides. In accordance with one embodiment of the invention, the novel polysaccharide synthesis. genes are the same as those expressed in a wild-type plant of a species of *Pinus* or *Eucalyptus*. Specific exemplary novel plant polysaccharide synthesis gene sequences of the invention are set forth in TABLE 1, which comprises *Eucalyptus grandis* sequences, and TABLE 2, which comprises *Pinus radiata* sequences. Corresponding gene products, i.e., oligonucleotides and polypeptides, are also listed in TABLE 3, TABLE 4, and TABLE 5.

The sequences of the invention have polysaccharide synthesis activity and encode proteins that are active in polysaccharide synthesis, such as proteins of the cellulose synthase and cellulose synthase-like families discussed above. As discussed in more detail below, manipulation of the expression of the polysaccharide synthesis genes and polynucleotides, or manipulation of the activity of the encoded proteins and polypeptides, can result in a transgenic plant with a desired phenotype that differs from the phenotype of a wild-type plant of the same species.

Throughout this description, reference is made to polysaccharide synthesis gene products. As used herein, a "polysaccharide synthesis gene product" is a product encoded by a polysaccharide synthesis gene, and includes both nucleotide products, such as RNA, and amino acid products, such as proteins and polypeptides. Examples of specific polysaccharide synthesis genes of the invention include SEQ ID NOs: 1-29. Examples of specific polysaccharide synthesis gene products of the invention include products encoded by any one of SEQ ID NOs: 1-29. Reference also is made herein to polysaccharide synthesis proteins and polysaccharide synthesis polypeptides. Examples of specific polysaccharide synthesis proteins and polypeptides of the invention include polypeptides encoded by any of SEQ ID NOs: 1-29 or polypeptides comprising the amino acid sequence of any of SEQ ID NOs: 30-58. One aspect of the invention is directed to a subset of these polysaccharide synthesis genes and polysaccharide synthesis gene products, namely SEQ ID 1-2, 7-14, 16-18, 20-21, 24-25, and 27-30, their respective conservative variants (as that term is defined below), and the nucleotide and amino acid products encoded thereby.

The present invention also includes sequences that are complements, reverse sequences, or reverse complements to the nucleotide sequences disclosed herein.

The present invention also includes conservative variants of the sequences disclosed herein. The term "variant," as used herein, refers to a nucleotide or amino acid sequence that differs in one or more nucleotide bases or amino acid residues from the reference sequence of which it is a variant.

Thus, in one aspect, the invention includes conservative variant polynucleotides. As used herein, the term "conservative variant polynucleotide" refers to a polynucleotide that hybridizes under stringent conditions to an oligonucleotide probe that, under comparable conditions, binds to the reference gene the conservative variant is a variant of. Thus, for example, a conservative variant of SEQ ID NO: 1 hybridizes under stringent conditions to an oligonucleotide probe that, under comparable conditions, binds to SEQ ID NO: 1. For example, sequences are considered to hybridize when they form a double-stranded complex in a hybridization solution of 6×SSC, 0.5% SDS, 5×Denhardt's solution and 100 µg of non-specific carrier DNA. See Ausubel et al., section 2.9, supplement 27 (1994). "Moderate stringency" is defined as a temperature of 60° C. in a hybridization solution of 6×SSC, 0.5% SDS, 5×Denhardt's solution and 100 µg of non-specific carrier DNA. Id. "High stringency" hybridization conditions are, for example, 68° C. in a hybridization solution of 6×SSC, 0.5% SDS, 5×Denhardt's solution and 100 µg of non-specific carrier DNA. Id. Following the moderate stringency hybridization reaction, the nucleotides are washed in a solution of 2×SSC plus 0.05% SDS for five times at room temperature, with subsequent washes with 0.1×SSC plus 0.1% SDS at 60° C. for 1 h.

One aspect of the invention provides conservative variant polynucleotides that exhibit at least about 75% sequence identity to their respective reference sequences. "Sequence identity" has an art-recognized meaning and can be calculated using published techniques. See COMPUTATIONAL MOLECULAR BIOLOGY, Lesk, ed. (Oxford University Press, 1988), BIOCOMPUTING: INFORMATICS AND GENOME PROJECTS, Smith, ed. (Academic Press, 1993), COMPUTER ANALYSIS OF SEQUENCE DATA, PART I, Griffin & Griffin, eds., (Humana Press, 1994), SEQUENCE ANALYSIS IN MOLECULAR BIOLOGY, Von Heinje ed., Academic Press (1987), SEQUENCE ANALYSIS PRIMER, Gribskov & Devereux, eds. (Macmillan Stockton Press, 1991), Gish et al., *J. Mol. Biol.* 215: 403 (1990); Gish and States, *Nature Genet.* 3: 266 (1993); Madden et al., *Meth. Enzymol.* 266:131 (1996); Altschul et al., *Nucleic Acids Res.* 25: 3389 (1997); and Zhang and Madden, *Genome Res.* 7: 649-656 (1997), and Carillo and Lipton, SIAM *J. Applied Math.* 48: 1073 (1988). Methods commonly employed to determine identity or similarity between two sequences include but are not limited to those disclosed in GUIDE TO HUGE COMPUTERS, Bishop, ed., (Academic Press, 1994) and Carillo & Lipton, supra.

Methods to determine identity and similarity are codified in computer programs. Preferred computer program methods to determine identity and similarity between two sequences include but are not limited to the GCG program package (Devereux et al., *Nucleic Acids Research* 12: 387 (1984)), BLASTP, BLASTN, FASTA (Atschul et al., *J. Mol. Biol.* 215: 403 (1990)), and FASTDB (Brutlag et al., *Comp. App. Biosci.* 6: 237 (1990)).

The invention includes conservative variant polynucleotides having a sequence identity that is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% to any one of 1-29. In such variants, differences between the variant and the reference sequence can occur at the 5' or 3' terminal positions of the reference nucleotide sequence or anywhere between those terminal positions, interspersed either individually among nucleotides in the reference sequence or in one or more contiguous groups within the reference sequence.

Additional conservative variant polynucleotides contemplated by and encompassed within the present invention include polynucleotides comprising sequences that differ from the polynucleotide sequences of SEQ ID NOs: 1-29 or complements, reverse complements or reverse sequences thereof, as a result of deletions and/or insertions totaling less than 30% of the total sequence length. In one embodiment, deletions and/or insertions total less than 20% or less than 10% of the total length.

The invention also includes conservative variant polynucleotides that, in addition to sharing a high degree of similarity in their primary structure (sequence) to SEQ ID NOs have at least one of the following features: (i) they contain an open reading frame or partial open reading frame encoding a polypeptide having substantially the same functional properties in polynucleotide synthesis as the polypeptide encoded by the reference polynucleotide, or (ii) they have nucleotide domains or encoded protein domains in common. The invention includes conservative variants of SEQ ID NOs: 1-29 that encode proteins having the enzyme or biological activity or binding properties of the protein encoded by the reference polynucleotide. Such conservative variants are functional variants, in that they have the enzymatic or binding activity of the protein encoded by the reference polynucleotide.

In accordance with the invention, polynucleotide variants can include a "shuffled gene" such as those described in e.g. U.S. Pat. Nos. 6,500,639, 6,500,617, 6,436,675, 6,379,964, 6,352,859 6,335,198 6,326,204, and 6,287,862. A variant of a nucleotide sequence of the present invention also can be a polynucleotide modified as disclosed in U.S. Pat. No. 6,132,970, which is incorporated herein by reference.

In accordance with one embodiment, the invention provides a polynucleotide that encodes a polysaccharide synthesis protein such as cellulose synthase and cellulose synthase-like protein. SEQ ID NOs: 1-29 provide examples of such polynucleotides.

In accordance with another embodiment, a polynucleotide of the invention encodes the catalytic or protein binding domain of a polypeptide encoded by any of SEQ ID NOs: 1-29 or of a polypeptide comprising any of SEQ ID NOs: 30-58. The catalytic and protein binding domains of the polysaccharide synthesis proteins of the invention are known in the art. The conserved sequences of these proteins are shown in FIGS. 1-29 as underlined text.

The invention also encompasses as conservative variant polynucleotides that differ from the sequences discussed above but that, as a consequence of the degeneracy of the genetic code, encode a polypeptide which is the same as that encoded by a polynucleotide of the present invention. The invention also includes as conservative variants polynucleotides comprising sequences that differ from the polynucleotide sequences discussed above as a result of substitutions that do not affect the amino acid sequence of the encoded polypeptide sequence, or that result in conservative substitutions in the encoded polypeptide sequence.

The present invention also includes an isolated polypeptide encoded by a polynucleotide comprising any of SEQ ID NOs: 1-29 or any of the conservative variants thereof discussed above. The invention also includes polypeptides comprising SEQ ID NOs: 30-58 and conservative variants of these polypeptides.

In accordance with the invention, a variant polypeptide or protein refers to an amino acid sequence that is altered by the addition, deletion or substitution of one or more amino acids.

The invention includes conservative variant polypeptides. As used herein, the term "conservative variant polypeptide" refers to a polypeptide that has similar structural, chemical or biological properties to the protein it is a conservative variant of. Guidance in determining which amino acid residues can be substituted, inserted, or deleted can be found using computer programs well known in the art such as Vector NTI Suite (InforMax, MD) software. In one embodiment of the invention, conservative variant polypeptides that exhibit at least about 75% sequence identity to their respective reference sequences.

Conservative variant protein includes an "isoform" or "analog" of the polypeptide. Polypeptide isoforms and analogs refers to proteins having the same physical and physiological properties and the same biological function, but whose amino acid sequences differs by one or more amino acids or whose sequence includes a non-natural amino acid.

Polypeptides comprising sequences that differ from the polypeptide sequences of SEQ ID NO: 30-58 as a result of amino acid substitutions, insertions, and/or deletions totaling less than 10% of the total sequence length are contemplated by and encompassed within the present invention.

One aspect of the invention provides conservative variant polypeptides function in polysaccharide synthesis, as determined by one or more appropriate assays, such as those described below. The invention includes variant polypeptides which are cellulose synthase or cellulose synthase-like proteins, such as those capable of converting an activated glucose into a cellulose polymer and those genes that encode a peptide having the biological activity of glycosyltransferase. As discussed above, the invention includes variant polynucleotides that encode polypeptides that function as polysaccharide synthesis proteins.

The activities and physical properties of polysaccharide synthesis proteins can be examined using any method known in the art. The following examples of assay methods are not exhaustive and are included to provide some guidance in examining the activity and distinguishing protein characteristics of polysaccharide synthesis protein variants.

Cellulose synthase activity can be assessed as described in, for example, Blanton et al, *Planta* 180:324 (1990) and Blanton, *Development* 119:703 (1993).

Gycosyltransferase activity can be examined as described in, for example, Stults et al., *Anal. Biochem.* 174: 151 (1988), Stults et al., *Arch. Biochem. Biophys.* 280:20-26. (1990), Stults and Macher, *Arch. Biochem. Biophys.* 303: 125 (1993), 4) Crawley et al., *Anal. Biochem.* 185:112 (1990), and Yan et al., *Anal. Biochem.* 223: 111 (1994).

2. Methods of Using Polysaccharide Synthesis Genes, Polynucleotide and Polypeptide Sequences The present invention provides methods of using polysaccharide synthesis genes and conservative variants thereof. The invention includes methods and constructs for altering expression of cellulose synthase and cellulose synthase-like genes and/or gene products for purposes including, but not limited to (i) investigating function during polysaccharide synthesis and ultimate effect on plant phenotype and (ii) to effect a change in plant phenotype. For example, the invention includes methods and tools for modifying wood quality, fiber development, cell wall polysaccharide content, fruit ripening, and plant growth and yield by altering expression of one or more polysaccharide synthesis genes.

The invention comprises methods of altering the expression of any of the polysaccharide synthesis genes and variants discussed above. Thus, for example, the invention comprises altering expression of a polysaccharide synthesis gene present in the genome of a wild-type plant of a species of *Eucalyptus* or *Pinus*. In one embodiment, the polysaccharide synthesis gene comprises a nucleotide sequence selected from SEQ ID NOs: 1-29 sequences or the conservative variants thereof, as discussed above.

Techniques which can be employed in accordance with the present invention to alter gene expression, include, but are not limited to: (i) over-expressing a gene product, (ii) disrupting a gene's transcript, such as disrupting a gene's mRNA transcript; (iii) disrupting the function of a polypeptide encoded by a gene, or (iv) disrupting the gene itself. Over-expression of a gene product, the use of antisense RNAs, ribozymes, and the use of double-stranded RNA interference (dsRNAi) are valuable techniques for discovering the functional effects of a gene and for generating plants with a phenotype that is different from a wild-type plant of the same species.

Over-expression of a target gene often is accomplished by cloning the gene or cDNA into an expression vector and introducing the vector into recipient cells. Alternatively, over-expression can be accomplished by introducing exogenous promoters into cells to drive expression of genes residing in the genome. The effect of over-expression of a given gene on cell function, biochemical and/or physiological properties can then be evaluated by comparing plants transformed to over-express the gene to plants that have not been transformed to over-express the gene.

Antisense RNA, ribozyme, and dsRNAi technologies typically target RNA transcripts of genes, usually mRNA. Antisense RNA technology involves expressing in, or introducing into, a cell an RNA molecule (or RNA derivative) that is complementary to, or antisense to, sequences found in a particular mRNA in a cell. By associating with the mRNA, the antisense RNA can inhibit translation of the encoded gene product. The use of antisense technology to reduce or inhibit the expression of specific plant genes has been described, for example in European Patent Publication No. 271988, Smith et al., *Nature,* 334:724-726 (1988); Smith et. al., *Plant Mol. Biol.,* 14:369-379 (1990)).

A ribozyme is an RNA that has both a catalytic domain and a sequence that is complementary to a particular mRNA. The ribozyme functions by associating with the mRNA (through the complementary domain of the ribozyme) and then cleaving (degrading) the message using the catalytic domain.

RNA interference (RNAi) involves a post-transcriptional gene silencing (PTGS) regulatory process, in which the steady-state level of a specific mRNA is reduced by sequence-specific degradation of the transcribed, usually fully processed mRNA without an alteration in the rate of de novo transcription of the target gene itself. The RNAi technique is discussed, for example, in Elibashir, et al., *Methods Enzymol.* 26: 199 (2002); McManus & Sharp, *Nature Rev. Genetics* 3: 737 (2002); PCT application WO 01/75164; Martinez et al., *Cell* 110: 563 (2002); Elbashir et al., supra; Lagos-Quintana et al., *Curr. Biol.* 12: 735 (2002); Tuschl et al., Nature Biotechnol. 20:446 (2002); Tuschl, *Chembiochem.* 2: 239 (2001); Harborth et al., *J. Cell Sci.* 114: 4557 (2001); et al., *EMBO J.* 20:6877 (2001); Lagos-Quintana et al., *Science.* 294: 8538 (2001); Hutvagner et al., *loc cit,* 834; Elbashir et al., *Nature.* 411: 494 (2001).

The present invention provides a DNA construct comprising at least one polynucleotide of SEQ ID NOs: 1-29 or conservative variants thereof, such as the conservative variants discussed above. Any method known in the art can be used to generate the DNA constructs of the present invention. See, e.g. Sambrook et al., supra.

The invention includes DNA constructs that optionally comprise a promoter. Any suitable promoter known in the art can be used. A promoter is a nucleic acid, preferably DNA, that binds RNA polymerase and/or other transcription regulatory elements. As with any promoter, the promoters of the invention facilitate or control the transcription of DNA or RNA to generate an mRNA molecule from a nucleic acid molecule that is operably linked to the promoter. The RNA can encode a protein or polypeptide or can encode an antisense RNA molecule or a molecule useful in RNAi. Promoters useful in the invention include constitutive promoters, inducible promoters, temporally regulated promoters and tissue-preferred promoters.

Examples of useful constitutive plant promoters include: the cauliflower mosaic virus (CaMV) 35S promoter, which confers constitutive, high-level expression in most plant tissues (Odel et al. *Nature* 313:810 (1985)); the nopaline synthase promoter (An et al. *Plant Physiol.* 88:547 (1988)); and the octopine synthase promoter (Fromm et al., *Plant Cell* 1: 977 (1989)). It should be noted that, although the CaMV 35S promoter is commonly referred to as a constitutive promoter, some tissue preference can be seen. The use of CaMV 35S is envisioned by the present invention, regardless of any tissue preference which may be exhibited during use in the present invention.

Inducible promoters regulate gene expression in response to environmental, hormonal, or chemical signals. Examples of hormone inducible promoters include auxin-inducible promoters (Baumann et al. *Plant Cell* 11:323-334 (1999)), cytokinin-inducible promoters (Guevara-Garcia, *Plant Mol. Biol.* 38:743-753 (1998)), and gibberellin-responsive promoters (Shi et al. *Plant Mol. Biol.* 38:1053-1060 (1998)). Additionally, promoters responsive to heat, light, wounding, pathogen resistance, and chemicals such as methyl jasmonate or salicylic acid, can be used in the DNA constructs and methods of the present invention.

Tissue-preferred promoters allow for preferred expression of polynucleotides of the invention in certain plant tissue. Tissue-preferred promoters are also useful for directing the expression of antisense RNA or siRNA in certain plant tissues, which can be useful for inhibiting or completely blocking the expression of targeted genes as discussed above. As used herein, vascular plant tissue refers to xylem, phloem or vascular cambium tissue. Other preferred tissue includes apical meristem, root, seed, and flower. In one aspect, the tissue-preferred promoters of the invention are either "xylem-preferred," "cambium-preferred" or "phloem-preferred," and preferentially direct expression of an operably linked nucleic acid sequence in the xylem, cambium or phloem, respectively. In another aspect, the DNA constructs of the invention comprise promoters that are tissue-specific for xylem, cambium or phloem, wherein the promoters are only active in the xylem, cambium or phloem.

A vascular-preferred promoter is preferentially active in any of the xylem, phloem or cambium tissues, or in at least two of the three tissue types. A vascular-specific promoter is specifically active in any of the xylem, phloem or cambium, or in at least two of the three. In other words, the promoters are only active in the xylem, cambium or phloem tissue of plants. Note, however, that because of solute transport in plants, a product that is specifically or preferentially expressed in a tissue may be found elsewhere in the plant after expression has occurred.

Additionally, the promoters of particular polysaccharide synthesis genes may be expressed only within the cambium in developing secondary vasculature. Within the cambium, particular polysaccharide synthesis gene promoters may be expressed exclusively in the stem or in the root. Moreover, the polysaccharide synthesis promoters may be expressed only in the spring (for early wood formation) or only in the summer.

A promoter may be operably linked to the polynucleotide. As used in this context, operably linked refers to linking a polynucleotide encoding a structural gene to a promoter such that the promoter controls transcription of the structural gene. If the desired polynucleotide comprises a sequence encoding a protein product, the coding region can be operably linked to regulatory elements, such as to a promoter and a terminator, that bring about expression of an associated messenger RNA transcript and/or a protein product encoded by the desired polynucleotide. In this instance, the polynucleotide is operably linked in the 5'- to 3'-orientation to a promoter and, optionally, a terminator sequence.

Alternatively, the invention provides DNA constructs comprising a polynucleotide in an "antisense" orientation, the transcription of which produces nucleic acids that can form secondary structures that affect expression of an endogenous polysaccharide synthesis gene in the plant cell. In another variation, the DNA construct may comprise a polynucleotide that yields a double-stranded RNA product upon transcription that initiates RNA interference of a polysaccharide synthesis gene with which the polynucleotide is associated. A polynucleotide of the present invention can be positioned within a t-DNA, such that the left and right t-DNA border sequences flank or are on either side of the polynucleotide.

It should be understood that the invention includes DNA constructs comprising one or more of any of the polynucleotides discussed above. Thus, for example, a construct may comprise a t-DNA comprising one, two, three, four, five, six, seven, eight, nine, ten, or more polynucleotides.

The invention also includes DNA constructs comprising a promoter that includes one or more regulatory elements. Alternatively, the invention includes DNA constructs comprising a regulatory element that is separate from a promoter. Regulatory elements confer a number of important characteristics upon a promoter region. Some elements bind transcription factors that enhance the rate of transcription of the operably linked nucleic acid. Other elements bind repressors that inhibit transcription activity. The effect of transcription factors on promoter activity can determine whether the promoter activity is high or low, i.e. whether the promoter is "strong" or "weak."

A DNA construct of the invention can include a nucleotide sequence that serves as a selectable marker useful in identifying and selecting transformed plant cells or plants. Examples of such markers include, but are not limited to, a neomycin phosphotransferase (nptII) gene (Potrykus et al., *Mol. Gen. Genet.* 199:183-188 (1985)), which confers kanamycin resistance. Cells expressing the nptII gene can be selected using an appropriate antibiotic such as kanamycin or G418. Other commonly used selectable markers include a mutant EPSP synthase gene (Hinchee et al., *Bio/Technology* 6:915-922 (1988)), which confers glyphosate resistance; and a mutant acetolactate synthase gene (ALS), which confers imidazolinone or sulphonylurea resistance (European Patent Application No. 154,204).

The present invention also includes vectors comprising the DNA constructs discussed above. The vectors can include an origin of replication (replicons) for a particular host cell. Various prokaryotic replicons are known to those skilled in the art, and function to direct autonomous replication and maintenance of a recombinant molecule in a prokaryotic host cell.

For example, pMON530 is an *Agrobacterium*-based plant transformation vector for use in transformation of dicotyledonous plants is plasmid vector (Rogers et al. "Improved vectors for plant transformation: expression cassette vectors and new selectable markers," in METHODS IN ENZYMOLOGY. Ed. R. Wu and L. Grossman. p 253-277. San Diego: Academic Press). Another useful plasmid is pMON530, a derivative of pMON505, prepared by transferring the 2.3 kb StuI-HindIII fragment of pMON316 into pMON526. Plasmid pMON526 is a simple derivative of pMON505 in which the SmaI site is removed by digestion with XmaI, treatment with Klenow polymerase and ligation. Plasmid pMON530 retains all the properties of pMON505 and the CaMV35S-NOS expression cassette, but contains a unique cleavage site for SmaI between the promoter and polyadenylation signal.

Binary vector pMON505 is a derivative of pMON200 (Rogers et al., supra,) in which the Ti plasmid homology region, LIH, is replaced with a 3.8 kb HindIII to SmaI segment of the mini RK2 plasmid, pTJS75 (Schmidhauser and Helinski. (1985) *J. Bacteriol.* 164-155). This segment contains the RK2 origin of replication, oriV, and the origin of transfer, oriT, for conjugation into *Agrobacterium* using the tri-parental mating procedure. Horsch and Klee., *Proc. Natl. Acad. Sci. U.S.A.*, 83:4428 (1986). Plasmid pMON505 retains all the important features of pMON200 including the synthetic multi-linker for insertion of desired DNA fragments, the chimeric NOS/NPTII'/NOS gene for kanamycin resistance in plant cells, the spectinomycin/streptomycin resistance determinant for selection in *E. coli* and *A. tumefaciens*, an intact nopaline synthase gene for facile scoring of transformants and inheritance in progeny, and a pBR322 origin of replication for ease in making large amounts of the vector in *E. coli*. Plasmid pMON505 contains a single T-DNA border derived from the right end of the pTiT37 nopaline-type T-DNA. Southern blot analyses demonstrate that plasmid pMON505 and any DNA that it carries are integrated into the plant genome, that is, the entire plasmid is the T-DNA that is inserted into the plant genome. One end of the integrated DNA is located between the right border sequence and the nopaline synthase gene and the other end is between the border sequence and the pBR322 sequences.

A particularly useful Ti plasmid cassette vector is pMON17227. This vector is described in WO 92/04449 and contains a gene encoding an enzyme conferring glyphosate resistance (denominated CP4), which is an excellent selection marker gene for many plants, including potato and tomato. The gene is fused to the *Arabidopsis* EPSPS chloroplast transit peptide (CTP2), and expression is driven by the promoter of choice.

Figure 31:
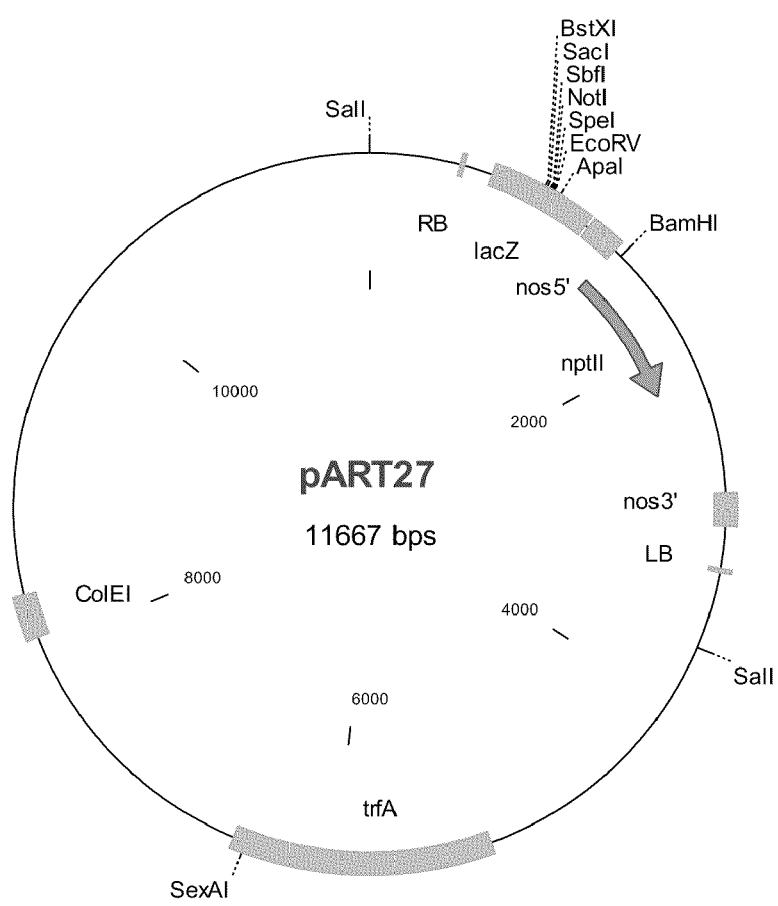
FIG. 31. Vector map of pART27.

In one embodiment, the present invention utilizes a pWVR8 vector as shown in FIG. 30 or pART27 as described in Gleave, *Plant Mol. Biol.*, 20:1203-27 (1992) and shown in FIG. 31.

The invention also provides host cells which are transformed with the DNA constructs of the invention. As used herein, a host cell refers to the cell in which a polynucleotide of the invention is expressed. Accordingly, a host cell can be an individual cell, a cell culture or cells that are part of an organism. The host cell can also be a portion of an embryo, endosperm, sperm or egg cell, or a fertilized egg. In one embodiment, the host cell is a plant cell.

The present invention further provides transgenic plants comprising the DNA constructs of the invention. The invention includes transgenic plants that are angiosperms or gymnosperms. The DNA constructs of the present invention can be used to transform a variety of plants, both monocotyledonous (e.g. grasses, corn, grains, oat, wheat and barley), dicotyledonous (e.g., *Arabidopsis*, tobacco, legumes, alfalfa, oaks, eucalyptus, maple), and Gymnosperms (e.g., Scots pine; see Aronen, Finnish Forest Res. Papers, Vol. 595, 1996), white spruce (Ellis et al., *Biotechnology* 11:84-89, 1993), and larch (Huang et al., *In Vitro Cell* 27:201-207, 1991).

The plants also include turfgrass, wheat, maize, rice, sugar beet, potato, tomato, lettuce, carrot, strawberry, cassaya, sweet potato, geranium, soybean, and various types of woody plants. Woody plants include trees such as palm oak, pine, maple, fir, apple, fig, plum and acacia. Woody plants also include rose and grape vines.

In one embodiment, the DNA constructs of the invention are used to transform woody plants, i.e., trees or shrubs whose stems live for a number of years and increase in diameter each year by the addition of woody tissue. The invention includes methods of transforming plants including eucalyptus and pine species of significance in the commercial forestry industry such as plants selected from the group consisting of *Eucalyptus grandis* and its hybrids, and *Pinus taeda*, as well as the transformed plants and wood and wood pulp derived therefrom. Other examples of suitable plants include those selected from the group consisting of *Pinus banksiana, Pinus brutia, Pinus caribaea, Pinus clausa, Pinus contorta, Pinus coulteri, Pinus echinata, Pinus eldarica, Pinus ellioti, Pinus jeffreyi, Pinus lambertiana, Pinus massoniana, Pinus monticola, Pinus nigra, Pinus palustris, Pinus pinaster, Pinus ponderosa, Pinus radiata, Pinus resinosa, Pinus rigida, Pinus serotina, Pinus strobus, Pinus sylvestris, Pinus taeda, Pinus virginiana, Abies amabilis, Abies balsamea, Abies concolor, Abies grandis, Abies lasiocarpa, Abies magnifica, Abies procera, Chamaecyparis lawsoniona, Chamaecyparis nootkatensis, Chamaecyparis thyoides, Juniperus virginiana, Larix decidua, Larix laricina, Larix leptolepis, Larix occidentalis, Larix siberica, Libocedrus decurrens, Picea abies, Picea engelmanni, Picea glauca, Picea mariana, Picea pungens, Picea rubens, Picea sitchensis, Pseudotsuga menziesii, Sequoia gigantea, Sequoia sempervirens, Taxodium distichum, Tsuga canadensis, Tsuga heterophylla, Tsuga mertensiana, Thuja occidentalis, Thuja plicata, Eucalyptus alba, Eucalyptus bancroftii, Eucalyptus botryoides, Eucalyptus bridgesiana, Eucalyptus calophylla, Eucalyptus camaldulensis, Eucalyptus citriodora, Eucalyptus cladocalyx, Eucalyptus coccifera, Eucalyptus curtisii, Eucalyptus dalrympleana, Eucalyptus deglupta, Eucalyptus delagatensis, Eucalyptus diversicolor, Eucalyptus dunnii, Eucalyptus ficifolia, Eucalyptus globulus, Eucalyptus gomphocephala, Eucalyptus gunnii, Eucalyptus henryi, Eucalyptus laevopinea, Eucalyptus macarthurii, Eucalyptus macrorhyncha, Eucalyptus maculata, Eucalyptus marginata, Eucalyptus megacarpa, Eucalyptus melliodora, Eucalyptus nicholii, Eucalyptus nitens, Eucalyptus nova-angelica, Eucalyptus obliqua, Eucalyptus occidentalis, Eucalyptus obtusiflora, Eucalyptus oreades, Eucalyptus pauciflora, Eucalyptus polybractea, Eucalyptus regnans, Eucalyptus resinifera, Eucalyptus robusta, Eucalyptus rudis, Eucalyptus saligna, Eucalyptus sideroxylon, Eucalyptus stuartiana, Eucalyptus tereticornis, Eucalyptus torelliana, Eucalyptus urnigera, Eucalyptus urophylla, Eucalyptus viminalis, Eucalyptus viridis, Eucalyptus wandoo*, and *Eucalyptus youmanni*.

As used herein, the term "plant" also is intended to include the fruit, seeds, flower, strobilus, etc. of the plant. A transformed plant of the current invention can be a direct transfectant, meaning that the DNA construct was introduced directly into the plant, such as through *Agrobacterium*, or the plant can be the progeny of a transfected plant. The second or subsequent generation plant can be produced by sexual reproduction, i.e., fertilization. Furthermore, the plant can be a gametophyte (haploid stage) or a sporophyte (diploid stage).

As used herein, the term "plant tissue" encompasses any portion of a plant, including plant cells. Plant cells include suspension cultures, callus, embryos, meristematic regions, callus tissue, leaves, roots, shoots, gametophytes, sporophytes, pollen, seeds and microspores. Plant tissues can be grown in liquid or solid culture, or in soil or suitable media in pots, greenhouses or fields. As used herein, "plant tissue" also refers to a clone of a plant, seed, progeny, or propagule, whether generated sexually or asexually, and descendents of any of these, such as cuttings or seeds.

In accordance with one aspect of the invention, a transgenic plant that has been transformed with a DNA construct of the invention has a phenotype that is different from a plant that has not been transformed with the DNA construct.

As used herein, "phenotype" refers to a distinguishing feature or characteristic of a plant which can be altered according to the present invention by integrating one or more DNA constructs of the invention into the genome of at least one plant cell of a plant. The DNA construct can confer a change in the phenotype of a transformed plant by modifying any one or more of a number of genetic, molecular, biochemical, physiological, morphological, or agronomic characteristics or properties of the transformed plant cell or plant as a whole.

For example, cellulose synthase-like proteins have been shown to be involved in plant growth. (Favery et al., *Genes*

Dev. 15:79 (2001)). Therefore, plant cell growth can be modulated by altering the levels of polysaccharides in a plant by changing the expression of one or more polysaccharide synthesis genes. Plant cell growth is accomplished through loosening of the plant cell wall and expansion due to the turgor pressure of the plant cell. The relationship between the looseness of the plant cell wall and the turgor pressure of the cell is such that looser cell walls require less turgor pressure to expand, while stronger cell walls require more turgor pressure to expand. In this manner, the polynucleotides of the invention can be used to modulate the levels of polysaccharide synthesis and thus to mediate plant growth.

Similarly, under conditions of drought or stress, there is a decrease in both turgor pressure of a plant cell and polysaccharide synthesis. Ray, *Curr. Topics in Plant Biochem. & Phys.* 11:18-41 (1992). Thus, the interplay between low turgor pressure and the strength of the cell wall prevents or slows growth. Thus, increasing polysaccharides synthesis by altering polysaccharide gene expression would allow the plant cell wall to loosen and allow growth in conditions resulting in decreased turgor pressure, such as drought conditions. Furthermore, the use of stress-responsive promoters would allow regulated expression of the polysaccharide synthases of the invention (see U.S. Pat. No. 5,891,859; U.S. Pat. No. 5,929,305; U.S. Pat. No. 5,965,705; U.S. Pat. No. 5,892,009).

In one embodiment, transformation of a plant with a DNA construct of the present invention can yield a phenotype including, but not limited to any one or more of increased drought tolerance, herbicide resistance, reduced or increased height, reduced or increased branching, enhanced cold and frost tolerance, improved vigor, enhanced color, enhanced health and nutritional characteristics, improved storage, enhanced yield, enhanced salt tolerance, enhanced resistance of the wood to decay, enhanced resistance to fungal diseases, altered attractiveness to insect pests, increased disease tolerance, increased insect tolerance, increased water-stress tolerance, improved texture, increased germination, increased micronutrient uptake, production of novel resins, and production of novel proteins or peptides.

In another embodiment, the affected phenotype includes one or more of the following traits: propensity to form reaction wood, a reduced period of juvenility, an increased period of juvenility, self-abscising branches, accelerated reproductive development or delayed reproductive development, as compared to a plant of the same species that has not been transformed with the DNA construct.

In a further embodiment, the phenotype that is different in the transgenic plant includes one or more of the following: lignin quality, lignin structure, wood composition, wood appearance, wood density, wood strength, wood stiffness, cellulose polymerization, fiber dimensions, lumen size, proportion of rays, proportion of vessel elements, other plant components, plant cell division, plant cell development, number of cells per unit area, cell size, cell shape, cell wall composition, rate of wood formation, aesthetic appearance of wood, formation of stem defects, average microfibril angle, width of the S2 cell wall layer, rate of growth, rate of root formation ratio of root to branch vegetative development, leaf area index, and leaf shape.

Phenotype can be assessed by any suitable means. The plants can be evaluated based on their general morphology. Transgenic plants can be observed with the naked eye, can be weighed and their height measured. The plant can be examined by isolating individual layers of plant tissue, namely phloem and cambium, which is further sectioned into meristematic cells, early expansion, late expansion, secondary wall formation, and late cell maturation. See, e.g., Hertzberg, supra. The plants also can be assessed using microscopic analysis or chemical analysis.

Microscopic analysis includes examining cell types, stage of development, and stain uptake by tissues and cells. Fiber morphology, such as fiber wall thickness and microfibril angle of wood pulp fibers can be observed using, for example, microscopic transmission ellipsometry. See Ye and Sundström, *Tappi J.*, 80:181 (1997). Wood strength, density, and grain slope in wet wood and standing trees can be determined by measuring the visible and near infrared spectral data in conjunction with multivariate analysis. See, U.S. Patent Application Publication Nos. 2002/0107644 and 2002/0113212. Lumen size can be measured using scanning electron microscopy. Lignin structure and chemical properties can be observed using nuclear magnetic resonance spectroscopy as described in Marita et al., *J. Chem. Soc., Perkin Trans.* 12939 (2001).

The biochemical characteristic of lignin, cellulose, carbohydrates and other plant extracts can be evaluated by any standard analytical method known including spectrophotometry, fluorescence spectroscopy, HPLC, mass spectroscopy, and tissue staining methods.

As used herein, "transformation" refers to a process by which a nucleic acid is inserted into the genome of a plant cell. Such insertion encompasses stable introduction into the plant cell and transmission to progeny. Transformation also refers to transient insertion of a nucleic acid, wherein the resulting transformant transiently expresses the nucleic acid. Transformation can occur under natural or artificial conditions using various methods well known in the art. See, e.g., Glick and Thompson, eds., METHODS IN PLANT MOLECULAR BIOLOGY, CRC Press, Boca Raton, Fla. (1993)). Transformation can be achieved by any known method for the insertion of nucleic acid sequences into a prokaryotic or eukaryotic host cell, including *Agrobacterium*-mediated transformation protocols (see, e.g., Horsch et al., *Science*, 227:1229-31 (1985), viral infection, whiskers, electroporation (see, e.g., Rhodes et al., *Science* 240(4849):204-207 (1988), microinjection, polyethylene glycol-treatment (see, e.g., Lyznik et al., *Plant Mol. Biol.* 13:151-161 (1989), heat shock, lipofection, and particle bombardment (see, e.g., Klein et al., *Plant Physiol.* 91:440-444 (1989) and Boynton et al., *Science* 240(4858):1534-1538 (1988)). Transformation can also be accomplished using chloroplast transformation as described in e.g. Svab et al., *Proc. Natl. Acad. Sci.* 87:8526-30 (1990).

Plant transformation strategies are described in, for example, U.S. Pat. Nos. 5,159,135 (cotton), 5,981,840 (corn), 5,914,451 (soybean), and WO 00/12715 (eucalyptus), which are incorporated by reference in their entirety. Additional plant transformation strategies and techniques are reviewed in Birch, R. G., *Ann. Rev. Plant Physiol. Plant Mol. Biol.* 48:297 (1997) and Forester et al., *Exp. Agric.* 33:15-33 (1997), and are incorporated by reference in their entirety Methods for transforming tree species are well known in the art. In accordance with one embodiment of the invention, genotype-independent transformation of *Eucalyptus* explants and generation of transgenic progeny can be accomplished by transformation using *Agrobacterium*. A tree explant can be, although need not be, harvested and cultured on a pre-culture medium before transformation. Although a pre-culture medium is not necessary, use of such a medium can increase transformation efficiency and plant regeneration. A pre-culture medium is a nutrient medium upon which plant explants can be cultured before transformation with *Agrobacterium*. Any pre-culture media and time periods of culture can be used. The pre-culture medium contains an *Agrobacterium* inducer, such as acetosyringone. The pre-culture medium can optionally contain plant growth regulators, including auxin and cytokinin. Pre-culture medium can be prepared using and appropriate salt medium, including, but not limited to Woody Plant Medium (WPM) salts (Lloyd and McCown, *Combined Proceedings of the International Plant Propagators Society*, 30:421-427,1980), Murashige and Skoog medium (Sigma Aldrich, St. Louis, Mo.) or Lepoivre medium. The pre-culture medium can contain *Agrobacterium* inducers, such as, for example acetosyringone. Optionally, pre-culture medium can contain auxin, cytokinin, or both auxin and cytokinin. An exemplary plant pre-culture medium is shown below.

| Medium Components | Amount per Liter of Medium |
|---|---|
| WPM salts | 1 package (Sigma) |
| $Ca(NO_3)_2 \cdot 4H_2O$ | 3.7 g |
| $MgSO_4 \cdot 4H_2O$ | 0.37 g |
| Nicotinic Acid | 0.5 mg |
| Thiamine•HCl | 0.5 mg |
| Pyridoxin•HCl | 0.5 mg |
| D-Pantothenic Acid | 1.0 mg |
| Myo-inositol | 0.1 g |
| BA | 0.1-1 mg |
| BACTO-AGAR ® | 5-8 g |
| Acetosyringone | 5-200 mg |
| NAA | 0.2-3 mg |
| zeatin | 1-6 mg |

In this transformation method, plant explants can be pre-cultured for four days in the dark on the pre-culture medium. Induced *Agrobacterium* culture can be prepared by methods known in the art. The induced culture is applied to a plant explant. Explants can be transformed by application of *Agrobacterim* culture to the explant, vacuum infiltration, floral dip, etc. Following transformation, *Agrobacterium* culture-treated explants can be co-cultivated with *Agrobacterium* under light or dark conditions for 2-10 days. In one embodiment, the explants are co-cultivated with *Agrobacterium* under light or dark conditions for 4 days.

Following co-cultivation, explants can be transferred to regeneration medium with 400 mg/L TIMENTIN®. Explants can be cultured on regeneration medium before transfer to a selection medium. In one embodiment, explants are cultured on regeneration medium for four days. Any suitable selection medium can be used. In one embodiment, the selection medium is the regeneration medium supplemented with both TIMENTIN® and an herbicide selection agent. The table below provides an exemplary regeneration medium

| Components for 1 Liter of Medium | |
|---|---|
| $KNO_3$ | 1 |
| $NH_4H_2PO_4$ | 0.25 |
| $MgSO_4 \cdot 7H_2O$ | 0.25 |
| $CaCl_2 \cdot 2H_2O$ | 0.10 |
| $FeSO_4 \cdot 7H_2O$ | 0.0139 |
| $Na_2EDTA \cdot 2H_2O$ | 0.01865 |
| MES (Duchefa m1501) | 600.0 |
| MS Micro (½ strength) | |
| $MnSO_4 \cdot H_2O$ | 0.00845 |
| $ZnSO_4 \cdot 7H_2O$ | 0.0043 |
| $CuSO_4 \cdot 5H_2O$ | 0.0000125 |
| $CoCl_2 \cdot 6H_2O$ | 0.0000125 |
| KI | 0.000415 |
| $H_3BO_3$ | 0.0031 |
| $Na_2MoO_4 \cdot 2H_2O$ | 0.000125 |
| Zeatin | |
| NAA (naphthalene acetic acid) | |
| Glucose/Sucrose | 20.0 |
| Myo-inositol | 0.100 |
| Nicotinic Acid | 0.010 |
| Thiamine | 0.010 |
| Ca Pantothenate | 0.001 |
| Pyridoxine | 0.001 |
| Biotin | 0.00001 |
| Ascorbic Acid | 0.050 |
| L-glutamine | 0.1 |
| Arginine | 0.0258 |
| Glycine | 0.00199 |
| Lysine | 0.0508 |
| Methionine | 0.0132 |
| Phenylalanine | 0.0257 |
| Serine | 0.00904 |
| Threonine | 0.00852 |
| Tryptophan | 0.0122 |
| Tyrosine | 0.0127 |
| GELRITE ® | 3.0 |

Shoot clumps that survive selection are maintained on regeneration medium containing herbicide and TIMENTIN®. The shoot clumps can be transferred until shoots proliferate and initially elongate. In one embodiment, the shoot clumps are transferred every 3 weeks.

Any reporter gene can be used, such as, for example, GFP, luciferase, or GUS.

In one embodiment, GUS staining can performed to monitor the frequency of *Agrobacterium* infection and to ensure that the selected shoots are not escapes or chimeras. Leaf and stem tissues from the regenerated shoots can be stained for reporter gene expression immediately upon shoot development. For example, to determine GUS activity, the explants can be incubated in a substrate comprising 100 mM phosphate buffer (pH 7.0), 0.05% dimethyl suphoxide, 0.05% Triton X-100, 10 mM EDTA, 0.5 mM potassium ferrocyanide, and 1.5 mg/ml 5-bromo-4-chloro-3-indolyl-β-D-glucuronide (X-gluc). The explants can then be subjected to 10 minutes of vacuum before an overnight incubation at 37° C. prior to counting GUS foci.

In accordance with another embodiment, transformation of *Pinus* is accomplished using the methods described in U.S. Patent Application Publication No. 2002/0100083.

Another aspect of the invention provides methods of obtaining wood and/or making wood pulp from a plant transformed with a DNA construct of the invention. Methods of producing a transgenic plant are provided above and are known in the art. A transformed plant can be cultured or grown under any suitable conditions. For example, pine can be cultured and grown as described in U.S. Patent Application Publication No. 2002/0100083. *Eucalyptus* can be cultured and grown as in, for example, Rydelius, et al., "Growing Eucalyptus for Pulp and Energy," presented at the Mechanization in Short Rotation, Intensive Culture Forestry Conference, Mobile, Ala., 1994. Wood and wood pulp can be obtained from the plant by any means known in the art.

As noted above, the wood or wood pulp obtained in accordance with this invention may demonstrate improved characteristics including, but not limited to any one or more of lignin composition, lignin structure, wood composition, cellulose polymerization, fiber dimensions, ratio of fibers to other plant components, plant cell division, plant cell development, number of cells per unit area, cell size, cell shape, cell wall composition, rate of wood formation, aesthetic appearance of wood, formation of stem defects, rate of growth, rate of root formation ratio of root to branch vegetative development, leaf area index, and leaf shape include increased or decreased lignin content, increased accessibility of lignin to chemical treatments, improved reactivity of lignin, increased or decreased cellulose content increased dimensional stability, increased tensile strength, increased shear strength, increased compression strength, increased shock resistance, increased stiffness, increased or decreased hardness, decreased spirality, decreased shrinkage, and differences in weight, density, and specific gravity.

B. Expression Profiling of Polysaccharide Synthesis Genes

The present invention also provides methods and tools for performing expression profiling of polysaccharide synthesis genes. Expression profiling is useful in determining whether genes are transcribed or translated, comparing transcript levels for particular genes in different tissues, genotyping, estimating DNA copy number, determining identity of descent, measuring mRNA decay rates, identifying protein binding sites, determining subcellular localization of gene products, correlating gene expression to a phenotype or other phenomenon, and determining the effect on other genes of the manipulation of a particular gene. Expression profiling is particularly useful for identifying gene expression in complex, multigenic events. For this reason, expression profiling is useful in correlating polysaccharide synthesis gene expression to plant phenotype and formation of plant tissues and the interconnection thereof to the polysaccharide biosynthesis.

Only a small fraction of a plant's polysaccharide synthesis genes are expressed at a given time in a given tissue sample, and all of the expressed genes may not affect the plant phenotype. To identify genes capable of affecting a phenotype of interest, the present invention provides methods and tools for determining, for example, a polysaccharide synthesis gene expression profile at a given point in plant development and a polysaccharide synthesis gene expression profile a given tissue sample. The invention also provides methods and tools for identifying polysaccharide synthesis genes whose expression can be manipulated to alter plant phenotype. In support of these methods, the invention also provides methods and tools that distinguish expression of different genes of the same family, such as cellulose synthases or cellulose synthase-like proteins.

As used herein, "gene expression" refers to the process of transcription of a DNA sequence into an RNA sequence, followed by translation of the RNA into a protein, which may or may not undergo post-translational processing. Thus, the relationship between plant phenotype and polysaccharide synthesis gene expression can be observed by detecting, quantitatively or qualitatively, changes in the level of an RNA or a protein. As used herein, the term "biological activity" includes, but is not limited to, the activity of a protein gene product, including enzyme activity, such as, for example, glycosyltransferase activity.

The present invention provides oligonucleotides that are useful in these expression profiling methods. Each oligonucleotide is capable of hybridizing under a given set of conditions to a polysaccharide synthesis gene or gene product. In one aspect of the invention, a plurality of oligonucleotides is provided, wherein each oligonucleotide hybridizes under a given set of conditions to a different polysaccharide synthesis gene product. Examples of oligonucleotides of the present invention include SEQ ID NOs: 59-83. Each of the oligos of SEQ ID NOs 59-83 hybridizes under standard conditions to a different gene product of one of SEQ ID NOs: 1-29. The oligonucleotides of the invention are useful in determining the expression of one or more polysaccharide synthesis genes in any of the above-described methods.

1. Cell, Tissue, Nucleic Acid, and Protein Samples

Samples for use in methods of the present invention may be derived from plant tissue. Suitable plant tissues include, but are not limited to, somatic embryos, pollen, leaves, stems, calli, stolons, microtubers, shoots, xylem, male strolbili, pollen cones, vascular tissue, apical meristem, vascular cambium, xylem, root, flower, and seed.

According to the present invention "plant tissue" is used as described previously herein. Plant tissue can be obtained from any of the plants types or species described supra.

In accordance with one aspect of the invention, samples can be obtained from plant tissue at different developmental stages, from plant tissue at various times of the year (e.g. spring versus summer), from plant tissues subject to different environmental conditions (e.g. variations in light and temperature) and/or from different types of plant tissue and cells. In accordance with one embodiment, plant tissue is obtained during various stages of maturity and during different seasons of the year. In a further embodiment, plant tissue is obtained from plants displaying different phenotypes. For example, plant tissue can be collected from stem dividing cells, differentiating xylem, early developing wood cells, differentiated early wood cells, and differentiated late wood cells. As another example, gene expression in a sample obtained from a plant with developing wood can be compared to gene expression in a sample obtained from a plant which does not have developing wood. As a further example, gene expression in a sample obtained from a plant displaying a reaction wood phenotype can be compared to gene expression in a sample obtained from a plant which does not have reaction wood.

Differentiating xylem includes samples obtained from reaction wood. Reaction wood includes compression wood, side-wood, and normal vertical xylem. Methods of obtaining samples for expression profiling from pine and eucalyptus are known. See, e.g., Allona et al., *Proc. Nat'l Acad. Sci.* 95:9693-8 (1998) and Whetton et al., *Plant Mol. Biol.* 47:275-91, and Kirst et al., Int'l Union of Forestry Research Organizations Biennial Conference, S6.8 (June 2003, Umea, Sweden).

In one embodiment of the invention, gene expression in one type of tissue is compared to gene expression in a different type of tissue or to gene expression in the same type of tissue in a difference stage of development. Gene expression can also be compared in one type of tissue which is sampled at various times during the year (different seasons). For example, gene expression in juvenile secondary xylem can be compared to gene expression in mature secondary xylem. Similarly, gene expression in cambium can be compared to gene expression in xylem. Furthermore, gene expression in apical meristems can be compared to gene expression in cambium.

In another embodiment of the invention, a sample is obtained from a plant having a specific phenotype and gene expression in that sample is compared to a sample obtained from a plant of the same species that does not have that phenotype. For example, a sample can be obtained from a plant exhibiting a fast rate of growth and gene expression can be compared with that of a sample obtained from a plant exhibiting a normal or slow rate of growth. Differentially expressed genes identified from such a comparison can be correlated with growth rate and, therefore, useful for manipulating growth rate.

In a further embodiment, a sample is obtained from clonally propagated plants. In one embodiment the clonally propagated plants are of the species *Pinus* or *Eucalyptus*.

Figure 32:
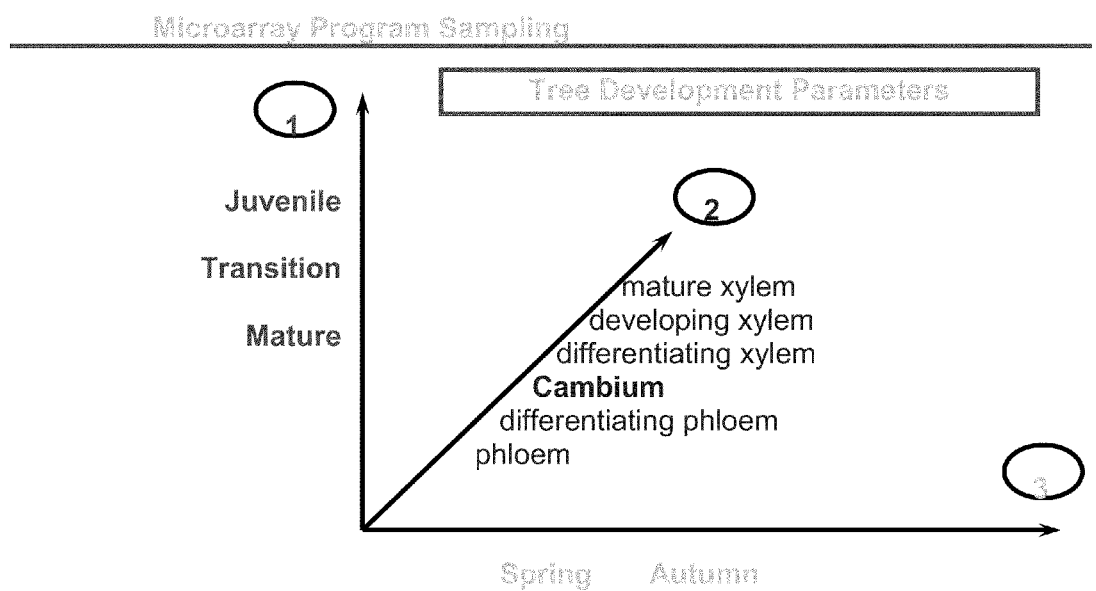
FIG. 32. Exemplary microarray sampling parameters.

Individual ramets from the same genotype can be sacrificed at different times of year. Thus, for any genotype there can be at least two genetically identical trees sacrificed, early in the season and late in the season. Each of these trees can be divided into juvenile (top) to mature (bottom) samples. Further, tissue samples can be divided into, for example, phloem to xylem, in at least 5 layers of peeling. Each of these samples can be evaluated for phenotype and gene expression. See FIG. 32.

Where cellular components may interfere with an analytical technique, such as a hybridization assay, enzyme assay, a ligand binding assay, or a biological activity assay, it may be desirable to isolate the gene products from such cellular components. Gene products, including nucleic acid and amino acid gene products, can be isolated from cell fragments or lysates by any method known in the art.

Nucleic acids used in accordance with the invention can be prepared by any available method or process, or by other processes as they become known in the art. Conventional techniques for isolating nucleic acids are detailed, for example, in Tijssen, LABORATORY TECHNIQUES IN BIOCHEMISTRY AND MOLECULAR BIOLOGY, Hybridization With Nucleic Acid Probes, chapter 3 (Elsevier Press, 1993), Berger and Kimmel, *Methods Enzymol.* 152:1 (1987), and Gibco BRL & Life Technologies Trizol RNA Isolation Protocol, Form No. 3786 (2000). Techniques for preparing nucleic acid samples, and sequencing polynucleotides from pine and eucalyptus are known. See, e.g., Allona et al., supra and Whetton et al., supra.

A suitable nucleic acid sample can contain any type of nucleic acid derived from the transcript of a polysaccharide synthesis gene, i.e., RNA or a subsequence thereof or a nucleic acid for which an mRNA transcribed from a polysaccharide synthesis gene served as a template. Suitable nucleic acids include cDNA reverse-transcribed from a transcript, RNA transcribed from that cDNA, DNA amplified from the cDNA, and RNA transcribed from the amplified DNA. Detection of such products or derived products is indicative of the presence and/or abundance of the transcript in the sample. Thus, suitable samples include, but are not limited to, transcripts of the gene or genes, cDNA reverse-transcribed from the transcript, cRNA transcribed from the cDNA, DNA amplified from the genes, and RNA transcribed from amplified DNA. As used herein, the category of "transcripts" includes but is not limited to pre-mRNA nascent transcripts, transcript processing intermediates, and mature mRNAs and degradation products thereof.

It is not necessary to monitor all types of transcripts to practice the invention. For example, the expression profiling methods of the invention can be conducted by detecting only one type of transcript, such as mature mRNA levels only.

In one aspect of the invention, a chromosomal DNA or cDNA library (comprising, for example, fluorescently labeled cDNA synthesized from total cell mRNA) is prepared for use in hybridization methods according to recognized methods in the art. See Sambrook et al., supra.

In another aspect of the invention, mRNA is amplified using, e.g., the MessageAmp kit (Ambion). In a further aspect, the mRNA is labeled with a detectable label. For example, mRNA can be labeled with a fluorescent chromophore, such as CyDye (Amersham Biosciences).

In some applications, it may be desirable to inhibit or destroy RNase that often is present in homogenates or lysates, before use in hybridization techniques. Methods of inhibiting or destroying nucleases are well known. In one embodiment of the invention, cells or tissues are homogenized in the presence of chaotropic agents to inhibit nuclease. In another embodiment, RNase is inhibited or destroyed by heat treatment, followed by proteinase treatment.

Protein samples can be obtained by any means known in the art. Protein samples useful in the methods of the invention include crude cell lysates and crude tissue homogenates. Alternatively, protein samples can be purified. Various methods of protein purification well known in the art can be found in Marshak et al., STRATEGIES FOR PROTEIN PURIFICATION AND CHARACTERIZATION: A LABORATORY COURSE MANUAL (Cold Spring Harbor Laboratory Press 1996).

2. Detecting Level of Gene Expression

For methods of the invention that comprise detecting a level of gene expression, any method for observing gene expression can be used, without limitation. Such methods include traditional nucleic acid hybridization techniques, polymerase chain reaction (PCR) based methods, and protein determination. The invention includes detection methods that use solid support-based assay formats as well as those that use solution-based assay formats.

Absolute measurements of the expression levels need not be made, although they can be made. The invention includes methods comprising comparisons of differences in expression levels between samples. Comparison of expression levels can be done visually or manually, or can be automated and done by a machine, using for example optical detection means. Subrahmanyam et al., *Blood.* 97: 2457 (2001); Prashar et al., *Methods Enzymol.* 303: 258 (1999). Hardware and software for analyzing differential expression of genes are available, and can be used in practicing the present invention. See, e.g., GenStat Software and GeneExpress® GX Explorer™ Training Manual, supra; Baxevanis & Francis-Ouellette, supra.

In accordance with one embodiment of the invention, nucleic acid hybridization techniques are used to observe gene expression. Exemplary hybridization techniques include Northern blotting, Southern blotting, solution hybridization, and 51 nuclease protection assays.

Nucleic acid hybridization typically involves contacting an oligonucleotide probe and a sample comprising nucleic acids under conditions where the probe can form stable hybrid duplexes with its complementary nucleic acid through complementary base pairing. For example, see PCT application WO 99/32660; Berger & Kimmel, *Methods Enzymol.* 152: 1 (1987). The nucleic acids that do not form hybrid duplexes are then washed away leaving the hybridized nucleic acids to be detected, typically through detection of an attached detectable label. The detectable label can be present on the probe, or on the nucleic acid sample. In one embodiment, the nucleic acids of the sample are detectably labeled polynucleotides representing the mRNA transcripts present in a plant tissue (e.g., a cDNA library). Detectable labels are commonly radioactive or fluorescent labels, but any label capable of detection can be used. Labels can be incorporated by several approached described, for instance, in WO 99/32660, supra. In one aspect RNA can be amplified using the MessageAmp kit (Ambion) with the addition of aminoallyl-UTP as well as free UTP. The aminoallyl groups incorporated into the amplified RNA can be reacted with a fluorescent chromophore, such as CyDye (Amersham Biosciences)

Duplexes of nucleic acids are destabilized by increasing the temperature or decreasing the salt concentration of the buffer containing the nucleic acids. Under low stringency conditions (e.g., low temperature and/or high salt) hybrid duplexes (e.g., DNA:DNA, RNA:RNA or RNA:DNA) will form even where the annealed sequences are not perfectly complementary. Thus, specificity of hybridization is reduced at lower stringency. Conversely, at higher stringency (e.g., higher temperature and/or lower salt and/or in the presence of destabilizing reagents) hybridization tolerates fewer mismatches.

Typically, stringent conditions for short probes (e.g., 10 to 50 nucleotide bases) will be those in which the salt concentration is at least about 0.01 to 1.0 M at pH 7.0 to 8.3 and the temperature is at least about 30° C. Stringent conditions can also be achieved with the addition of destabilizing agents such as formamide.

Under some circumstances, it can be desirable to perform hybridization at conditions of low stringency, e.g., 6×SSPE-T (0.9 M NaCl, 60 mM $NaH_2PO_4$, pH 7.6, 6 mM EDTA, 0.005% Triton) at 37° C., to ensure hybridization. Subsequent washes can then be performed at higher stringency (e.g., 1×SSPE-T at 37° C.) to eliminate mismatched hybrid duplexes. Successive washes can be performed at increasingly higher stringency (e.g., down to as low as 0.25×SSPE-T at 37° C. to 50° C.) until a desired level of hybridization specificity is obtained.

In general, standard conditions for hybridization is a compromise between stringency (hybridization specificity) and signal intensity. Thus, in one embodiment of the invention, the hybridized nucleic acids are washed at successively higher stringency conditions and read between each wash. Analysis of the data sets produced in this manner will reveal a wash stringency above which the hybridization pattern is not appreciably altered and which provides adequate signal for the particular oligonucleotide probes of interest. For example, the final wash may be selected as that of the highest stringency that produces consistent results and that provides a signal intensity greater than approximately 10% of the background intensity.

a. Oligonucleotide Probes

Oligonucleotide probes useful in nucleic acid hybridization techniques employed in the present invention are capable of binding to a nucleic acid of complementary sequence through one or more types of chemical bonds, usually through complementary base pairing via hydrogen bond formation. A probe can include natural bases (i.e., A, G, U, C or T) or modified bases (7-deazaguanosine, inosine, etc.). In addition, the nucleotide bases in the probes can be joined by a linkage other than a phosphodiester bond, so long as it does not interfere with hybridization. Thus, probes can be peptide nucleic acids in which the constituent bases are joined by peptide bonds rather than phosphodiester linkages.

Oligonucleotide probes can be prepared by any means known in the art. Probes useful in the present invention are capable of hybridizing to a nucleotide product of a polysaccharide synthesis gene, such as one of SEQ ID NOs: 1-29. Probes useful in the invention can be generated using the nucleotide sequences disclosed in SEQ ID NOs: 1-29. The invention includes oligonucleotide probes having at least a 2, 10, 15, 20, 30, 35, 40, 45, 50, 55, 60, 65, 70, 75, 80, 85, or 100 nucleotide fragment of a corresponding contiguous sequence of any one of SEQ ID NOs: 1-29. The invention includes oligonucleotides of less than 2, 1, 0.5, 0.1, or 0.05 kb in length. In one embodiment, the oligonucleotide is 60 nucleotides in length.

Oligonucleotide probes can be designed by any means known in the art. See, e.g., Li and Stormo, *Bioinformatics* 17: 1067-76 (2001). Oligonucleotide probe design can be effected using software. Exemplary software includes ArrayDesigner, GENESCAN®, and ProbeSelect. Probes complementary to a defined nucleic acid sequence can be synthesized chemically, generated from longer nucleotides using restriction enzymes, or can be obtained using techniques such as polymerase chain reaction (PCR). PCR methods are well known and are described, for example, in Innis et al. eds., PCR Protocols: A Guide to Methods and Applications, Academic Press Inc. San Diego, Calif. (1990). The probes can be labeled, for example, with a radioactive, biotinylated, or fluorescent tag. Optimally, the nucleic acids in the sample are labeled and the probes are not labeled. Oligonucleotide probes generated by the above methods can be used in solution or solid support-based methods.

The invention includes oligonucleotide probes that hybridize to a product of the coding region or a 3' untranslated region (3' UTR) of a polysaccharide synthesis gene. In one embodiment, the oligonucleotide probe hybridizes to the 3'UTR of any one of SEQ ID NOs: 1-29. The 3' UTR is generally a unique region of the gene, even among members of the same family. Therefore, the probes capable of hybridizing to a product of the 3' UTR can be useful for differentiating the expression of individual genes within a family where the coding region of the genes likely are highly homologous. This allows for the design of oligonucleotide probes to be used as members of a plurality of oligonucleotides, each capable of uniquely binding to a single gene. In another embodiment, the oligonucleotide probe comprises any one of SEQ ID NOs: 59-83. In another embodiment, the oligonucleotide probe consists of any one of SEQ ID NOs: 1-29.

b. Oligonucleotide Array Methods

One embodiment of the invention employs two or more oligonucleotide probes in combination to detect a level of expression of one or more polysaccharide synthesis genes, such as the genes of SEQ ID NOs: 1-29. In one aspect of this embodiment, the level of expression of two or more different genes is detected. The two or more genes may be from the same or different polysaccharide synthesis gene families discussed above. Each of the two or more oligonucleotides may hybridize to a different one of the genes.

One embodiment of the invention employs two or more oligonucleotide probes, each of which specifically hybridize to a polynucleotide derived from the transcript of a gene provided by SEQ ID NOs: 1-29. Another embodiment employs two or more oligonucleotide probes, at least one of which comprises a nucleic acid sequence of SEQ ID NOs: 59-83. Another embodiment employs two or more oligonucleotide probes, at least one of which consists of SEQ ID NOs: 59-83.

The oligonucleotide probes may comprise from about 5 to about 60, or from about 5 to about 500, nucleotide bases, such as from about 60 to about 100 nucleotide bases, including from about 15 to about 60 nucleotide bases.

One embodiment of the invention uses solid support-based oligonucleotide hybridization methods to detect gene expression. Solid support-based methods suitable for practicing the present invention are widely known and are described, for example, in PCT application WO 95/11755; Huber et al., *Anal. Biochem.* 299: 24 (2001); Meiyanto et al., Biotechniques. 31: 406 (2001); Relogio et al., *Nucleic Acids Res.* 30:e51 (2002). Any solid surface to which oligonucleotides can be bound, covalently or non-covalently, can be used. Such solid supports include filters, polyvinyl chloride dishes, silicon or glass based chips, etc.

One embodiment uses oligonucleotide arrays, i.e. microarrays, which can be used to simultaneously observe the expression of a number of genes or gene products. Oligonucleotide arrays comprise two or more oligonucleotide probes provided on a solid support, wherein each probe occupies a unique location on the support. The location of each probe may be predetermined, such that detection of a detectable signal at a given location is indicative of hybridization to an oligonucleotide probe of a known identity. Each predetermined location can contain more than one molecule of a probe, but each molecule within the predetermined location has an identical sequence. Such predetermined locations are termed features. There can be, for example, from 2, 10, 100, 1,000, 2,000 or 5,000 or more of such features on a single solid support. In one embodiment, each oligonucleotide is located at a unique position on an array at least 2, at least 3, at least 4, at least 5, at least 6, or at least 10 times.

Oligonucleotide probe arrays for detecting gene expression can be made and used according to conventional techniques described, for example, in Lockhart et al., Nat'l Biotech. 14: 1675 (1996), McGall et al., *Proc. Nat'l Acad. Sci. USA* 93: 13555 (1996), and Hughes et al., *Nature Biotechnol.* 19:342 (2001). A variety of oligonucleotide array designs is suitable for the practice of this invention.

In one embodiment the one or more oligonucleotides include a plurality of oligonucleotides that each hybridize to a different gene expressed in a particular tissue type. For example, the tissue can be developing wood. In one embodiment, a nucleic acid sample obtained from a plant can be amplified and, optionally labeled with a detectable label. Any method of nucleic acid amplification and any detectable label suitable for such purpose can be used. For example, amplification reactions can be performed using, e.g. Ambion's MessageAmp, which creates "antisense" RNA or "aRNA" (complementary in nucleic acid sequence to the RNA extracted from the sample tissue). The RNA can optionally be labeled using CyDye fluorescent labels. During the amplification step, aaUTP is incorporated into the resulting aRNA. The CyDye fluorescent labels are coupled to the aaUTPs in a non-enzymatic reaction. Subsequent to the amplification and labeling steps, labeled amplified antisense RNAs are precipitated and washed with appropriate buffer, and then assayed for purity. For example, purity can be assay using a NANODROP® spectrophotometer. The nucleic acid sample is then contacted with an oligonucleotide array having, attached to a solid substrate (a "microarray slide"), oligonucleotide sample probes capable of hybridizing to nucleic acids of interest which may be present in the sample. The step of contacting is performed under conditions where hybridization can occur between the nucleic acids of interest and the oligonucleotide probes present on the array. The array is then washed to remove non-specifically bound nucleic acids and the signals from the labeled molecules that remain hybridized to oligonucleotide probes on the solid substrate are detected.

The step of detection can be accomplished using any method appropriate to the type of label used. For example, the step of detecting can accomplished using a laser scanner and detector. For example, on can use and Axon scanner which optionally uses GenePix Pro software to analyze the position of the signal on the microarray slide.

Data from one or more microarray slides can analyzed by any appropriate method known in the art.

Oligonucleotide probes used in the methods of the present invention, including microarray techniques, can be generated using PCR. PCR primers used in generating the probes are chosen, for example, based on the sequences of SEQ ID NOs: 1-29, to result in amplification of unique fragments of the polysaccharide synthesis genes (i.e., fragments that hybridize to only one polynucleotide of any one of SEQ ID NOs: 1-29 under standard hybridization conditions). Computer programs are useful in the design of primers with the required specificity and optimal hybridization properties. For example, Li and Stormo, supra at 1075, discuss a method of probe selection using ProbeSelect which selects an optimum oligonucleotide probe based on the entire gene sequence as well as other gene sequences to be probed at the same time.

In one embodiment, oligonucleotide control probes also are used. Exemplary control probes can fall into at least one of three categories referred to herein as (1) normalization controls, (2) expression level controls and (3) negative controls. In microarray methods, one or more of these control probes may be provided on the array with the inventive polysaccharide synthesis gene-related oligonucleotides.

Normalization controls correct for dye biases, tissue biases, dust, slide irregularities, malformed slide spots, etc. Normalization controls are oligonucleotide or other nucleic acid probes that are complementary to labeled reference oligonucleotides or other nucleic acid sequences that are added to the nucleic acid sample to be screened. The signals obtained from the normalization controls, after hybridization, provide a control for variations in hybridization conditions, label intensity, reading efficiency and other factors that can cause the signal of a perfect hybridization to vary between arrays. In one embodiment, signals (e.g., fluorescence intensity or radioactivity) read from all other probes used in the method are divided by the signal from the control probes, thereby normalizing the measurements.

Virtually any probe can serve as a normalization control. Hybridization efficiency varies, however, with base composition and probe length. Preferred normalization probes are selected to reflect the average length of the other probes being used, but they also can be selected to cover a range of lengths. Further, the normalization control(s) can be selected to reflect the average base composition of the other probes being used. In one embodiment, only one or a few normalization probes are used, and they are selected such that they hybridize well (i.e., without forming secondary structures) and do not match any test probes. In one embodiment, the normalization controls are mammalian genes.

Expression level controls probes hybridize specifically with constitutively expressed genes present in the biological sample. Virtually any constitutively expressed gene provides a suitable target for expression level control probes. Typically, expression level control probes have sequences complementary to subsequences of constitutively expressed "housekeeping genes" including, but not limited to certain photosynthesis genes.

"Negative control" probes are not complementary to any of the test oligonucleotides (i.e., the inventive polysaccharide synthesis gene-related oligonucleotides), normalization controls, or expression controls. In one embodiment, the negative control is a mammalian gene which is not complementary to any other sequence in the sample.

The terms "background" and "background signal intensity" refer to hybridization signals resulting from non-specific binding or other interactions between the labeled target nucleic acids (i.e., mRNA present in the biological sample) and components of the oligonucleotide array. Background signals also can be produced by intrinsic fluorescence of the array components themselves.

A single background signal can be calculated for the entire array, or a different background signal can be calculated for each target nucleic acid. In a one embodiment, background is calculated as the average hybridization signal intensity for the lowest 5 to 10 percent of the oligonucleotide probes being used, or, where a different background signal is calculated for each target gene, for the lowest 5 to 10 percent of the probes for each gene. Where the oligonucleotide probes corresponding to a particular polysaccharide synthesis gene hybridize well and, hence, appear to bind specifically to a target sequence, they should not be used in a background signal calculation. Alternatively, background can be calculated as the average hybridization signal intensity produced by hybridization to probes that are not complementary to any sequence found in the sample (e.g., probes directed to nucleic acids of the opposite sense or to genes not found in the sample). In microarray methods, background can be calculated as the average signal intensity produced by regions of the array that lack any oligonucleotides probes at all.

c. PCR-Based Methods

In another embodiment, PCR-based methods are used to detect gene expression. These methods include reverse-transcriptase-mediated polymerase chain reaction (RT-PCR) including real-time and endpoint quantitative reverse-transcriptase-mediated polymerase chain reaction (Q-RTPCR). These methods are well known in the art. For example, methods of quantitative PCR can be carried out using kits and methods that are commercially available from, for example, Applied BioSystems and Stratagene®. See also Kochanowski, QUANTITATIVE PCR PROTOCOLS (Humana Press, 1999); Innis et al., supra.; Vandesompele et al., Genome Biol. 3: RESEARCH0034 (2002); Stein, Cell Mol. Life. Sci. 59: 1235 (2002).

Gene expression can also be observed in solution using Q-RTPCR. Q-RTPCR relies on detection of a fluorescent signal produced proportionally during amplification of a PCR product. See Innis et al., supra. Like the traditional PCR method, this technique employs PCR oligonucleotide primers, typically 15-30 bases long, that hybridize to opposite strands and regions flanking the DNA region of interest. Additionally, a probe (e.g., TaqMan®, Applied Biosystems) is designed to hybridize to the target sequence between the forward and reverse primers traditionally used in the PCR technique. The probe is labeled at the 5' end with a reporter fluorophore, such as 6-carboxyfluorescein (6-FAM) and a quencher fluorophore like 6-carboxy-tetramethyl-rhodamine (TAMRA). As long as the probe is intact, fluorescent energy transfer occurs which results in the absorbance of the fluorescence emission of the reporter fluorophore by the quenching fluorophore. As Taq polymerase extends the primer, however, the intrinsic 5' to 3' nuclease activity of Taq degrades the probe, releasing the reporter fluorophore. The increase in the fluorescence signal detected during the amplification cycle is proportional to the amount of product generated in each cycle.

The forward and reverse amplification primers and internal hybridization probe is designed to hybridize specifically and uniquely with one nucleotide derived from the transcript of a target gene. In one embodiment, the selection criteria for primer and probe sequences incorporates constraints regarding nucleotide content and size to accommodate TaqMan® requirements.

SYBR Green® can be used as a probe-less Q-RTPCR alternative to the Taqman®-type assay, discussed above. ABI Prism® 7900 Sequence Detection System User Guide Applied Biosystems, chap. 1-8, App. A-F. (2002).

A device measures changes in fluorescence emission intensity during PCR amplification. The measurement is done in "real time," that is, as the amplification product accumulates in the reaction. Other methods can be used to measure changes in fluorescence resulting from probe digestion. For example, fluorescence polarization can distinguish between large and small molecules based on molecular tumbling (see, e.g., U.S. Pat. No. 5,593,867).

d. Protein Detection Methods

Proteins can be observed by any means known in the art, including immunological methods, enzyme assays and protein array/proteomics techniques.

Measurement of the translational state can be performed according to several protein methods. For example, whole genome monitoring of protein—the "proteome"—can be carried out by constructing a microarray in which binding sites comprise immobilized, preferably monoclonal, antibodies specific to a plurality of proteins having an amino acid sequence of any of SEQ ID NOs: 30-48 or proteins encoded by the genes of SEQ ID NOs: 1-29 or conservative variants thereof. See Wildt et al., Nature Biotechnol. 18: 989 (2000). Methods for making polyclonal and monoclonal antibodies are well known, as described, for instance, in Harlow & Lane, ANTIBODIES: A LABORATORY MANUAL (Cold Spring Harbor Laboratory Press, 1988).

Alternatively, proteins can be separated by two-dimensional gel electrophoresis systems. Two-dimensional gel electrophoresis is well-known in the art and typically involves isoelectric focusing along a first dimension followed by SDS-PAGE electrophoresis along a second dimension. See, e.g., Hames et al, GEL ELECTROPHORESIS OF PROTEINS: A PRACTICAL APPROACH (IRL Press, 1990). The resulting electropherograms can be analyzed by numerous techniques, including mass spectrometric techniques, western blotting and immunoblot analysis using polyclonal and monoclonal antibodies, and internal and N-terminal micro-sequencing.

3. Correlating Gene Expression to Phenotype and Tissue Development

As discussed above, the invention provides methods and tools to correlate gene expression to plant phenotype. Gene expression may be examined in a plant having a phenotype of interest and compared to a plant that does not have the phenotype or has a different phenotype. Such a phenotype includes, but is not limited to, increased drought tolerance, herbicide resistance, reduced or increased height, reduced or increased branching, enhanced cold and frost tolerance, improved vigor, enhanced color, enhanced health and nutritional characteristics, improved storage, enhanced yield, enhanced salt tolerance, enhanced resistance of the wood to decay, enhanced resistance to fungal diseases, altered attractiveness to insect pests, increased disease tolerance, increased insect tolerance, increased water-stress tolerance, improved texture, increased germination, increased micronutrient uptake, production of novel resins, increased cellulose content, decreased lignin content and production of novel proteins or peptides.

In another embodiment, the phenotype includes one or more of the following traits: propensity to form reaction wood, a reduced period of juvenility, an increased period of juvenility, self-abscising branches, accelerated reproductive development or delayed reproductive development.

In a further embodiment, the phenotype that is differs in the plants compares includes one or more of the following: lignin quality, lignin structure, wood composition, wood appearance, wood density, wood strength, wood stiffness, cellulose polymerization, fiber dimensions, lumen size, proportion of rays, proportion of vessel elements, other plant components, plant cell division, plant cell development, number of cells per unit area, cell size, cell shape, cell wall composition, rate of wood formation, aesthetic appearance of wood, formation of stem defects, average microfibril angle, width of the S2 cell wall layer, rate of growth, rate of root formation ratio of root to branch vegetative development, leaf area index, and leaf shape. Phenotype can be assessed by any suitable means as discussed above, such as, for example Hertzberg, supra, Ye and Sundström, supra, U.S. Patent Application Publication Nos. 2002/0107644 and 2002/0113212, Marita et al., supra.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference in their entirety.

EXAMPLES

Example 1

Example 1 demonstrates how cellulose synthase and cellulose synthase-like genes are isolated and characterized in *E. grandis* and *P. radiata*.

Total RNA was extracted from plant tissue (using the protocol of Chang et al., *Plant Mol. Biol. Rep.* 11:113-116 (1993). Plant tissue samples were obtained from phloem (P), cambium (C), expanding xylem (X1), and differentiating and lignifying xylem (X2).

mRNA was isolated from the total RNA preparation using either a Poly(A) Quik mRNA Isolation Kit (Stratagene, La Jolla, Calif.) or DYNABEADS® Oligo (dT)25 (Dynal, Skogen, Norway). cDNA expression libraries were constructed from the purified mRNA by reverse transcriptase synthesis followed by insertion of the resulting cDNA clones in Lambda ZAP using a ZAP Express cDNA Synthesis Kit (Stratagene), according to the using the manufacturer's protocol. The resulting cDNAs were packaged using a GIGA-PACK II® Packaging Extract (Stratagene) using an aliquot (1-5 µL) from the 5 µL ligation reaction dependent upon the library. Mass excision of the library was done using XL1-Blue MRF' cells and XLOLR cells (Stratagene) with ExAssist helper phage (Stratagene). The excised phagemids were diluted with NZY broth (Gibco BRL, Gaithersburg, Md.) and plated out onto LB-kanamycin agar plates containing X-gal and isopropylthio-beta-galactoside (IPTG).

Of the colonies plated and selected for DNA miniprep, 99% contained an insert suitable for sequencing. Positive colonies were cultured in NZY broth with kanamycin and cDNA was purified by means of alkaline lysis and polyethylene glycol (PEG) precipitation. Agarose gel at 1% was used to screen sequencing templates for chromosomal contamination. Dye primer sequences were prepared using a Turbo Catalyst 800 machine (Perkin Elmer/Applied Biosystems Division, Foster City, Calif.) according to the manufacturer's protocol.

DNA sequence for positive clones was obtained using a Perkin Elmer/Applied Biosystems Division Prism 377 sequencer. cDNA clones were sequenced first from the 5' end and, in some cases, also from the 3' end. For some clones, internal sequence was obtained using either Exonuclease III deletion analysis, yielding a library of differentially sized subclones in pBK-CMV, or by direct sequencing using gene-specific primers designed to identified regions of the gene of interest. The determined cDNA sequences are provided in SEQ ID NOS: 1-29. The predicted polypeptide sequences are SEQ ID NOs: 30-58.

To identify the cellulose synthase (Ces) and cellulose synthase-like (Csl) candidates in *P. radiata* and *E. grandis* databases, the cDNA sequences were compared to the *Arabidopsis* cellulose synthase superfamily. Richmond and Somerville, *Plant Physiol.* 124:495 (2000).

Next, public domain sequences (by SWISS-PROT/TrEMBL ID's) were used to search against the pine and eucalyptus databases (non-redundant by contig, expect $<1.0e^{-2}$). 80 hits for pine and 82 hits for eucalyptus were obtained. Of these hits, 26 pine and 15 eucalyptus were potentially full length (i.e. contained start Met) or near full length sequences.

The contig consensus DNA and protein sequences were then obtained for all 162 hits, and duplicate sequences were identified. A multiple alignment was then carried out with the protein sequences. The protein alignment was created using the remaining 29 pine and eucalyptus sequences along with the *Arabidopsis* members, and 2 callose synthases and 2 cellulases. From the protein alignment, a dendogram was created. This dendogram grouped the sequence hits with the ces family or the csl family. These sequences were analyzed by primer walking to provide a full length sequence (best HT pick from the contig analyzed for full length sequence).

The public domain cellulose synthase sequences from maize, cotton, rice, and poplar were also extracted and blasted against the pine and eucalyptus databases. The completed primer walked pine and eucalyptus sequences were also blasted against ownseq and the top 500 hits were taken. This was done so that the sequences could be used to search further and ensure that nothing in the pine and eucalyptus databases had been missed by using the *Arabidopsis* superfamily. This search resulted in an additional 4 sequences which were not found in the previous searches. These sequences were then also sent for primer walked full length sequence.

After removing a small number of additional duplicates after primer walking, 30 pine and eucalyptus primer walked cellulose synthase superfamily members were identified. The classification of these sequences as CES or CSL was confirmed by alignment with ClustalX, the corresponding dendogram, and MEME/MAST analysis.

Example 2

To identify additional sequence 5' or 3' of a partial cDNA sequence in a cDNA library, 5' and 3' rapid amplification of cDNA ends (RACE) was performed. using the SMART RACE cDNA amplification kit (Clontech Laboratories, Palo Alto, Calif.). Generally, the method entailed first isolating poly(A) mRNA, performing first and second strand cDNA synthesis to generate double stranded cDNA, blunting cDNA ends, and then ligating of the SMART RACE. Adaptor to the cDNA to form a library of adaptor-ligated ds cDNA. Gene-specific primers were designed to be used along with adaptor specific primers for both 5' and 3' RACE reactions. Using 5' and 3' RACE reactions, 5' and 3' RACE fragments were obtained, sequenced, and cloned. The process may be repeated until 5' and 3' ends of the full-length gene were identified. A full-length cDNA may generated by PCR using primers specific to 5' and 3' ends of the gene by end-to-end PCR.

For example, to amplify the missing 5' region of a gene from first-strand cDNA, a primer was designed 5'→3' from the opposite strand of the template sequence, and from the region between ~100-200 bp of the template sequence. A successful amplification should give an overlap of ~100 bp of DNA sequence between the 5' end of the template and PCR product.

RNA was extracted from four pine tissues, namely seedling, xylem, phloem and structural root using the Concert Reagent Protocol (Invitrogen, Carlsbad, Calif.) and standard isolation and extraction procedures. The resulting RNA was then treated with DNase, using 10U/µl DNase I (Roche Diagnostics, Basel, Switzerland). For 100 μg of RNA, 9 μl 10×DNase buffer (Invitrogen, Carlsbad, Calif.), 10 μl of Roche DNase 1 and 90 μl of Rnase-free water was used. The RNA was then incubated at room temperature for 15 minutes and ¹/₁₀ volume 25 mM EDTA is added. A RNEASY® mini kit (Qiagen, Venlo, The Netherlands) was used for RNA purification according to manufacturer's protocol.

To synthesize cDNA, the extracted RNA from xylem, phloem, seedling and root was used and the SMART RACE cDNA amplification kit (Clontech Laboratories Inc, Palo Alto, Calif.) was followed according to manufacturer's protocol. For the RACE PCR, the cDNA from the four tissue types was combined. The master mix for PCR was created by combining equal volumes of cDNA from xylem, phloem, root and seedling tissues. PCR reactions were performed in 96 well PCR plates, with 1 μl of primer from primer dilution plate (10 mM) to corresponding well positions. 49 μl of master mix is aliquoted into the PCR plate with primers. Thermal cycling commenced on a GENEAMP® 9700 (Applied Biosystems, Foster City, Calif.) at the following parameters:

94° C. (5 sec),
72° C. (3 min), 5 cycles;
94° C. (5 sec),
70° C. (10 sec),
72° C. (3 min), 5 cycles;
94° C. (5 sec),
68° C. (10 sec),
72° C. (3 min), 25 cycles.

cDNA was separated on an agarose gel following standard procedures. Gel fragments were excised and eluted from the gel by using the Qiagen QIAGEN® 96-well Gel Elution kit, following the manufacturer's instructions.

PCR products were ligated into pGEMTeasy (Promega, Madison, Wis.) in a 96 well plate overnight according to the following specifications: 60-80 ng of DNA, 5 μl 2× rapid ligation buffer, 0.5 μl pGEMT easy vector, 0.1 μl DNA ligase, filled to 10 μl with water, and incubated overnight.

Each clone was transformed into *E. coli* following standard procedures and DNA was extracted from 12 clones picked by following standard protocols. DNA extraction and the DNA quality was verified on an 1% agarose gel. The presence of the correct size insert in each of the clones was determined by restriction digests, using the restriction endonuclease EcoRI, and gel electrophoresis, following standard laboratory procedures.

The transformation of *Eucalyptus* elite clones with a sense UDP-glucose binding domain sequence operably-linked to a constitutive promoter confers an enhanced growth phenotype, as evidenced by increases in cellulose synthesis, primary cell wall synthesis, wood density, and tensile strength. Leaf explants are harvested from stock *Eucalyptus* plants and the explants are cultured on a pre-treatment medium. The pre-culture medium comprises auxin, cytokinin, and an *Agrobacterium* inducer, such as acetosyringone, to stimulate cell division along the excised edges of the tissue explant. Following four days of pre-culture, the explants are inoculated with *Agrobacterium* strain GV2260 containing a plasmid bearing a portion of the UDP-glucose binding domain operably linked to a ubiquitin promoter. The explants are co-cultivated for 3 days prior to transfer to Euc Regeneration medium. The explants are cultured on Euc Regeneration medium for 4 days before transfer to selection medium containing an herbicide.

Following the selection of herbicide-resistant transformants, the transformants are assayed for GUS expression. Upon the confirmation of GUS expression, shoots are harvested and transferred to a rooting medium. The rooting medium comprises BTM-1 salts supplemented with 5 g/l MeadWestvaco Nuchar activated carbon, and rooting development usually occurs after 2-4 weeks. Upon development of the primary root system, the transformed plants are transferred to soil. The transgenic Eucalyptus plants carrying any one of SEQ ID NOs. 1-29 operably linked to a ubiquitin promoter exhibit enhanced growth.

Example 3

Example 3 illustrates a procedure for RNA extraction and purification, which is particularly useful for RNA obtained from conifer needle, xylem, cambium, and phloem.

Tissue is obtained from conifer needle, xylem, cambium or phloem. The tissue is frozen in liquid nitrogen and ground. The total RNA is extracted using Concert Plant RNA reagent (Invitrogen). The resulting RNA sample is extracted into phenol:chloroform and treated with DNase. The RNA is then incubated at 65° C. for 2 minutes followed by centrifugation at 4° C. for 30 minutes. Following centrifugation, the RNA is extracted into phenol at least 10 times to remove contaminants.

The RNA is further cleaned using RNEASY® columns (QIAGEN®). The purified RNA is quantified using RIBOGREEN® reagent (Molecular Probes) and purity assessed by gel electrophoresis.

RNA is then amplified using MessageAmp (Ambion). Aminoallyl-UTP and free UTP are added to the in vitro transcription of the purified RNA at a ratio of 4:1 aminoallyl-UTP-to-UTP. The aminoallyl-UTP is incorporated into the new RNA strand as it is transcribed. The amino-allyl group is then reacted with Cy dyes to attach the colorimetric label to the resulting amplified RNA using the Amersham procedure modified for use with RNA. Unincorporated dye is removed by ethanol precipitation. The labeled RNA is quantified spectrophotometrically (NANODROP®). The labeled RNA is fragmented by heating to 95° C. as described in Hughes et al., *Nature Biotechnol.* 19:342 (2001).

Example 4

Example 4 illustrates how cellulose synthase or cellulose synthase-like genes important for wood development in *P. radiata* can be determined and how oligonucleotides which uniquely bind to those genes can be designed and synthesized for use on a microarray.

Pine trees of the species *P. radiata* are grown under natural light conditions. Tissue samples are prepared as described in, e.g., Sterky et al., *Proc. Nat'l Acad. Sci.* 95:13330 (1998). Specifically, tissue samples are collected from woody trees having a height of 5 meters. Tissue samples of the woody trees are prepared by taking tangential sections through the cambial region of the stem. The stems are sectioned horizontally into sections ranging from juvenile (top) to mature (bottom). The stem sections separated by stage of development are further separated into 5 layers by peeling into sections of phloem, differentiating phloem, cambium, differentiating xylem, developing xylem, and mature xylem. Tissue samples, including leaves, buds, shoots, and roots are also prepared from seedlings of the species *P. radiata*.

RNA is isolated and ESTs generated as described in Example 1 or Sterky et al., supra. The nucleic acid sequences of ESTs derived from samples containing developing wood are compared with nucleic acid sequences of genes known to be involved in polysaccharide synthesis. ESTs from samples that do not contain developing wood are also compared with sequences of genes known to be involved in the plant cell cycle. An in silico hybridization analysis is performed using BLAST (NCBI). TABLES 6 and 7, below, show in silico hybridization data for cellulose synthase and cellulose synthase-like proteins in *E. grandis* (TABLE 6) and *P. radiata* (TABLE 7).

cDNA libraries using techniques well known in the art of molecular biology. Using the sequence information, oligonucleotides are designed such that each oligonucleotide is specific for only one cDNA sequence in the library. The oligonucleotide sequences are provided in TABLE 5. 60-mer oligonucleotide probes are designed using the method of Li

TABLE 6

In silico hybridization data for *E. grandis*

| SEQ ID | Cons ID | Total number of ESTs | reproductive tissues | reproductive buds | vegetative buds | fruit | leaf | phloem | cambium | xylem | stem | root |
|---|---|---|---|---|---|---|---|---|---|---|---|---|
| 14 | eucalyptus Spp_017462 | 4 | | | | | | | 0.82 | 0.17 | | |
| 5 | eucalyptus Spp_005009 | 8 | | | 0.08 | | | 0.06 | | | | 0.24 |
| 18 | eucalyptus Spp_023490 | 9 | 2.73 | 2.90 | | | | | | | | |
| 10 | eucalyptus Spp_016249 | 17 | 0.33 | 0.24 | | 1.00 | 0.17 | 0.06 | 3.43 | 0.13 | | 0.08 |
| 16 | eucalyptus Spp_017722 | 1 | | | | | | | | 0.38 | | |
| 3 | eucalyptus Spp_003922 | 7 | | 1.45 | | | | | 0.19 | 1.56 | | |
| 8 | eucalyptus Spp_008896 | 64 | 0.68 | | | | 0.17 | | 0.37 | 17.48 | | 0.08 |
| 9 | eucalyptus Spp_012804 | 14 | 1.84 | | | 0.69 | 0.17 | 0.06 | | | | |
| 11 | eucalyptus Spp_016939 | 3 | | | 0.08 | | 0.99 | | | 0.17 | | |
| 12 | eucalyptus Spp_017058 | 2 | | | | | 0.83 | | | | | |
| 17 | eucalyptus Spp_022868 | 64 | 0.68 | | | | 0.17 | | 0.37 | 17.48 | | 0.08 |
| 7 | eucalyptus Spp_008124 | 47 | 0.11 | | | 0.54 | 0.17 | | 0.57 | 9.60 | | 0.04 |
| 15 | eucalyptus Spp_017488 | 6 | 1.37 | | | 0.15 | | 0.11 | 0.16 | 0.29 | | |
| 19 | eucalyptus Spp_027512 | 2 | | | | | | 0.06 | 0.90 | | | |
| 4 | eucalyptus Spp_004683 | 7 | | 1.61 | 0.23 | 0.34 | | | | | 0.24 | |

TABLE 7

In silico hybridization data for *P. radiata*

| SEQ ID NO | Cons ID | Total number of ESTs | female cones | Reproductive buds | Vegetative buds | Vegetative meristem | callus | vascular | phloem | Cambium | xylem | root |
|---|---|---|---|---|---|---|---|---|---|---|---|---|
| 20 | pinusRadiata_000531 | 17 | | | | | | | | 0.19 | 1.91 | 0.11 |
| 21 | pinusRadiata_002922 | 3 | | | | | | 0.18 | | | 0.15 | |
| 23 | pinusRadiata_017730 | 11 | | | | 0.38 | | | | | 0.46 | |
| 24 | pinusRadiata_027109 | 9 | | | | | | | | | 1.45 | |
| 25 | pinusRadiata_000892 | 26 | 0.15 | | 0.14 | | | 0.36 | 0.82 | 0.58 | 1.12 | |
| 27 | pinusRadiata_013907 | 16 | 0.11 | 0.16 | | | | | 0.41 | | 0.17 | 0.26 |
| 28 | pinusRadiata_026937 | 3 | 0.39 | | | | | | | | | |
| 29 | pinusRadiata_027496 | 2 | | | | | | | | | 0.37 | |
| 22 | pinusRadiata_003920 | 94 | | | 0.14 | 0.27 | | 0.18 | 0.06 | 1.99 | 22.24 | 0.60 |
| 26 | pinusRadiata_008513 | 12 | 0.15 | | | | 0.22 | | 0.06 | 0.05 | | 0.22 |

Sequences from among the known cellulose synthase and cellulose synthase-like protein genes that show hybridization in silico to ESTs made from samples containing developing wood, but that do not hybridize to ESTs from samples not containing developing wood are selected for further examination.

cDNA clones containing sequences that hybridize to the genes showing wood-preferred expression are selected from and Stormo, supra or using software such as ArrayDesigner, GENESCAN®, and ProbeSelect.

The oligonucleotides are then synthesized in situ described in Hughes et al., *Nature Biotechnol.* 19:324 (2002) or as described in Kane et al., *Nucleic Acids Res.* 28:4552 (2000) and affixed to an activated glass slide (Sigma-Genosis, The Woodlands, Tex.) using a 5' amino linker. The position of each oligonucleotide on the slide is known.

Example 5

Example 5 illustrates how RNAs of tissues from multiple pine species, in this case both *P. radiata* and loblolly pine *P. taeda* trees, are selected for analysis of the pattern of gene expression associated with wood development in the juvenile wood and mature wood forming sections of the trees using the microarrays derived from *P. radiata* cDNA sequences described in Example 4.

Open pollinated trees of approximately 16 years of age are selected from plantation-grown sites, in the United States for loblolly pine, and in New Zealand for radiata pine. Trees are felled during the spring and summer seasons to compare the expression of genes associated with these different developmental stages of wood formation. Trees are felled individually and trunk sections are removed from the bottom area approximately one to two meters from the base and within one to two meters below the live crown. The section removed from the basal end of the trunk contains mature wood. The section removed from below the live crown contains juvenile wood. Samples collected during the spring season are termed earlywood or springwood, while samples collected during the summer season are considered latewood or summerwood. Larson et al., *Gen. Tech. Rep.* FPL-GTR-129. Madison, Wis.: U.S. Department of Agriculture, Forest Service, Forest Products Laboratory. p. 42.

Tissues are isolated from the trunk sections such that phloem, cambium, developing xylem, and maturing xylem are removed. These tissues are collected only from the current year's growth ring. Upon tissue removal in each case, the material is immediately plunged into liquid nitrogen to preserve the nucleic acids and other components. The bark is peeled from the section and phloem tissue removed from the inner face of the bark by scraping with a razor blade. Cambium tissue is isolated from the outer face of the peeled section by gentle scraping of the surface. Developing xylem and lignifying xylem are isolated by sequentially performing more vigorous scraping of the remaining tissue. Tissues are transferred from liquid nitrogen into containers for long term storage at −70° C. until RNA extraction and subsequent analysis is performed.

Example 6

Example 6 illustrates procedures alternative to those used in Example 3 for RNA extraction and purification, particularly useful for RNA obtained from a variety of tissues of woody plants, and a procedure for hybridization and data analysis using the arrays described in Example 4.

RNA is isolated according to the protocol of Chang et al., Plant Mol. Biol. Rep. 11:113. DNA is removed using DNase I (Invitrogen, Carlsbad, Calif.) according to the manufacturer's recommendations. The integrity of the RNA samples is determined using the Agilent 2100 Bioanalyzer (Agilent Technologies, USA).

10 μg of total RNA from each tissue is reverse transcribed into cDNA using known methods.

In the case of *Pinus radiata* phloem tissue, it can be difficult to extract sufficient amounts of total RNA for normal labelling procedures. Total RNA is extracted and treated as previously described and 100 ng of total RNA is amplified using the Ovation™ Nanosample RNA Amplification system from NuGEN™ (NuGEN, CA, USA). Similar amplification kits such as those manufactured by Ambion may alternatively be used. The amplified RNA is reverse transcribed into cDNA and labelled as described above.

Hybridization and stringency washes are performed using the protocol as described in the US patent application for "Methods and Kits for Labeling and Hybridizing cDNA for Microarray Analysis" (supra) at 42 C. The arrays (slides) are scanned using a ScanArray 4000 Microarray Analysis System (GSI Lumonics, Ottawa, ON, Canada). Raw, non-normalized intensity values are generated using QUANTARRAY software (GSI Lumonics, Ottawa, ON, Canada).

A fully balanced, incomplete block experimental design (Kerr and Churchill, *Gen. Res.* 123:123, 2001) is used in order to design an array experiment that would allow maximum statistical inferences from analyzed data.

Gene expression data is analyzed using the SAS® Microarray Solution software package (The SAS Institute, Cary, N.C., USA). Resulting data was then visualized using JMP® (The SAS Institute, Cary, N.C., USA).

Analysis done for this experiment is an ANOVA approach with mixed model specification (Wolfinger et al., *J. Comp. Biol.* 8:625-637). Two steps of linear mixed models are applied. The first one, normalization model, is applied for global normalization at slide-level. The second one, gene model, is applied for doing rigorous statistical inference on each gene. Both models are stated in Models (1) and (2).

$$\log_2(Y_{ijkls}) = \theta_{ij} + D_k + S_l + DS_{kl}\omega_{ijkls} \quad (1)$$

$$R_{ijkls}^{(g)} = \mu_{ij}^{(g)} + D_k^{(g)} + S_l^{(g)} + DS_{kl}^{(g)} + SS_{ls}^{(g)}\epsilon_{ijkls}^{(g)} \quad (2)$$

$Y_{ijkls}$ represents the intensity of the $s^{th}$ spot in the $l^{th}$ slide with the $k^{th}$ dye applying the $j^{th}$ treatment for the $i^{th}$ cell line. $\theta_{ij}$, $D_k$, $S_l$, and $DS_{kl}$ represent the mean effect of the jth treatment in the ith cell line, the kth dye effect, the $l^{th}$ slide random effect, and the random interaction effect of the $k^{th}$ dye in the $l^{th}$ slide. $\omega_{ijkls}$ is the stochastic error term. represent the similar roles as $\theta_{ij}$, $D_k$, $S_l$, and $DS_{kl}$ except they are specific for the $g^{th}$ gene. $R_{ijkls}^{(g)}$ represents the residual of the $g^{th}$ gene from model (1). $\mu_{ij}^{(g)}$, $D_k^{(g)}$, $S_l^{(g)}$, and $DS_{kl}^{(g)}$ represent the similar roles as $\theta_{ij}$, $D_k$, $S_l$, and $DS_{kl}$ except they are specific for the $g^{th}$ gene. $SS_{ls}^{(g)}$ represent the spot by slide random effect for the $g^{th}$ gene. $\epsilon_{ijkls}^{(g)}$ represent the stochastic error term. All random terms are assumed to be normal distributed and mutually independent within each model.

According to the analysis described above, certain cDNAs, some of which are shown in Table 4, are found to be differentially expressed.

| SEQ ID NO | Expression pattern |
|---|---|
| 22 | Increased expression |
| 28 | Specific expression in X2 xylem. |

The involvement of these specific genes in wood development is inferred through the association of the up-regulation or down-regulation of genes to the particular stages of wood development. Both the spatial continuum of wood development across a section (phloem, cambium, developing xylem, maturing xylem) at a particular season and tree trunk position and the relationships of season and tree trunk position are considered when making associations of gene expression to the relevance in wood development.

Example 7

Example 7 demonstrates how one can correlate polysaccharide gene expression with agronomically important wood phenotypes such as density, stiffness, strength, distance between branches, and spiral grain.

Mature clonally propagated pine trees are selected from among the progeny of known parent trees for superior growth characteristics and resistance to important fungal diseases. The bark is removed from a tangential section and the trees are examined for average wood density in the fifth annual ring at breast height, stiffness and strength of the wood, and spiral grain. The trees are also characterized by their height, mean distance between major branches, crown size, and forking.

To obtain seedling families that are segregating for major genes that affect density, stiffness, strength, distance between branches, spiral grain and other characteristics that may be linked to any of the genes affecting these characteristics, trees lacking common parents are chosen for specific crosses on the criterion that they exhibit the widest variation from each other with respect to the density, stiffness, strength, distance between branches, and spiral grain criteria. Thus, pollen from a tree exhibiting high density, low mean distance between major branches, and high spiral grain is used to pollinate cones from the unrelated plus tree among the selections exhibiting the lowest density, highest mean distance between major branches, and lowest spiral grain. It is useful to note that "plus trees" are crossed such that pollen from a plus tree exhibiting high density are used to pollinate developing cones from another plus tree exhibiting high density, for example, and pollen from a tree exhibiting low mean distance between major branches would be used to pollinate developing cones from another plus tree exhibiting low mean distance between major branches.

Seeds are collected from these controlled pollinations and grown such that the parental identity is maintained for each seed and used for vegetative propagation such that each genotype is represented by multiple ramets. Vegetative propagation is accomplished using micropropagation, hedging, or fascicle cuttings. Some ramets of each genotype are stored while vegetative propagules of each genotype are grown to sufficient size for establishment of a field planting. The genotypes are arrayed in a replicated design and grown under field conditions where the daily temperature and rainfall are measured and recorded.

The trees are measured at various ages to determine the expression and segregation of density, stiffness, strength, distance between branches, spiral grain, and any other observable characteristics that may be linked to any of the genes affecting these characteristics. Samples are harvested for characterization of cellulose content, lignin content, cellulose microfibril angle, density, strength, stiffness, tracheid morphology, ring width, and the like. Samples are also examined for gene expression as described in Example 6. Ramets of each genotype are compared to ramets of the same genotype at different ages to establish age:age correlations for these characteristics.

Example 8

Example 8 demonstrates how responses to environmental conditions such as light and season alter plant phenotype and can be correlated to polysaccharide synthesis gene expression using microarrays. In particular, the changes in gene expression associated with wood density are examined.

Trees of three different clonally propagated *E. grandis* hybrid genotypes are grown on a site with a weather station that measures daily temperatures and rainfall. During the spring and subsequent summer, genetically identical ramets of the three different genotypes are first photographed with north-south orientation marks, using photography at sufficient resolution to show bark characteristics of juvenile and mature portions of the plant, and then felled. The age of the trees is determined by planting records and confirmed by a count of the annual rings. In each of these trees, mature wood is defined as the outermost rings of the tree below breast height, and juvenile wood as the innermost rings of the tree above breast height. Each tree is accordingly sectored as follows:
NM—NORTHSIDE MATURE
SM—SOUTHSIDE MATURE
NT—NORTHSIDE TRANSITION
ST—SOUTHSIDE TRANSITION
NJ—NORTHSIDE JUVENILE
SJ—SOUTHSIDE JUVENILE Tissue is harvested from the plant trunk as well as from juvenile and mature form leaves. Samples are prepared simultaneously for phenotype analysis, including plant morphology and biochemical characteristics, and gene expression analysis. The height and diameter of the tree at the point from which each sector was taken is recorded, and a soil sample from the base of the tree is taken for chemical assay. Samples prepared for gene expression analysis are weighed and placed into liquid nitrogen for subsequent preparation of RNA samples for use in the microarray experiment.

The tissues are denoted as follows:
P—phloem
C—cambium
X1—expanding xylem
X2—differentiating and lignifying xylem Thin slices in tangential and radial sections from each of the sectors of the trunk are fixed as described in Ruzin, PLANT MICROTECHNIQUE AND MICROSCOPY, Oxford University Press, Inc., New York, N.Y. (1999) for anatomical examination and confirmation of wood developmental stage. Microfibril angle is examined at the different developmental stages of the wood, for example juvenile, transition and mature phases of *Eucalyptus grandis* wood. Other characteristics examined are the ratio of fibers to vessel elements and ray tissue in each sector. Additionally, the samples are examined for characteristics that change between juvenile and mature wood and between spring wood and summer wood, such as fiber morphology, lumen size, and width of the S2 (thickest) cell wall layer. Samples are further examined for measurements of density in the fifth ring and determination of modulus of elasticity using techniques well known to those skilled in the art of wood assays. See, e.g., Wang, et al., *Non-destructive Evaluations of Trees*, EXPERIMENTAL TECHNIQUES, pp. 28-30 (2000).

For biochemical analysis, 50 grams from each of the harvest samples are freeze-dried and analyzed, using biochemical assays well known to those skilled in the art of plant biochemistry for quantities of simple sugars, amino acids, lipids, other extractives, lignin, and cellulose. See, e.g., Pettersen & Schwandt, *J. Wood Chem. & Technol.* 11:495 (1991).

In the present example, the phenotypes chosen for comparison are high density wood, average density wood, and low density wood. Nucleic acid samples are prepared as described in Example 3, from trees harvested in the spring and summer. Gene expression profiling by hybridization and data analysis is performed as described above.

Using similar techniques and clonally propagated individuals one can examine polysaccharide gene expression as it is related to other complex wood characteristics such as strength, stiffness and spirality.

Example 9

Example 9 demonstrates how a cellulose synthase can be linked to a tissue-preferred promoter and expressed in pine resulting in a plant with increased wood density.

A polysaccharide synthesis gene, which is more highly expressed during the early spring, is identified by the method described in Example 7. A DNA construct having the density-related polypeptide operably linked to a promoter is placed into an appropriate binary vector and transformed into pine using the methods described herein. Pine plants are transformed as described in herein and the transgenic pine plants are used to establish a forest planting. Increased density even in the spring wood (early wood) is observed in the transgenic pine plants relative to control pine plants which are not transformed with the density related DNA construct.

Example 10

Using techniques well known to those skilled in the art of molecular biology, the sequence of the cellulose synthase isolated in Example 9 is analyzed in genomic DNA isolated from alfalfa. This enables the identification of an orthologue in alfalfa whose sequence is then used to create an RNAi knockout construct. This construct is then transformed into alfalfa. See, e.g., Austin et al., *Euphytica* 85, 381 (1995). The regenerated transgenic plants show lower fiber content and increased ray cell content in the xylem. Such properties improve digestability which results in higher growth rates in cattle fed on this alfalfa as compared to wild-type alfalfa of the same species.

Example 11

Example 11 demonstrates how gene expression analysis can be used to find gene variants which are present in mature plants having a desirable phenotype. The presence or absence of such a variant can be used to predict the phenotype of a mature plant, allowing screening of the plants at the seedling stage. Although this example employs eucalyptus, the method used herein is also useful in breeding programs for pine and other tree species.

The sequence of a putative density-related gene is used to probe genomic DNA isolated from *Eucalyptus* that vary in density as described in previous examples. Non-transgenically produced *Eucalyptus* hybrids of different wood phenotypes are examined. One hybrid exhibits high wood density and another hybrid exhibits lower wood density. A molecular marker in the 3' portion of the coding region is found which distinguishes a high-density gene variant from a lower density gene variant.

This molecular marker enables tree breeders to assay non-transgenic *Eucalyptus* hybrids for likely density profiles while the trees are still at seedling stage, whereas in the absence of the marker, tree breeders must wait until the trees have grown for multiple years before density at harvest age can be reliably predicted. This enables selective outplanting of the best trees at seedling stage rather than an expensive culling operation and resultant erosion at thinning age. This molecular marker is further useful in the breeding program to determine which parents will give rise to high density outcross progeny.

Molecular markers found in the 3' portion of the coding region of the gene that do not correspond to variants seen more frequently in higher or lower wood density non-transgenic *Eucalyptus* hybrid trees are also useful. These markers are found to be useful for fingerprinting different genotypes of *Eucalyptus*, for use in identity-tracking in the breeding program and in plantations.

Example 12

This Example describes microarrays for identifying gene expression differences that contribute to the phenotypic characteristics that are important in commercial wood, namely wood appearance, stiffness, strength, density, fiber dimensions, coarseness, cellulose and lignin content, extractives content and the like.

Woody trees of genera that produce commercially important wood products, in this case *Pinus* and *Eucalyptus*, are felled from various sites and at various times of year for the collection and isolation of RNA from developing xylem, cambium, phloem, leaves, buds, roots, and other tissues. RNA is also isolated from seedlings of the same genera.

All contigs are compared to both the ESTs made from RNA isolated from samples containing developing wood and the sequences of the ESTs made from RNA of various tissues that do not contain developing wood. Contigs containing primarily ESTs that show more hybridization in silico to ESTs made from RNA isolated from samples containing developing wood than to ESTs made from RNA isolated from samples not containing developing wood are determined to correspond to possible novel genes particularly expressed in developing wood. These contigs are then used for BLAST searches against public domain sequences. Those contigs that hybridize in silico with high stringency to no known genes or genes annotated as having only a "hypothetical protein" are selected for the next step. These contigs are considered putative novel genes showing wood-preferred expression.

The longest cDNA clones containing sequences hybridizing to the putative novel genes showing wood-preferred expression are selected from cDNA libraries using techniques well known to those skilled in the art of molecular biology. The cDNAs are sequenced and full-length gene-coding sequences together with untranslated flanking sequences are obtained where possible. Stretches of 45-80 nucleotides (or oligonucleotides) are selected from each of the sequences of putative novel genes showing wood-preferred expression such that each oligonucleotide probe hybridizes at high stringency to only one sequence represented in the ESTs made from RNA isolated from trees or seedlings of the same genus.

Oligomers are then chemically synthesized and placed onto a microarray slide as described in Example 4. Each oligomer corresponds to a particular sequence of a putative novel gene showing wood-preferred expression and to no other gene whose sequence is represented among the ESTs made from RNA isolated from trees or seedlings of the same genus.

Sample preparation and hybridization are carried out as in Example 4. The technique used in this example is more effective than use of a microarray using cDNA probes because the presence of a signal represents significant evidence of the expression of a particular gene, rather than of any of a number of genes that may contain similarities to the cDNA due to conserved functional domains or common evolutionary history. Thus, it is possible to differentiate homologous genes, such as those in the same family, but which may have different functions in phenotype determination.

This hybridization data, gained using the method of Example 6, enables the user to identify which of the putative novel genes actually possesses a pattern of coordinate expression with known genes, a pattern of expression consistent with a particular developmental role, and/or a pattern of expression that suggests that the gene has a promoter that drives expression in a valuable way.

The hybridization data obtained using this method can be used, for example, to identify a putative novel gene that shows an expression pattern particular to the tracheids with the lowest cellulose microfibril angle in developing spring wood (early wood). The promoter of this gene can also be isolated as in Example 8, and operably linked to a gene that has been shown as in Example 9 to be associated with late wood (summer wood). Transgenic pine plants containing this construct are generated using the methods of Example 9, and the early wood of these plants is then shown to display several characteristics of late wood, such as higher microfibril angle, higher density, smaller average lumen size, etc.

Example 13

Example 13 demonstrates the use of a xylem-specific promoter functionally linked to a polysaccharide synthesis gene for increased plant biomass.

Xylem-specific polysaccharide synthesis transcripts are identified via array analyses of different secondary vasculature layers as described in Example 6. Candidate promoters linked to the genes corresponding to these transcripts are cloned from pine genomic DNA using, e.g., the BD Clontech GenomeWalker kit and tested in transgenic tobacco via a reporter assay(s) for cambium specificity/preference. The xylem-specific promoter overexpressing a polysaccharide synthesis gene involved in secondary xylem cell division is used to increase wood biomass. A tandem xylem-specific promoter is constructed driving the polysaccharide synthesis gene ORF. Boosted transcript levels of the candidate polysaccharide synthesis gene result in an increased xylem biomass phenotype.

While the invention is described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention. All references and publications cited herein are incorporated by reference in their entireties.

TABLE 1

*Eucalyptus grandis* polysaccharide synthesis genes

| DNA SEQ ID | Consensus ID | Target | Curated DNA seq |
|---|---|---|---|
| 1 | | Cellulose synthase GDP forming | GGGGAAAAAGCAACCATATAAAACTATTGCCA TTCGCACAGGAACAGAACGACGAGATCATGGA GGCCAGGGCGGGACTTGTTGCAGGTTCCTATA AGCGGAACGAGCTTATGGTAGTCCCTGGACAC GATGGGCCCAAGCCCATCAGGCTATCCACCCT CCAGGATTGCCAAGTCTGCGGAGATAAAATCG GCTGCAACCCGAATGGGGAACTATTCGTGGCC TGCAACGAGTGTGGATTCCCTGTGTGTCGTCCC TGTTATGAGTACGAGAGAAAGGATGGGAACCG GTGCTGCCCTCAGTGCAAGACTCGGTACAGGC GTCACAAAGGGAGTCCCCGGGTTGAAGGCGAT GATGAAGAAGATGGCATGGACGACTTAGAACA AGAATTCAACATGGAAAGAGATCGCCAAAGCG TAGTCAGTCACAGAGGAAACGCCTTCGACGCT ACTCCTCGGGCTGCCCACAGTATCGCTAACCG CTCGATAAATGGAGATAATTATGCACTTTCCCT TCCTCCGATCATGGATGGCGACAGTTTAAGTGT TCAGCGTTTTCCACATGCAGCTACTGTGATTGG AAATGGATTAGATCCAGTCAAAGAGAACTATG GGAGTGCTGCATGGAAGGAGAGAGTGGAGAA TTGGAAAGCGAAGCACGATAAGAAAAGTGGC AGCATCAAGGATGGCATATATGATCCAGACGA GGCCGATGATATAATGATGACTGAAGCCGAAG CGAGACAGCCTTTTTCGCGTAAGGTGCCAATC CCCTCCAGTCTAATCAATCCCTACAGAATTGTT ATTGTGTTGCGTTTGATAATTCTGGGATTCTTC TTCCGCTACCGATTGATGAATCCTGCCAAGGA CGCACTTGGCCTCTGGTTGACCTCCATTATCTG CGAGATCTGGTTCGCCTTCTCCTGGATTCTTGA TCAGTTCCCCAAGTGGTTTCCCATCACTAGAGA AACTTATCTCGACAGATTATCTATGAGATACG AGAGGGAAGGAGAGCCTTGCAAGCT |
| 2 | eucalyptusSpp_000984 | Cellulose synthase GDP forming | CTGACGTGCTCGTTGACTCCCCGGAGATTGGTC CGCAGAGATAGCCGATGGGTCCGGCGACAAGG AGGAGCCTGGATCGTCGGATGACGGCGGGGTC GACACTGCGAAGGTTGATGGGGCTAAGGGTGG CGGTGAAGCCTATGATCCTGCTTCTAAGAAGC TCAGGAGAGAGAATATGAGGAGTTCAAGGTGC AAATCAATGCTTTGGTTGCAAAGGCACAAAAG ATGCCAGAAGAAGGGTGGACAATGCAGGATG GCACTGCCTGGGCTGGAAATAACCCCAGGGAT CACCCTGGAATGATACAGGTTTTCCTGGGCCA CAGTGGGGACTTGATACTGATGGAAATGAGC TACCTCGACTTGTTTATGTTTCTCGTGAAAAGC GACCTGGTTTCCAACATCACGAGAAAGCTGGA GCCATGATTGCTTTGATCCGGGTCTCAGCTGTC CTAACCAACGGACCGTATCTTTTGAATGTTGAC TGTGATCATTACTTTAATAAAGTAAAGCATTGA |

TABLE 1-continued

Eucalyptus grandis polysaccharide synthesis genes

| DNA SEQ Consensus ID ID | Target | Curated DNA seq |
|---|---|---|
| | | AAGAAGCAATGTGTTTCATGATGGATCCCGCT TATGGAAAGAAGACGTGCTATGTGCAGTTCCC ACAACGTTTTGATGGGATTGACTTGCACGATC GATATGCTAACCGCAACATCGTCTTCTTTGATA TAGATTAACTTGAAAGGGCTTGACGTCATCCA AGGTCCTGTCTATGTTGGAATTGGATGTTGTTT CAACAGGCAAGCCCTTTATGGATATGACCCTG TATTAACCGAGGAAGATCTGGAACCAAATATT ATTGTAAAGAGTTGTGGTTCAAGAAAGAAGGG GAAGGGTGGCAATAAGTACATTGACAAGAAA AGAGCAATGAAAAGAACTGAATCCACTGTTCC AATTTTCAATATAGAAGATGTTGAGGAGGGGG TTGAAGGATATGATGATGAGACGTCGCTCCTG ATGTCTCAGAAAGTCTAGAGAAAAGATTCGG TCAGTCTCCTGTTTTCATTGCGGCTACTTTCAT GGAACAGGGTGGCCTACGACCATCTA |
| 3 eucalyptusSpp_003922 | Cellulose synthase GDP forming | CTCGACACATTGCTTTCTTCCGAGTTCACAGTT AACATGAGATCTCTCTGTGTGACTATCCTCAGT CTCTTTGCCACTTAGATCTGAACCGCAATTCTG TTGCTTTCTTTCGTATTCTTTGTTCTTTCGCTAA GAAGGGCTGAAAATCAAGAACGGTAGTAAGA GCAAAGAGAAATGGAGGTGAGTTCTGGTTTAG TAGCGGGCTCTCACAACAGGAACGAGCTGGTT GTCATCCGCCGCGAGAATGAACTCGGACAAAA GCCGTTGCAGAAGTTGAGCGGGCAAATTTGCC AGATTTGCGGCGACGACGTTGGATTGACCGTG GACGGCGAGCTATTCGTCGCCTGCAATGAGTG TGCGTTCCCCATTTGCAGGACTTGCTATGAGTA CGAACGGCGCGAGGGAAGCCAAATTTGTCCTC AGTGCAAAACCAGATTCAAGTGCTTAAGGGGG TGTGCAAGAGTGGATGGAGATGAGGAAGAGG ATGGTGTGGATGACTTGGAGAACGAGTTCAAC TTTGATGGGAGGCATAGGCAAGAGATGGATCG CCAGGGATATGGTGCAGAGGCAATGCTTCATG GCCATATGAGCTATGGCCGTGGCTCGGATTTG GATCTGTCTCACGTTCATCCACTGCCCCAAGTC CCACTCCTCACCAATGGTCAAATGGTTGATGAT ATTCCTCCGGAGCACCATGCTTTGGTGCCAGCC TACATGGGAGCTGGAGGCGGCGGTGGCGGAG GTGGCAAAAGGATTCACCCACTTCCTTTCACTG ATTCTGGTCTTCCAGTGCAACCTCGATCCATGG ATCCTTCAAAGGACTTGGCTGCTTATGGATATG GAAGCGTTGCTTGGAAAGAGAGGATGGAGAGT TGGAAACAAAAGCAAGAGAAACTACAGACGA TGAAGAACGAGAAAGGTGGCAAGGAATGGGA CGATGATGGGGACAACCCAGATCTACCACTAA TGGATGAGGCGAGACAGCCGCTGTCAAGAAAG TTGCCTATATCCTCCAGCCAAATCA |
| 4 eucalyptusSpp_004683 | Cellulose synthase like | GTCCTTTGGCGCTCCGTTGCCTCCTCCTCGTTC ACGGCTCATGAACACCCCCTCTCTGCACGTCGT CCATCATTTTCTTCTCTAATCCTCATTGGCATTA GCATTTTGATCTGATAAAAGCCACTTGGTCGCA ACACGTTCGGTGTTTCTTGGCTCGCCTTCCCTG AAGTGAATCTTCTACGAAAGCTGAAAGCTTGG CCTTTCCTGCGAAGTGGGTGTGCTTCAAGAATC GAGATTCGAGAAAATCAAGACTTCAAAATGGC ACCTTCGCTCGATTCGTGGGCAAAACAGAACG TTCACAAGGGCACCCCCGTCGTCGTCAAGATG GAGAACCTGAACTGGTCCATGCTCGAGCTGGA GAGCCCGTCGGACGAGGACATCTTCCCCGCCG GCGCCCCGCCGCCGGCGAGGGGCGGCGCCG GAGCGGACGCGCAACAAGAACGCGAAGCAGC TCACGTGGGTCCTGCTCCTCAGGGCCCACAGG GCCGCCGGCTGCCTGGCCTCCATGGCCGCCGC CTTCCTCGGCCTCGCCTCCGCCGTCAGGCGCCG CGTGGCCGCCGGCAGGACCGACAACGACGTCA GCGAGGCTTCTCGTCGCGGCGGGGAGTGAGA GAGAGCCCCACTCTCAAGGCCAGGTTCTATAC TTGCACAAAAGTGTTCCTTTGGCTGTCCATTGT CCTGTTAGGGTTTGAAGTGGCTGCTTACTTCAA GGGTTGGCACTATGGTGCGCACAATGTCGAGT TGCAACACCTGTTGGCAACTTCTTTCTCAGTTA |

TABLE 1-continued

Eucalyptus grandis polysaccharide synthesis genes

| DNA SEQ ID | Consensus ID | Target | Curated DNA seq |
|---|---|---|---|
| | | | AGGGTGTTTTCGATCGGTTGTATTCGAAGTGGG TTTCGATCCGGGTGGAATATCTTGCTCCTCCAT TGCAGTTCTTGGCCAATGCTTGCATAGTGCTCT TCCTTATCCAGAGCTTGGACAGGCTTGTCCTGT GTTTGGGTTGTTTCTGGATCAAATTCAAAAACA TCAAGCCGATCCCAAAGGAGGACGCCTCAGTC GATGTCGAATCCGGCGAGAAGGGATACTTCCC TATGGTCCTAGTGCAAC |
| 5 | eucalyptusSpp_005009 | Cellulose synthase like | CTCTCCCCTCTTCATCGACTCCACTCGCTCTCTT TCCCTCCCCTCTCTCTCTCTCTTCCGCAGCAAT GCGTCTGTTCCTTTCCTTCCTGGCTTCGCTCTAG TCGAGGACAAGAACAGAGGCATTCCGTCGGCA CGAACTCAGAGAGAGAGAAAGAGAGAGAGGG ACTGAAGAAGCAGGTGGTCTTGGAAGGGTGCA AAAGGAAAGTGAGGAAAAGGGGAGAGAAGGA AGCCGAACGGAGGCAGCATTTCCCCTCTGCTT GCCTCATTTGCTCGAGAGAGAGAGAAAGAGAG AGAGGGGGAGGCAGCGAGTGAGATCTACCTTT TTCGTACACTAGCTTCTCAAAATGCCTGCTTTG ACCTAGTTAAGACACCCCTCGATTACCATTCCA TCTGAGGAACGATTTCCTAGTCCAAACCCAAC TTTCCAAATCCTAGATAATAACATCCCCTGTTT TTCTCCTCTGTTTTGCTTTCTGTGCTCTGCTCCA GAAAACAGAGCAGCGCCAAACAGAGCAGGGT AGAAAACAGAGTCTCGAGCCTCTGTCTCGAAA TGGCGCAAATCTCGGCCAAGGACCTGATCCCG GACTCGTTAACCATGTCCCGGGAGGACATCGC GGGCCAGCTGGGGATGGTGTGGGAGCTGATCA AGGCGCCGCTGATCGTCCCGGTGCTGCGGCTC TCGGTCTACGTATGCCTCGCGATGGCGCTCATG CTTTTCATGGAGAGGGTCTACATGGGCATCGTC ATCGTCCTCGTCAAGCTCTTCTGGAAGAAGCC GGAGAAGCGCTACAATTGGGAGCCCATCGAGG AGGACCTCGAGTCCGGAAGCTCCAACTTCCCC TTCGTCCTCGTCCAAATCCCAATGTACAACGAG AAAGAGGTGTACAAGATTTCGATCGGGAGCAGC GTGCGGGCTGTCCTGGCCGGCGGACCGCCTCG TGATCCAAGTCCTCGACGACTCCACCGATCCC GTAATTAAGCAAATGGTGGAGCTGGAGTGCCA GAGGTGGGCGAGCAAGGGGATC |
| 6 | eucalyptusSpp_007860 | Cellulose synthase GDP forming | CTCCTCGGCGCCTCCCCCTCGCGATCGCTTCCC GCTCGGCCCGTGGCCTCCCCGACACCATGTCC GGCTTCGCCGTGGGCTCTCACTCCCGGAACGA GCTCCATGTCACGAATGGTGGCGCTGCTGACG AACACCGCTCTCCTCCCCGCCAAAACGCGGCC AGAACCTGCCGCGTCTGCGGCGACGAGATCGG CCTGAAGGACGACGGCGCTCCGTTCGTCGCCT GCCACGAGTGCGGCTTCCCCGTCTGCCGCCCT GCTACGTCTACGAGCGCAGCGACGGCACCCAG TGCTGCCCCCAGTGCAACGCCCGCTACAAGCG CCACAAAGGGTGCCCCCGGGTCGCGGGAGACG ACGAGGACGACCACTTCGAAGGCGAGGATTTC GAGGACGAGTTTCAGATCAGGAACGCGGCGA GAATGAAGTTCGCCCCACCGGTTTCGATCGTTC GGAAAATGGGGACAGTCACGCGCCGCAAGTCC ATCCGAACGGTCAGGTTTTCTCTTCGGCCGGAA GCGTCGTCGGCGCGGAGTTGGAAGGAGAAGGC AATGCGGAGTGGAAGGAGAGGATCGAGAAGT GGAAAATCAGGCAAGAAAAGAGGGGCTTAGT GGGCAAGGACGATGGCGGGAACGGCGATGGA GAGGAAGATGACTACCTGATGGCTGAAGCTCG GCAACCACTTTCGAGAAAAGTACCGATTTCTTC GAGCAAAATAAGCCCATACCGAATTGTCATCG TCCTGCGCCTCGTAGTCCTAGGCTTTTTCCTCC ATTTCCGTATCTTAACCCCTGCAACTGATGCAT TCCCTCTATGGCTTATCTCAGTTATATGTGAAA CATGGTTTGCCTTGTCGTGGATTCTTGATCAAT TCCCTAAGTGGAACCCGATAAACAGAGAAACT TATTTGGATAGATTATCCATAAGGTTTGAGAG GGAGGGTGAGCCCAGTCGCTTAACTCCTGTGG ATGTGTTCGTCAGTTCTGTGGACCCTCTTAAGG AACCACCAATAATCACTGCAAATACTGTCCCTCT |

TABLE 1-continued

Eucalyptus grandis polysaccharide synthesis genes

| DNA SEQ ID | Consensus ID | Target | Curated DNA seq |
|---|---|---|---|
| | | | CAATCCTGGCCGTTGATTACCCGGTGGACAAA |
| | | | GTTTGTTGCTATGTATCTGATGATGGCGCTTCG |
| | | | ATGCTGCTTTTTGACACTCTCTCTGAAACTGCT |
| | | | GAGTTTGCGAGGAGGTGGGTCCCATTCTGCAA |
| | | | GAAGTATAGCATCGAGCCGAGGACTCCAGAGT |
| | | | TTTACTTTTCTCAAAAGATTGATTACCTGAAAG |
| | | | ATAAGGTGGAGCCCAGCTTTGTGAAGGAACGT |
| | | | AGAGCCATGAAAAGAGAGTATGAAGAGTTCA |
| | | | AAGTGAGGGTCAATGCATTGGTGGCAAAAGCT |
| | | | CAGAAAAAACCTGAAGAAGGATGGGTAATGC |
| | | | AAGATGGTACCCCCTGGCCTGGAAATAATACG |
| | | | CGCGATCATCCTGGCATGATCCAGGTTTATTTG |
| | | | GGAAGTGCTGGAGCATTGGACGTGGAAGGTAA |
| | | | GGAGTTGCCTCGACTTGTATATGTGTCCCGTGA |
| | | | GAAGCGACCTGGTTACCAGCACCACAAGAAGG |
| | | | CTGGTGCAATGAATGCTCTGGTTCGAGTGTCG |
| | | | GCAGTGCTAACAAACGCACCCTTCTTGTTGAA |
| | | | CTTGGATTGTGACCACTACATCAACAACAGTA |
| | | | AGGCTATCAGGGAAGCTATGTGTTTTCTAATG |
| | | | GATCCCCAACTTGGAAAGAAGCTTTGCTATGTT |
| | | | CAATTTCCTCAGAGGTTCGATGGCATTGATCGA |
| | | | CATGACAGATATGCTAATAGGAACATAGTTTT |
| | | | CTTTGATATCAACATGAGAGGGCTTGATGGGA |
| | | | TACAAGGACCAGTGTATGTTGGAACTGGATGT |
| | | | GTGTTCAATCGGCAGGCATTGTATGGGTATGA |
| | | | TCCTCCAGTGTCCCAAAAGCGGCCAAAGATGA |
| | | | CATGTGATTGCTGGCCTTCATGGTGCTCTTGTT |
| | | | GCTGCGGTGGTTCAAGGAAGTCAAAGTCAAAG |
| | | | AAGAAGGATGATACGAGTTTGCTTGGGCCTGT |
| | | | TCATGCGAAGAAGAAAAAGATGACAGGAAAG |
| | | | AACTACTTGAAGAAGAAAGGGTCTGGACCTGT |
| | | | CTTTGATCTAGAAGACATTGAAGAAGGACTTG |
| | | | AGGGTTTTGATGAGCTAGAAAAATCATCGCTC |
| | | | ATGTCTCAGAAGAATTTTGAGAAGCGGTTTGG |
| | | | ACAGTCACCTGTATTCATTGCCTCCACACTAAT |
| | | | GGAAGATGGTGGCTTGCCAGAAGGGACTAACT |
| | | | CCACTTCACTTATTAAGGAAGCTATCCATGTCA |
| | | | TAAGTTGTGGCTATGAAGAGAAAACAGAATGG |
| | | | GGCAAAGAGATTGGATGGATTTATGGCTCCGT |
| | | | TACAGAAGATATCTTGACAGGCTTCAAGATGC |
| | | | ATTGTAGAGGATGGAAGTCTGTATATTGCATG |
| | | | CCCAAAAGACCAGCTTTCAAGGGATCAGCACC |
| | | | TATAAATCTGTCAGATCGACTCCATCAAGTTCT |
| | | | GAGATGGGCTCTTGGCTCCGTTGAGATTTTCCT |
| | | | CAGTCGTCATTGTCCTTTGTGGTATGCTTGGGG |
| | | | AGGAAAACTCAAACTGCTTGAGAGGCTTGCCT |
| | | | ATATCAACACCATTGTCTACCCTTTCACTTCCA |
| | | | TTCCTTTGCTTTTCTACTGTACAATACCTGCCGT |
| | | | TTGCCTTCTCACTGGGAAATTCATTATCCCCAC |
| | | | GCTCACTAACTTTGCGAGCATATGGTTCTTGGC |
| | | | CCTTTTCCTATCCATCATAGCCACTGGCGTGCT |
| | | | TGAACTACGGTGAGTGGTGTCAGCATCGAGG |
| | | | ACTGGTGGCGTAATGAACAATTCTGGGTCATT |
| | | | GGTGGAGTATCTGCACACCTCTTCGCTGTATTC |
| | | | CAAGGCCTCCTCAAGGTGCTTGCCGGAGTTGA |
| | | | TACTAACTTCACTGTTACAGCAAAGGCAGCCG |
| | | | AGGACAGTGAGTTTGGTGAACTCTACCTTTTCA |
| | | | AGTGGACTACCCTTCTCAAACCACCAACCACT |
| | | | CTAATAATCTTGAACATGGTCGGTGTCGTCGCC |
| | | | GGTGTTTCGGATGCCATAAACAATGGATACGG |
| | | | ATCGTGGGCCCTCTGTTCGGGAAGCTCTTCTT |
| | | | CGCCTTTTGGGTGATCGTCCATCTCTACCCTTT |
| | | | CCTCAAAGGTCTGATGGGAAAACAGAACAGGA |
| | | | CACCCACGATCGTGGTCCTTTGGTCCGTACTTC |
| | | | TCGCCTCTATTTTCTCATTGGTCTGGGTCCGGA |
| | | | TCGATCCGTTCCTGCCGAAGCAAACCGGTCCA |
| | | | GTTCTCAAACCGTGTGGGGTGGAGTGCTGATT |
| | | | CTGGCGTCGGATTTCATTCAACATGCCGTCTCT |
| | | | CCGACCCGATTAGATGTGTCGCTTTACGGAGCT |
| | | | GTTTCTTTCTGTCTCTTACTTGGGACATATTGTA |
| | | | ATGCACTAGGGGAAATCTTCCCGATTGAAATC |
| | | | TCTTGATTAGCATAGGTTTTGCTTGAAGAGTGT |
| | | | GGAACTGAAATGTGCAAAGTCCTGGTTTTGAA |

TABLE 1-continued

_Eucalyptus grandis_ polysaccharide synthesis genes

| DNA SEQ ID | Consensus ID | Target | Curated DNA seq |
|---|---|---|---|
| | | | CTTTTTGCAATATATTCTGCTCAAGATTAAGCA AAAAAAAA |
| 7 | eucalyptusSpp_008124 | Cellulose synthase GDP forming | GCTAAGTCCTGTTCTAGCACCACCGCCATCCTC CTCCTCCTCCTCCTCCCATGGAAGCCGGAGCTG GACTTGTCGCCGGTTCTCACAACCGCAACGAG CTCGTTGTGATTCACGGCCATGAGGAGTCGAA GCCTTTGAAGAACTTGGATGGGCAAGTGTGTG AGATCTGTGGGGATGAGGTTGGGCTCACGGTT GATGGAGATTTGTTCGTGGCATGCAACGAGTG CGGATTTCCGGTTTGTCGGCCTTGCTATGAGTA TGAGAGGAGAGAAGGGAGCCAGTTGTGCCCTC AGTGCAAGACTCGATACAAGCGTCTCAAAGGG AGCCCAAGAGTGGAGGGTGATGATGATGAAG AAGACATTGATGATCTCGAGCACGAATTCAAC ATTGAAGATGAGCAGAACAAGCACAAGTACAT GGCAGAAGCTATGCTTCATGGGAAGATGAGCT ATGGAAGAGGTCCTGAGGATGACGATAACGCT CAATTTCCATCAGTTATAGCTGGTGGCAGATCC CGACCTGTTAGTGGCGAGTTCCCAATATCATCT TATGGTCACGGAGAGATGCCCTCTTCCCTTCAC AAACGAGTTCATCCATATCCAATTTCTGAACCC GGAAGTGAAAGATGGGATGAAAAGAAAGAGG GAGGGTGGAAAGAAAGAATGGACGACTGGAA GCTGCAGCAGGGCAACCTCGGCCCTGAACCTG ATGACATCAATGACCCGGACATGGCAATGATA GATGAGGCAAGGCAGCCACTCTCCAGGAAAGT ACCAATTGCATCGAGCAAGATCAACCCATACC GGATGGTGATAGTTGCTCGGCTTGCCATATTGG CTTTCTTCCTTCGATACAGGATATTGAACCCAG TACATGATGCATTTGGTCTTTGGTTAACATCCA TCATCTGTGAGATATGGTTCGCTTTCTCCTGGA TCCTGGATCAGTTTCCCAAATGGTTCCCTATTG ATCGTGAGACCTATCTTGATCGCCTCTCTCTCA GATATGAAAGGGAAGGTGAACC |
| 8 | eucalyptusSpp_008896 | Cellulose synthase like | AGAGAGAGAGAGAGAGAGAGAGAGAGAGCTT TCGTCTTCGTTCTCATTTCCTCTCTCCTCCCCCC TTGTTCATTCGTTTCTCGTTTCTGCTTCCGTCTT CGTTTGAGGGCAGCGGCAGAGAAAAAGCTTCC ATTTTTCTTCGATAGAGTTCGTCCGTCCGTCTT CATCGATAAGTAATTGTCTTATTTTGCTCAGCT GTTGGATTCGTGATCAGGCCCTTCTTTTCCATG TCGTTTTTTTCAGTGGGTCTCTCTGCAATGCAT CAAGAGGAGTGACCTTTGAGCGAGCGATTCAC TGACATTTCCAGCTCTGCCTTCCTTTTTTTCCCA CTTCTGCTTTGCTTGACCCAGAAGCAATATTGC AAAGCAAATATTCTCTCCAACTCTCTGCTTT TTTCAGATAATTCAATTGCCAGATCACAGAGA TCTACTTGCTCTCATCAGCTCTGGTCCCTAGCA TCACATTCTCCCTCTCTCGCATTGCTCTGTTTCG CGATCGAAAAACAGAGCAAACGAGTCTCTGCC GAAATGGACCGGCTCTCTGCAACTGGTCTCCTT CCCGACACGTTCGGAGGAGCAAGAGACGACAT CTCCATGCAACTTTCGCTGATTTGGGCTCAGAT CAAGGCGCCGTTGCTCGTCCCGTTGCTCCGGCT CGCGGTGTTCCTTTGCCTGGCCATGTCGCTGAT GCTGTTCCTCGAGAGGGTGTACATGGCCGTCG TGATCCTCTTGGTGAAGCTCTTCGGCCGGAAGC CGGAGAAGCGGTACAGGTGGGAGCCCATGAA GGACGACGTCGAGCTGGGCAACTCGGCCTACC CCATGGTCCTGGTTCAAATCCCAATGTACAAC GAGCGAGAGGTTTATCAGCTCTCGATCGGAGC CGCATGCGGTCTCTCGTGGCCGTCCGACCGCAT CATCATTCAAGTCCTCGACGATTCCACCGACCC GACGATCAAGGACCTGGTGGAGCTGGAGTGCC AGAGGTGGGCGAGCAAAGGGATCAACATCAG GTACGAGATCCGG |
| 9 | eucalyptusSpp_012804 | Cellulose synthase like | GTCCCTAGTTCCTTACTTGCTCTTCTTTCTCTCC ACATAAAGCTGGCCTCTTGTTCCTCTCTCCTCC TCCTCCTCCTCCTCTATTAACCACCGTCGACGA GCATCGATCAGAAAGGCTAGTGGCATCGCCTC AAGGACAGAGAACGAAAGAACTATGGAGCAT |

TABLE 1-continued

Eucalyptus grandis polysaccharide synthesis genes

| DNA SEQ ID | Consensus ID | Target | Curated DNA seq |
|---|---|---|---|
| | | | CGGTTCGCGCCCTCTAAACCTTTGCCATGTAGA CCCGAAATTGATCGCCGTCAACCGTGCACACA TGCTCATCCATGGAGCAGCTCTACTTATCCTTA TACACTATAGAGCTTCCTTTTTCTTCGCCGAAG AAGCTAGCTCACCGGGCCAACCCACCACTTTG GCTTGGCTCATTATTTTCCTGGGCGAGCTAACG CTGTCCCTCACGTGGCTTCTCCACCAGGCCTTC CGATGGCGGCCCGTGTCGCGGACCGCCTTTCC CGAGAGGTTGCCCGGCGATGGGGAGCTCCCAT CGATAGACGTGCTGGTGTGCACAGCGGACCCC GATAAGGAGCCCACCGTGGCAGTGATGAACAC AGTGATATCGGCAATGGCGCTCGACTATCCAC CGGAGAAGCTCCACGTGTACCTCTCAGACGAC GGCGGCTCGCTGCTCACGCTGCACGGGATGAG GGAGGCGTACGATTTCGCGAGACGGTGGTTGC CGTTTTGCAAGAGGTTTGGAATAAAGACGAGG TGCCCCAAGGCTTACTTCATCGAAGACGAGGA TGTGAGCGCTAGCGTGGGGTACGAATCCGAGA AGAAGGAGGTCAAGGAGAAGTATGAATTGTTC GAGGCGTATATAAATGGATATAGAAACAGGAA CTATGGTGAATCACGGGATGGGAGGCTGGATC ATCCGTCTACCATTGAGGTGATCCATGGAAATT CCTCAGACGAAGTTGTGCAAGCTGACCAACAG CAAATGCCTCTGCTTGTTTACGTCTCCAGGGAA AAAAGGCCTTCTTACCCTCATAACTTCAAAGCT GGGAGCTCTCAATGTTCTGCTTCGCGTGTCGGGG GTGATGAGCAACTCGCCGTA |
| 10 | eucalyptusSpp_016249 | Cellulose synthase GDP forming | CCCTTCCCTTCCCTTCCCTGTCACGCCTCTCCCC TCTCTCTCTCTAGACGCTCGCGAATACGCAG GCGAGACCCATTTCCTCCCTTCCTTTCTCTCTCT GTGAATCTACCCGTCTAAAAAAGGCTGTCCGC AGCACATTGATCGAGATCGAGAGCGCAGCAGA GCATCCCCCGCTCGACAAGCATTCTCCCCCGCC AGATCGGCCGCTGCATTCCTCGTCGTAGAGGG GGAGGCAGCCTTTCTTGGTGGGTGGCTCCGGG CGGCAATGCGGAGATCCGGGTCTGTTCTGAAG AGCTGAGACTGCTGCTGGGTTTCTCTTCTTTCT TTCCTTTCTTGTGCCGTTCGCTTCCTTGCGTTCT TGTCGGTGGTGGGTGAGTCGGGTCCTCTCGTTC TGGTCCCGCCATGAACACTGGAGGGAGGCTCA TCGCCGGGTCGCACAACCGGAACGAGTTCGTG CTCATCAATGCCGATGAGAGTTCACGGATCAA ATCTGTGAAAGAACTGAGCGGGCAAATATGTC AGATATGTGGGGATGAAGTGGAGATAGCAGAT GGCGAGCTCTTCGTTGCCTGTAATGAATGTGCT TTTCCAGTGTGTCGGCCTTGCTATGAGTATGAG AGAAGAGAAGGAAATCAGGCCTGCCCGCAAT GTAAAACTAGATACAAGCGCCTCAAAGGCAGT CCGAGGGTCGAAGGCGATGAGGAAGAAGATG ACATTGATGATTTGGACAATGAGTTCGATTATG ACCCTTCGGATCCTCAGCATGTCGCTGAGAAA ACGTTCTCTTCACGGCTTAATTATGGCCGTGGT GCCCATCGGAACGCATCTGGAATGCCCACTGA CGTTGAATCCTCTCCGCTTAGTTCACAAATTCC TCTCTTGACATATGGCCAAGAGGATGCTGAGA TTTCTCCTGATCAACACGCTCTTATTGTTCCCC CTGCCACGGGTCATGCATATAGAGTTCATCCG ATGCCATATCCGGATTCTTCTAATCCTCTTCAT CCCAGACCAATGGCCCC |
| 11 | eucalyptusSpp_016939 | Cellulose synthase like | TGCCGCTTGTTTCTTCTTCTTCTTCTTCTTCTTC CACGCGATGTTGTTCAGCTCGAGCCAGGGGTA GCGCTCGGTCCGGGTCGTTAGCCCTCCGAGTTT TCAGCTGCTGCTGCTTTCACTTCAGCGGGTGTT GCTCTGAGCTGAGGGCTCTTGTAGTGGGACCA AGATGGATACCGGAGTTCACATGAGAAGAATG AGCACGCCCGGGATCCGACAAGTGAATAACTC CAGGGACGATACTGACAGCGTGGTCAGCAGCG CCGAGTTCGCTAGCTACACGGTCCACATACCC CCCACGCCGGAGTACCAACCGATGTACATGTC GATTGAGACTTCGAATGCCGAGAAAGTCGAGG ACCTGTACGCGTCGAACTCGCTCTTCACAGGA GGGTACAACCGCGCCACCCGCTCCTTTCTGAA |

TABLE 1-continued

Eucalyptus grandis polysaccharide synthesis genes

| DNA SEQ ID | Consensus ID | Target | Curated DNA seq |
|---|---|---|---|
| | | | GGAGAAGATGACCGACTCTGTGTCGAACCACC CTCAGATGGCGGGCATGAATGGGTCGATGTGC GAAATTCCCGGGTGTGATGCGAAGATCATGAG GGACGAGCGAGGAGAAGACATCGTCCCCTGCG ACTGTGACTTCAAGATATGCAGGGACTGTTTC AGGGACGCGGTGAGAGGGGGAGATGTGATTTG CTTGGGGTGCAAGGAGCCTTACAAGGGGCTGG ACATGGCCGAGCCTGAGATGAATGATGGGCGG CGGGTATCTTCTGGCGGGATGTCGAAGAGGGA GCGGAGGATGTCCATGATCAAATCGAGGATGT CACTGAAGAGGTCGGAAATGGACGACTTCGAC CATAGGAACTGGCTCTTCGAAACCAAGGGGAG CTACGGATATGGGAACGCGATGTGGCCTAAAG AGGACGTCGATGGGGATGACGATGGATTCGGT AACCCTCAAGTGCTCCATGACAAAAAGTGGAG GCCCCTTACTCGCAAGGTCAATGTCTCCCCAAA AATCCTTAGTCCCTACAGGCTCTTGATTTTCCT CCGAATTATTGCTCTGGCACTACTTTTGATGTG GCGGATTAAGCATCCTAATGAAGAT |
| 12 | eucalyptusSpp_017058 | Cellulose synthase like | GTATAACCCTATGTGCTAAAATCTTGGAGAAC TTCCTATTCATATCAGAAGAAGAACCGATCCT GTCATATGGAGCATAGCTCAGGCCCTCTCAAT CTCTGTCATGTCCTCACAAAATCAATCATCATC AACCGCACCCACATGCTCGTTCACGCCACAGC TCTATCCGCTCTCATATACTATAGAGCTTCGTT TTTCTTCAGTGAGAGTAAATCGAGAGACAGAG CCACAACTTTGGCATGTCTCACCATGTTCCTTG CCGAGCTAGGGCTATCTTTCCTGTGGCTGCTCA GCCAAGCCTTCCGGTGGCGGCCCGTCAGACGG ACTGCCTTCCCCAAGCGGCTGCCAGAGGACAA GGAGCTGCCACCCATCGATGTGTTTGTGTGCAC GGCGGACCCAGATAAGGAGCCGACTGTTGACG TGATGAACACGGTGGTGTCGGCAATGGCGCTT GACTATCCCCCGGAGAAGCTCCATGTGTACCT CTCGGACGATGGCGGCTCGACACTGACCTTGC ATGGGACGAGGGAGGCCTACGATTTCGCAAGA TGGTGGCTGCCCTTCTGCAAGAGGTATGGGAT AAAGACGAGGTGTCCGAAGGCATTTTTTAAGG AGGAAGAGGATGGTGAGGGGATTGGCATGAG TTCTGATAATGAGTTTGGCTCTGAGAAGAAGA TAGTCAAGGAGAAATATGAGTTGTTCAAAGAA CGAGTAAATGAGTACCGAAAGAGGCACCGAG GTGACTCCAGCCACACTGGCCGAGACCATCCG CCTACCATCGAGGTGGTCCGAGGGAATGTCCC TGATGAAGTTATGCAAGCACACCAAGACCCCA TGCCTAAGCTTATATACGTCTCAAGAGAAAAG AGACCTTCTCATCACCATCACTTCAAAGCTGGA GCTCTCAACGTTCTTCTCCGGGTATCAGGAGTG ATGAGCAACTCGCCTTACATTTTAGTGTTGGAT TGCGACATGTACTGCAACGACCCTTCTTCGGCT CGGCAGGCGATGTGTTTTCATTTGG |
| 13 | eucalyptusSpp_017442 | Cellulose synthase GDP forming | AAAGCACTGAGTGAGAGCTGGAACTGAAGTGA CTGACTGATGTTAGAGAGAGAGAGAATTGAGA TAGAGATGGAGTGACGAGGAAGCCTCCCCTCC CTTCTTCACCAAACGTTCGCTCTCTCCCGCTCC ACACCTCCTTCGCTGCTGCCCCCTCCATTGCGT AGCACCGTCGCCGCCGCTCGCCGCCGATCTCCT CTTCTCCGAGACCCGGAATCGCGAACCGCTTG TCGAGCACCGCGATCGCCCCCGAGCGAGCGAG AGCGAGAGCGAGAGGGGAGGACATGGAAGCG AATGCCGGGATGGTGGCCGGATCCTACAAGCG GAACGAGCTGGTCCGGATACGCCACGACTCCG ACAGCGCGCCCAAGCCCCTGAAGCACTTGGAT GGCCACATGTGTCAGATTTGTGGTGATACCGTT GGACTTTCGGCCAGTGGTGATGTGTTTGTTGCG TGTAATGAGTGCGCATTCCCAGTGTGCCGTCCC TGTTATGAGTATGAGAGGAAAGATGGAAACCA GTGTTGTCCTCAGTGTAAGACTCGCTACAAAA GGCAAAAAGGGAGTCCTCGAGTGGAAGGAGA TGATGACGAAGATGGTGTCGATGATTTAGAGA ACGAGTTCAGCTACACCCGAGGAAATGCCAGG AGGCGCCAATGGCAGGGAGACGATCCTGACCT |

TABLE 1-continued

Eucalyptus grandis polysaccharide synthesis genes

| DNA SEQ ID | Consensus ID | Target | Curated DNA seq |
|---|---|---|---|
| | | | CTCGTCTTCTTCTAGACGTGAATCTCAACATCC AGTCCCCCTTCTCACTAATGGACTGCCAATATC TGGTGAAATCCCCTGTGCTACACCTGACAACC AATCTGTTCGGACAACATCTGGACCTTTGGGCC CTTCTGATAGGCATTCAGTTCATTCTGTTGATC CTAGACAGCCAGTTCCTGTGCGAATTGTGGAC CCCTCCAGGGACTTGAACTCTTATGGCCTTGGA AATGTTGATTGGAAAGAAAGGGTTGAAAGTTG GAAACTCAAGCAGGAAAAGAACATCCCCCACA TGACCAGTAGATTCCCGGAAGGAAAAGGAGAC ATAGAAGGAACTGGCTCTTATGG |
| 14 | eucalyptusSpp_017462 | Cellulose synthase like | CCCACACCGCCACCCGCTGACGTCATCGCCGT CGCCTCGTTCGTCATCTTCTTCTTCTTCTTCTTC GTCGTCGTCGTCGTCGTCGTCGGCGTCGTC CTCGCCGCGTCGTTCTCCGGATCCCTCGCACTG ACGATGCCCGCGCTCCATCGGGGCGAATCCGC GCTGTGATCCTTCTCGCTCCCCCCGCCCGCACC GCCATTGATGTCTCGAGCGCCGAACCGCGAGT TCCAGGAATGGTGGAACAAGCAGCGCGAGCGC GGCCTCGACCTCTCCTCCCCCCTCCTCCGCCGAC GGCCCCTCCACCAGCGGCGGCGGCGGCGGCGG CGGCGGCCCGCTCCTCGCCGTCGAGATCCGGA CCCCGCGGTCCGATCAGGCCGTCGAGAAGTCC CGCGCACGCAGCGCCCGTCAGCTCTCCTGGGT CTGCCTCCTCCGGTTCCAGCAGATCGCCTCCCT CCTCGCCTCCGCCGCGGGGTCATTCCTCTCCGT CCTCCGCACCGCCAACCGGAGGATCGCCGCCT CCCCCGCGGACTCCTCCTCGTCGCGGCTGTACC GGATCATCAGGTTCTTCCTGATCCTCGTCCTGG TGCTGCTAGGGTTCGAGCTGCTGGCGTATTCCA AGGGGTGGCATTTCAGCCCCCCCTCCGTCGGG TCCAAGGAGGTGCTGGGATTCGTGGAGCTGGT GTACGCGAATTGGCTCGAGATTAGGGCTACGT ACCTGGCGCCGCCGCTGCAGAGCTTGACCAAC GTGTGCATTGTGCTGTTCCTTATACAGTCCGTG GATCGAGTGGTGTTGGTGTTGGGCTGCATTTGG ATCAAGATCAAGGGGATAAAGCCGGTGGCGTC GGCTGATTATGAGAAGAAGGAAGATTTGGAGA GCGAAAGTGGGGATGAGGCGTATCCCATGGTG TTGGTGCAGATTCCGATGTGCAACGAGAGGGA GGTTTATCAACAGTCTATTGCAGCAGTATGCAT TCAAGACTGGCCGAGGGAAAGAATGCTTGTGC AGGTTCTTGATGATTCTG |
| 15 | eucalyptusSpp_017488 | Cellulose synthase GDP forming | GGCTTATTACAGATCCAGAAGCCGAGCGACAG TGAGCGTGTTTCAGAGGCAAGTACCATGGCGT GCCGAGAAAGGCGAAGAAGAACTCGGTCTCTC CTCTCTCTCCTCTCCTCCTCCTCCGCCAGATC CTCTCGCTTCCGCCTTCGATCTCGGGGAGAAGG AAGGAAGGAAGAGGACGACGATGGAGGCCAA TGGCGGCATGGCCGCCGGATCTTACAAGAGGA ACGAGCTGGTCCGGATTCGCCACGACTCGGAC GGCGGACCCAAACCCCTGAAGAATTTGAATGG CCAGATTTGTCAGATATGTGGCGATACTGTTGG ACTTACGGCCAGCGGCGATGTTTTTGTTGCTTG CAATGAGTGTGCATTCCCTGTGTGCCGTCCCTG TTATGAGTACGAGAGGAAAGATGGTAACCAAT CATGTCCTCAGTGCAAGTCTCGATATAAGAGG CACAAAGGTAGTCCTCGAGTTGACGGAGATGA TGATGAGGATGAGGTTGATGACCTGGAGAATG AGTTCAATTATGCCCAGGGAACCAGTGCTGCA AGGCAACAGTGGCAGGGAGAAGATCCAGATCT TTCTTCTTCTTCTAGACATGAATCTCGACATCC AATCCCTCTTCTAACCAATGGGCAGCCGATGTC TGGTGAAATCCCTTGTGCTAGTATTGACAGCCA ATCTGTGAGGACTACATCTGGACCTCTGGGTCC TTCTGATAAACATGTGCACTCGCTTCCCTATGT TGATCCCAGACAGCCAGTTCCTGTGCGGATTGT GGATCCATCAAAGGATTTGAATACTTATGGCC TCGGAAATGTTGACTGGAAGGAAAGGGTTGAA GGATGGAAACTTAAACAAGAGAAAAACATGA CGCAGATGCCAAACAAATATCATGAAGGGAAG AACGACATAGAGGGCACTGGCTCTAATGGAGA |

TABLE 1-continued

Eucalyptus grandis polysaccharide synthesis genes

| DNA SEQ ID | Consensus ID | Target | Curated DNA seq |
|---|---|---|---|
| | | | AGAACTTCAAATGGCTGATGATGCACGTCAAC CTATGAGTCGTGTGGTGCCTATATCGTCGTCTC ACCTCACTCCGTACCGTGTTG |
| 16 | eucalyptusSpp_017722 | Cellulose synthase GDP forming | GAGAGAACCAGAGGAGCGACAGCTAGCGTTTC CCCGCACACCGCTCTCTCTCTCTCTCTCTCTC TGCTCATCCTCTTCTCTCTCTCAGCTCTGGTCA GTTTCGATCTGCATTTTTTCATGCTCTCCCTCTG GGTTCGGTTCGGTTCTGTTGGATTCGATTCGAT GGAGAGTTGAAGAAAGTGCTCTTCTTTGTGCA GGAACTGAGCGTTTCGCCTCCCGTCCTCCGTCG TTCTATCCGGTCAAGATCGGATTTTGAGGAATT TACTCACGGATCTGTGTTTTACTGGAAAACAA GTTGCTTCTGAATGCAACACTAGAGATCTCTAC AGCTTCTGCTAATGCCACATCAAGTTCGGAATC AGTGAAGTCATCCTCTCTTAGCATCCGAGCCA GGAGGAGCTATTGCGATGGAGTCGGAAGGAG AAACTGGGGAAAGTCAATGAAAATTCTGGGT GGTCAAGTCTACCAGATTTGTGGTGATAACGTT GGCAAAAGTGTTGATGGCGAGCCGTTTGTTGC TTGCAATGTCTGTGCATTTCCTGTCTGTAGGCC ATGCTATGAGTATGAGAGGAAAGACGGGAATC AGTCATGTCCTCAATGCAAAACCAGATACAAG AGGCACAGAGGAAGTCCGGCTATTCTTGGTGA CCAAGAAGAAGATGCTGATGCTGATGATAGTG TGAGTGATTTCAATTACTCAGAAAATCAAAAT CTAAACCGGAAGACTGAAGAGCGCATCTTGAG TTGGCACATGCAGTATGGACAGAATGAGGATG TGAGTGCACCAAACTACGATAAGGAGGTTTCT CACAACCATATTCCTCGACTTACAAGTGGCCA AGAGGTTTCTGGGGAGTTATCTGCTGCTTCGCC TGAACGCCTCTCTGTGGCATCTCCTGATGTTGG TGCTGGGAAGCGCATCCATTCTCTACCTTATGT AGCCGATGCTAATCAATCACCTAACATCAGGG TGGTGGACCCAGTGCGGGAATTTGGTTCATCA GGACTGAACAACGTTGC |
| 17 | eucalyptusSpp_022868 | Cellulose synthase like | AGAGAGAGAGAGAGAGAGAGAGAGAGAGCTT TCGTCTTCGTTCTCATTTCCTCTCTCCTCCCCCC TTGTTCATTCGTTTCTCGTTTCTGCTTCCGTCTT CGTTTGAGGGCAGCGGCAGAGAAAAAGCTTCC ATTTTTCTTCGATAGAGTTCGTCCGTCCGTCTT CATCGATAAGTAATTGTCTTATTTTGCTCAGCT GTTGGATTCGTGATCAGGCCCTTCTTTTCCATG TCGTTTTTTTCAGTGGGTCTCTCTGCAATGCAT CAAGAGGAGTGACCTTTGAGCGAGCGATTCAC TGACATTTCCAGCTCTGCCTTCCTTTTTTTCCCA CTTCTGCTTTGCTTGACCCAGAAGCAATATTGC AAAGCAAATATTCTCTCCAACTCTCTGCTTT TTTCAGATAATTCAATTGCCAGATCACAGAGA TCTACTTGCTCTCATCAGCTCTGGTCCCTAGCA TCACATTCTCCCTCTCTCGCATTGCTCTGTTTCG CGATCGAAAAACAGAGCAAACGAGTCTCTGCC GAAATGGACCGGCTCTCTGCAACTGGTCTCCTT CCCGACACGTTCGGAGGAGCAAGAGACGACAT CTCCATGCAACTTTCGCTGATTTGGGCTCAGAT CAAGGCGCCGTTGCTCGTCCCGTTGCTCCGGCT CGCGGTGTTCCTTTGCCTGGCCATGTCGCTGAT GCTGTTCCTCGAGAGGGTGTACATGGCCGTCG TGATCCTCTTGGTGAAGCTCTTCGGCCGGAAGC CGGAGAAGCGGTACAGGTGGGAGCCCATGAA GGACGACGTCGAGCTGGGCAACTCGGCCTACC CCATGGTCCTGGTTCAAATCCCAATGTACAAC GAGCGAGAGGTTTATCAGCTCTCGATCGGAGC CGCATGCGGTCTCTCGTGGCCGTCCGACCGCAT CATCATTCAAGTCCTCGACGATTCCACCGACCC GACGATCAAGGACCTGGTGGAGCTGGAGTGCC AGAGGTGGGCGAGCAAAGGGATCAACATCAG GTACGAGATCCGG |

TABLE 1-continued

Eucalyptus grandis polysaccharide synthesis genes

| DNA SEQ ID | Consensus ID | Target | Curated DNA seq |
|---|---|---|---|
| 18 | eucalyptusSpp_023490 | Cellulose synthase like | GCTCTCCAGAACGCTCTCTGTTCCTTCTTCTTCT TCTTCTTCTCATTAGCCCCCGTATCACTCATCTC CCAATGTCGCCATGATCTAGAGACGCCTTGCTC CGGTGCTCCTTCCACGCGTCCCTCTCCCTCTGC CTGTCCCTCTCTCTCTCTCTCTTCCTCTGAAG CAGTTGGTTTATCTGAATCCACACAAGCGCTCT CTTTCTCTCTCTCTCCCTTTCGCCGCGGCTGGTG TGTCTCTCCCATACTAGGACAAGAATGAGGCT AAATTCCTAGCTCCTTTTGGCTTTTCCTCTTCTG GGACTCGGCTAAATCTTGCGAAAATTGGAAAA GCTCCAATCTTTATCCCGTGGAACCAAATTGTA CGAAGTGGGTGTTTTTTCTAGATCAAGGTTGAC GAAGACCAAGACCAAGAATGGCGCCCTCGTTT GATTGGTGGGCGAAAGGAGGCCACAAGGGCA CCCCGGTCGTCGTCAAGATGGAGAACCCCAAC TGGTCCATGGTCGAGCTCGAGTCGCCGTCCGA GGAGGACTTCCTCATCGGCGGCGACTCCGCGC CGTCGGGGCGGGTCCGCGACAAGGGCCGGAAC AAGAACGCCAAGCAGCTCACTTGGGTCCTCCT CCTCAAGGCCCACAAAGCCGCCGGCTGCCTCA CCTCCATTGCCGGCGCGGCGTTCACTCTCGCCT CCGCGGTGCGGCGCCGCGTCGCCTCCGGAAGG ACTGACGCTGATGCCGACGAAGCCGAGACCGG CGAATCTCGCAGCGGCAGAGAGAAGGAGAAC CCCACTGTGAAGTCCAGGATCTATGCGTGTAT AAAAGCGTTTCTTTGGTTGTCGATTTTGTTGCT AGGATTTGAGGTTGCTGCATACTTTAAGGGTTG GCATTTCGGAGCTCTCGAATTGCAATACTTGTT AGCTGCACCTTTAGGGGTTAAGGGTGCCTTCA ATTCCTTGTATTCGAGGTGGGTTTTGATTCGGG TGGAGTATCTCGCTCCGCCGTTGCAGTTCTTGG CCAATGTGTGCAT |
| 19 | eucalyptusSpp_027512 | Cellulose synthase GDP forming | GTCATATCCAGCTATCCAGTGGCTTTGGCATGG GAGGCTGACGCATCGACATCGACCCCGCGCTT TGATGATCCCCATCGTCGCTGTCCTTCGTTCTC CATTTCCCCCTCTTCGATTCGATCACCCCCCCG ACCTTCCGCTCGATTTCAGATCAGTTTCGGATT TCGAGGCTTTTGCAGAAGTATAGAAGCTGCCT TGGAAGTGGAAGGACTCCGATAAAGCAGATTC CGATTGCCTCTTTAGCACGTGCGAAGGTGCAT GTGAGCCTCTACATATGCACCGATCTTGTTGAC GCCGAGTCAGTTTTGCGTTCTTCTCTTGACGTC TCGGCAAAGAGGTGCTCCAGCGATGGAATCCG ATGCTGAAAATGGGGAAAGCCCTTGAAAAGT CTGGGGGGCCAAGTCTGCCAGATATGTGGTGA AAATGTCGGCAAAACTCTTGATGGGGAACCCT TCATTGCTTGCGATGTCTGTGCATTTCCTGTCT GTCGGCCCTGCTACGAATACGAGAGGAAGGAT GGAAATCAGTCGTGCCCACAATGCAAGACCAG ATACAAGAGGCACAAAGGAAGTCCTGCCATTC TTGGTGACCATGAAGAGGATGGAGATGCTGGC GATGACTACCATTACTCTTCTGAAGATCAAACT CAAAAGGAGAAAATTGCAGAACGCATGTTGAG CTGGCATATGACATATGGACGAGGGGAAAATG TTGCTCCGGCCAACTATGATGGAGAGGTTTCTC GTAACCATATTCCTCTGCTTACTAGTAGACAAG AGGTTTCTGGAGAGTTATCTGCTGCTTCACCTG AGCGACTTTCTATGGCATCTCCTGGAGTTGGTA GAGTGCATCGCGTTCGTCCACTTTCTTATGCAT CTGATGTTACTCAATCACCTAACATAAGGGTTG TGGATCCAGCGAGGGAATTTGGTTCACCTGGA ATTGGCAATGTTGCTTGGAAGGAGAGAGTAGA TGGCTGGAAGATGAAACAAGAGAAAAATGTTG GACCAATGAGCACTGGCC |

TABLE 2

*Pinus radiata* polysaccharide synthesis genes

| DNA SEQ ID | Consensus ID | Target | Curated DNA seq |
|---|---|---|---|
| 20 | pinusRadiata_000531 | Cellulose synthase GDP forming | GATGGCTCGCACCTTGAGCGTCATGGATGAATT TCTGTATATGGATCTGATCTGATAGAAATTCAG TGTCTGAATCTTGTCTTTTTTTATCACAGGGGCG AAGCTTTCATGCAGGACTTTTTAGCTTAAATTTT TTGAATTTGGCAGAGAATTGAACTTAACAATGG AAGCCAGCGCCGGCTTGGTTGCCGGTTCTCATA ACAGAAACGAGTTCGTGGTCATCCATGGACATG AGGAGCCGAAGCCTTTGAACACGTTGAGTGGCC ACGTCTGCCAGATTTGTGGCGAGGACGTCGGGC TTAACACAGACGGCGAGCTGTTCGTTGCCTGTA ATGAGTGCGGGTTTCCTGTCTGTCGGCCGTGCT ATGAGTACGAGAGACGAGAAGGAAATCAGTCG TGCCCGCAGTGCAATACTCGTTACAAGCGTCAA AAAGGGAGTCCACGGGTGGAAGGTGACGATGA TGAAGAAGACGTTGATGACATAGAACATGAAT TTAATGTGGAGACTCAGCAAAGAAACAGGCAG CAGATCACCGAGGCGATGCTCCACGGACGCAT GAGCTATGGCCGAGGTCCCGACGACGAAAATT CGCAGATTGCTCATAATCCAGAGCTTCCTCCGC AGATTCCTGTACTTGCAAACGGCCACTCGGTTG TGAGTGGGGAGATTCCAACGTCATACTACGCAG ACAACCAATTGCTTGCCAACCCTGCAATGCTGA AGCGTGTGCATCCAAGCTCCGAGCCGGGGAGT GGAAGGATCATCATGGATCCAAACAGGGATAT TGGTTCTTATGGCTTTGGGAACGTGTCTTGGAA GGAGCGAGGCGATGGTTATAAATCGAAGGAAA ACAAATCAGGCCAGTTGGATATGACGGAAGGG AGATATCAATATAATGGGGGGTTTGCACCAAAT GAGCCTGAAGATTATATTGATCCCGATATGCCA ATGACCGATGAAGCAAGGCAGCCACTGTCCCG AAAAGTGCCAATTCCTTCAAGCAAATAAATCC ATACCGAATG |
| 21 | pinusRadiata_002922 | Cellulose synthase GDP forming | CGATACACTAAGAAAAGTAGTCGTGCAAGTATT AGATGGCTGGCTGGGATAGTTGGAAAAGGAAT AGTAGAAATGGGACAGAAGTTTCATTCTGTAAG CTTTTTCATGGACTGTTAGTCTTCTCTTTGCTTTC AGCTTAAGCAGCTTTAGTGCTGGCATTTTGATG CTCAGTAATCACAAGTTGGAGCTTTGGTCTGGA TTAGAAGGATTTGAGCCTGTTTTAGTGCATTAC AGACCGTTTTAAGGTTGCTTTTTGCAGTTTTGAT AAGGCTGGGATTGAAGTGGGGAGTTTAATGAT GGCTAGGATGAAGGAGAGGCTGAGATACTGGG CATTTTGATGTGGGTTAAGCTGGATTTCAGCTG ATTTCAATACCTTTTTGTTCTGGGGAGCAGAAA TCAGTGAACGGGACTTTAGCAGGAAGAACCCA TTTTGACGTGGAGCTAAGTGTTGTTAGGATTCA AAGGTGATCAATTAGTGCGCGGGAGGTTCAGTG GCAATGGAGGCTAGAACAAACACAGCAGCAGG TTCTAACAAAAGGAATGTGCGTGTTTCGGTTCG AGATGATGGAGAACTTGGGCCTAAGCCTCCACA ACACATAAATAGCCACATTTGCCAGATATGTGG AGAAGATGTTGGCTTAGCAGCAGATGGGGAGT TCTTTGTAGCTTGCAATGAGTGTGCATTTCCAGT ATGCAGGCCTTGCTATGAATATGAGTGGAAGGA TGGAAATCAATCTTGTCCACAATGCAAGACTAG ATACAAGTGGCATAAAGGTAGCCCTCAAGTGG ATGGTGACAAGGAAGATGAATGTGCAGATGAT TTGGATCATGACTTCAACTCCACTCAGGGTAAC AGGAATGAAAAACAGCAGATTGCAGAGGCCAT GTTGCATTGGCAAATGGCCTATGGACGAGGGG AGGATGTTGGTCCATCACGCTCAGAAAGTCAGG AGCTTCCTCAGCTTCAAGTTCCCCTTATTACCAA TGGACAAGCGATTTCTGGTGAGTTGCCAGCAGG ATCCTC |
| 22 | pinusRadiata_003920 | Cellulose synthase GDP forming | GTCATGGCTTCCAACGGGACTATGAACTCTCAA GTTTGTCAAGTTTGCGGGGACAACGTTGGGGTT GATGCAAACAGTGAGCCCTTCGTTGCCTGCCAT GACTGTGGCTTTCCTGTTTGTCGTCCCTGCCAGC AGTACGAGAGAGACGAAGCAAGTCAGTGCTGC CTGCATTGCAAAGCTCCGTATCGGCGCTACGAA GGCGGCCCAGCTGATGAGGTTGAAGAGAACGG AGATCCCAACTTTGAAAAAGTAGAAGCAACTG |

TABLE 2-continued

Pinus radiata polysaccharide synthesis genes

| DNA SEQ ID | Consensus ID | Target | Curated DNA seq |
|---|---|---|---|
| | | | ACTATGAAGGGGAAGGCTATCGTGTTGATTCAT TTAATGATAGTGAGATTAATAATGCTGAAACAA AGGATGGCAACAGCAAGGGCGTGGCGTGGAAG GAAAGAGTTGAGAGCTGGAAGTCCAAAAAAAA TAAGAAAAAAACTGCCGCCAGCAAAACAGTTA ATCCCGGCGTGGAAGGAATCCCAGAGCAGACA AGGGATCCAGAGGCGGAGGAAGCAATGATGGC TGAGGCCGGGCAGCCGCTATCGTGTATAATACC CATTCCACGCACCAAACTCCAACCGTATAGGAT GGTTGTTATTATGCGGCTGATCGTTCTAGGGTT ATTCTTCAGCTACCGAGTACAGAATCCTGTGGA GAGCGCATTTGGCCTGTGGATGACCTCAGTTAT TTGTGAGATCTGGTTCGCTTTATCCTGGATTCTT GATCAGTTTCCCAAGTGGAATCCGATCAATCGC GAAACATTCACAGACAGATTGTCTTTAAGGTAC GAGAGACCGGGCGAGCCCTGTGAGCTTGCGGC CGTGGACTTCTTCGTGAGTACCGTGGACCCACT GAAAGAGCCTCCTTTAGTTACGGCCAACACCGT TCTGTCCATTCTGGCTGTGGATTACCCTGTGGA GAAAGTTTCTTGCTATGTCTCTGACGATGGTGC GGCCATGCTCACGTTCGAGACCATGTCGGAGAC AGCTGAGTTCGCTAGGAAGTGGGTTCCTTTCTG CAAGAACTTTAACATCGAGCCTCGAGCTCCTGA ATTCTACT |
| 23 | pinusRadiata_017730 | Cellulose synthase GDP forming | GAGATGGTGGCTATCTTTAACTGAAGAAAAGA GGGCCCTTAGGTATACAAGAAGCTGGAGAGAGG AGAAGCCAAGGTGCCAGCCAGTCCTTCAGCTTT TGGGACTCTGCCTGCCCATAGCCGGAGGCCTGA ACATATGATTCTAGGTTCATTTTTGGCGTATGCT CACAAGTTTCCTCGTGGAGAAAACACCAGGGA ACTTGATAAAATTCATGTTTTTTCTATTGCAGAA GTACCCCAAAATGGATTTTGAGCTGATAATGGT ATGAGGATTCGACAAGGACGAGTTTGTTGGGTT GTGCTGAAAAGCAAAGCAGATCTGCTGCGCAA TCTGGAATTCAGCTTATATCCACTCTGCGATCA GGAATCCACTTTTCTCTAAAGACTGATAGCAAT GGAGGCCAATGCTGGACTGGTTGCTGGTTCTCA CAACAGGAATGAATTTGTAGTCATCAGGCCTGA AGGCGAAGTGGGTCCTAAGCCTCTACATCATTT AAGTGTACAAATTTGCCATATCTGTAATGAAGA CGTTGGTCTCACAGTGGATGGGGAACTGTTTGT TGCCTGCAACGAATGTGCATTCCCAATCTGCAG GACTTGCTACGAGTACGAGCGGAGTGAGGGTA ACCAGGTCTGCCCTCAATGCAAAACGAGATTCA AACGACATAAGGGAAGTGCCAGAGTTGAAGGA GATGAAGATGAAGATGATGTTGATGACCTTGAA AATGAGTTCAATTTTGGGGACCGAGACAAACA AGATATGCAGTACATTGCAGAAGCGATGCTTCA TGGGCATATGAGCTATGGCCGAGGTGGTGATAC AGATATGCCTCATGTAGTTCAGACAACTCTTCC ACAAGTGCCACTACTTACCAATGGCCACATGGA TCCCGGGATCCCTCCAGAACACCATGCTCTAGT CCCTTCATATATGGGTGGGGAAAAAGAATTCA TCCATTCCCTTATGCCGATTCTAATCTTCCAGTC CAAGCCAGGTCAATGGATCCAACCAAGGACTT GGCAGC |
| 24 | pinusRadiata_027109 | Cellulose synthase GDP forming | AGATGTGAGATGGTGGCTATCTTTAACTGAAGA AAAGAGGGCCCTTAGGTATACAAGAAGCTGGAG AGAGGAGAAGCCAAGGTGCCAGCCAGTCCTTC AGCTTTTGGGACTCTGCCTGCCCATAGCCGGAG GCCTGAACATATGATTCTAGGTTCATTTTTGGC GTATGCTCACAAGTTTCCTCGTGGAGAAAACAC CAGGGAACTTGATAAAATTCATGTTTTTTCTATT GCAGAAGTACCCCAAAATGGATTTTGAGCTGAT AATGGTATGAGGATTCGACAAGGACGAGTTTGT TGGGTTGTGCTGAAAAGCAAAGCAGATCTGCTG CGCAATCTGGAATTCAGCTTATATCCACTCTGC GATCAGGAATCCACTTTTCTCTAAAGACTGATA GCAATGGAGGCCAATGCTGGACTGGTTGCTGGT TCTCACAACAGGAATGAATTTGTAGTCATCAGG CCTGAAGGCGAAGTGGGTCCTAAGCCTCTACAT CATTTAAGTGTACAAATTTGCCATATCTGTAAT |

TABLE 2-continued

Pinus radiata polysaccharide synthesis genes

| DNA SEQ ID | Consensus ID | Target | Curated DNA seq |
|---|---|---|---|
| | | | GAAGACGTTGGTCTCACAGTGGATGGGGAACT GTTTGTTGCCTGCAACGAATGTGCATTCCCAAT CTGCAGGACTTGCTACGAGTACGAGCGGAGTG AGGGTAACCAGGTCTGCCCTCAATGCAAAACG AGATTCAAACGACATAAGGGAAGTGCCAGAGT TGAAGGAGATGAAGATGAAGATGATGTTGATG ACCTTGAAAATGAGTTCAATTTTGGGGACCGAG ACAAACAAGATATGCAGTACATTGCAGAAGCG ATGCTTCATGGGCATATGAGCTATGGCCGAGGT GGTGATACAGATATGCCTCATGTAGTTCAGACA ACTCTTCCACAAGTGCCACTACTTACCAATGGC CACATGGATCCCGGGATCCCTCCAGAACACCAT GCTCTAGTCCCTTCATATATGGGTGGGGGAAAA AGAATTCATCCATTCCCTTATGCCGATTCTAATC TTCCAGTCCAAGCCAGGTCAATGGATCCAACCA AGGACTT |
| 25 | pinusRadiata_000892 | Cellulose synthase like | GGTTCACGTTCATTCATTCACTCATCGTGAGCA GCAGTACATCAACAGTTCTTGAAGAACATTGAT AGGTTGGCTATTTCAATCCTTTCATGGGAATA TTTAAGTCTGGATCCGAGCCTGAACTCAATGGA TTTTCAGCGATCCTTGTGCTTGGGAAGCCTGGA TCTCCTTAATCATAGGATCTGCTAGTTCTGTATC AAATGCATTTTGAGTTCACGGAGCTGTATTTAC AACATTTTAGGTTGCTGTTTTGCTATCTTAAAAG TCATTAGGAGTAGTGACATAAACTGTAGTTTTT AGGCCATAGGTTGCAATTCAGAGTAACTAGAAC GGTTGATTTTCATTGTACTGATTTTTTTGATGGC ACCCAATTTCGGTGTTGGGCAATGGTGGAGTAA GCAGAGCCACAAGGGAACCTCTGTTGTTGTGAA AATGGAGAACCCAAATTACTCAATGCTAGAATT AGAGAGCCCTGCAAATGGTTTTCAGGTCGATAA GGGGGGTCGAGGCAAGAATGCTAAGCAGCTCA CATGGGTTCTTCTGCTGAAGGCTCATAAGGCAG CAGGATGCCTGGCTTGGCTTGCCAATGGAGTTT GGGCACTTTTTGCTTCAGTCAGAAGACGTTTCA CTGCGCCTTCTGATGAATCAGGGAAGTCTTCTG AGAAAAGCAAGCTTTACAGAGTTATCAGGTGTT TCCTTATAGCTTCCATTTTCTTGTTAGGGTTTGA GCTATTGGCTTATTGGAAGGGGTGGCATTTCAG CCGGCCAAATCTGCATATTCCCCCATCTCTAAG CATAAATGGCCTTCTGCAATCTATATATTCAGG ATGGCTTTATACCAGAGCGAATTACCTAGCTCC TCCTCTTCAGTATTTGGCCAATGTGTGCATCATA TTGTTCCTTATCCAGTCGGCGGATCGAGCCCTG TTATGCGTTGGTTGTTTTTGGATTAAACTGAAG AAGATCAAGCCAGTTCCCAAATGTGAGTTGGGA GATGCAGCTGATTTGGAGCAGGGAGACAAT |
| 26 | pinusRadiata_008513 | Cellulose synthase like | GACAACATACGTGTGCTTGCTTCGCCTTTGGTG ATTGAAGCAAGCTGCTGATGGAGCCTAACGACT TTCCTTTGTATACTACACTGGAAAAGAAATCAC TCTTATACAGAGCTTATTCGTGCACCCACTTTTC TGCAATAATCGGTCTCATATGTTATCGCTTGTTG TATATCCCAAGTGAGGATTCTTGGCCATGGATT CTGATATTTGTCGCAGAACTAGGCTTCTCGTAC AGCTGGATTCTGGATCAGGCCCTAAGATGGTGG CCAGTTGAACGAACAGTCTTCCCAAACAGACTT TCTAAGAGGTTTCAGAGCAAGTTACCGCCTGTG GATATCTTTATTTGCACTGCTGATCCTTTCAAAG AACCTCCACTGACTGTTATAAACACAGTATTGT CCGCTCTCGCCGTAGATTATCCCATGGGAAAAT TGTCATGTTATGTTTCTGACGACGGAGGATCAC CTCTGACATTTTATGCTCTCTTGGAAGCTTCACG TTTTGCAAAGATCTGGATTCCATTTTGTGATAA ATACTCCATTCAAGACAGATGTCCGGAGGTTTA CTTCTCAAATCCCAGTGCTCTGGAAAACGTAAA TCTGCCCTTCATGAAAGACTGGAAGCATGTAAA TAAAATGTATTCTGAATTGAAGGATCGAATCAA CAACGTCATGGAGATGGGCAGTGTTCCACCAGA TAAACAGAATGAACACCAAGGATTCAAGGACT GGGCTTCTGGAAGCAGTAGGCGAGATCATCCA AGTATAGTTCAGATTTTACTGGAGAAGGGAGAG GACAGGGACATTGACGGAAATGATCTGCCCGA |

TABLE 2-continued

Pinus radiata polysaccharide synthesis genes

| DNA SEQ ID | Consensus ID | Target | Curated DNA seq |
|---|---|---|---|
| | | | TCTTATATATGTCTCCCGTGAGAAGCGACCTGG<br>AATTCCCCACCATTATAAGGCTGGTGCTCTTAA<br>TGTTCTGCTAAGAGTCTCTGGCGTAATGAGCAA<br>TGCTCCCTTCATTCTCACTCTTGATTGCGACATG<br>TACACCAACAATCCTGAGGCCCTTCGGCAAGCC<br>ATGTGCTTTTCTTGGACCCTAAAACAGGTGA |
| 27 | pinusRadiata_013907 | Cellulose synthase like | CTGGTGTGCTGTTGCAGGAGAATGTGGGATCGC<br>GGGTTCGAACTTCGTGGAGTGTAGGGTTTTGGC<br>TTGGAATGAGGATAGAAGGGCGAACGAGAAGA<br>GTAGGGAAGGGCAGTTATTGATTGCGTGCGCGC<br>CTGGCTTATCGCATCTCGACATTCGCGGATCGA<br>ATCTCACAAACTCCAGGCGGCCTCCGCATTGTG<br>AGATCGGCGCAGCTTCTATGTAGGCGGGGCTGC<br>CGATGGGTTCGTTTTCTATCAGTTAGAAGACGG<br>AGGAAGCGGAGGAGGACAACGTACTTACTATT<br>ATTGTTATCGTTGTCAAAAGTCTTTCCAACTTAT<br>GCCAAAGATCCATTCTTGCATTCACTGAAGTGA<br>AAAGATCCAGGTTTGGGCAGAGTGCTTTTTCCA<br>TTTTTTGTTCATGTGACTCCCCGGGGGGTGGGG<br>CGTCGTTTGGTTCTTATGTATGGCAACCAATTTT<br>GAGTTTCAAGAATGGTGGAACAAGGAGAAAGA<br>AACCCACAGGGGCACTTCCGTGGTAGTGAAAAT<br>GGAGAATCCAAATTGGTCCATGGTGGAATTGCA<br>AAGCCCCGACGACGATTTCCAGCATTCAGATAA<br>GCAGGGCCGAGGCAAAAATGCCAGGCAACTTA<br>CCTGGGTTTGGCTGCTGAAAGCCCATCGCGCCG<br>CGGGCTGTGTCGCCTGGCTCGCGCAGGGGCTAT<br>GGAGCCTTCTCTCCGCCGTAAAAAGAAGGGTCA<br>CTTTGAACAAGAATCAAAATCGTGTGACAGAG<br>GAGGACAAACCAGGGAAAAGTAAACTGTATAG<br>AGTCATTAGAGGGTTTCTGTTATTTGCCATTTTG<br>ATGCTAGGGTTTGAGATTGCGGCTTATATGAAA<br>GGCTGGCACTTTAGCCGCCCTCCTTTCGACTTTT<br>CTCCGTCGCTGGACTTGCAGGGCGTTTTGCATT<br>CCATTTATTCTGAATGGGTATTTGTTAGGGCCA<br>CTTATCTTGCCCCTCCTCTTCAGACATTGGCCAA<br>CATCTGTATTGTGCTGTTTCTTATCCAGTCGGCAG |
| 28 | pinusRadiata_026937 | Cellulose synthase like | AAGTAGAGAAGCCAAAAAGATATGAGGTCTTT<br>GTGTGCCTTTGATCATTGGTAACTGAAGCAAGT<br>TGCCAATGGAGCCTAATGGCTTTCCTCTGTATA<br>CGACACTGGAAAAGAAATCCTTCGTATACAGA<br>GCTTATGCCTGTGCCCACTTTTCTGCAATAATTG<br>GTCTCCTATATTATCGCATTGTGTATATCCCAAG<br>TGAAGATTATTGGCCATGGATTATGATATTTGT<br>GGCAGAACTAGGCTTCGCCTACGGTTGGATTTT<br>GGAGCAGGCCTTCAGGTGGCGGCCTGTTGAGCG<br>AAAAGTCTTCCCAGAAAGACTTTCTAAGAGGTT<br>TAAGAGCGATCTACCGCCTGTTGATATATTTAT<br>ATGCACTGCTGATCCTATCAAAGAACCTCCACT<br>CGCTGTCATAAACACAGTACTGTCGGCTTTGGC<br>TGTAGACTATCCCGTAGAAAAACTGTCATGTTA<br>TGTTTCTGATGATGGAGTATCCTGCTTACATTT<br>TATGCTCTCTTCGAAGCTTCACGTTTTGCAAAG<br>ATTTGGCTTCCATTTTGTTATAACTACTCGATTC<br>AAGACAGATCACCAGAGGCATATTTCTCGGCAA<br>GATCTGGTCAGGAAAAGGAAAATATGTCCTTTA<br>CTAGAGAATGTAAGAGTGTAAAGAAAGCGTAT<br>TTGGAAATGAAGGATCGTATCAATAACGCTGTG<br>GAGATGGGAAGTGTTCCGGATGACAAACAGAA<br>AGAACACACGGGCTTCAAAGACTGGATTTTGGG<br>AAGCACTAGGCGAGATCATCCGAGTATTGTTCA<br>GATTCTACTGGAGAACGGAGAGGACAAGGACA<br>TTCAGGGTAATGATCTGCCCAGTCTTATTTATGT<br>CTCCCGTGAAAAGCGACCGGGAATTCCTCACCA<br>TTACAAGGCCGGCGCTCTTAATGCTCTGATTAG<br>AATCTCCGGCTTAATGAGCAATGCTCCCTTCAT<br>TATCACTCTTGATTGCGACATGTGCACCAACAA<br>TTGTGAAGCACTTCGTCAAGCCATGTGCTTTTTC |
| 29 | pinusRadiata_027496 | Cellulose synthase like | GCTGCTGCCAATTGCATAGATCTGCTCAAGGCA<br>CCACCATGGATCGGTTGTCTTATTCCAGTGCCA<br>ACATATTGCCACAGACATTTCAAGGCACAAGGG |

TABLE 2-continued

Pinus radiata polysaccharide synthesis genes

| DNA SEQ ID | Consensus ID | Target | Curated DNA seq |
|---|---|---|---|
| | | | ATGACATAGTTGAGCAGATTGCGTTGCTTTGGC AGCAGATTCGGGCTCCTCTGGTTGCCCCATTGC TGAATATCTGTATTTACTTCTGCCTGCTCATGTC TGTCATGCTCTTCATTGAAAGAGTTTATATGGC AGTAGTCATTGTGTTGATTAAGGTGTTTGGAAA GAAGCCAGAGAAGAGATACAAGTGGGGGGCCA TTAAGGAGGACGTGGAGCTTGGCAACAGTGTTT ATCCCATGGTCTTAGTGCAGATACCAATGTACA ATGAGAGGGAGGTTTATCAGCTCTCAATTGGAG CAGCATGTGCATTGTCATGGCCTTCAAATCGGG TTATCATTCAAGTGCTCGATGATTCCACTGACCT TACAATCAAGGATTTGGTGGAGATGGAATGTCA GAAATGGGCGAGTAAAGGCATAAATATCAAGT ACGAAATCAGAGGCAACAGAAATGGGTACAAA GCTGGTGCCCTGAAAGAGGGAATGAAGCATAG CTACGTAAGGGAATGCGATTACGTTGTAATATT TGATGCAGATTTTCAGCCCGATCGAGACTTTCT GAGCAGAACGATTCCATTCTTAGTGCACAATCC AGAATTGGCCTTAGTTCAAGCTCGTTGGAAGTT TGCATGAATGGTGGATTGATTGATTGATT AGCCTATCAACCACAACACACACAGAAAAGGC TGAAGGCCGTCAGGACTCAGGGGGGCCTCCCTC CGGTCTCCGTTGGTCCTGTTTTTCCACTCCCCCA CCCATCTCATTCCAAGTGTTTGGCCTGCAGCAG GCTGGCCAACCTGGCAGCCGCGCCAGTGGTAAC AGCGATGTGTACTTTTCACCTTCAGTCTATTCGT CCAGGACTGTAACACGTAAAGTTTTACGAAGTT CATTATCAGCTCTGTTGTATCAATCAATGAACA AA |

TABLE 3

Eucalyptus grandis polysaccharide synthesis peptides

| SEQ ID | Consensus ID | Gene Product | Curated Peptide Sequence |
|---|---|---|---|
| 30 | | Cellulose synthase GDP forming | MEARAGLVAGSYKRNELMVVPGHDGP KPIRLSTLQDCQVCGDKIGCNPNGELFV ACNECGFPVCRPCYEYERKDGNRCCPQ CKTRYRRHKGSPRVEGDDEEDGMDDL EQEFNMERDRQSVVSHRGNAFDATPRA AHSIANRSINGDNYALSLPPIMDGDSLS VQRFPHAATVIGNGLDPVKENYGSAA WKERVENWKAKHDKKSGSIKDGIYDP DEADDIMMTEAEARQPFSRKVPIPSSLI NPYRIVIVLRLIILGFFFRYRLMNPAKDA LGLWLTSIICEIWFAFSWILDQFPKWFPI TRETYLDRLSMRYEREGEPCKLAPVDF FVSTVDPLKEPPLITANTVLSILAADYPV DRVSCYVSDDGASMLTFDSMTETSEFA RKWVPFCKKYSIEPRAPDFYFSQKIDYL KDKVQPTFVKERRAMKREYEEFKVRIN ALVSTAQNTFDEGWVMQDGTPWPGNN TRDHPGMIQVFLGSSGAHDIEGNELPRL VYVSREKRPGYQHHKKAGAMNALVRV SAVLTNAPFILNLDCDHYLNNSKAVRE AMCFLMDPQLGKKLCYVQFPQRFDGID RHDRYANRNTVFFDINMKGLDGIQGPV YVGTGCVFNRQALYGYDPPVSQKKPK MTCDCWPSWCCCCFGSRKKTKKSSKK FFGRKKSSKPTEIAAPIFSLEEIEEGLEGY EEHEKSWLMSQKSFEKRFGQSPVFITST LMENGGVPESVNSPALIKEAIHVISIGYE EKTEWGKEIGWIYGSVTEYILTGFKMH CRGWRSVYCMPPRPAFKGSAPINLSDR LHQVLRWALGSIEIFLSRHCPLWYAYG GNLKWLERLAYINTIVYPFTSIPLVAYC TLPAICLLTGKFITPTLTSLASVWFMGLF ISIIATGVLELRWSGVSIEEFWRNEQFW VIGGVSAHLFAVFQGLLKVLGGVDTNF TVTAKGSDEEDQFGELYMFKWTTLLIP |

TABLE 3-continued

Eucalyptus grandis polysaccharide synthesis peptides

| SEQ ID | Consensus ID | Gene Product | Curated Peptide Sequence |
|---|---|---|---|
| | | | PTTLLIINLVSLVAGVSAAVNNNYQSW GPLFGKLFFACWVILHLYPFLKGLLGRQ NRTPTIVILWS |
| 31 | eucalyptusSpp_000984 | Cellulose synthase GDP forming | AQEREYEEFKVQINALVAKAQKMPEEG WTMQDGTAWAGNNPRDHPGMIQVFL GHSGGLDTDGNELPRLVYVSREKRPGF QHHKKAGAMNALIRVSAVLTNGAYLL NVDCDHYFNNSKALKEAMCFMMDPA YGKKTCYVQFPQRFDGIDLHDRYANRN IVFFDINLKGLDGIQGPVYVGTGCCFNR QALYGYDPVLTEEDLEPNIIVKSCCGSR KKGKGGNKKYIDKKRAMKRTESTVPIF NMEDVEEGVEGYDDERSLLMSQKSLE KRFGQSPVFISATFMEQGGLPPSTNPAT LLKEAIHVISCGYEDKTEWGKEIGWIYG SVTEDILTGFKMHARGWISIYCMPPRPA FKGSAPINLSDRLNQVLRWALGSIEILLS RHCPIWYGYNGKLRLLERLAYINTIVYP LTSIPLIAYCILPAFCLLTNKFIIPEISNFA SMWFILLFVSIFTTGILELRWSGVSIEDW WRNEQFWVIGGTSAHLFAVFQGLLKVL AGIDTNFTVTSKAGDEDGDFAELYVFK WTSLLIPPTTVLIVNIIGIVAGVSYAINSG YQSWGPLFGKLFFAIWVIAHLYPPLKGL LGRQNRTPTIVIVWSILLASIFSLLWVRI DPFTSATTASTANGQCGINC |
| 32 | eucalyptusSpp_003922 | Cellulose synthase GDP forming | MEVSSGLVAGSHNRNELVVIRRENELG QKPLQKILSGQICQICGDDVGLTVDGELF VACNECAFPICRTCYEYERREGSQICPQ CKTRFKCLRGCARVDGDEEEDGVDDLE NEFNFDGRHRQEMDRQGYGAEAMLHG HMSYGRGSDLDLSHVHPLPQVPLLTNG QMVDDIPPEHHALVPAYMGAGGGGGG GGKRIHPLPFTDSGLPVQPRSMDPSKDL AAYGYGSVAWKERMESWKQKQEKLQ TMKNEKGGKEWDDDGDNPDLPLMDE ARQPLSRKLPISSSQINPYRMIIVIRLVVL GFFFHYRVMHPVNDAYALWLISVICEI WFGLSWILDQFPKWLPIDRETYLDRLSL RYEKEGQPSQLAPVDIFVSTVDPLKEPP LVTANTVLSILAVDYPVDKVSCYVSDD GAAMLTFEALSETSEFARKWVPFCKKF NIEPRAPEFYFAQKIDYLKDKVEASFVK ERRAMKREYEEFKVRINALVAKAQKVP EEGWTMQDGTPWPGNNVRDHPGMIQV FLGQSGGHDSDGNELPRLVYVSREKRP GYNHHKKAGAMNALVRVSAVLTNAPY LLNLDCDHYFNNSKAIREAMCFMMDPL IGKRVCYVQFPQRFDGIDRHDRYANRN TVFFDINMKGLDGIQGPIYVGTGCVFRR LALYGYDAPKAKKPPTRTCNCLPKWCC CGCCCSGTKKKKKTTKPKTELKKRFFK KKDAGTPPPLEGIEEGIEVIESENPTPQH KLEKKFGQSSVFVASTLLEDGGTLKGTS PASLLKEAIHVISCGYEDKTEWGKEVG WIYGSVTEDILTGFKMHCHGWRSIYCIP ARPAFKGSAPINLSDRLHQVLRWALGSI EIFLSRHCPLWYGYGGGLKWLERLSYI NATVYPWTSIPLLAYCTLPAVCLLTGKF ITPELSNVASLWFLSLFICIFATSILEMR WSGVGIEEWWRNEQFWVIGGVSAHLF AVFQGLLKVLAGVDTNFTVTSKGGDD KEFSELYAFKWTTLLIPPTTLLIINLIGVV AGVSNAINNGYESW |
| 33 | eucalyptusSpp_004683 | Cellulose synthase like | MAPSLDSWAKQNVHKGTPVVVKMENL NWSMLELESPSDEDIFPAGAPAAGEGA APERTRNKNAKQLTWVLLLRAHRAAG CLASMAAAFLGLASAVRRRVAAGRTD NDVSEASRRGGGVRESPTLKARFYTCT KVFLWLSIVLLGFEVAAYFKGWHYGA HNVELQHLLATSFSVKGVFDRLYSKWV SIRVEYLAPPLQFLANACIVLFLIQSLDR LVLCLGCFWIKFKNIKPIPKEDASVDVE |

TABLE 3-continued

Eucalyptus grandis polysaccharide synthesis peptides

| SEQ ID | Consensus ID | Gene Product | Curated Peptide Sequence |
|---|---|---|---|
| | | | SGEKGYFPMVLVQLPMCNEKEVYQQSI
AAVCNLDWPKSKLLIQVLDDSDDPTAQ
SLIKEEVNKWQQEGARIVYRHRVIREG
YKAGNLKSAMNCSYVKEYEFVSIFDAD
FQPAPDFLKRTVPHFKDNDELGLVQAR
WSFVNKDENLLTRLQHINLAFHFEVEQ
QVNGVFLNFFGFNGTAGVWRIKALEDS
GGWLERTTVEDMDIAVRAHLHGWKFIF
LNDVEAQCELPESYEAYRKQQHRWHS
GPMQLFRLCLPAIIKSKISIWKKFNLIFLF
FLLRKLILPFYSFTLFCIILPMTMFVPEAE
LPAWVVCYIPATMSFLNILPAPKSFPFIV
PYLLFENTMSVTKFNAMISGLFQLGSAY
EWVVTKKSGRSSEGDLLSLVEKETKHK
RGNSAPDLEALKEEISRQEKKASRKKK
HNRIYTKELTLAFLLLTASARSLLSAQG
VHFYFLLFQGISFLLVGLDLIGEQVE |
| 34 | eucalyptusSpp_005009 | Cellulose synthase like | MAQISAKDLIPDSLTMSREDIAGQLGM
VWELIKAPLIVPVLRLSVYVCLAMALM
LFMERVYMGIVIVLVKLFWKKPEKRYN
WEPIEEDLESGSSNFPFVLVQIPMYNEK
EVYKISIGAACGLSWPADRLVIQVLDDS
TDPVIKQMVELECQRWASKGINIVYQIR
ETRGGYKAGALKEGLKRSYVKHCEFV
AIFDADFRPEPDYLKRAIPYFLRNPDLA
LVQARWRFVNSNECLLTRMQEMSLDY
HFTVEQEVGSATHAFFGFNGTAGVWRI
GAINEAGGWKDRTTVEDMDLAVRASL
RGWKFVYLGDLQVKSELPSTFKAFRFQ
QHRWSCGPANLFRKMVMEIVRNKKVR
FWKKVYVIYSFFFVRKIIAHMVTFFFYC
VVLPLTIWVPEVHVPIWGAVYIPSIITIL
NSVGTPRSIHLLFYWILFENVMSMHRTK
ATFIGLLEAGRANEWVVTEKLGDTLKN
KSKKLRFTFNFADRLHLLELGFGVFLFV
TGCYDFLYGKNNYFVYLWLQTITFFIA
GFGYIGTIV |
| 35 | eucalyptusSpp_007860 | Cellulose synthase GDP forming | MSGFAVGSHSRNELHVTNGGAADEHR
SPPRQNAARTCRVCGDEIGLKDDGAPF
VACHECGFPVCRPCYVYERSDGTQCCP
QCNARYKRHKGCPRVAGDDEDDHFEG
EDFEDEFQIRNRGENEVRPTGFDRSENG
DSHAPQVHPNGQVFSSAGSVVGAELEG
EGNAEWKERIEKWKIRQEKRGLVGKD
DGGNGDGEEDDYLMAEARQPLSRKVPI
SSSKISPYRIVIVLRLVVLGFFLHFRILTP
ATDAFPLWLISVICETWFALSWILDQFP
KWNPINRETYLDRLSIRFEREGEPSRLTP
VDVFVSSVDPLKEPPIITANTVLSILAVD
YPVDKVCCYVSDDGASMLLFDTLSETA
EFARRWVPFCKKYSIEPRTPEFYFSQKID
YLKDKVEPSFVKERRAMKREYEEFKVR
VNALVAK420AQKKPEEGWVMQDGTP
WPGNNTRDHPGMIQVYLGSAGALDVE
GKELPRLVYVSREKRPGYQHHKKAGA
MNALVRVSAVLTNAPFLLNLDCDHYIN
NSKAIREAMCFLMDPQLGKKLCYVQFP
QRFDGIDRHDRYANRNIVFFDINMRGL
DGIQGPVYVGTGCVFNRQALYGYDPPV
SQKRPKMTCDCWPSWCSCCCGGSRKS
KSKKKDDTSLLGPVHAKKKKMTGKNY
LKKKGSGPVFDLEDIEEGLEGFDELEKS
SLMSQKNFEKRFGQSPVFIASTLMEDGG
LPEGTNSTSLIKEAIHVISCGYEEKTEWG
KEIGWIYGSVTEDILTGFKMHCRGWKS
VYCMPKRPAFKGSAPINLSDRLHQVLR
WALGSVEIFLSRHCPLWYAWGGKLKLL
ERLAYINTIVYPFTSIPLLFYCTIPAVCLL
TGKFIIPTLTNFASIWFLALFLSIIATGVL
ELRWSGVSIEDWWRNEQFWVIGGVSA
HLFAVFQGLLKVLAGVDTNFTVTAKAA
EDSEFGELYLFKWTTLLKPPTTLIILNM
VGVVAGVSDAINNGYGSWGPLFGKLFF
AFWVIVHLYPFLKGLMGKQNRTPTIVV |

TABLE 3-continued

Eucalyptus grandis polysaccharide synthesis peptides

| SEQ ID | Consensus ID | Gene Product | Curated Peptide Sequence |
|---|---|---|---|
| | | | LWSVLLASIFSLVWVRIDPFLPKQTGPV<br>LKPCGVEC |
| 36 | eucalyptusSpp_008124 | Cellulose synthase GDP forming | MEAGAGLVAGSHNRNELVVIHGHEESK<br>PLKNLDGQVCEICGDEVGLTVDGDLFV<br>ACNECGFPVCRPCYEYERREGSQLCPQ<br>CKTRYKRLKGSPRVEGDDDEEDIDDLE<br>HEFNIEDEQNKHKYMAEAMLHGKMSY<br>GRGPEDDDNAQFPSVIAGGRSRPVSGEF<br>PISSYGHGEMPSSLHKRVHPYPISEPGSE<br>RWDEKKEGGWKERMDDWKLQQGNLG<br>PEPDDINDPDMAMIDEARQPLSRKVPIA<br>SSKINPYRMVIVARLAILAFFLRYRILNP<br>VHDAFGLWLTSIICEIWFAFSWILDQFP<br>KWFPIDRETYLDRLSLRYEREGEPNMLS<br>PVDVFVSTVDPMKEPPLVTGNTVLSILA<br>MDYPVDKISCYVSDDGASMLTFESLSE<br>TAEFARKWVPFCKKFSIEPRAPEMYFTL<br>KIDYLKDKVQPTFVKERRAMKREYEEF<br>KVRINALVAKAAKVPPEGWIMQDGTP<br>WPGNNTKDHPGMIQVFLGHSGGLDAD<br>GNELPRLVYVSREKRPGFQHHKKAGA<br>MNALVRVSGVLTNAPFMLNLDCDHYI<br>NNSKAVREAMCFLMDPQIGRKVCYVQ<br>FPQRFDGIDTNDRYANRNTVFFDINMK<br>GLDGIQGPVYVGTGCVFRRQALYGYEP<br>PKGPKRPKMVSCDCCPCFGRRKKLPKY<br>SKHSANGDAADLQGMDDDKELLMSEM<br>NFEKKFGQSAIFVTSTLMEQGGVPPSSS<br>PAALLKEAIHVISCGYEDKTEWGTELG<br>WIYGSITEDILTGFKMHCRGWRSIYCMP<br>KRPAFKGSAPINLSDRLNQVLRWALGS<br>VEIFFSHHSPVWYGYKGGKLKWLERFA<br>YVNTTIYPFTSLPLLAYCTLPAICLLTDK<br>FIMPAISTFASLFFIALFMSIFATGILELR<br>WSGVSIEEWWRNEQFWVIGGVSAHLF<br>AVVQGLLKVLAGIDTNFTVTSKASDDE<br>DFGELYAFKWTTLLIPPTTILIINLVGVV<br>AGISDAINNGYQAWGPLFGKLFFAFWV<br>ILHLYPFLKGLMGRQNRTPTIVVIWSVL<br>LASIFSLLWVRIDPF |
| 37 | eucalyptusSpp_008896 | Cellulose synthase like | MDRLSATGLLPDTFGGARDDISMQLSLI<br>WAQIKAPLLVPLLRLAVFLCLAMSLML<br>FLERVYMAVVILLVKLFGRKPEKRYRW<br>EPMKDDVELGNSAYPMVLVQIPMYNE<br>REVYQLSIGAACGLSWPSDRIIIQVLDDS<br>TDPTIKDLVELECQRWASKGINIRYEIR<br>DNRNGYKAGALKEGMKRSYVKQCDY<br>VAILDADFQPEPDFLWRTIPFLVHNPEV<br>ALVQARWKFVNADECLMTRMQEMSL<br>DYHFTVEQEVGSSTHAFFGFNGTAGVW<br>RISALNEAGGWKDRTTVEDMDLAVRA<br>SLKGWKFVYLGSLKVKNELPSTFKAYR<br>FQQHRWSCGPANLFRKMAMEIIRNKKV<br>TLWKKVHVIYSFFLVRKIVAHIVTFIFYC<br>VVLPATVFVPEVTVPKWGAVYIPSIITV<br>LNAVGTPRSLHLVVFWILFENVMSFHR<br>TKATFIGLLEAGRVNEWIVTEKLGDAL<br>KVKASNKVPKKPKFRFGDRLHVLELGV<br>GAYLFFCGCYDIAFGRNHYFMYLFAQA<br>IAFFIMGFGYIGTFVPNS |
| 38 | eucalyptusSpp_012804 | Cellulose synthase like | MEHRSRPLNLCHVDPKLIAVNRAHMLI<br>HGAALLILIHYRASFFFAEEASSPGQPTT<br>LAWLIIFLGELTLSLTWLLHQAFRWRPV<br>SRTAFPERLPGDGELPSIDVLVCTADPD<br>KEPTVAVMNTVISAMALDYPPEKLHVY<br>LSDDGGSLLTLHGMREAYDFARRWLPF<br>CKRFGIKTRCPKAYFMDDEDVSASVGY<br>ESEKKEVKEKYELFEAHINGYRNRNYG<br>ESRDGRLDHPSTIEVIHGNSSDEVVQAD<br>QQQMPLLVYVSREKRPSYPHNFKAGAL<br>NVLLRVSGVISNSPYVLVLDCDMYCND<br>PSSARRAMCFHLDPTLSPSLSFVQFPQSF<br>HNISKNDIYDSKIRSPFGTLLCGMDGLQ |

TABLE 3-continued

Eucalyptus grandis polysaccharide synthesis peptides

| SEQ ID | Consensus ID | Gene Product | Curated Peptide Sequence |
|---|---|---|---|
| | | | GPLIAGTGFYIKRESLYSEPMQEGTTAN |
| | | | LMDLKAIFGHSNEFIKHLHWSDKLNKNI |
| | | | LSEPGTVCRDTEHLASCHYENGTKW |
| 39 | eucalyptusSpp_016249 | Cellulose synthase GDP forming | MNTGGRLIAGSHNRNEFVLINADESSRI |
| | | | KSVKELSGQICQICGDVEIADGELFVA |
| | | | CNECAFPVCRPCYEYERREGNQACPQC |
| | | | KTRYKRLKGSPRVEGDEEEDDIDDLDN |
| | | | EFDYDPSDPQHVAEKTFSSRLNYGRGA |
| | | | HRNASGMPTDYESSPLSSQIPLLTYGQE |
| | | | DAEISPDQHALIVPPATGHAYRVHPMPY |
| | | | PDSSNPLHPRPMAPEKDITLYGYGSVA |
| | | | WKDKMEKWRKKQNEKLQVVKHEGAG |
| | | | DGGDFGSDELDDPDLPMMDEGRQPLSR |
| | | | KLPIPSSKINPYRLLIILRLVILGLFLHYRI |
| | | | LHPVNDAYGLWLTSVICEIWFAVSWIL |
| | | | DQFPKWYPIERETYLDRLSLRYEREGKP |
| | | | SELAPVDVFVSTVDPMKEPPLITANTVL |
| | | | SILAVDYPVDKVACYVSDDGAAMLTFE |
| | | | ALSETSEFAKKWVPFCKRFNIEPRAPEW |
| | | | YFSQKMDYLKNKVHPEFVRERRAIKRE |
| | | | YEEFKVRINALVAMAQKVPEEGWTMQ |
| | | | DGTPWPGNNVRDHPGMIQVFLGHSGV |
| | | | CDDDGNELPRLVYVSREKRPGFEHHKK |
| | | | AGAMNALIRVSAVISNAPYLLNVDCDH |
| | | | YINNSKALREAMCFMMDPTSGKKVCY |
| | | | VQFPQRFDGIDRHDRYSNRNVVFFDIN |
| | | | MKGLDGLQGPIYVGTGCVFRRQALYG |
| | | | HDAPSKKKPPSKTCNCWPKWCCLCCG |
| | | | GRKNKGKTKKERSKKTKNRETSKQIH |
| | | | ALENIEEGVSEVSNEKSSEMTQIKLEKK |
| | | | FGQSPVFVASTTLEDGGVPPDASPASLL |
| | | | KEAIQVISCGYEDKTEWGKEVGWIYGS |
| | | | VTEDILTGFKMHCHGWRSVYCIPKRPA |
| | | | FKGSAPINLSDRLHQVLRWALGSVEIFL |
| | | | SRHCPIWYGYGGGLKWLERFSYINSVV |
| | | | YPWTSIPLIVYCSLPAICLLTGQFIVPEIS |
| | | | NYASLVFMALFISIAATGILEMQWGGV |
| | | | GIDDWWRNEQFWVIGGVSSHLFALVQ |
| | | | GLLKVLGGVNTNFTVTSKAADDGAFSE |
| | | | LYIFKWTSLLIPPMTLLIMNIVGVVVGIS |
| | | | DAINNGYDSWGPLF |
| 40 | eucalyptusSpp_016939 | Cellulose synthase like | MDTGVHMRRMSTPGIRQVNNSRDDTD |
| | | | SVVSSAEFASYTVHIPPTPEYQPMYMSI |
| | | | ETSNAEKVEDLYASNSLFTGGYNRATR |
| | | | SFLKEKMTDSVSNHPQMAGMNGSMCE |
| | | | IPGCDAKIMRDERGEDIVPCDCDFKICR |
| | | | DCFRDAVRGGDVICLGCKEPYKGLDM |
| | | | AEPEMNDGRRVSSGGMSKRERRMSMI |
| | | | KSRMSLKRSEMDDFDHRNWLFETKGS |
| | | | YGYGNAMWPKEDVDGDDDGFGNPQV |
| | | | LHDKKWRPLTRKVNVSPKILSPYRLLIF |
| | | | LRIIALALLLMWRIKHPNEDAMWLWA |
| | | | MSVVCEIWFGFSWLLDQLPKLCPINRTT |
| | | | DLGALKMKFETPSPTNPTGKCDLPGIDI |
| | | | FVSTADPEKEPPLVTANTILSILAADYPV |
| | | | EKLACYVSDDGGALLTFEAMAEAASFA |
| | | | NLWVPFCRKHRIEPRNPESYFSLKRDPY |
| | | | KDKVRQDFVRDRRRVKREYDEFKVRIN |
| | | | GLSNSIRRRSDAYNACEEIKAAKLQNK |
| | | | NESGEGVESLKIPKATWMADGTHWPG |
| | | | TWTGPAAEHSRGDHASVIQVMLKPPSD |
| | | | EPLRGTESTSPIDLAEVDIRLPMLVYISR |
| | | | EKRPGYDHNKKAGAMNALVRASAIMS |
| | | | NGPFILNLDCDHYIYNSQAMREGMCFM |
| | | | MDRGGDRICYVQFPQRFEGIDPSDRYA |
| | | | NHNTVFFDVNMRALDGLQGPVYVGTG |
| | | | CLFRRTALYGFDPPRVKEHGGCFSQIFK |
| | | | RHRSAATVASTPEVSLVENRFLGMGDS |
| | | | SQEEVNLLPNKFGNSVLFVESIHIAEFQG |
| | | | RPLADDPSVKNGRPPGALTIPRQLLDAP |
| | | | TVAEAISVISCWYEDKTEWGQRIGWIY |
| | | | GSVTEDVVTGYRMHNRGWRSIYCVTK |
| | | | RDAFRGTAPINLTDRLHQVLRWATGSV |
| | | | EIFFSRNNALLASRRMKFLQRIAYMNV |

TABLE 3-continued

*Eucalyptus grandis* polysaccharide synthesis peptides

| SEQ ID | Consensus ID | Gene Product | Curated Peptide Sequence |
|---|---|---|---|
| | | | GLYPFTSIFLVVYCFLPALSLFSGQFIVQ SLDVTFLTYLLAITVTLCILAMLEIKWS GIELEEWWRNEQFWLIGGTSAHLAAVI QGLLKVIAGIEISFTLTSKSAGDENDDEF AELYLFKWTSLMILPITI |
| 41 | eucalyptusSpp_017058 | Cellulose synthase like | MEHSSGPLNLCHVLTKSIIINRTHMLVH ATALSALIYYRASFFFSESKSRDRATTL ACLTMFLAELGLSFLWLLSQAFRWRPV RRTAFPKRLPEDKELPPIDVFVCTADPD KEPTVDVMNTVVSAMALDYPPEKLHV YLSDDGGSTLTLHGTREAYDFARWWL PFCKRYGIKTRCPKAFFKEEEDGEGIGM SSDNEFGSEKKIVKEKYELFKERVNEYR KRHRGDSSHTGRDHPPTIEVVRGNVPD EVMQAHQDPMPKLIYVSREKRPSHHHH FKAGALNVLLRVSGVMSNSPYILVLDC DMYCNDPSSARQAMCFHLDPRLSPSLM LVQFPQMFHNISENDIYDSKLRPYFWTC WYGMDGLKGPVLSGTCFYIKRESLYRK PVQEGYDLMDLKKLFGHSNEFIKYLGQ KEKPSKNTIAGDSAALMKETQLLTSCG YEYGTKWGQEVGFKYYSVVEDYFTSFT LHCRGWTSVFYTPSKPQFLGTATTNFN DMLIQGMRWYSGLSQVGISRFCPLIYGS LRMPILQSMCYAELSLFPLYCLPICCFAT IPQICLVNGISIYPEVPSSYIMLFAFIFLSS LCKHLYEVVASGHSVQTFLNEQRIWMI KSTTCYVYGTIDAIMTQIGMRTASFLPT NKVDDDEQSKRYEMGIFDFQTSIMFLA PMVTLVILNMASFFGGVARVLTLGGFD KLFMQIALSLFVLVMSYPVIKAMVLRT DKGRIPRSVTTLSAFLSLVLLLQGSSFLM |
| 42 | eucalyptusSpp_017442 | Cellulose synthase GDP forming | MEANAGMVAGSYKRNELVRIRHDSDS APKPLKHLDGHMCQICGDTVGLSASGD VFVACNECAFPVCRPCYEYERKDGNQC CPQCKTRYKRQKGSPRVEGDDDEDGV DDLENEFSYTRGNARRRQWQGDDPDL SSSSRRESQHPVPLLTNGLPISGEIPCATP DNQSVRTTSGPLGPSDRHSVHSVDPRQP VPVRIVDPSRDLNSYGLGNVDWKERVE SWKLKQEKNIPHMTSRFPEGKGDIEGT GSYGEELQMADDARLPLSRVVPISSSHL TPYRVVIILRLIILGFFLQYRATHPVKDA YPLWLTSVICEIWFALSWLLDQFPKWFP INRETYLDRLALRYDREGEPSQLAPIDIF VSTVDPLKEPPLVTANTVLSILAVDYPV DKVSCYVSDDGSAMLTFEALSETAEFA KKWVPFCKKHNIEPRAPEFYFAQIDYLK DKIQPSFVKERRAMKREYEEFKVRINAL VAKAQKVPEEGWTMQDGTPWPGNNPR DHPGMIQVFLGHSGGLDTDGNELPRLV YVSREKRPGFQHHKKAGAMNALIRVSA VLTNGAYLLNVDCDHYFNNSKALKEA MCFMMDPALGKKTCYVQFPQRFDGID LHDRYANRNIVFFDINLKGLDGIQGPVY VGTGCCFNRQALYGYDPVLTEADLEPN IIVKSCCGPRKKGKGGDKNYIDKKRAV KRTESNIPIFNMEDIEEGMEGYDDERSL LMSQKSLEKRFGQSPVFIAATFMEQGG LPPSTNPASLLKEAIHVISCGYEDKTEW GKEIGWIYGSVTEDILTGFKMHARGWIS IYCMPPRPAFKGSAPINLSDRLNQVLRW ALGSIEILLSRHCPIWYGYNGRLKWLER LAYINTIVYPLTSIPLIAYCILPAFCLLTG KFIIPEISNFASMWFILLFVSIFATGILELR WSGVSIEDWWRNEQFWVIGGTSAHLF AVFQGLLKVLAGIDTNFTVTSKASDED GDFAELYVFKWTSLLIPPTTVLIVNLVGI VAGVSYAINSGYQSWGPLFGKLFFAIW VIAH |
| 43 | eucalyptusSpp_017462 | Cellulose synthase like | MSRAPNREFQEWWNKQRERGLDLSSPS SADGPSTSGGGGGGGGPLLAVEIRTPRS DQAVEKSRARSARQLSWVCLLRFQQIA |

TABLE 3-continued

*Eucalyptus grandis* polysaccharide synthesis peptides

| SEQ ID | Consensus ID | Gene Product | Curated Peptide Sequence |
|---|---|---|---|
| | | | SLLASAAGSFLSVLRTANRRIAASPADS
SSSRLYRIIRFFLILVLVLLGFELLAYSKG
WHFSPPSVGSKEVLGFVELVYANWLEI
RATYLAPPLQSLTNVCIVLFLIQSVDRV
VLVLGCIWIKIKGIKPVASADYEKKEDL
ESESGDEAYPMVLVQIPMCNEREVYQQ
SIAAVCIQDWPRERMLVQVLDDSDDLD
VQLLIKSEVQKWQQRGIRIVYRHRLIRT
GYKAGNLKSAMSCDYVKDYEFVAIFD
ADFQPGPDFLKKTIPYFKGNDDLALVQ
TRWAFVNKDENLLTRLQNINLSFHFEV
EQQVNGVFINFFGFNGTAGVWRIKALE
ECGGWLERTTVEDMDIAVRAHLCGWK
FIYLNDVKCLCELPESYEAYKKQQHRW
HSGPMQLFRLCFFDIIRSKVSLAKKANLI
FLFFLLRKLILPFYSFTLFCIILPLTMFLPE
AQLPAWVVCYVPGVMSILNILPAPRSFP
FIVPYLLFENTMSVTKFNAMISGLFKFG
SSYEWIVTKKLGRSSEADLLTFGEKGSD
PLLETSNLHRSSSESGLAELNKMEMTK
KAGKLRRNRLYRKELGLAFILLTAAVR
SLLSAQGIHFYFLLFQGISFLVVGLDLIG
EQVS |
| 44 | eucalyptusSpp_017488 | Cellulose synthase GDP forming | MACRERRRRTRSLLSLLSPPPPPDPLAS
AFDLGEKEGRKRTTMEANGGMAAGSY
KRNELVRIRHDSDGGPKPLKNLNGQIC
QICGDTVGLTASGDVFVACNECAFPVC
RPCYEYERKDGNQSCPQCKSRYKRHKG
SPRVDGDDDEDEVDDLENEFNYAQGTS
AARQQWQGEDPDLSSSSRHESRHPIPLL
TNGQPMSGEIPCASIDSQSVRTTSGPLGP
SDKHVHSLPYVDPRQPVPVRIVDPSKDL
NTYGLGNVDWKERVEGWKLKQEKNM
TQMPNKYHEGKNDIEGTGSNGEELQM
ADDARQPMSRVVPISSSHLTPYRVVIILR
LIILGFFLQYRVTHPVKDAYPLWLTSVI
CEIWFALSWLLDQFPKWSPINRETYLDR
LALRHDREGEPSQLAPVDVFVSTVDPL
KEPPLITANTVLSILAVDYPVDKVSCYV
SDDGSAMLTFEALSETAEFARKWVPFC
KKHNIEPRAPEFYFAQKIDYLKDKIQPSF
VKERRAMKREYEEFKVRINALVAKAQ
KMPEEGWTMQDGTAWPGNNPRDHPG
MIQVFLGHSGGLDTDGNELPRLVYVSR
EKRPGFQHHKKAGAMNALIRVSAVLTN
GAYLLNVDCDHYFNNSKALKEAMCFM
MDPAYGKKTCYVQPFPQRFDGIDLHDRY
ANRNIVFFDINLKGLDGIQGPVYVGTGC
CFNRQALYGYDPVLTEEDLEPNIIVKSC
CGSRKKGKGGNKKYIDKKRAMKRTES
TVPIFNMEDVEEGVEGYDDERSLLMSQ
KSLEKRFGQSPVFISATFMEQGGLPPST
NPATLLKEAIHVISCGYEDKTEWGKEIG
WIYGSVTEDILTGFKMHARGWISIYCMP
PRPAFKGSAPINLSDRLNQVLRWALGSI
EILLSRHCPIWYGYNGKLRLLERLAYIN
TIVYPLTSIPLIAYCILPAFCLFTNKFIIPEI
SNFASMWFILLFVSIFTTGILELRWSGVS
IEDWWRNEQFWVIGGTSAHLFAVFQGL
LKVLAGIDTNFTVTSKAGDEDGDFAEL
YVFKWTSL |
| 45 | eucalyptusSpp_017722 | Cellulose synthase GDP forming | MESEGETGGKSMKILGGQVYQICGDNV
GKSVDGEPPFVACNVCAFPVCRPCYEYE
RKDGNQSCPQCKTRYKRHRGSPAILGD
QEEDADADDSVSDFNYSENQNLNRKTE
ERILSWHMQYGQNEDVSAPNYDKEVS
HNHIPRLTSGQEVSGELSAASPERLSVA
SPDVGAGKRIHSLPYVADANQSPNIRVV
DPVREFGSSGLNNVAWKERVDGWKM
KQEKNVAPMSTAQATSERGVGDIDAST
DVLVDDSLLNDEARQPLSRKVSVPSSRI
NPYRMVIVLRLIILSIFLHYRITNPVPNA
YALWLISVICEIWFAISWILDQFPKWFPV
NRETYLDRLAIRYDREGEPSQLAAVDIF |

TABLE 3-continued

Eucalyptus grandis polysaccharide synthesis peptides

| SEQ ID | Consensus ID | Gene Product | Curated Peptide Sequence |
|---|---|---|---|
| | | | VSTVDPLKEPPLVTANTVLSILAVDYPV |
| | | | DKVSCYVSDDGAAMLTFEALSETSEFA |
| | | | RKWVPFCKKYSIEPRAPEWYFALKIDY |
| | | | LKDKVHPSFVKDRRAMKREYEEFKVRI |
| | | | NGLVAKAAKIPEEGWIMQDGTPWPGN |
| | | | NTRDHPGMIQVFLGQSGGLDAEGNELP |
| | | | RLVYVSREKRPGFQHHKKAGAMNALV |
| | | | RVSAVLTNGPFLLNLDCDHYINNSKAL |
| | | | REAMCFLMDPNLGKHVCYVQFPQRFD |
| | | | GIDRNDRYANRNTVFFDINLRGLDGIQG |
| | | | PVYVGTGCVFNRTALYGYEPPHKPKQR |
| | | | KSGFLSSLCGGSRKKSRSSKKGSDKKKS |
| | | | SKHVDPTVPIFSLEDIEEGVEGAGFDDE |
| | | | KSLLMSQMSLEKRFGQSAVFVASTLME |
| | | | NGGVPQSATPETLLKEAIHVISCGYEDK |
| | | | SDWGSEIGWIYGSVTEDILTGFKMHAR |
| | | | GWRSIYCMPKRPAFKGSAPINLSDRLNQ |
| | | | VLRWALGSVEILFSRHCPIWYGYGGRL |
| | | | KWLERFAYVNTTIYPITAIPLLMYCTLP |
| | | | AVCLLTNKFIIPQISNVASIWFISLFLSIFA |
| | | | TGILEMRWSGVGIDEWWRNEQFWVIG |
| | | | GVSAHLFAVFQGLLKVLAGIDTNFTVTS |
| | | | KASDEDGDSAELYMFKWTTLLIPPTTLL |
| | | | IINLVGVVAGISYAINSGYQSWGPLFGK |
| | | | LFFAFWVIVH |
| 46 | eucalyptusSpp_022868 | Cellulose synthase like | MDRLSATGLLPDTFGGARDDISMQLSLI |
| | | | WAQIKAPLLVPLLRLAVFLCLAMSLML |
| | | | FLERVYMAVVILLVKLFGRKPEKRYRW |
| | | | EPMKDDVELGNSAYPMVLVQIPMYNE |
| | | | REVYQLSIGAACGLSWPSDRIIIQVLDDS |
| | | | TDPTIKDLVELECQRWASKGINIRYEIR |
| | | | DNRNGYKAGALKEGMKRSYVKQCDY |
| | | | VAILDADFQPEPDFLWRTIPFLVHNPEV |
| | | | ALVQARWKFVNADECLMTRMQEMSL |
| | | | DYHFTVEQEVGSSTHAFFGFNGTAGVW |
| | | | RISALNEAGGWKDRTTVEDMDLAVRA |
| | | | SLKGWKFVYLGSLKVKNELPSTFKAYR |
| | | | FQQHRWSCGPANLFRKMAMEIIRNKKV |
| | | | TLWKKVHVIYSFFLVRKIVAHIVTFIFYC |
| | | | VVLPATVFVPEVTVPKWGAVYIPSIITV |
| | | | LNAVGTPRSLHLVVFWILFENVMSFHR |
| | | | TKATFIGLLEAGRVNEWIVTEKLGDAL |
| | | | KVKASNKVPKKPKFRFGDRLHVLELGV |
| | | | GAYLFFCGCYDIAFGRNHYFMYLFAQA |
| | | | IAFFIMGFGYIGTFVPNS |
| 47 | eucalyptusSpp_023490 | Cellulose synthase like | MAPSFDWWAKGGHKGTPVVVKMENP |
| | | | NWSMVELESPSEEDFLIGGDSAPSGRVR |
| | | | DKGRNKNAKQLTWVLLLKAHKAAGCL |
| | | | TSIAGAAFTLASAVRRRVASGRTDADA |
| | | | DEAETGESRSGREKENPTVKSRIYACIK |
| | | | AFLWLSILLLGFEVAAYFKGWHFGALE |
| | | | LQYLLAAPLGVKGAFNSLYSRWVLIRV |
| | | | EYLAPPLQFLANVCIVLFLIQSIDRLVLC |
| | | | LGCFWIKFKKIKPVPKESGAAVDPESGE |
| | | | NGFFPMVLVQIPMCNEKEVYQQSIAAV |
| | | | CNLDWPKSSLLIQVLDDSDDPTTQSLIK |
| | | | EEVQKWQQEGANILYRHRVIRDGYKA |
| | | | GNLKSAMNCSYVKDYEFVAIFDADFQP |
| | | | TPDFLKRTVPHFKDNEELGLVQARWSF |
| | | | VNKDENLLTRLQNVNLSFHFEVEQQVN |
| | | | GIFINFFGFNGTAGVWRIKALEDAGGW |
| | | | LERTTVEDMDIAVRAHLRGWKFVFLND |
| | | | VECQCELPESYEAYRKQQHRWHSGPM |
| | | | QLFRLCLLDIIRSKISVWKKFNMIFLFFL |
| | | | LRKLILPFYSFTLFCIILPMTMFVPEAELP |
| | | | AWVVCYIPATMSFLNILPAPKSFPFIVPY |
| | | | LLFENTMSVTKFNAMISGLFQLGSAYE |
| | | | WVVTKKSGRSSEGDLVALIDKEPKHQR |
| | | | GVSVPDLEEMKEEIQKQEKLASRKKKH |
| | | | NRIYVKELSLAFLLLTASARSLLSAQGIH |
| | | | FYFLLFQGISFLLVGLDLIGEQVE |

TABLE 3-continued

*Eucalyptus grandis* polysaccharide synthesis peptides

| SEQ ID | Consensus ID | Gene Product | Curated Peptide Sequence |
|---|---|---|---|
| 48 | eucalyptusSpp_027512 | Cellulose synthase GDP forming | MESDAENGGKPLKSLGGQVCQICGENV GKTLDGEPFIACDVCAFPVCRPCYEYER KDGNQSCPQCKTRYKRHKGSPAILGDH EEDGDAGDDYHYSSEDQTQKEKIAERM LSWHMTYGRGENVAPANYDGEVSRNH IPLLTSRQEVSGELSAASPERLSMASPGV GRVHRVRPLSYASDVTQSPNIRVVDPA REFGSPGIGNVAWKERVDGWKMKQEK NVGPMSTGQAASERGAGDIDASTDVLV DDSLLNDEARQPLSRKVSIPSSRINPYR MVIMLRLVILCIFLHYRITNPVPNAYAL WLISVICEIWFAISWILDQFPKWFPVNRE TYLDRLALRYDREGEPSQLAAVDIFVST VDPLKEPPLVTANTVLSILAVDYPVDKV SCYVSDDGAAMLTFEALSETAEFARKW VPPFCKKYNIEPRAPEWYFTKKIDYLKD KIQPSFVKDRRAMKREYEEFKVRINGL VAKAQKIPEEGWVMQDGTPWPGNNTR DHPGMIQVFLGQSGGLDAEGNELPRLV YVSREKRPGFQHHKKAGAMNSLVRVS AVLTNGPFLLNLDCDHYINNSKALREA MCFLMDPNLGKHVCYVQFPQRFDGIDK NDRYANRNTVFFDINLRGLDGIQGPVY VGTGCVFNRTALYGYEPPLKPKHKKPG VLSLLCGGSRKKSSKSSKKSSDRKRSGK HVDTTVPIFSLEDIEEGVEGAGFDDEKS LLMSQMSLEKRFGQSAVFVASTLMENG GVPQSATPETLLKEAIHVISCGYEDKSE WGSEIGWIYGSVTEDILTGFKMHARGW RSIYCMPKLPAFKGSAPINLSDRLNQVL RWALGSVEILFSRHCPIWYGYGGRLKW LERFAYVNTTIYPVTAIPLLMYCTLPAV CLLTNKFIIPQISNIASIWFISLFLSIFATGI LEMRWSGVGIDEWWRNEQFWVIGGVS SHLFAVFQGLLKVLAGIDTNFTVTSKAS DEEGDFTELYTFKWTTLLIPPTTLLIINL VGVVAGISYAINSGYQSWGPLFGKLFF AFWVIIHL |

TABLE 4

*Pinus radiata* polysaccharide synthesis peptides

| SEQ ID | Consensus ID | Gene Product | Curated Peptide Sequence |
|---|---|---|---|
| 49 | pinusRadiata_000531 | Cellulose synthase GDP forming | MEASAGLVAGSHNRNEFVVIHGHEEPK PLNTLSGHVCQICGEDVGLNTDGELFV ACNECGFPVCRPCYEYERREGNQSCPQ CNTRYKRQKGSPRVEGDDDEEDVDDIE HEFNVETQQRNRQQITEAMLHGRMSY GRGPDDENSQIAHNPELPPQIPVLANGH SVVSGEIPTSYYADNQLLANPAMLKRV HPSSEPGSGRIIMDPNRDIGSYGFGNVS WKERGDGYKSKENKSGQLDMTEGRYQ YNGGFAPNEPEDYIDPDMPMTDEARQP LSRKVPIPSSKINPYRMVIVIRLIVLGIFL RYRLLNPVKNAYGLWATSIVCEIWFAL SWILDQFPKWLPISRETYLDRLSLRYER EGEPSMLAPVDLFVSTVDPLKEPPLVTA NTVLSILSVDYPVDNVSCYVSDDGASM LTFESLSETSEFARKWVPFCKKFDIEPRA PEIYFSQKIDYLKDKFQPTFVKERRAMK REYEEFKVRINRLVAKASKVPKEGWTM QDGTPWPGNNTRDHPGMIQVFLGHSG GLDTEGNELPRLVYVSREKRPGFQHHK KAGAMNALVRVSAVLTNAPFMLNLDC DHYINNSKAIREGMCFMMDPQVGRKV CYVQFPQRFDGIDRNDRYANRNTVFFDI NMKGLDGIQGPVYVGTGCMFRRQALY GYGPPKGPKRPKMVTCDCLPCCGPRKK SPKKNSSKKSAGIPAPAYNLDGIEEGVE GYDDERALLMSQLDFEKKFGQSSAFVQ |

TABLE 4-continued

Pinus radiata polysaccharide synthesis peptides

| SEQ ID | Consensus ID | Gene Product | Curated Peptide Sequence |
|---|---|---|---|
| | | | STLMENGGVPQTANPAELLKEAIHVISC
GYEDKTEWGKELGWIYGSVTEDILTGF
KMHTRGWRSIYCMPKRAAFKGSAPINL
SDRLNQVLRWALGSVEIFMSRHCPIWY
GYGGGLKWLERFAYINTIVYPFTSLPLI
AYCTLPAVSLLTGKFVIPQISTFASLFFIA
LFISIFATGILEMRWSGVSIEEWWRNEQ
FWVIGGVSAHFFAVIQGLLKVLAGIDTN
FTVTAKASDDGEFGELYAFKWTTLLIPP
TTLLVINLVGVVVGVADAINNGFQSWG
PLLGKLFFAFW |
| 50 | pinusRadiata_002922 | Cellulose synthase GDP forming | MEARTNTAAGSNKRNVRVSVRDDGEL
GPKPPQHINSHICQICGEDVGLAADGEF
FVACNECAFPVCRPCYEYEWKDGNQSC
PQCKTRYKWHKGSPQVDGDKEDECAD
DLDHDFNSTQGNRNEKQQIAEAMLHW
QMAYGRGEDVGPSRSESQELPQLQVPLI
TNGQAISGELPAGSSEYRRIAAPPTGGG
SGKRVHPLPFPDSTQTGQVRAEDPAKD
FNSYGFGNVAWKERVESWKNKQDKNT
LQVTSDTYYASEGKDGDIDGCVADEED
LQMSDEARQPLSRKVPIASSKINPYRMV
IVLRLVILCFFFRYRILNPVRNAYGLWFT
SVICEIWFAISWILDQFPKWLPINRETYL
DRLCLRYDREGEPSQLAAVDIFVSTVDP
MKEPPLVTANTVLSILSVDYPVDKVSC
YVSDDGAAMLTFEALSETSEFARKWVP
FVKKFDIEPRAPEWYFAQKIDYLKDKV
QPSFVKERRAMKREYEEFKVRINALVA
KAQKVPEEGWIMQDGTPWPGNNTRDH
PGMIQVFLGHSGGLDTDGNELPRLVYV
SREKRPGFEHHKKAGAMNSLVRVSAVL
TNGPYMLNLDCDHYINNSRALREAMCF
MMDPTLGKKVCYVQFPQRFDGIDRND
RYANHNTVFFDINLKGLDGIQGPVYVG
TGCVFNRQALYGYEPPHKGKIHFSSCC
GPRKKSRKSNKKYNDTKKLDRPTDSTV
PIFSSLEDIEGGVEGFDDEKSPLVFQKSL
EKKFGQSLVFVASTQMENGGVPQSATP
ADLLKEAIHVISCGYEDKSDWGKEIGWI
YGSVTEDILTGFKMHARGWRSIYCMPP
RPAFKGSAPINLSDRLNQVLRWALGSV
EILLSRHCPIWYGYTGRLKWLERLAYIN
TTVYPITSIPLLAYCTLPAICLLTGKFIIPE
ISTLASLWFISLFLSIFATGILEMRWSGV
GIDEWWRNEQFWVIGGVSAHLFAVIQG
LLKVLAGVDTNFTVTSKASDEGGDFAE
LYIIKWTALLIPPTTLLIINIVGVVAGISY
AISTGYRSW |
| 51 | pinusRadiata_003920 | Cellulose synthase GDP forming | MASNGTMNSQVCQVCGDNVGVDANG
EPFVACHDCGFPVCRPCQQYERDEASQ
CCLHCKAPYRRYEGGPADEVEENGDPN
FEKVEATDYEGEGYRVDSFNDSEINNA
ETKDGNSKGVAWKERVESWKSKKNKK
KTAASKTVNPGVEGIPEQTRDPEAEEA
MMAEAGQPLSCIIPIPRTKLQPYRMVVI
MRLIVLGLFFSYRVQNPVESAFGLWMT
SVICEIWFALSWILDQFPKWNPINRETFT
DRLSLRYERPGEPCELAAVDFFVSTVDP
LKEPPLVTANTVLSILAVDYPVEKVSCY
VSDDGAAMLTFETMSETAEFARKWVPF
CKNFNIEPRAPEFYFSLKVDYLKDKVQP
NFVKERRAMKREYEEYKVRINALVAK
AQKTPDEGWIMQDGTAWPGNNIRDHP
GMIQVFLGHTGAHDVEGNELPRLVYVS
REKRPGYQHHKKAGAMNALVRVSAVL
TNAPYLLNLDCDHYVNNSKAVREAMC
FMMDPEVGRNVCYVQFPQRFDGIDRSD
RYANRNTVFFDINMKGLDGIQGPVYVG
TGCCFNRQALYGYGPPAAARPKASRGC
LPSLCCCCCCCPKSKTIDPKKSAPQEDL
NAAIFNLQEMQSYDDYERQLLVSQRSF
EKSFGQSSVFIASTLMDNGGVPESTNPA
SLIKEAIHVISCGYEEKTEWGKEVGWIY |

TABLE 4-continued

Pinus radiata polysaccharide synthesis peptides

| SEQ ID | Consensus ID | Gene Product | Curated Peptide Sequence |
|---|---|---|---|
| | | | GSVTEDILTGFKMHCRGWRSIYCMPKR
PAFKGSAPINLSDRLHQVLRWALGSIEIL
FSRHCPLWYGFGAGRLKWLERLAYTN
TIVYPLTSLPLIAYCTLPAICLLTGEFIIPT
LSNLASIYFMLLFISIIVTGVLELRWSGV
SIEEWWRNEQFWVIGGVSAHFFAVFQG
LLKVLAGIDTNFTVTAKASDDNEFGEL
YAFKWTTLLIPPTTLLVINLVGIVAGFSD
ALNNGYQSWGPLFGKLFFSVWVILHLY
PFLKGLMGRQNRTPTIVVLWSILLASIFS
LLWVKIDPFLGPAETPTLQKCMAIDC |
| 52 | pinusRadiata_017730 | Cellulose synthase GDP forming | MEANAGLVAGSHNRNEFVVIRPEGEVG
PKPLHHLSVQICHICNEDVGLTVDGELF
VACNECAFPICRTCYEYERSEGNQVCPQ
CKTRFKRHKGSARVEGDEDEDDVDDL
ENEFNFGDRDKQDMQYIAEAMLHGHM
SYGRGGDTDMPHVVQTTLPQVPLLTNG
HMDPGIPPEHHALVPSYMGGGKRIHPFP
YADSNLPVQARSMDPTKDLAAYGYGSI
AWKERVENWKMRQEKMQVMRNEGGP
LGGGKDWDPDGNGPDGPDLPLMDEAR
QPLSRKLPIPSSRINPYRMVIILRLVVIGF
FFHYRVMHPVNDAFGIWLTSVICEIWFA
FSWILDQFPKWLPIDRETYLDRLSLRYE
KEGQPSGLAPVDIFVSTVDPLKEPPLVT
ANTVLSILAVDYPVDKVSCYVSDDGAA
MLTFEALSETSEFARKWVPFCKKFNIEP
RAPEWYFQQKIDYLKDKVQPSFVKDRR
AMKREYEEFKVRMNALVAKAQKVPEE
GWTMQDGTPWPGNNVRDHPGMIQVFL
GHTGGHDTDGNELPRLVYVSREKRPGF
NHHKKAGAMNSLVRVSAVLTNAPYML
NLDCDHYINNSKAIRESMCFMMDPTVG
KKVCYVQFPQRFDGIDRHDRYANRNV
VFFDINMKGLDGIQGPIYVGTGCVFRRQ
ALYGFDAPKAEKEPTRTCNCWPKWCC
CKSRKKNKKVKAKQEKKKKKSKRSDA
SLPIFNSEDIEAVEGVDSEKLAFISQIKLE
KKFGQSPVFVASTLLENGGVPQNASPA
SLLKEAIHVISCGYEDKTDWGKEVGWI
YGSVTEDILTGFKMHCHGWRSIYCIPPR
PAFKGSAPINLSDRHQVLRWALGSVEI
FLSRHCPVWYGYGGGLKWLERLSYINA
TVYPWTSIPLVAYCTLPAICLLTGKFIIPE
LSNIASLWFLALFICIFTTGILEMRWSGV
PIDDWWRNEQFWVIGGVSAHLFAVFQ
GLLKVLAGVDTNFTVTSKAGDDDDFSE
LYAFKWTTLLIPPTTLLIVNLIGVVAGVS
NAINNGYESWGPLF |
| 53 | pinusRadiata_027109 | Cellulose synthase GDP forming | MEANAGLVAGSHNRNEFVVIRPEGEVG
PKPLHHLSVQICHICNEDVGLTVDGELF
VACNECAFPICRTCYEYERSEGNQVCPQ
CKTRFKRHKGSARVEGDEDEDDVDDL
ENEFNFGDRDKQDMQYIAEAMLHGHM
SYGRGGDTDMPHVVQTTLPQVPLLTNG
HMDPGIPPEHHALVPSYMGGGKRIHPFP
YADSNLPVQARSMDPTKDLAAYGYGSI
AWKERVENWKMRQEKMQVMRNEGGP
LGGGKDWDPDGNGPDGPDLPLMDEAR
QPLSRKLPIPSSRINPYRMVIILRLVVIGF
FFHYRVMHPVNDAFGIWLTSVICEIWFA
FSWILDQFPKWLPIDRETYLDRLSLRYE
KEGQPSGLAPVDIFVSTVDPLKEPPLVT
ANTVLSILAVDYPVDKVSCYVSDDGAA
MLTFEALSETSEFARKWVPFCKKFNIEP
RAPEWYFQQKIDYLKDKVQPSFVKDRR
AMKREYEEFKVRMNALVAKAQKVPEE
GWTMQDGTPWPGNNVRDHPGMIQVFL
GHTGGHDTDGNELPRLVYVSREKRPGF
NHHKKAGAMNSLVRVSAVLTNAPYML
NLDCDHYINNSKAIRESMCFMMDPTVG
KKVCYVQFPQRFDGIDRHDRYANRNV
VFFDINMKGLDGIQGPIYVGTGCVFRRQ
ALYGFDAPKAEKEPTRTCNCWPKWCC |

TABLE 4-continued

Pinus radiata polysaccharide synthesis peptides

| SEQ ID | Consensus ID | Gene Product | Curated Peptide Sequence |
|---|---|---|---|
| | | | CKSRKKNKKVKAKQEKKKKKSKRSDA SLPIFNSEDIEAVEGVDSEKLAFISQIKLE KKFGQSPVFVASTLLENGGVPQNASPA SLLKEAIHVISCGYEDKTDWGKEVGWI YGSVTEDILTGFKMHCHGWRSIYCIPPR PAFKGSAPINLSDRLHQVLRWALGSVEI FLSRHCPVWYGYGGGLKWLERLSYINA TVYPWTSIPLVAYCTLPAICLLTGKFIIPE VLPLTFMPYINIVSELACEGLSHFDILF |
| 54 | pinusRadiata_000892 | Cellulose synthase like | MAPNFGVGQWWSKQSHKGTSVVVKM ENPNYSMLELESPANGFQVDKGGRGKN AKQLTWVLLLKAHKAAGCLAWLANG VWALFASVRRRFTAPSDESGKSSEKSKL YRVIRCFLIASIFLLGFELLAYWKGWHF SRPNLHIPPSLSINGLLQSIYSGWLYTRA NYLAPPLQYLANVCIILFLIQSADRALLC VGCFWIKLKKIKPVPKCELGDAADLEQ GDNAAYPMVLVQMPMCNEREVYQQSI AAVCNLDWPKDHMLVQVLDDSDDVE VQFLIAAEVQKWQQKGVHIVYRHRVV RTGYKAGNLKSAMNCDYVKDYEFVAI FDADFRPDPDFLKRTVPHFKDNDELAL VQARWSFVNRDENLLTRLQNINLSFHF EVEQQVNSVFVNFFGFNGTAGVWRIKA LEESGGWLERTTVEDMDIAVRAHLNG WKFIFLDDVKCLCELPESYEAYRKQQH RWHSGPMQLFRLCLPDIIRSKIAFWKKA NLIFLFFLLRKLILPFYSFTLFCIILPMTM FLPEAELPAWVVCYVPAIMSLLNILPAP RSFPFIIPYLLFENTMSVTKFNAMISGLF QLGSAYEWVVTKKSGRASETDLLALVE RESHVQLEHPKHHRGVSESGLDALSKL DEQKHQQPPKKKLNRIYKKELALAFLL LTASARSLMSAQGIHFYFLLFQGISFLV VGLDLIGEQTS |
| 55 | pinusRadiata_008513 | Cellulose synthase like | MEPNDFPLYTTLEKKSLLYRAYSCTHFS AIIGLICYRLLYIPSEDSWPWILIFVAELG FSYSWILDQALRWWPVERTVFPNRLSK RFQSKLPPVDIFICTADPFKEPPLTVINTV LSALAVDYPMGKLSCYVSDDGGSPLTF YALLEASRFAKIWIPFCDKYSIQDRCPE VYFSNPSALENVNLPFMKDWKHVNKM YSELKDRINNVMEMGSVPPDKQNEHQ GFKDWASGSSRRDHPSIVQILLEKGEDR DIDGNDLPDLIYVSREKRPGIPHHYKAG ALNVLLRVSGVMSNAPFILTLDCDMYT NNPEALRQAMCFFLDPKTGDQFGFVQF PQVFHGITKNDIYGNNLRIFIEIDFKGQD GIDGPFYVGTGCIHRREALCRTERRQSS SNYHKVASTIVCAEETVAKDKACPSKM LKNARELANCTYEDNTLWGKEFGMIY GCAVEDILSGFVIQCKGWRSIYCNPRRS AFLGCAPNNLIDTLTQHKRWAVGHLQL FVSKFCPYIYGIHRMQIAQRMCYSYCPL WSLSSMHKLCYGLIPGLCMLRGISLFPK LSSSCFFLFAFLAISAYGYSLFEYIWNVG SLNRWCNEQRMWMIKGVSAYLFALIEF AGKMIGVSEVGFEVTNKVVDSEAAKR YETEIFEFGVASPLFVRPATLVVINLISV VGGLARILREGYSAFECITLQLILCSFIVI TGYPILEAMFLSKAKGRIPTSITIFFTLDA VSVWSVASMAIPSR |
| 56 | pinusRadiata_013907 | Cellulose synthase like | MATNFEFQEWWNKEKETHRGTSVVVK MENPNWSMVELQSPDDDFQHSDKQGR GKNARQLTWVWLLKAHRAAGCVAWL AQGLWSLLSAVKRRVTLNKNQNRVTE EDKPGKSKLYRVIRGFLLFAILMLGFEIA AYMKGWHFSRPPFDFSPSLDLQGVLHSI YSEWVFVRATYLAPPLQTLANICIVLFLI QSADRLVLAMGCLWIHIKKIKPVPQFEF PSSAADLEKGASADYPMVLVQIPMCNE MEVYQQSIAAVCNLDWPKERMLVQVL DDSDDVDVQLLIKSEVQKWQQKDINIV |

TABLE 4-continued

Pinus radiata polysaccharide synthesis peptides

| SEQ ID | Consensus ID | Gene Product | Curated Peptide Sequence |
|---|---|---|---|
| | | | YKHRVVRTGYKAGNLKSAMACDYVK DYEFVAIFDADFQPSPDFLKKTVPHFKG NEDLALVQARWAFVNKDENLLTRLQNI NLAFHFEVEQQVNGVFINFFGFNGTAG VWRIKALEESGGWLERTTVEDMDIAVR AHLNGWKFIYLNDVQCLCELPESYEAY RKQQHRWHSGPMQLFRLCLPDIIRSKEI GFSKKANLIFLFFLLRKLILPFYSFTLFCII LPMTMFLPEAQLPSWVICYVPVIMSFFN ILPAPRSFPFIVPYLLFENTMSVTKFNAM ISGLFQLGSAYEWVVTKKLGRSSEADL VAFMEKESHPQLEHPRHHRGVSESGLD VLNKLTEQQQKQPFKKKANRLYRKEL ALAFLLLTASARSLLSAQGIHFYFLLFQ GISFLLVGLDLIGEQVS |
| 57 | pinusRadiata_026937 | Cellulose synthase like | MEPNGFPLYTTLEKKSFVYRAYACAHF SAIIGLLYYRIVYIPSEDYWPWIMIFVAE LGFAYGWILEQAFRWRPVERKVFPERL SKRFKSDLPPVDIFICTADPIKEPPLAVIN TVLSALAVDYPVEKLSCYVSDDGVSSL TFYALFEASRFAKIWLPFCYNYSIQDRS PEAYFSARSGQEKENMSFTRECKSVKK AYLEMKDRINNAVEMGSVPDDKQKEH TGFKDWILGSTRRDHPSIVQILLENGED KDIQGNDLPSLIYVSREKRPGIPHHYKA GALNALIRISGLMSNAPFIITLDCDMCTN NCEALRQAMCFFLDPQTGHQFAYVQFP QGFHGITRNDLYANDHLRISYWQFKGM DGLEGPLYAGTGCIHRRDALCGKEGRL ASSTSKAQTSPSKMLKDARHLANCACE ENTLWGKEVGMIYGCAEEDALTGFVIQ SRGWKSIYCTPRRKAFLGGAPVNMNDT LIQIKRWSAGYLEFFLSKFCPYVYGIQR TSTVQCMCYGVCCLWAPSSLYILCYGL LPALAMLNGLSLFPKASNPWFILFVSLA ASTYGYSLIEFMCIGGSFKSWWNEQRM WLIKGVSSYLFALIQVVCKMLGLSEVG FEVTSKVVDSEAAKRHEEEMLEFGVAS AMFVPPASLAITNLISLVGGLARIMREG YQTFDSMIWQLLLCSFIVLISYPILEAMF LRKDKGRIPTSITIVSIFVAVSACSVASIL IPTW |
| 58 | pinusRadiata_027496 | Cellulose synthase like | MDRLSYSSANILPQTFQGTRDDIVEQIA LLWQQIRAPLVAPLLNICIYFCLLMSVM LFIERVYMAVVIVLIKVFGKKPEKRYK WGAIKEDVELGNSVYPMVLVQIPMYNE REVYQLSIGAACALSWPSNRVIIQVLDD STDLTIKDLVEMECQKWASKGINIKYEI RGNRNGYKAGALKEGMKHSYVRECDY VVIFDADFQPDRDFLSRTIPFLVHNPELA LVQARWKFA |

TABLE 5

Oligonucleotide sequences

| SEQ ID | Consensus ID Target | Oligonucleotide Sequence |
|---|---|---|
| 59 | eucalyptusSpp_003922 | AGGCGGTTTGAAATGGTTAGAGCGATTATCTTACATAA ACGCCACAGTATACCCCTGGAC |
| 60 | eucalyptusSpp_004683 | GTGAGAGAGAGCCCCACTCTCAAGGCCAGGTTCTATAC TTGCACAAAAGTGTTCCTTTGG |
| 61 | eucalyptusSpp_005009 | TCATGCTTTTCATGGAGAGGGTCTACATGGGCATCGTCA TCGTCCTCGTCAAGCTCTTCT |
| 62 | eucalyptusSpp_008124 | ACACAGTTCTGTCAATATTGGCTATGGACTATCCAGTCG ATAAGATTCCTGCTACGTTT |

TABLE 5-continued

Oligonucleotide sequences

| SEQ ID | Consensus ID Target | Oligonucleotide Sequence |
|---|---|---|
| 63 | eucalyptusSpp_008896 | CGTCCGTCTTCATCGATAAGTAATTGTCTTATTTTGCTC AGCTGTTGGATTCGTGATCAG |
| 64 | eucalyptusSpp_012804 | GAGAGTCCTTGTACAGCGAACCCATGCAAGAAGGTACT ACAGCTAATCTCATGGATTTGA |
| 65 | eucalyptusSpp_016249 | GATGGGATTGATCGTCACGATCGATACTCTAACAGGAA TGTCGTATTCTTCGATATCAAC |
| 66 | eucalyptusSpp_016939 | TTTTGATGTCCCTACGGTGACAATGGTACATGCTCGTTA CTTGGTGTAGTTATTCTTGTT |
| 67 | eucalyptusSpp_017058 | CAAGTCAACGACTTGTTATGTATACGGAACCATAGACG CGATTATGACACAAATCGGCAT |
|  | eucalyptusSpp_017442 | no oligo |
| 68 | eucalyptusSpp_017462 | AAAAAGACCATTCCTTATTTTAAGGGAAACGATGATCT AGCATTGGTCCAGACGAGATGG |
| 69 | eucalyptusSpp_017488 | AATCCCTCTTCTAACCAATGGGCAGCCGATGTCTGGTGA AATCCCTTGTGCTAGTATTGA |
| 70 | eucalyptusSpp_017722 | TCCGAAGTGGTTTCCAGTAAATCGTGAAACGTATCTCG ACAGACTAGCCATTAGGTATGA |
| 71 | eucalyptusSpp_022868 | AAAATAAACACGTTTGAGTGAAATTTGTTTGTTGTGAG GAGCATTTGTATATTTGTGCCC |
| 72 | eucalyptusSpp_023490 | GTTCGGTTCCAGGTAATTCATGAGTATAATTTAGTCCAT TAGGGTTGTAGGACCCTTGTC |
| 73 | eucalyptusSpp_027512 | ATTCCGATTGCCTCTTTAGCACGTGCGAAGGTGCATGTG AGCCTCTACATATGCACCGAT |
| 74 | pinusRadiata_000531 | TTTATATCCGTGGAATGTAATTCATTAACGCGTGCCCAT AATTAGGCAGCTTTTACGAGT |
| 75 | pinusRadiata_002922 | TCAAACATCCATTTGCTGGTCAACCATGTCTATTCCAAA ATTAATTTGCCATTCGGAAAG |
| 76 | pinusRadiata_003920 | GAATTTGATGTTTTTAACGGCTGTGATTGCCTATATTTT GTTTCATTCTGTACTACGGAT |
| 77 | pinusRadiata_017730 | TCTGTATCTCAGATGTTGTCTAGCTTTAATGTATTCAGC AAGCGGTGTGAGATAAAGTTT |
| 78 | pinusRadiata_027109 | TATTCCAGAGGTACTACCCTTGACATTCATGCCCTATAT TAACATTGTATCTGAGTTGGC |
| 79 | pinusRadiata_000892 | TGATGATGTCACATAATCCACAGGAATGATCCGTCAAC AATTCAGATACTTTGCAATTGA |
| 80 | pinusRadiata_008513 | GAACAAGGTTCCGTTGTAAACTCATGGTCCCTGATTAG AAGTTTGTTTATGTGATAGTTT |
| 81 | pinusRadiata_013907 | TTGCCCTTGTAATGTTCTTTGACACTAACTGGAGACCTG ATTTTAGGCCAAGATTCAAGT |
| 82 | pinusRadiata_026937 | AAATTGCCAAAGTCGCGACATATATAGATAGTACAACT GTTCTAATTTACCGCGTTTTTC |
| 83 | pinusRadiata_027496 | GGGGTTTTAATATGATTTCCACGAAACCAAGTGGTCTA AGTGGTATAAGGACAAGTCAAT |

What is claimed is:

1. An isolated polynucleotide comprising the nucleic acid sequence of SEQ ID NO: 20.

2. A DNA construct comprising the polynucleotide of claim 1.

3. The DNA construct of claim 2, further comprising a promoter, wherein the promoter and the polynucleotide are operably linked.

4. A plant cell transformed with the construct of claim 3.

5. A transgenic plant transformed with the construct of claim 3.

6. The DNA construct of claim 3, wherein the promoter is selected from the group consisting of a constitutive promoter, an inducible promoter, a regulatable promoter, a temporally regulated promoter, and a tissue-preferred promoter.

7. The DNA construct of claim 3, wherein the polynucleotide encodes an RNA transcript.

8. The DNA construct of claim 7, wherein the polynucleotide is in a sense or antisense orientation relative to the promoter.

9. The DNA construct of claim 7, wherein the RNA transcript induces RNA interference of a polynucleotide having the nucleic acid sequence of SEQ ID NO: 20.

10. A plant cell transformed with the DNA construct of claim 9, wherein the plant cell is from the genus *Pinus*.

11. A transgenic plant comprising the plant cell of claim 10.

12. A method of making a transformed *Pinus* plant comprising (A) transforming a plant cell with the DNA construct of claim 9; and (B) culturing the transformed plant cell under conditions that promote growth of a plant.

13. An isolated polynucleotide encoding the protein of SEQ ID NO: 49.

14. A plant cell transformed with a DNA construct comprising the isolated polynucleotide of claim 13 operably linked to a promoter.

15. A transgenic plant comprising the plant cell of claim 14.

16. The transgenic plant of claim 15, wherein a phenotype of the plant is different from a phenotype of a plant of the same species that has not been transformed with the DNA construct.

* * * * *